US009957519B2

(12) United States Patent
Roberts et al.

(10) Patent No.: US 9,957,519 B2

(45) Date of Patent: May 1, 2018

(54) ACYLTRANSFERASE POLYNUCLEOTIDES, POLYPEPTIDES AND METHODS OF USE

(71) Applicant: Agresearch Limited, Hamilton (NZ)

(72) Inventors: Nicholas John Roberts, Feilding (NZ); Amy Christina Curran, San Diego, CA (US); Somrutai Winichayakul, Palmerston North (NZ); Marissa Roldan, Palmerston North (NZ); Richard William Scott, Palmerston North (NZ)

(73) Assignee: Agresearch Limited, Hamilton (NZ)

( * ) Notice: Subject to any disclaimer, the term of this patent is extended or adjusted under 35 U.S.C. 154(b) by 0 days. days.

(21) Appl. No.: 14/438,784

(22) PCT Filed: Oct. 22, 2013

(86) PCT No.: PCT/IB2013/059525
§ 371 (c)(1),
(2) Date: Apr. 27, 2015

(87) PCT Pub. No.: WO2014/068438
PCT Pub. Date: May 8, 2014

(65) Prior Publication Data

US 2015/0252378 A1 Sep. 10, 2015

Related U.S. Application Data

(60) Provisional application No. 61/720,136, filed on Oct. 30, 2012.

(51) Int. Cl.
*C12N 9/10* (2006.01)
*C12N 15/82* (2006.01)
*C12P 7/64* (2006.01)

(52) U.S. Cl.
CPC ....... *C12N 15/8247* (2013.01); *C12N 9/1029* (2013.01); *C12P 7/6445* (2013.01); *C12Y 203/0102* (2013.01)

(58) Field of Classification Search
None
See application file for complete search history.

(56) References Cited

U.S. PATENT DOCUMENTS 4,795,855 A 1/1989 Fillatti et al.
4,943,674 A 7/1990 Houck et al.
(Continued)

FOREIGN PATENT DOCUMENTS

WO WO 1998/055631 A1 12/1998
WO WO 2000/001713 A2 1/2000
(Continued)

OTHER PUBLICATIONS

Genseq Accession No. AKT19954, published Nov. 29, 2007.*
(Continued)

*Primary Examiner* — Richard C Ekstrom
(74) *Attorney, Agent, or Firm* — Lathrop Gage LLP

(57) ABSTRACT

The invention provides a novel DGAT1 protein with improved properties over known DGAT proteins, particularly known DGAT1 proteins from plants. The novel DGAT1 protein of the invention can be expressed in cells to increase cellular lipid accumulation. Expression of the DGAT1 protein of the invention in cells results in a higher level of lipid than any of several other plant DGAT1 proteins tested by the applicants. The invention provides polynucleotides encoding the novel DGAT1 protein of SEQ ID NO:39, constructs, cells, plant, plant parts and progeny comprising the polynucleotides, and methods of use of the polynucleotides and polypeptides of the invention.

30 Claims, 21 Drawing Sheets

(56) References Cited

U.S. PATENT DOCUMENTS

| | | | | |
|---|---|---|---|---|
| 5,004,863 | A | 4/1991 | Umbeck | |
| 5,086,169 | A | 2/1992 | Mascarenhas | |
| 5,159,135 | A | 10/1992 | Umbeck | |
| 5,177,010 | A | 1/1993 | Goldman et al. | |
| 5,187,073 | A | 2/1993 | Goldman et al. | |
| 5,188,958 | A | 2/1993 | Moloney et al. | |
| 5,412,085 | A | 5/1995 | Allen et al. | |
| 5,416,011 | A | 5/1995 | Hinchee et al. | |
| 5,463,174 | A | 10/1995 | Moloney et al. | |
| 5,536,653 | A | 7/1996 | Barry et al. | |
| 5,545,169 | A | 8/1996 | Yarger | |
| 5,545,546 | A | 8/1996 | Allen et al. | |
| 5,563,055 | A | 10/1996 | Townsend et al. | |
| 5,569,834 | A | 10/1996 | Hinchee et al. | |
| 5,591,616 | A | 1/1997 | Hiei et al. | |
| 5,608,150 | A | 3/1997 | Conner | |
| 5,639,952 | A | 6/1997 | Quail et al. | |
| 5,656,496 | A | 8/1997 | Quail et al. | |
| 5,750,385 | A | 5/1998 | Shewmaker et al. | |
| 5,750,871 | A | 5/1998 | Moloney et al. | |
| 5,792,935 | A | 8/1998 | Arntzen et al. | |
| 5,795,855 | A | 8/1998 | Schneider et al. | |
| 5,824,877 | A | 10/1998 | Hinchee et al. | |
| 5,837,848 | A | 11/1998 | Ely et al. | |
| 5,846,797 | A | 12/1998 | Strickland | |
| 5,952,543 | A | 9/1999 | Firoozabady et al. | |
| 5,968,830 | A | 10/1999 | Dan et al. | |
| 5,981,840 | A | 11/1999 | Zhao et al. | |
| 6,020,539 | A | 2/2000 | Goldman et al. | |
| 6,037,522 | A | 3/2000 | Dong et al. | |
| 6,074,877 | A | 6/2000 | D'Halluin et al. | |
| 6,100,077 | A | 8/2000 | Sturley et al. | |
| 6,127,179 | A | 10/2000 | Dellapenna et al. | |
| 6,184,443 | B1 | 2/2001 | Pedersen et al. | |
| 6,228,643 | B1 | 5/2001 | Greenland et al. | |
| 6,229,067 | B1 | 5/2001 | Sonnewald et al. | |
| 6,342,657 | B1 | 1/2002 | Thomas et al. | |
| 6,344,548 | B1 | 2/2002 | Farese, Jr. et al. | |
| 6,552,250 | B1 * | 4/2003 | Nykiforuk | C12N 15/8247 435/419 |
| 7,081,565 | B2 | 7/2006 | Ohlrogge et al. | |
| 7,141,424 | B2 | 11/2006 | Shin et al. | |
| 7,153,953 | B2 | 12/2006 | Marraccini et al. | |
| 7,371,928 | B2 | 5/2008 | Suh et al. | |
| 7,405,345 | B2 | 7/2008 | Ohlrogge et al. | |
| 7,629,454 | B2 | 12/2009 | Chan et al. | |
| 7,642,346 | B2 | 1/2010 | Chaudhary et al. | |
| 7,667,097 | B2 | 2/2010 | Scheirlinck et al. | |
| 7,745,697 | B2 | 6/2010 | Perez et al. | |
| 2001/0047525 | A1 | 11/2001 | Bruce et al. | |
| 2003/0074695 | A1 * | 4/2003 | Farese, Jr. | C12P 7/64 800/281 |
| 2003/0115632 | A1 | 6/2003 | Lardizabal et al. | |
| 2004/0067506 | A1 | 4/2004 | Scheres et al. | |
| 2009/0094717 | A1 | 4/2009 | Troukhan et al. | |
| 2009/0293152 | A1 * | 11/2009 | Roesler | C12N 9/1029 800/281 |
| 2010/0024079 | A1 | 1/2010 | Andersen et al. | |
| 2011/0167514 | A1 | 7/2011 | Brover et al. | |
| 2012/0156360 | A1 | 6/2012 | Roesler et al. | |
| 2012/0278951 | A1 * | 11/2012 | Roberts | C07K 14/415 800/298 |
| 2015/0275223 | A1 | 10/2015 | Roberts et al. | |
| 2015/0284736 | A1 | 10/2015 | Roberts et al. | |

FOREIGN PATENT DOCUMENTS

| | | | |
|---|---|---|---|
| WO | WO 2000/032756 | A2 | 6/2000 |
| WO | WO 2002/000894 | A2 | 1/2002 |
| WO | WO 2004/011671 | A2 | 2/2004 |
| WO | WO 2006/052914 | A1 | 5/2006 |
| WO | WO 2009/143397 | A2 | 11/2009 |
| WO | WO 2011/053169 | A1 | 5/2011 |

OTHER PUBLICATIONS

U.S. Appl. No. 14/438,758, filed Apr. 27, 2015, 2015/0275223, Oct. 1, 2015.

U.S. Appl. No. 14/438,768, filed Apr. 27, 2015, 2015/0284736, Oct. 8, 2015.

Alam et al. (1999) "Transgenic insect-resistant maintainer line (IR68899B) for improvement of hybrid rice," Plant Cell Rep. 18:572-575.

Altpeter et al. (2004) "Comparison of Transgene Expression Stability after Agrobacterium-mediated or Biolistic Gene Transfer into Perennial Ryegrass (*Lolium perenne* L.)," Developments in Plant Breeding. 11(7):255-260.

Altschul et al. (1997) "Gapped BLAST and PSI-BLAST: a new generation of protein database search programs," Nucleic Acids Res. 25:3389-3402.

Andrianov et al. (2009) "Tobacco as a production platform for biofuel: overexpression of *Arabidopsis* DGAT and LEC2 genes increases accumulation and shifts the composition of lipids in green biomass," Plant Biotechnol. J. 8:277-287.

Bairoch et al. (1994) "PROSITE: recent developments," Nucleic Acids Res. 22:3583-3589.

Baxevanis (2001) "The Molecular Biology Database Collection: an updated compilation of biological database resources," Nucleic Acids Res. 29:1-10.

Beopoulos et al. (Mar. 31, 2011) "An overview of lipid metabolism in yeasts and its impact on biotechnological processes," Appl. Microbiol. Biotechnol. 90:1193-1206.

Birch (1997) "Plant Transformations: Problems and Strategies for Practical Applications," Ann. Rev. Plant Phys. Plant Mol. Biol. 48:297-326.

Birney et al. (2004) "GeneWise and Genomewise," Genome Res. 14:988-995.

Bolton et al. (1962) "A General Method for The Isolation of RNA Complementary to DNA," Proc. Natl. Acad. Sci. USA. 48:1390-1397.

Bouvier-Navé et al. (2000) "Expression in yeast and tobacco of plant cDNAs encoding acyl CoA:diacylglycerol acyltransferase," Eur. J. Biochem. 267:85-96.

Bowie et al. (1990) "Deciphering the message in protein sequences: tolerance to amino acid substitutions," Science. 247:1306-1310.

Browse et al. (1986) "Fatty acid composition of leaf lipids determined after combined digestion and fatty acid methyl ester formation from fresh tissue," Anal. Biochem. 152:141-145.

Cahoon et al. (2007) "Engineering oilseeds for sustainable production of industrial and nutritional feedstocks: solving bottlenecks in fatty acid flux," Current Opinion in Plant Biology. 10:236-244.

Cardoza et al. (2006) "Canola (*Brassica napus* L.)," Methods Mol. Biol. 343:257-266.

Christou et al. (1991) "Production of Transgenic Rice (*Oryza sativa* L.) Plants from Agronomically Important Indica and Japonica Varieties via Electric Discharge Particle Acceleration of Exogenous DNA into Immature Zygotic Embryos," Nature Biotech. 9:957-962.

Clough et al. (1998) "Floral dip: a simplified method for Agrobacterium-mediated transformation of *Arabidopsis thaliana*," Plant J. 16(6):735-743.

Dan et al. (2006) "MicroTom—a high-throughput model transformation system for functional genomics," Plant Cell Reports. 25:432-441.

Durrett et al. (2008) "Plant triacylglycerols as feedstocks for the production of biofuels," Plant J. 54:593-607.

Elble (1992) "A simple and efficient procedure for transformation of yeasts," BioTechniques. 13:18-20.

Ellerström et al. (1996) "Functional dissection of a napin gene promoter: identification of promoter elements required for embryo and endosperm-specific transcription," Plant Molecular Biology. 32(6):1019-1027.

Falquet et al. (2002) "The PROSITE database, its status in 2002," Nucleic Acids Res. 30:235-238.

Feng et al. (1987) "Progressive sequence alignment as a prerequisite to correct phylogenetic trees," J. Mol. Evol. 25:351-360.

(56) References Cited

OTHER PUBLICATIONS

Folta et al. (2006) "Characterization of LF9, an octoploid strawberry genotype selected for rapid regeneration and transformation," Planta. 224(5):1058-1067.
Fortman et al. (2008) "Biofuel alternatives to ethanol: pumping the microbial well," Trends Biotechnol. 26:375-381.
Frohman (1993) "Rapid amplification of complementary DNA ends for generation of full-length complementary DNAs: thermal RACE," Methods Enzymol. 218:340-356.
GenBank (Jul. 25, 2006) "diacylglycerol acyltransferase [Oryza sativa Japonica Group]," Accession No. AAW47581. Accessible on the Internet at URL: http://www.ncbi.nlm.nih.gov/protein/AAW47581. [Last Accessed Dec. 17, 2015].
GenBank (Feb. 25, 2009) "unknown [*Zea mays*]," Accession No. ACN35495. Accessible on the Internet at URL: http://www.ncbi.nlm.nih.gov/protein/ACN35495. [Last Accessed Dec. 17, 2015].
Giesen et al. (1998) "A formula for thermal stability (Tm) prediction of PNA/DNA duplexes," Nucleic Acids Res. 26(21):5004-5006.
Gonzalez Padilla et al. (2003) "Early antibiotic selection and efficient rooting and acclimatization improve the production of transgenic plum plants (*Prunus domestica* L.)," Plant Cell Rep. 22(1):38-45.
Graham et al. (1995) "Agrobacterium-mediated transformation of soft fruit Rubus, Ribes, and Fragaria," Methods Mol. Biol. 44:129-133.
Guiheneuf et al. (2011) "Cloning and molecular characterization of a novel acyl-CoA:diacylglycerol acyltransferase 1-like gene (PtDGAT1) from the diatom Phaeodactylum tricornutum," The FEBS Journal. 278:3651-3666.
Halford et al. (1998) "SNF1-related protein kinases: global regulators of carbon metabolism in plants?" Plant Mol. Biol. 37:735-748.
Hellens et al. (2000) "pGreen: a versatile and flexible binary Ti vector for Agrobacterium-mediated plant transformation," Plant Mol. Biol. 42:819-832.
Hellens et al. (2005) "Transient expression vectors for functional genomics, quantification of promoter activity and RNA silencing in plants," Plant Methods. 1:13 pp. 1-14.
Herrera-Estrella et al. (1993) "Expression of chimaeric genes transferred into plant cells using a Ti-plasmid-derived vector," Nature. 303:209-213.
Hofmann et al. (1999) "The PROSITE database, its status in 1999," Nucleic Acids Res. 27:215-219.
Horsch et al. (1985) "A simple and general method for transferring genes into plants," Science. 227:1229-1231.
Huang (1994) "On Global Sequence Alignment," Computer Applications in the Biosciences. 10:227-235.
James et al. (Sep. 27, 2010) "Disruption of the *Arabidopsis* CGI-58 homologue produces Chanarin-Dorfman-like lipid droplet accumulation in plants," Proc. Natl. Acad. Sci. USA. 107:17833-17838.
Jang et al. (2006) "Functional classification, genomic organization, putatively cis-acting regulatory elements, and relationship to quantitative trait loci, of sorghum genes with rhizome-enriched expression," Plant Physiol. 142:1148-1159.
Jeanmougin et al. (1998) "Multiple sequence alignment with Clustal X," Trends Biochem. Sci. 23:403-405.
Josefsson et al. (1987) "Structure of a gene encoding the 1.7 S storage protein, napin, from *Brassica napus*," J. Biol. Chem. 262(25):12196-12201.
Kaup et al. (2002) "A role for diacylglycerol acyltransferase during leaf senescence," Plant Physiol. 129(4):1616-1626.
Krens et al. (1997) "Transgenic caraway, *Carum carvi* L.: a model species for metabolic engineering," Plant Cell Rep. 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Li et al. (1996) "Genetic transformation of cassava (*Manihot esculenta* Crantz)," Nat. Biotechnol. 14:736-740.
Li et al. (2003) "Transgenic rose lines harboring an antimicrobial protein gene, Ace-AMP1, demonstrate enhanced resistance to powdery mildew (*Sphaerotheca pannosa*)," Planta, 218:226-232.
Li et al. (Jan. 27, 2010) "DGAT1, DGAT2 and PDAT expression in seeds and other tissues of epoxy and hydroxy fatty acid accumulating plants," Lipids. 45:145-157.
Lung et al. (2006) "Diacylglycerol acyltransferase: a key mediator of plant triacylglycerol synthesis," Lipids. 41(12):1073-1088.
Matsuda et al. (2005) "Development of an Agrobacterium-mediated transformation method for pear (*Pyrus communis* L.) with leaf-section and axillary shoot-meristem explants," Plant Cell Rep. 24(1):45-51.
McFie et al. (Sep. 27, 2010) "Topological orientation of acyl-CoA:diacylglycerol acyltransferase-1 (DGAT1) and identification of a putative active site histidine and the role of the n terminus in dimer/tetramer formation," J. Biol. Chem. 285:37377-37387.
Michelmore et al. (1987) "Transformation of lettuce (*Lactuca sativa*) mediated by Agrobacterium tumefaciens," Plant Cell Rep. 6:439-442.
Moloney et al. (1989) "High efficiency transformation of *Brassica napus* using Agrobacterium vectors," Plant Cell Rep. 8:238-242.
Mu et al. (2008) "LEAFY COTYLEDON1 is a key regulator of fatty acid biosynthesis in *Arabidopsis*," Plant Physiol. 148:1042-1054.
Needleman et al. (1970) "A general method applicable to the search for similarities in the amino acid sequence of two proteins," J. Mol. Biol. 48:443-453.
Nielsen et al. (1991) "Sequence-selective recognition of DNA by strand displacement with a thymine-substituted polyamide," Science. 254(5037):1497-1500.
Niu et al. (1998) "Transgenic peppermint (*Mentha x piperita* L.) plants obtained by cocultivation with Agrobacterium tumefaciens," Plant Cell Rep. 17:165-171.
Notredame et al. (2000) "A novel method for fast and accurate multiple sequence alignment," J. Mol. Biol. 302:205-217.
Nykiforuk et al. (2002) "Characterization of cDNAs encoding diacylglycerol acyltransferase from cultures of *Brassica napus* and sucrose-mediated induction of enzyme biosynthesis," Biochimica et Biophysica Acta. 1580:95-109.
Ohlrogge et al. (2009) "Energy. Driving on biomass," Science. 324:1019-1020.
Oosumi et al. (2006) "High-efficiency transformation of the diploid strawberry (*Fragaria vesca*) for functional genomics," Planta. 223(6):1219-1230.
Orlikowska et al. (1995) "Factors influencing Agrobacterium tumefaciens-mediated transformation and regeneration of the safflower cultivar 'centennial,'" Plant Cell Tissue and Organ Culture. 40:85-91.
Ortiz et al. (1996) "Hygromycin resistance as an efficient selectable marker for wheat stable transformation," Plant Cell Rep. 15:877-881.
Pena et al. (1995) "High efficiency Agrobacterium-mediated transformation and regeneration of citrus," Plant Sci.104:183-191.
Potrykus et al.: Eds, (1995) Gene Transfer to Plants. Springer-Verlag. Berlin, Germany. pp. i-xxii.
Ramesh et al. (2006) "Improved methods in Agrobacterium-mediated transformation of almond using positive (mannose/pmi) or negative (kanamycin resistance) selection-based protocols," Plant Cell Rep. 25(8):821-828.
Rice et al. (2000) "EMBOSS: The European Molecular Biology Open Software Suite," Trends in Genetics. 16(6):276-277.
Rose et al. (1989) "KAR2, a karyogamy gene, is the yeast homolog of the mammalian BiP/GRP78 gene," Cell. 57:1211-1221.
Salse et al. (2008) "Identification and characterization of shared duplications between rice and wheat provide new insight into grass genome evolution," Plant Cell. 20:11-24.
Sandager et al. (2002) "Storage lipid synthesis is non-essential in yeast," The Journal of Biological Chemistry. 277:6478-6482.
Sanjaya et al. (Oct. 2011) "Increasing the energy density of vegetative tissues by diverting carbon from starch to oil biosynthesis in transgenic *Arabidopsis*," Plant Biotechnol. J. 9:874-883.

(56) References Cited

OTHER PUBLICATIONS

Santos-Mendoza et al. (2008) "Deciphering gene regulatory networks that control seed development and maturation in *Arabidopsis*," Plant J. 54:608-620.
Schenk et al. (2001) "Promoters for pregenomic RNA of banana streak badnavirus are active for transgene expression in monocot and dicot plants," Plant Molecular Biology. 47:399-412.
Schrott (1995) "Selectable Marker and Reporter Genes," Ch. 31 In; Potrykus et al.: Eds. Gene Transfer to Plants. Springer-Verlag. Berlin, Germany. pp. 325-336.
Scott et al. (Oct. 2010) "Elevation of oil body integrity and emulsion stability by polyoleosins, multiple oleosin units joined in tandem head-to-tail fusions," Plant Biotechnology Journal. 8:912-927.
Shockey et al. (2006) "Tung tree DGAT1 and DGAT2 have nonredundant functions in triacylglycerol biosynthesis and are localized to different subdomains of the endoplasmic reticulum," Plant Cell. 18:2294-2313.
Smeets et al. (1997) "Developmental Regulation of Lectin and Alliinase Synthesis in Garlic Bulbs and Leaves," Plant Physiol. 113:765-771.
Song et al. (2005) "Transformation of Montmorency sour cherry (*Prunus cerasus* L.) and Gisela 6 (*P. cerasus x P. canescens*) cherry rootstock mediated by Agrobacterium tumefaciens," Plant Cell Rep. 25(2):117-123.
Tatusova et al. (1999) "Blast 2 sequences—a new tool for comparing protein and nucleotide sequences," FEMS Microbiol. Lett. 174:247-250.
Tatusova et al. (1999) "Erratum: Blast 2 sequences—a new tool for comparing.protein and nucleotide sequences [FEMS Microbiol. 174 (1999) 247-250]," FEMS Microbiol. Lett. 177:187-188.
Thompson et al. (1994) "CLUSTAL W: improving the sensitivity of progressive multiple sequence alignment through sequence weighting, position-specific gap penalties and weight matrix choice," Nucleic Acids Res. 22:4673-4680.
Triglia et al. (1988) "A procedure for in vitro amplification of DNA segments that lie outside the boundaries of known sequences," Nucleic Acids Res. 16:8186.
Wang et al. (2006) "Transformation of Actinidia eriantha: a potential species for functional genomics studies in Actinidia," Plant Cell Rep. 25(5):425-431.
Wang et al. (2009) "Maize Transformation," In; Handbook of Maize. Bennetzen, J. L.; Hake, S. C.: Eds. Springer-Verlag. New York, New York. pp. 609-639.
Wheeler et al. (2001) "Database resources of the National Center for Biotechnology Information," Nucleic Acids Res. 29:11-16.
Xu et al. (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content," Plant Biotechnol. J. 6:799-818.
Yang et al. (2009) "Turnover of fatty acids during natural senescence of *Arabidopsis*, Brachypodium, and switchgrass and in *Arabidopsis* beta-oxidation mutants," Plant Physiol. 150:1981-1989.
Yao et al. (1995) "Regeneration of transgenic plants from the commercial apple cultivar Royal Gala," Plant Cell Reports. 14:407-412.

* cited by examiner

Figure 1

```
     N  P  F   S  F  L   L  L  L  L   F  R  E   N  F  A
    E  S  F   F  L  S  S   S  S  S   L  Q  R   K  L  C  F ·
   *  I  L  F   P  F  F   F  F  F   S  S  E  K   T  L  L ·
  1 TGAATCCTTT TTCCTTTCTT CTTCTTCTTC TCTTCAGAGA AAACTTTGCT
    S  L  S  I   R  N  Q   T  R  I   P  F  P  P   I  S  * ·
   · S  F  Y   K  E  P   D  T  N  P   I  P  T   D  F  L
   · L  F  L   *  G  T  R   H  E  S   H  S  H   R  F  L  S ·
 51 TCTCTTTCTA TAAGGAACCA GACACGAATC CCATTCCCAC CGATTTCTTA
   · L  L  P   S  I  R  S   F  P  L   H  *  I   L  F  P  L ·
    A  S  S  F   N  P  L   F  P  S   P  L  D  S   V  S  S ·
   ·  F  F  L   Q  S  A   L  S  L  S   I  R  F   C  F  L
101 GCTTCTTCCT TCAATCCGCT CTTTCCCTCT CCATTAGATT CTGTTTCCTC
   ·  S  I  S   S  A  C   F  S  I  L   S  D  A   S  F  L
   · F  N  F   F  C  M  L   L  D  S   L  *  R   L  F  S  P ·
    F  Q  F  L   L  H  A   S  R  F   S  L  T  P   L  F  S ·
151 TTTCAATTTC TTCTGCATGC TTCTCGATTC TCTCTGACGC CTCTTTTCTC
    P  T  L  F   R  Q  T   L  F  E   M  A  I  L   D  S  A ·
   ·  D  A  V   S  S  N   A  F  R  N   G  D  F   G  F  C
   · R  R  C   F  V  K  R   F  S  K   W  R  F   W  I  L  L ·
201 CCGACGCTGT TTCGTCAAAC GCTTTTCGAA ATGGCGATTT TGGATTCTGC
   · G  V  T   T  V  T  E   N  G  G   G  E  F   V  D  L  D ·
    W  R  Y  Y   G  D  G   E  R  W   R  R  V  R   R  S  * ·
   ·  A  L  L   R  *  R   R  T  V  A   E  S  S   S  I  L
251 TGGCGTTACT ACGGTGACGG AGAACGGTGG CGGAGAGTTC GTCGATCTTG
   ·  R  L  R   R  R  K   S  R  S  D   S  S  N   G  L  L
   · *  A  S   S  T  E  I   E  I  G   F  F  *   R  T  S  S ·
    I  G  F  V   D  G  N   R  D  R   I  L  L  T   D  F  F ·
301 ATAGGCTTCG TCGACGGAAA TCGAGATCGG ATTCTTCTAA CGGACTTCTT
    L  S  G  S   D  N  N   S  P  S   D  D  V  G   A  P  A ·
   ·  L  W  F   R  *  *   F  S  F  G   *  C  W   S  S  R
   · S  L  V   P  I  I  I   L  L  R   M  M  L   E  L  P  P ·
351 CTCTCTGGTT CCGATAATAA TTCTCCTTCG GATGATGTTG GAGCTCCCGC
   · D  V  R   D  R  I  D   S  V  V   N  D  D   A  Q  G  T ·
    R  R  *  G   S  D  *   F  R  C   *  R  *  R   S  G  N ·
   ·  T  L  G   I  G  L   I  P  L  L   T  M  T   L  R  E
401 CGACGTTAGG GATCGGATTG ATTCCGTTGT TAACGATGAC GCTCAGGGAA
   ·  A  N  L   A  G  D   N  N  G  G   G  D  N   N  G  G
   · S  Q  F   G  R  R  *   *  R  W   W  R  *   *  R  W  W ·
    Q  P  I  W   P  E  I   I  T  V   V  A  I  I   T  V  V ·
451 CAGCCAATTT GGCCGGAGAT AATAACGGTG GTGGCGATAA TAACGGTGGT
    G  R  G  G   G  E  G   R  G  N   A  D  A  T   F  T  Y ·
   ·  K  R  R   R  R  R   K  R  K  R   R  C  Y   V  Y  V
   · E  E  A   A  E  K  E   E  E  T   P  M  L   R  L  R  I ·
501 GGAAGAGGCG GCGGAGAAGG AAGAGGAAAC GCCGATGCTA CGTTTACGTA
   · R  P  S   V  P  A  H   R  R  A   R  E  S   P  L  S  S ·
    S  T  V  G   S  S  S   S  E  G   E  R  E  S   T  *  L ·
   ·  D  R  R   F  Q  L   I  G  G  R   E  R  V   H  L  A
551 TCGACCGTCG GTTCCAGCTC ATCGGAGGGC GAGAGAGAGT CCACTTAGCT
   ·  D  A  I   F  K  Q   V  *  N  L   R  N  L   R  I  W
   · R  R  N   L  Q  T  G   L  K  S   Q  K  S   S  N  L  V ·
    P  T  Q  S   S  N  R   F  K  I   S  E  I  F   E  F  G ·
601 CCGACGCAAT CTTCAAACAG GTTTAAAATC TCAGAAATCT TCGAATTTGG
    C  L  L  V   V  L  Y   G  I  E   F  G  D  C   F  A  L ·
   ·  F  A  C   C  F  I   W  N  *  V   W  *  L   F  C  I
   · V  C  L   L  F  Y  M   E  L  S   L  V  I   V  L  H  C ·
651 TGTTTGCTTG TTGTTTTATA TGGAATTGAG TTTGGTGATT GTTTTGCATT
   · Q  S  H   A  G  L  F   N  L  C   V  V  V   L  I  A  V ·
    A  E  P  C   R  I  I   Q  P  L   C  S  S  S   Y  C  C ·
   ·  R  A  M   P  D  Y   S  T  S  V   *  *  F   L  L  L
701 GCAGAGCCAT GCCGGATTAT TCAACCTCTG TGTAGTAGTT CTTATTGCTG
   ·  N  S  R   L  I  I   E  N  L  M   K  V  C   C  Y  L
   · K  Q  *   T  H  H  R   K  S  Y   E  G  L   L  L  L  V ·
    *  T  V  D   S  S  S   K  I  L   *  R  F  A   V  T  C ·
751 TAAACAGTAG ACTCATCATC GAAAATCTTA TGAAGGTTTG CTGTTACTTG
    F  L  L  L   G  I  E   L  L  E   N  L  S  E   T  N  N ·
   ·  S  P  F   R  N  *   I  A  *  K   F  I  R   D  E  *
   · F  S  F   *  E  L  N   C  L  K   I  Y  Q   R  R  I  T ·
801 TTTCTCCTTT TAGGAATTGA ATTGCTTGAA AATTTATCAG AGACGAATAA
```

Figure 1 Cont.

```
     ·F  V  V   A  I  I  H   V  V  W   L  V  D   Q  N  G  F·
      L  C  C  C   Y  H  S   C  S  M   V  G  *  S   E  R  I·
     · L  L  L   L  S  F   M  *  Y  G   W  L  I   R  T  D
 851 CTTTGTTGTT GCTATCATTC ATGTAGTATG GTTGGTTGAT CAGAACGGAT
     · L  V  *   F  K  I   A  A  R  L   A  A  F   H  V  L
     ·S  G  L   V  Q  D  R   C  E  I   G  R  F   S  C  V  G·
      F  W  F  S   S  R  S   L  R  D   W  P  L  F   M  C  W·
 901 TTCTGGTTTA GTTCAAGATC GCTGCGAGAT TGGCCGCTTT TCATGTGTTG
      V  K  E  D   V  F  Y   F  Q  Q   C  Y  I  V   I  R  I·
     · K  R  R   C  F  L   F  P  A  M   L  H  C   Y  T  Y
     ·*  K  K   M  F  F  I   S  S  N   V  T  L   L  Y  V  *·
 951 GTAAAAGAAG ATGTTTTTTA TTTCCAGCAA TGTTACATTG TTATACGTAT
     ·M  M  S   L  V  I  K   F  L  F   D  S  S   F  L  L  Q·
      N  D  E  F   S  D  Q   V  P  L   *  F  F  F   L  V  A·
     · *  *  V   *  *  S   S  S  S  L   I  L  L   S  C  C
1001 AATGATGAGT TTAGTGATCA AGTTCCTCTT TGATTCTTCT TTCTTGTTGC
     · Y  I  P   F  D  L   S  F  G  C   L  Y  G   *  E  I
     ·V  Y  P   F  R  S  F   L  W  L   P  L  R   L  R  N  W·
      S  I  S  L   S  I  F   P  L  A   A  F  T  V   E  K  L·
1051 AGTATATCCC TTTCGATCTT TCCTTTGGCT GCCTTTACGG TTGAGAAATT
      G  T  S  E   I  H  I   R  T  C   E  *  L  L   F  S  S·
     · Y  F  R   N  T  Y   Q  N  L  *   V  I  T   I  L  Q
     ·V  L  Q   K  Y  I  S   E  P  V   S  N  Y   Y  S  P  A·
1101 GGTACTTCAG AAATACATAT CAGAACCTGT GAGTAATTAC TATTCTCCAG
     ·H  Y  C   N  F  Y  *   R  Q  V   C  I  M   K  N  L  Q·
      P  L  L  *   F  L  L   K  T  S   L  Y  H  E   E  L  T·
     · I  T  V   I  F  I   E  D  K  F   V  S  *   R  T  Y
1151 CCATTACTGT AATTTTTATT GAAGACAAGT TTGTATCATG AAGAACTTAC
     · V  L  F   *  K  C   S  R  L  S   S  F  F   I  L  L
     ·S  S  V   L  K  M  L   K  V  V   I  F  L   H  I  I  I·
      K  F  C  F   E  N  A   Q  G  C   H  L  S  S   Y  Y  Y·
1201 AAGTTCTGTT TTGAAAATGC TCAAGGTTGT CATCTTTCTT CATATTATTA
      S  P  *  Q   R  F  C   I  Q  F   T  S  P  *   G  D  T·
     · T  M  T   E  V  L   Y  P  V  Y   V  T  L   R  *  Y
     ·H  H  D   R  G  F  V   S  S  L   R  H  P   K  V  I  L·
1251 TCACCATGAC AGAGGTTTTG TATCCAGTTT ACGTCACCCT AAGGTGATAC
     ·V  F  L   V  S  V  C   D  T  V   F  K  F   S  C  L  T·
      C  F  S  G   L  S  L   *  Y  C   F  *  V  *   L  S  D·
     · F  F  W   S  Q  F   V  I  L  F   L  S  L   V  V  *
1301 TGTTTTTCTG GTCTCAGTTT GTGATACTGT TTTTAAGTTT AGTTGTCTGA
     · R  *  S   *  K  W   T  G  V  I   L  L  F   Y  Q  V
     ·P  V  I   L  K  M  D   R  C  D   S  A  F   L  S  G  V·
      P  G  D  L   E  N  G   Q  V  *   F  C  F  F   I  R  C·
1351 CCCGGTGATC TTGAAAATGG ACAGGTGTGA TTCTGCTTTT TTATCAGGTG
      S  L  *  C   S  S  L   A  L  C   G  *  S  W   F  L  M·
     · T  L  M   L  L  T   C  I  V  W   L  K  L   V  S  Y
     ·H  F  D   A  P  H  L   H  C  V   A  K  V   G  F  L  C·
1401 TCACTTTGAT GCTCCTCACT TGCATTGTGT GGCTAAAGTT GGTTTCTTAT
     ·L  I  L   A  M  T  *   D  P  *   P  M  Q   L  I  R  *·
      A  H  T  S   Y  D  I   R  S  L   A  N  A  A   D  K  V·
     · S  Y  *   L  *  H   K  I  P  S   Q  C  S   *  *  G
1451 GCTCATACTA GCTATGACAT AAGATCCCTA GCCAATGCAG CTGATAAGGT
     · N  T  K   K  K  R   M  Y  *  S   L  A  L   C  Y  C
     ·K  Y  E   K  E  A  Y   V  L  V   T  C  T   V  L  L  F·
      K  I  R  K   R  S  V   C  I  S   H  L  H  C   V  T  V·
1501 AAAATACGAA AAAGAAGCGT ATGTATTAGT CACTTGCACT GTGTTACTGT
      F  N  Q  T   L  L  *   T  L  G   Q  S  *  S   L  L  L·
     · *  P  N   T  V  M   N  F  R  P   I  L  K   S  P  T
     ·L  T  K   H  C  Y  E   L  *  A   N  P  E   V  S  Y  Y·
1551 TTTAACCAAA CACTGTTATG AACTTTAGGC CAATCCTGAA GTCTCCTACT
     ·R  *  L   E  E  L  G   I  F  H   G  R  S   H  I  V  L·
      T  L  A  *   R  A  W   H  I  S   W  S  L  P   H  C  V·
     · V  S  L   K  S  L   A  Y  F  M   V  A  P   T  L  C
1601 ACGTTAGCTT GAAGAGCTTG GCATATTTCA TGGTCGCTCC CACATTGTGT
     · S  G  N   C  K  V   H  Q  P  F   L  Y  L   Q  E  F
     ·I  R  *   L  Q  S  A   S  T  I   L  I  L   A  R  V  S·
      Y  Q  V  T   A  K  C   I  N  H   S  Y  T  C   K  S  F·
1651 TATCAGGTAA CTGCAAAGTG CATCAACCAT TCTTATACTT GCAAGAGTTT
      L  V  *  T   S  D  L   C  F  S   P  A  K  L   S  T  F·
     · C  L  N   L  G  S   L  L  F  P   S  Q  V   I  H  V
     ·L  S  K   P  R  I  F   A  F  P   Q  P  S   Y  P  R  S·
1701 CTTGTCTAAA CCTCGGATCT TTGCTTTTCC CCAGCCAAGT TATCCACGTT
```

Figure 1 Cont.

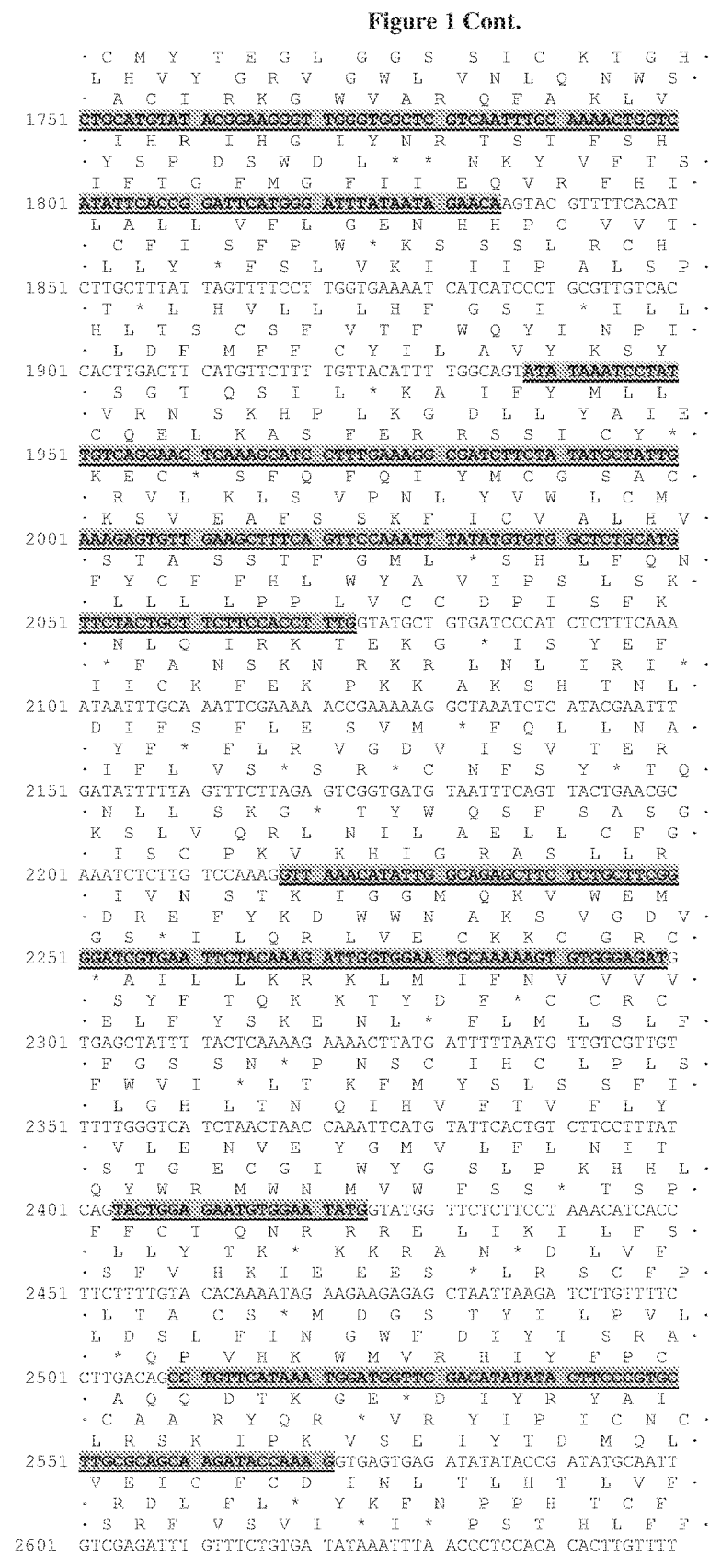

```
     ·C  M  Y   T  E  G  L   G  G  S   S  I  C   K  T  G  H·
      L  H  V  Y   G  R  V   G  W  L   V  N  L  Q   N  W  S·
     · A  C  I   R  K  G   W  V  A  R   Q  F  A   K  L  V
1751 CTGCATGTAT ACGGAAGGGT TGGGTGGCTC GTCAATTTGC AAAACTGGTC
     · I  H  R   I  H  G   I  Y  N  R   T  S  T   F  S  H
     ·Y  S  P   D  S  W  D   L  *  *   N  K  Y   V  F  T  S·
      I  F  T  G   F  M  G   F  I  I   E  Q  V  R   F  H  I·
1801 ATATTCACCG GATTCATGGG ATTTATAATA GAACAAGTAC GTTTTCACAT
      L  A  L  L   V  F  L   G  E  N   H  H  P  C   V  V  T·
     · C  F  I   S  F  P   W  *  K  S   S  S  L   R  C  H
     ·L  L  Y   *  F  S  L   V  K  I   I  I  P   A  L  S  P·
1851 CTTGCTTTAT TAGTTTTCCT TGGTGAAAAT CATCATCCCT GCGTTGTCAC
     ·T  *  L   H  V  L  L   L  H  F   G  S  I   *  I  L  L·
      H  L  T  S   C  S  F   V  T  F   W  Q  Y  I   N  P  I·
     · L  D  F   M  F  F   C  Y  I  L   A  V  Y   K  S  Y
1901 CACTTGACTT CATGTTCTTT TGTTACATTT TGGCAGTATA TAAATCCTAT
     · S  G  T   Q  S  I   L  *  K  A   I  F  Y   M  L  L
     ·V  R  N   S  K  H  P   L  K  G   D  L  L   Y  A  I  E·
      C  Q  E  L   K  A  S   F  E  R   R  S  S  I   C  Y  *·
1951 TGTCAGGAAC TCAAAGCATC CTTTGAAAGG CGATCTTCTA TATGCTATTG
      K  E  C  *   S  F  Q   F  Q  I   Y  M  C  G   S  A  C·
     · R  V  L   K  L  S   V  P  N  L   Y  V  W   L  C  M
     ·K  S  V   E  A  F  S   S  K  F   I  C  V   A  L  H  V·
2001 AAAGAGTGTT GAAGCTTTCA GTTCCAAATT TATATGTGTG GCTCTGCATG
     ·S  T  A   S  S  T  F   G  M  L   *  S  H   L  F  Q  N·
      F  Y  C  F   F  H  L   W  Y  A   V  I  P  S   L  S  K·
     · L  L  L   L  P  P   L  V  C  C   D  P  I   S  F  K
2051 TTCTACTGCT TCTTCCACCT TTGGTATGCT GTGATCCCAT CTCTTTCAAA
     · N  L  Q   I  R  K   T  E  K  G   *  I  S   Y  E  F
     ·*  F  A   N  S  K  N   R  K  R   L  N  L   I  R  I  *·
      I  I  C  K   F  E  K   P  K  K   A  K  S  H   T  N  L·
2101 ATAATTTGCA AATTCGAAAA ACCGAAAAAG GCTAAATCTC ATACGAATTT
      D  I  F  S   F  L  E   S  V  M   *  F  Q  L   L  N  A·
     · Y  F  *   F  L  R   V  G  D  V   I  S  V   T  E  R
     ·I  F  L   V  S  *  S   R  *  C   N  F  S   Y  *  T  Q·
2151 GATATTTTTA GTTTCTTAGA GTCGGTGATG TAATTTCAGT TACTGAACGC
     ·N  L  L   S  K  G  *   T  Y  W   Q  S  F   S  A  S  G·
      K  S  L  V   Q  R  L   N  I  L   A  E  L  L   C  F  G·
     · I  S  C   P  K  V   K  H  I  G   R  A  S   L  L  R
2201 AAATCTCTTG TCCAAAGGTT AAACATATTG GCAGAGCTTC TCTGCTTCGG
     · I  V  N   S  T  K   I  G  G  M   Q  K  V   W  E  M
     ·D  R  E   F  Y  K  D   W  W  N   A  K  S   V  G  D  V·
      G  S  *  I   L  Q  R   L  V  E   C  K  K  C   G  R  C·
2251 GGATCGTGAA TTCTACAAAG ATTGGTGGAA TGCAAAAAGT GTGGGAGATG
      *  A  I  L   L  K  R   K  L  M   I  F  N  V   V  V  V·
     · S  Y  F   T  Q  K   K  T  Y  D   F  *  C   C  R  C
     ·E  L  F   Y  S  K  E   N  L  *   F  L  M   L  S  L  F·
2301 TGAGCTATTT TACTCAAAAG AAAACTTATG ATTTTTAATG TTGTCGTTGT
     ·F  G  S   S  N  *  P   N  S  C   I  H  C   L  P  L  S·
      F  W  V  I   *  L  T   K  F  M   Y  S  L  S   S  F  I·
     · L  G  H   L  T  N   Q  I  H  V   F  T  V   F  L  Y
2351 TTTTGGGTCA TCTAACTAAC CAAATTCATG TATTCACTGT CTTCCTTTAT
     · V  L  E   N  V  E   Y  G  M  V   L  F  L   N  I  T
     ·S  T  G   E  C  G  I   W  Y  G   S  L  P   K  H  H  L·
      Q  Y  W  R   M  W  N   M  V  W   F  S  S  *   T  S  P·
2401 CAGTACTGGA GAATGTGGAA TATGGTATGG TTCTCTTCCT AAACATCACC
      F  F  C  T   Q  N  R   R  R  E   L  I  K  I   L  F  S·
     · L  L  Y   T  K  *   K  K  R  A   N  *  D   L  V  F
     ·S  F  V   H  K  I  E   E  E  S   *  L  R   S  C  F  P·
2451 TTCTTTTGTA CACAAAATAG AAGAAGAGAG CTAATTAAGA TCTTGTTTTC
     ·L  T  A   C  S  *  M   D  G  S   T  Y  I   L  P  V  L·
      L  D  S  L   F  I  N   G  W  F   D  I  Y  T   S  R  A·
     · *  Q  P   V  H  K   W  M  V  R   H  I  Y   F  P  C
2501 CTTGACAGCC TGTTCATAAA TGGATGGTTC GACATATATA CTTCCCGTGC
     · A  Q  Q   D  T  K   G  E  *  D   I  Y  R   Y  A  I
     ·C  A  A   R  Y  Q  R   *  V  R   Y  I  P   I  C  N  C·
      L  R  S  K   I  P  K   V  S  E   I  Y  T  D   M  Q  L·
2551 TTGCGCAGCA AGATACCAAA GGTGAGTGAG ATATATACCG ATATGCAATT
      V  E  I  C   F  C  D   I  N  L   T  L  H  T   L  V  F·
     · R  D  L   F  L  *   Y  K  F  N   P  P  H   T  C  F
     ·S  R  F   V  S  V  I   *  I  *   P  S  T   H  L  F  F·
2601 GTCGAGATTT GTTTCTGTGA TATAAATTTA ACCCTCCACA CACTTGTTTT
```

Figure 1 Cont.

```
     · Q  T  L   A  I  I  I   A  F  L   V  S  A   V  F  H  E ·
      S  D  T  R   H  Y  H   C  F  P   S  L  C  S   L  S  * ·
     ·  R  H  S   P  L  S   L  L  S  *   S  L  Q   S  F  M
2651 TCAGACACTC GCCATTATCA TTGCTTTCCT AGTCTCTGCA GTCTTTCATG
     ·  V  Y  I   L  S  T   L  P  C  L   *  T  H   E  H  T
     · G  I  H   T  F  Y  I   A  L  S   L  D  A   *  T  H  A ·
      R  Y  T  Y   F  L  H   C  P  V   S  R  R  M   N  T  R ·
2701 AGGTATACAT ACTTTCTACA TTGCCCTGTC TCTAGACGCA TGAACACACG
      L  V  K  E   M  L  I   F  K  A   L  F  L  L   N  D  L ·
     ·  S  E  R   N  A  N   I  Q  S  I   V  F  T   *  R  S
     · *  *  K   K  C  *  Y   S  K  H   C  F  Y   L  T  I  L ·
2751 CTAGTGAAAG AAATGCTAAT ATTCAAAGCA TTGTTTTTAC TTAACGATCT
     · V  L  Q   I  S  F  *   Q  L  C   I  A  V   P  C  R  L ·
      C  V  T  N   F  L  L   T  A  M   H  R  S  S   L  S  S ·
     ·  C  Y  K   F  P  F   D  S  Y  A   S  Q  F   L  V  V
2801 TGTGTTACAA ATTTCCTTTT GACAGCTATG CATCGCAGTT CCTTGTCGTC
     ·  F  K  L   W  A  F   L  G  I  M   F  Q  V   K  K  L
     · L  Q  A   M  G  F  S   W  D  Y   V  S  G   *  K  I  T ·
      S  S  S  Y   G  L  F   L  G  L   C  F  R  L   K  N  Y ·
2851 TCTTCAAGCT ATGGGCTTTT CTTGGGATTA TGTTTCAGGT TAAAAAATTA
      L  N  C  C   S  R  F   L  L  N   S  N  L  I   F  *  P ·
     ·  K  L  L   Q  S  I   F  T  K  L   *  S  H   I  L  T
     · *  T  A   A  V  D  F   Y  *  T   L  I  S   Y  S  D  Q ·
2901 CTAAACTGCT GCAGTCGATT TTTACTAAAC TCTAATCTCA TATTCTGACC
     · T  N  L   F  E  *  V   P  L  V   F  I  T   N  Y  L  Q ·
      N  Q  F  V   *  V  G   A  F  G   L  H  H  K   L  S  T ·
     ·  P  I  C   L  S  R   C  L  W  S   S  S  Q   T  I  Y
2951 AACCAATTTG TTTGAGTAGG TGCCTTTGGT CTTCATCACA AACTATCTAC
     ·  E  R  F   G  S  T   V  C  S  Q   N  P  R   K  *  N
     · G  K  V   W  L  N  G   M  L  S   K  P  E   K  I  E  R ·
      R  K  G  L   A  Q  R   Y  A  L   K  T  R  E   N  R  T ·
3001 AGGAAAGGTT TGGCTCAACG GTATGCTCTC AAAACCCGAG AAAATAGAAC
      E  *  L  F   L  S  *   P  S  H   L  N  R  N   A  E  T ·
     ·  I  T  L   S  F  I   A  *  P  F   K  S  Q   C  *  N
     · N  N  S   F  F  H  S   L  A  I   *  I  A   M  L  K  L ·
3051 GAATAACTCT TTCTTTCATA GCCTAGCCAT TTAAATCGCA ATGCTGAAAC
     · *  *  *   R  *  S  V   L  E  W   D  H  I   I  R  W  G ·
      L  I  I  K   V  I  C   F  G  M   G  S  Y  Y   *  V  G ·
     ·  N  N  K   G  D  L   F  W  N  G   I  I  L   L  G  G
3101 TTAATAATAA AGGTGATCTG TTTTGGAATG GGATCATATT ATTAGGTGGG
     ·  T  *  S   S  G  S   S  S  A  F   S  D  N   R  C  V
     · N  M  I   F  W  F  I   F  C  I   F  G  Q   P  M  C  V ·
      E  H  D  L   L  V  H   L  L  H   F  R  T  T   D  V  C ·
3151 GAACATGATC TTCTGGTTCA TCTTCTGCAT TTTCGGACAA CCGATGTGTG
      C  F  F  I   T  T  T   *  *  T   E  K  D  R   C  H  E ·
     ·  L  L  Y   Y  H  D   L  M  N  R   K  G  S   M  S  *
     · A  S  L   L  P  R  P   D  E  P   K  R  I   D  V  M  K ·
3201 TGCTTCTTTA TTACCACGAC CTGATGAACC GAAAAGGATC GATGTCATGA
     · T  T  V   Q  K  M  T   F  F  K   H  L  W   P  R  W  I ·
      N  N  C  S   K  N  D   F  L  Q   T  S  M  A   S  L  D ·
     ·  Q  L  F   K  K  *   L  S  S  N   I  Y  G   L  V  G
3251 AACAACTGTT CAAAAAATGA CTTTCTTCAA ACATCTATGG CCTCGTTGGA
     ·  S  V  D   V  V  V   V  L  M  L   K  R  Q   I  V  L
     · L  R  *   C  C  G  G   S  D  A   K  T  T   N  S  V  I ·
      S  P  L  M   L  W  W   F  *  C   *  N  D  K   *  C  Y ·
3301 TCTCCGTTGA TGTTGTGGTG GTTCTGATGC TAAAACGACA AATAGTGTTA
      *  P  L  K   K  K  R   K  L  E   L  L  Y  L   Q  K  F ·
     ·  T  I  E   E  E  K   K  I  R  V   V  V  S   A  K  I
     · N  H  *   R  R  K  E   N  *  S   C  C  I   C  K  N  F ·
3351 TAACCATTGA AGAAGAAAAG AAAATTAGAG TTGTTGTATC TGCAAAAATT
     · W  *  R   H  A  N  P   F  G  F   C  Y  G   V  K  K  F ·
      L  V  E  T   R  E  P   V  W  I   L  L  W  C   K  E  I ·
     ·  G  R  D   T  R  T   R  L  D  F   V  M  V   *  R  N
3401 TTGGTAGAGA CACGCGAACC CGTTTGGATT TTGTTATGGT GTAAAGAAAT
     ·  Q  S  K   N  C  C   N  N  C  Y   Q  K  E   M  L  F
     · S  I  K   K  L  L  *   *  L  L   P  K  R   N  A  F  L ·
      F  N  Q  K   T  V  V   I  I  V   T  K  K  K   C  F  S ·
3451 TTCAATCAAA AAACTGTTGT AATAATTGTT ACCAAAAAGA AATGCTTTTC
      W  K  R  G   E  K  *   *  F  C
     ·  E  T  R   G  K  I   V  V  L
     · G  N  E   G  K  N  S   S  F  V
3501 TGGAAACGAG GGGAAAAATA GTAGTTTTGT T (SEQ ID NO:116)
```

Figure 2

```
       G  P  A   P  L  H   A  C  R  L   R  S  R   R  P  W
      W  P  R   P  P  P  C   L  P  P   P  I  A   P  A  L  A ·
     M  A  P  P   P  S  M   P  A  A   S  D  R  A   G  P  G ·
   1 ATGGCCCCGC CCCCCTCCAT GCCTGCCGCC TCCGATCGCG CCGGCCCTGG
     P  R  R  G   R  L  V   L  P  S   P  P  P  R   P  L  S ·
     · A  T  R   A  T  R   P  P  F  A   S  A  A   P  P  Q
     · R  D  A   G  D  S  S   S  L  R   L  R  R   A  P  S  A ·
  51 CCGCGACGCG GGCGACTCGT CCTCCCTTCG CCTCCGCCGC GCCCCCTCAG
     · R  R  R   R  P  C  R   R  F  L   G  R  L   A  G  E  R ·
     P  T  P  A   T  L  P   A  I  P   R  *  A  C   G  R  T ·
     · D  A  G   D  L  A   G  D  S  S   V  G  L   R  E  N
 101 CCGACGCCGG CGACCTTGCC GGCGATTCCT CGGTAGGCTT GCGGGAGAAC
     · R  A  A   T  A  D   E  S  A  A   A  G  A   A  A  A
     · A  S  R   N  R  R  R   I  R  R   R  R  S   S  S  S  S ·
     G  E  P  Q   P  P  T   N  P  P   P  Q  E  Q   Q  Q  Q ·
 151 GGCGAGCCGC AACCGCCGAC GAATCCGCCG CCGCAGGAGC AGCAGCAGCA
     A  R  D  A   I  L  P   R  V  G   A  R  P  P   P  R  Q ·
     · T  R  C   Y  T  T   A  R  R  R   P  P  T   A  A  S
     · H  E  M   L  Y  Y  R   A  S  A   P  A  H   R  R  V  K ·
 201 GCACGAGATG CTATACTACC GCGCGTCGGC GCCCGCCCAC CGCCGCGTCA
     · G  E  P   P  Q  L  *   R  H  L   P  A  G   E  E  T  R ·
     R  R  A  P   S  A  L   T  P  S   S  G  R  *   G  D  A ·
     · E  S  P   L  S  S   D  A  I  F   R  Q  V   R  R  R
 251 AGGAGAGCCC CCTCAGCTCT GACGCCATCT TCCGGCAGGT GAGGAGACGC
     · I  L  G   S  L  F   V  S  D  C   L  I  P   A  L  V
     · N  F  R   L  A  V  C   K  R  L   F  D  P   R  A  C  A ·
     E  F  *  A   R  C  L   *  A  I   V  *  S  P   R  L  C ·
 301 GAATTTTAGG CTCGCTGTTT GTAAGCGATT GTTTGATCCC CGCGCTTGTG
     L  R  S  T   P  V  A   K  S  C   K  L  F  V   A  S  S ·
     · S  I  H   A  S  C   K  I  L  Q   I  V  C   C  F  Q
     · F  D  P   R  Q  L  Q   N  P  A   N  C  L   L  L  P  V ·
 351 CTTCGATCCA CGCCAGTTGC AAAATCCTGC AAATTGTTTG TTGCTTCCAG
     · Q  L  C   L  C  F  F   L  V  G   V  C  V   C  V  C  V ·
     S  T  L  P   L  F  F   F  G  W   C  V  C  V   C  V  C ·
     · N  S  A   S  V  F   F  W  L  V   C  V  C   V  C  V
 401 TCAACTCTGC CTCTGTTTTT TTTTGGTTGG TGTGTGTGTG TGTGTGTGTG
     · Q  I  T   L  C  A   I  G  S  L   T  L  P   V  A  I
     · S  N  H   T  L  C  Y   R  *  L   N  T  A   G  C  H  L ·
     F  K  S  H   F  V  L   S  V  A   *  H  C  R   L  P  S ·
 451 TTCAAATCAC ACTTTGTGCT ATCGGTAGCT TAACACTGCC GGTTGCCATC
     S  R  A  R   M  F  Y   C  G  P   W  A  S  E   L  W  I ·
     · A  R  T   D  V  L   L  W  A  L   G  F  G   I  V  D
     · R  A  H   G  C  F  I   V  G  L   G  L  R   N  C  G  * ·
 501 TCGCGCGCAC GGATGTTTTA TTGTGGGCCT TGGGCTTCGG AATTGTGGAT
     · D  C  A   R  V  L  E   W  A  Q   F  V  S   W  G  A  Y ·
     R  L  C  A   C  T  R   M  G  T   I  R  F  V   G  G  I ·
     · I  V  R   V  Y  S   N  G  H  N   S  F  R   G  G  H
 551 AGATTGTGCG CGTGTACTCG AATGGGCACA ATTCGTTTCG TGGGGGGCAT
     · A  A  A   I  E  V   G  V  Y  L   F  W  D   Q  G  D
     · C  C  C   D  *  G  R   C  L  L   V  L  G   S  G  G  P ·
     M  L  L  R   L  R  S   V  F  T   C  F  G  I   R  G  T ·
 601 ATGCTGCTGC GATTGAGGTC GGTGTTTACT TGTTTTGGGA TCAGGGGGAC
     Q  C  R  C   A  G  A   R  C  M   P  R  R  I   W  H  R ·
     · V  P  V   R  G  C   Q  M  H  A   T  Q  N   L  A  S
     · S  A  G   A  R  V  P   D  A  C   H  A  E   F  G  I  G ·
 651 CAGTGCCGGT GCGCGGGTGC CAGATGCATG CCACGCAGAA TTTGGCATCG
     · P  A  E   A  A  N  N   E  R  N   R  Y  H   W  R  S  F ·
     A  G  *  S   S  K  Q   R  A  *   P  L  P  L   E  E  L ·
     · R  L  K   Q  Q  T   T  S  V  T   V  T  T   G  G  A
 701 GCCGGCTGAA GCAGCAAACA ACGAGCGTAA CCGTTACCAC TGGAGGAGCT
     · G  L  S   K  R  M   T  G  *  A   N  E  S   L  N  S
     · W  L  V   E  T  D  D   W  M  S   E  *  I   I  E  F  I ·
     L  A  C  R   N  G  *   L  D  E   R  M  N  H   *  I  H ·
 751 TTGGCTTGTC GAAACGGATG ACTGGATGAG CGAATGAATC ATTGAATTCA
     L  L  A  V   L  T  I   V  M  W   T  V  V  G   T  A  P ·
     · V  G  G   T  H  Y   S  D  V  D   S  C  W   D  S  T
     · C  W  R   Y  S  L  *   *  C  G   Q  L  L   G  Q  H  L ·
 801 TTGTTGGCGG TACTCACTAT AGTGATGTGG ACAGTTGTTG GGACAGCACC
     · A  V  P   P  V  L  L   M  L  T   F  L  T   T  M  R  V ·
     C  S  A  P   S  I  I   N  A  D   F  S  N  Y   N  A  C ·
     · Q  C  P   Q  Y  Y   *  C  *  L   F  *  L   Q  C  V
 851 TGCAGTGCCC CCAGTATTAT TAATGCTGAC TTTTCTAACT ACAATGCGTG
```

Figure 2 Cont.

```
     · T  L  F   V  H  L   G  F  P  A   W  G  I   A  S  C
     ·Y  I  V   C  T  P  W   L  S  C   L  G  H   C  F  L  L·
      L  H  C  L   Y  T  L   A  F  L   L  G  A  L   L  L  V·
 901 TTACATTGTT TGTACACCTT GGCTTTCCTG CTTGGGGCAT TGCTTCTTGT
      *  G  P  Y   N  C  A   P  T  *   N  C  I  G   P  L  V·
     · R  T  I   *  L  C   T  Y  I  E   L  Y  W   T  T  C
     ·E  D  H   I  T  V  H   L  H  R   T  V  L   D  H  L  *·
 951 TGAGGACCAT ATAACTGTGC ACCTACATAG AACTGTATTG GACCACTTGT
     ·S  F  N   W  L  A  L   H  F  L   I  G  I   L  L  D  N·
      K  F  *  L   V  S  P   P  F  F   N  R  Y  I   I  R  Q·
     · V  L  T   G  *  P   S  I  F  *   *  V  Y   Y  *  T
1001 AAGTTTTAAC TGGTTAGCCC TCCATTTTTT AATAGGTATA TTATTAGACA
     · F  Y  C   H  *  H   Y  F  C  L   L  L  S   E  P  F
     ·F  L  L   S  L  T  L   F  L  F   A  T  L   G  A  L  F·
      I  F  I  V   I  D  I   I  F  V   C  Y  S  R   S  P  F·
1051 ATTTTTATTG TCATTGACAT TATTTTTGTT TGCTACTCTC GGAGCCCTTT
      S  Q  C  N   L  N  R   A  Q  I   T  A  E  T   R  E  T·
     · P  V  *   S  *  *   G  S  N  H   S  R  N   T  *  D
     ·P  S  V   I  L  I  G   L  K  S   Q  Q  K   H  V  R  R·
1101 TCCCAGTGTA ATCTTAATAG GGCTCAAATC ACAGCAGAAA CACGTGAGAC
     ·*  F  S   S  D  T  F   I  R  L   C  C  F   C  T  Y  S·
      V  I  F  *   *  Y  F   Y  *  T   L  L  F  L   H  I  L·
     · N  F  L   V  I  L   L  L  D  F   V  V  S   A  H  T
1151 GTAATTTTCT AGTGATACTT TTATTAGACT TTGTTGTTTC TGCACATACT
     · K  S  V   L  K  V   G  V  L  I   W  M  I   N  N  P
     ·*  I  C   F  E  G  R   S  A  Y   L  D  D   K  *  S  S·
      L  N  L  F   *  R  *   E  C  L   F  G  *  *   I  I  L·
1201 CTAAATCTGT TTTGAAGGTA GGAGTGCTTA TTTGGATGAT AAATAATCCT
      L  L  V  A   *  I  F   I  H  H   M  P  P  T   W  F  L·
     · V  S  C   M  N  I   Y  T  S  H   A  S  Y   M  V  P
     ·C  *  L   H  E  Y  L   Y  I  T   C  L  L   H  G  S  W·
1251 CTGTTAGTTG CATGAATATT TATACATCAC ATGCCTCCTA CATGGTTCCT
     ·G  L  H   S  G  Q  R   F  D  N   *  V  H   A  N  L  I·
      G  I  T  Q   W  T  T   L  *  *   L  S  P  C   *  L  D·
     · D  Y  T   V  D  N   A  L  I  I   E  S  M   L  T  *
1301 GGGATTACAC AGTGGACAAC GCTTTGATAA TTGAGTCCAT GCTAACTTGA
     · I  I  Y   Q  Y  S   I  Y  H  F   I  L  Y   F  N  *
     ·Y  N  I   S  V  F  H   I  S  F   Y  L  V   L  Q  L  R·
      L  *  Y  I   S  I  P   Y  I  I   L  S  C  T   S  T  E·
1351 TTATAATATA TCAGTATTCC ATATATCATT TTATCTTGTA CTTCAACTGA
      D  H  P  Y   F  L  Q   T  V  F   I  G  C  S   G  E  L·
     · S  S  L   F  F  A   N  R  I  Y   W  L  L   W  R  I
     ·I  I  L   I  F  C  K   P  Y  L   L  V  A   L  E  N  *·
1401 GATCATCCTT ATTTTTTGCA AACCGTATTT ATTGGTTGCT CTGGAGAATT
     ·K  S  *   N  *  A  L   L  L  I   A  E  P   C  W  S  S·
      E  V  L  K   L  S  T   S  P  D   C  R  A  M   L  V  F·
     · S  L  E   T  K  H   F  S  *  L   Q  S  H   A  G  L
1451 GAAGTCTTGA AACTAAGCAC TTCTCCTGAT TGCAGAGCCA TGCTGGTCTT
     · E  S  M   H  C  C   S  D  R  S   E  Q  Q   T  H  Y
     ·*  I  Y   A  L  L  F   *  S  Q   *  T  A   D  S  L  L·
      L  N  L  C   I  V  V   L  I  A   V  N  S  R   L  I  I·
1501 CTGAATCTAT GCATTGTTGT TCTGATCGCA GTGAACAGCA GACTCATTAT
      *  E  F  N   E  G  L   L  L  S   F  F  F  H   F  P  H·
     · R  I  *   *  R  F   I  T  F  F   L  F  S   F  S  S
     ·E  N  L   M  K  V  Y   Y  F  L   S  F  F   I  F  L  T·
1551 TGAGAATTTA ATGAAGGTTT ATTACTTTCT TTCTTTTTTC ATTTTCCTCA
     ·L  H  L   Q  I  P  Q   S  I  S   F  *  N   T  S  G  L·
      P  S  F  T   D  P  S   I  H  L   L  L  K  Y   I  W  S·
     · F  I  Y   R  S  L   N  P  S  P   S  E  I   H  L  V
1601 CCTTCATTTA CAGATCCCTC AATCCATCTC CTTCTGAAAT ACATCTGGTC
     · L  P  A   H  L  S   S  V  N  L   T  H  S   V  F  Y
     ·S  S  C   A  F  V  *   C  K  S   D  T  F   C  V  L  F·
      F  F  L  R   I  C  L   V  *  I   *  H  I  L   C  F  I·
1651 TTCTTCCTGC GCATTTGTCT AGTGTAAATC TGACACATTC TGTGTTTTAT
      L  N  W  L   V  Q  Y   G  L  L   I  R  A  G   F  W  F·
     · K  L  A   G  A  V   W  P  V  D   K  S  W   I  L  V
     ·*  I  G   W  C  S  M   A  C  *   *  E  L   D  F  G  L·
1701 TTAAATTGGC TGGTGCAGTA TGGCCTGTTG ATAAGAGCTG GATTTTGGTT
     ·S  A  R   S  L  G  D   W  P  L   L  M  C   W  *  K  L·
      *  C  K  I   A  G  *   L  A  P   S  N  V  L   V  E  I·
     · V  Q  D   R  W  V   T  G  P  F   *  C  A   G  R  N
1751 TAGTGCAAGA TCGCTGGGTG ACTGGCCCCT TCTAATGTGC TGGTAGAAAT
```

Figure 2 Cont.

· L S F L I Q M G F K * E L W S N
· V V I F N S D G F Q I R T V E * S ·
C C H F * F R W V S N K N C G V I ·
1801 TGTTGTCATT TTTAATTCAG ATGGGTTTCA AATAAGAACT GTGGAGTAAT
Q S V N F S L T L P V F P L V A L ·
· I C Q F Q P H S T S F P T S C T
· N L S I S A S L Y Q F S H * L H S ·
1851 CAATCTGTCA ATTTCAGCCT CACTCTACCA GTTTTCCCAC TAGTTGCACT
· M A E K L I T R K L I G E H V S L ·
H G * E A D H K K A H W * T C K F ·
· W L R S * S Q E S S L V N M * V
1901 CATGGCTGAG AAGCTGATCA CAAGAAAGCT CATTGGTGAA CATGTAAGTT
· T H K I A * Y F V E K F S F V I
· D S Q D C V V F C R E V L F C Y F ·
* L T R L R S I L * R S S L L L F ·
1951 TGACTCACAA GATTGCGTAG TATTTTGTAG AGAAGTTCTC TTTTGTTATT
S * V * V L R I E L D V K L D S P ·
· L G I S V E D * I R C K T R Q S
· L R Y K C * G L N * M * N * T V L ·
2001 TCTTAGGTAT AAGTGTTGAG GATTGAATTA GATGTAAAAC TAGACAGTCC
· L F C I F Q V P F I V Y D F Y T P ·
S I L H L P G A I Y R L * L L Y T ·
· Y S A S S R C H L S F M T S I H
2051 TCTATTCTGC ATCTTCCAGG TGCCATTTAT CGTTTATGAC TTCTATACAC
· L A G G Y S T P Y H Y Y N I C H
· S C R W L F Y S I S L L Q H L P L ·
L L Q V V I L L H I I I T T S A I ·
2101 CTCTTGCAGG TGGTTATTCT ACTCCATATC ATTATTACAA CATCTGCCAT
C L S S C C D S * V S I S F C F A ·
· S I Q L L * L L S K H F F L L C
· V Y P V V V T L K * A F L S A L Q ·
2151 TGTCTATCCA GTTGTTGTGA CTCTTAAGTA AGCATTTCTT TCTGCTTTGC
· V C L D A S Y F D I R * A L V F H ·
S L F G C I L F * H S L S S S I S ·
· F V W M H L I L T F V E L * Y F
2201 AGTTTGTTTG GATGCATCTT ATTTTGACAT TCGTTGAGCT CTAGTATTTC
· G M E Y I Q L I L F V I C C T S
· W Y G I H S I N L V R N L L Y F M ·
M V W N T F N * S C S * F A V L H ·
2251 ATGGTATGGA ATACATTCAA TTAATCTTGT TCGTAATTTG CTGTACTTCA
W Y G G Q L H Y C A P N I * S F P ·
· V W W P T T L L C P K H L V F P
· G M V A N Y I I V P Q T F S L S L ·
2301 TGGTATGGTG GCCAACTACA TTATTGTGCC CCAAACATTT AGTCTTTCCC
· S R Y V L Y Y A N W V D K K V A T ·
F K I R T I L C K L G G * K G S Y ·
· Q D T Y Y T M Q I G W I K R * L
2351 TTCAAGATAC GTACTATACT ATGCAAATTG GGTGGATAAA AAGGTAGCTA
· * H F Y L I V S G D S T L * Y K
· I T L L F N C I W * L H T I I Q R ·
H N T F I * L Y L V T P H Y N T K ·
2401 CATAACACTT TTATTTAATT GTATCTGGTG ACTCCACACT ATAATACAAA
E T Q L S S I F K K K M Y L V I K ·
· N A T L Q H I Q E K N V S G D K
· K R N S P A Y S R K K C I W * * K ·
2451 GAAACGCAAC TCTCCAGCAT ATTCAAGAAA AAAATGTATC TGGTGATAAA
· I Y C K C S F I S S R R N P Y Y L ·
N L L Q M F I Y L * * K K S L L S ·
· S I A N V H L S L V E E I L T I
2501 AATCTATTGC AAATGTTCAT TTATCTCTAG TAGAAGAAAT CCTTACTATC
· T L S * S V H * L H L I G K I C
· Y S V L I C S L T A S N R E D L L ·
L L C L D L F T D C I * * G R F V ·
2551 TTACTCTGTC TTGATCTGTT CACTGACTGC ATCTAATAGG GAAGATTTGT
* S I N I D T H F I M Q I F C F F ·
· V H Q Y * Y T F Y Y A D I L F L
· S P S I L I H I L L C R Y F V S F ·
2601 TAGTCCATCA ATATTGATAC ACATTTTATT ATGCAGATAT TTTGTTTCTT
· H V A S S L * P L S * H E A D L S ·
S C S F * L V T P F L T * S * S F ·
· M * L L A C N P F P N M K L I F
2651 TCATGTAGCT TCTAGCTTGT AACCCCTTTC CTAACATGAA GCTGATCTTT

Figure 2 Cont.

```
     · I V Q E K L D I F V H M L G N *
     ·H C T R K I G Y I C S H A W K L N·
      P L Y K K N W I Y L F T C L E I E·
2701 CCATTGTACA AGAAAAATTG GATATATTTG TTCACATGCT TGGAAATTGA
      I N K L * Y F * C * C A S S R L W·
     · K Q T V V F L M L M C K * * T L
     ·* T N C S I S D V D V Q V V D F G·
2751 ATAAACAAAC TGTAGTATTT CTGATGTTGA TGTGCAAGTA GTAGACTTTG
     ·L S Q L L S L K K S H * E Q V T F·
      V E S I V I S Q K E P L G A S Y L·
     · * V N C Y L S K R A I R S K L P
2801 GTTGAGTCAA TTGTTATCTC TCAAAAAGAG CCATTAGGAG CAAGTTACCT
     · S L I I F S V R L Q E L R M L Y
     ·F I D Y I F C E T A R V K N V V W·
      F H * L Y F L * D C K S * E C C M·
2851 TTTCATTGAT TATATTTTCT GTGAGACTGC AAGAGTTAAG AATGTTGTAT
      G * C L M L F S L S L L * L P R N·
     · L M P Y A V * F K F V I I A K K
     ·V D A L C C L V * V C Y N C Q E M·
2901 GGTTGATGCC TTATGCTGTT TAGTTTAAGT TTGTTATAAT TGCCAAGAAA
     ·V T * K D I V P C I N Y G L S V Q·
      C Y L K R Y C P M H Q L W I I S S·
     · L L E K I L S H A S I M D Y Q F
2951 TGTTACTTGA AAAGATATTG TCCCATGCAT CAATTATGGA TTATCAGTTC
     · S Y S E K F Q V * L S S T I W I
     ·V I F R K I S G V T Q Q Y Y L D L·
      S H I P K N F R C D S A V L S G F·
3001 AGTCATATTC CGAAAAATTT CAGGTGTGAC TCAGCAGTAC TATCTGGATT
      C A N V S C E H H V D E A C L L C·
     · C * C F L R A S C G * S L S L M
     ·V L M F L A S I M W M K L V S Y A·
3051 TGTGCTAATG TTTCTTGCGA GCATCATGTG GATGAAGCTT GTCTCTTATG
     ·T Y K L * Y K G I V Q K Y * E G N·
      H I Q I M I * G Y C P K V L R R *·
     · H T N Y D I R V L S K S T E K V
3101 CACATACAAA TTATGATATA AGGGTATTGT CCAAAAGTAC TGAGAAGGTA
     · A L T C * S E S V Q I F C * H V
     ·C I D M L I * I S S N I L L T C C·
      M H * H V N L N Q F K Y F V N M L·
3151 ATGCATTGAC ATGTTAATCT GAATCAGTTC AAATATTTTG TTAACATGTT
      A H F S K L I C * R S N F S * N S·
     · P F L K I D L L T F K L F L K L
     ·P I S Q N * F V D V Q T F L K T P·
3201 GCCCATTTCT CAAAATTGAT TTGTTGACGT TCAAACTTTT CTTAAAACTC
     ·F W W P N F S E A R I S P T C L N·
      L L V A K F F * S * N I S H L F K·
     · F G G Q I F L K L E Y L P L V *
3251 CTTTTGGTGG CCAAATTTTT CTGAAGCTAG AATATCTCCC ACTTGTTTAA
     · F F S S F I S * M S Y I * F Q F
     ·L L F Q F H F M N V L Y L V S I F·
      T S F P V S F H E C L I S S F N F·
3301 ACTTCTTTTC CAGTTTCATT TCATGAATGT CTTATATCTA GTTTCAATTT
      L H R M K C G A N Q Y T L P S R E·
     · A * D E M W C Q S I Y V T I K R
     ·C I G * N V V P I N I R Y H Q E S·
3351 TTGCATAGGA TGAAATGTGG TGCCAATCAA TATACGTTAC CATCAAGAGA
     ·* K N C S * L L I Q C F C Y M G *·
      V K K L F L T S H T V F L L H G L·
     · K K I V L N F S Y S V F V T W A
3401 GTAAAAAAAT TGTTCTTAAC TTCTCATACA GTGTTTTTGT TACATGGGCT
     · S Y I L S C V S L T V S V Y L Y
     ·I I Y T L M C * L N C * C I P L L·
      D H I Y S H V L A * L L V Y T S I·
3451 GATCATATAT ACTCTCATGT GTTAGCTTAA CTGTTAGTGT ATACCTCTAT
      C N G P W S T * P C Y I N A F P T·
     · * W A L V H L T L L Y Q C I P N
     ·V M G L G P P N P V I S M H S Q P·
3501 TGTAATGGGC CTTGGTCCAC CTAACCCTGT TATATCAATG CATTCCCAAC
     ·L I R V R V S L I L T S G N G S I·
      P N * G * G F P H S N F R Q R * H·
     · * L G L G F P S F * L Q A T V A
3551 CCTAATTAGG GTTAGGGTTT CCCTCATTCT AACTTCAGGC AACGGTAGCA
```

Figure 2 Cont.

```
     · * L Y  P F I  F I F H  A N N  H Y C
     ·M I I  S L H F  H F S  C K *  P L L L·
      Y D Y I  P S F  S F F  M Q I T  T I A·
3601 TATGATTATA TCCCTTCATT TTCATTTTTC ATGCAAATAA CCACTATTGC
      Y I L I  F R V  L H M  E I M S  I L R·
     · Y S Y  F * G  A A Y G  N Y V  D P E
     ·I F L  F L G C  C I W  K L C  R S * E·
3651 TATATTCTTA TTTTTAGGGT GCTGCATATG GAAATTATGT CGATCCTGAG
     ·I * K  I Q P L  K V *  C T S  C W P Q·
      N M K D  P T F  K S L  V Y F M  L A P·
     · Y E R  S N L  * K S S  V L H  V G P
3701 AATATGAAAG ATCCAACCTT TAAAAGTCTA GTGTACTTCA TGTTGGCCCC
     · H F V  T R Y  Y Y W T  N A P  F L F
     ·T L C  Y Q V L  L L D  Q C P  V F V F·
      N T L L  P G T  I I G  P M P R  F C F·
3751 AACACTTTGT TACCAGGTAC TATTATTGGA CCAATGCCCC GTTTTTGTTT
      L M S T  L C F  S S S  R L S S  Y A S·
     · N V Y  T L L  F F I A  S I *  L C Q
     ·* C L  H S A F  L H R  V Y L  V M P V·
3801 TTAATGTCTA CACTCTGCTT TTCTTCATCG CGTCTATCTA GTTATGCCAG
     ·D N M  N F L M  S L W  H V M  Q P T Y·
      * Q H E  F P D  V T L  A C Y A  A N L·
     · T T *  I S *  C H F G  M L C  S Q L
3851 TGACAACATG AATTTCCTGA TGTCACTTTG GCATGTTATG CAGCCAACTT
     · P Q T  T C I  R K G W  V T Q  Q L I
     ·S S N  Y M Y *  K G L  G D P  A T H K·
      I L K L  H V L  E R V  G * P S  N S *·
3901 ATCCTCAAAC TACATGTATT AGAAAGGGTT GGGTGACCCA GCAACTCATA
      K C V V  F T G  L M G  F I I E  Q V S·
     · V R G  F Y R  L D G L  H N *  A S E
     ·S A W  F L Q A  * W A  S * L  S K * A·
3951 AAGTGCGTGG TTTTTACAGG CTTGATGGGC TTCATAATTG AGCAAGTGAG
     ·L L Y  S L S N  L Y L  Y I T  L D * I·
      P P I F  L K *  L V F  I H N F  G L N·
     · S Y I  P * V  T C I Y  T * L  W I K
4001 CCTCCTATAT TCCTTAAGTA ACTTGTATTT ATACATAACT TTGGATTAAA
     · T N F  S S I  L Q Y I  N P I  V K N
     ·Y Q F  F F Y F  A V Y  K P N  C E E F·
      L P I F  L L F  C S I  * T Q L  * R I·
4051 TTACCAATTT TTCTTCTATT TTGCAGTATA TAAACCCAAT TGTGAAGAAT
      S K H P  L K G  N F L  N A I E  R V L·
     · Q T S  T E R  E F F E  C Y R  K S L
     ·P N I  H * K G  I F *  M L *  K E S *·
4101 TCCAAACATC CACTGAAAGG GAATTTTTTG AATGCTATAG AAAGAGTCTT
     ·K L S  V P T L  Y V W  L C M  F Y C F·
      K T L S  A N I  I C M  A L H V  L L L·
     · N S Q  C Q H  Y M Y G  F A C  S I A
4151 AAAACTCTCA GTGCCAACAT TATATGTATG GCTTTGCATG TTCTATTGCT
     · F H L  W L V  S C F S  S T V  P * I
     ·F S F  M V S I  L L Q  F N S  T L N L·
      F F I Y  G * Y  L A S  V Q Q Y  L K F·
4201 TTTTTCATTT ATGGTTAGTA TCTTGCTTCA GTTCAACAGT ACCTTAAATT
      C A A V  I G L  Y N R  L I G F  * P A·
     · C G S  D W F  I * Q V  N W V  L T C
     ·V R Q  * L V Y  I T G  * L G  F D L H·
4251 TGTGCGGCAG TGATTGGTTT ATATAACAGG TTAATTGGGT TTTGACCTGC
     ·W D F  D F H F  P W H  S C L  L F W L·
      M G L *  F P F  S M A  F L F A  L L V·
     · G T L  I S I  F H G I  L V C  S F G
4301 ATGGGACTTT GATTTCCATT TTCCATGGCA TTCTTGTTTG CTCTTTTGGT
     · V S G  * T L  * L N S  S V S  V T V
     ·G F R  L N I V  A E L  L C F  G D R E·
      W F Q A  E H C  S * T  P L F R  * P *·
4351 TGGTTTCAGG CTGAACATTG TAGCTGAACT CCTCTGTTTC GGTGACCGTG
      N S I R  T G G  M P K  L L K R  * D A·
     · F Y K  D W W  N A K T  V E E  V R C
     ·I L *  G L V E  C Q N  C * R  G E M P·
4401 AATTCTATAA GGACTGGTGG AATGCCAAAA CTGTTGAAGA GGTGAGATGC
     ·C * N  * V R F  F * S  E N F  K * D *·
      L L K L  S S F  L L K  * E L *  I G L·
     · V K I  E F V  S F E V  R T L  N R T
4451 CTGTTAAAAT TGAGTTCGTT TCTTTTGAAG TGAGAACTTT AAATAGGACT
```

Figure 2 Cont.

```
       · H  Q  L   Y  S  H   V  L  K  C   D  G  I   L  G  L
       · T  S  I   I  F  S  C   T  *  M   *  W  Y   F  G  A  L ·
        D  I  N  Y   I  L  M   Y  L  N   V  M  V  F   W  G  F ·
4501 GACATCAATT ATATTCTCAT GTACTTAAAT GTGATGGTAT TTTGGGGCTT
        Y  L  S  T   G  G  C   G  T  W   *  S  F  C   Y  F  Y ·
       · P  Q  Y   W  R  M   W  N  M  V   I  F  L   L  L  L
       · T  S  V   L  E  D  V   E  H  G   N  L  F   V  T  S  I ·
4551 TACCTCAGTA CTGGAGGATG TGGAACATGG TAATCTTTTT GTTACTTCTA
       · I  Q  I   L  Y  P  F   I  *  L   R  L  C   Y  L  T  K ·
        Y  S  D  S   I  P  F   Y  L  V   E  T  L  L   L  N  * ·
       · F  R  F   Y  T  L   L  F  S  *   D  F  V   T  *  L
4601 TATTCAGATT CTATACCCTT TTATTTAGTT GAGACTTTGT TACTTAACTA
       · D  S  C   D  G  S   G  T  L  L   F  S  *   D  F  L
       · G  Q  L   *  W  *  W   Y  S  S   I  *  L   R  L  P  * ·
        R  T  V  V   M  V  V   V  L  F   Y  L  V  K   T  S  L ·
4651 AGGACAGTTG TGATGGTAGT GGTACTCTTC TATTTAGTTA AGACTTCCTT
        N  F  C  H   *  A  *   D  I  C   L  I  I  S   F  K  * ·
       · L  L  S   L  S  L   R  Y  L  S   N  N  I   F  Q  I
       · T  S  V   T  E  L  E   I  F  V   *  *  Y   L  S  N  N ·
4701 AACTTCTGTC ACTGAGCTTG AGATATTTGT CTAATAATAT CTTTCAAATA
       · L  T  I   S  L  F  F   V  S  L   F  I  S   G  S  S  D ·
        T  D  N  *   S  I  F   C  Q  P   V  H  K  W   I  I  R ·
       · *  Q  L   V  Y  F   L  S  A  C   S  *  V   D  H  Q
4751 ACTGACAATT AGTCTATTTT TTGTCAGGCT GTTCATAAGT GGATCATCAG
       · T  Y  I   F  H  V   *  G  K  A   F  P  G   *  L  L
       · H  I  Y   F  P  C  I   R  K  G   F  S  R   V  I  A  S ·
        T  H  I  F   S  M  Y   K  E  R   L  F  Q  G   N  C  F ·
4801 ACACATATAT TTTCCATGTA TAAGGAAAGG CTTTTCCAGG GTAATTGCTT
        L  Y  V  Y   K  T  L   H  L  F   F  A  F  E   F  S  K ·
       · I  C  V   Q  N  S   T  F  V  L   C  F  *   I  L  Q
       · Y  M  C   T  K  L  Y   I  C  S   L  L  L   N  S  P  N ·
4851 CTATATGTGT ACAAAACTCT ACATTTGTTC TTTGCTTTTG AATTCTCCAA
       · C  S  L   V  W  N  I   D  A  I   *  N  S   Q  Y  T  N ·
        M  Q  F  S   L  E  H   R  C  N   I  E  F  T   I  Y  K ·
       · A  V  *   F  G  T   S  M  Q  Y   R  I  H   N  I  Q
4901 ATGCAGTTTA GTTTGGAACA TCGATGCAAT ATAGAATTCA CAATATACAA
       · D  V  L   *  K  M   G  K  Q  S   W  T  E   C  *  H
       · *  C  S   L  E  N  G   E  A  E   L  D  R   V  L  A  L ·
        M  M  F  F   R  K  W   G  S  R   A  G  Q  S   V  S  T ·
4951 ATGATGTTCT TTAGAAAATG GGGAAGCAGA GCTGGACAGA GTGTTAGCAC
        S  I  V  N   L  S  *   *  *  *   I  Q  L  N   K  W  L ·
       · N  C  Q   F  V  I   I  I  M  N   T  T  E   Q  V  A
       · Q  L  S   I  C  H  N   N  N  E   Y  N  *   T  S  G  * ·
5001 TCAATTGTCA ATTTGTCATA ATAATAATGA ATACAACTGA ACAAGTGGCT
       · K  L  L   *  E  N  Q   N  T  S   G  Q  Y   Y  L  H  S ·
        E  T  V  V   R  K  S   E  H  *   W  S  I  L   F  A  * ·
       · N  C  C   E  K  I   R  T  L  V   V  N  I   I  C  I
5051 GAAACTGTTG TGAGAAAATC AGAACACTAG TGGTCAATAT TATTTGCATA
       · K  S  I   W  *  C   K  L  R  Y   E  V  L   T  S  Y
       · *  I  N   L  V  M  *   I  K  I   *  S  S   Y  F  L  Y ·
        V  N  Q  F   G  N  V   N  *  D   M  K  F  L   L  L  I ·
5101 GTAAATCAAT TTGGTAATGT AAATTAAGAT ATGAAGTTCT TACTTCTTAT
        I  K  I  Y   Y  A  *   I  L  *   W  L  K  L   Y  C  S ·
       · K  D  L   L  C  L   N  F  I  V   A  E  T   L  L  F
       · *  R  F   T  M  L  E   F  Y  S   G  *  N   F  T  V  L ·
5151 ATAAAGATTT ACTATGCTTG AATTTTATAG TGGCTGAAAC TTTACTGTTC
       · W  I  K   I  L  N  K   N  K  G   Y  L  D   L  A  T  K ·
        L  D  K  D   F  K  *   K  Q  R   I  S  R  L   G  N  K ·
       · G  *  R   F  *  I   K  T  K  D   I  *  T   W  Q  Q
5201 TTGGATAAAG ATTTTAAATA AAAACAAAGG ATATCTAGAC TTGGCAACAA
       · C  C  L   L  L  T   G  K  S  K   L  D  N   V  N  T
       · M  L  P   S  A  D  W   Q  K  *   I  R  Q   C  E  Y  M ·
        N  A  A  F   C  *  L   A  K  V   N  *  T  M   *  I  H ·
5251 AATGCTGCCT TCTGCTGACT GGCAAAAGTA AATTAGACAA TGTGAATACA
        W  T  Y  I   K  F  C   W  S  F   H  F  C  R   T  D  M ·
       · D  I  H   K  I  L   L  V  L  S   F  L  Q   N  *  H
       · G  H  T   *  N  F  V   G  P  F   I  F  A   E  L  T  * ·
5301 TGGACATACA TAAAATTTTG TTGGTCCTTT CATTTTTGCA GAACTGACAT
       · I  F  T   A  Y  F  S   N  S  Y   C  I  Y   T  A  G  C ·
        D  F  H  C   L  L  L   K  F  V   L  Y  L  H   C  R  V ·
       · F  S  L   P  T  S   Q  I  R  I   V  S  T   L  Q  G
5351 GATTTTCACT GCCTACTTCT CAAATTCGTA TTGTATCTAC ACTGCAGGGT
```

Figure 2 Cont.

```
      · S  Y  S   N  L  V   S  G  F  S   C  I  P   *  G  T
      ·*  L  F   *  S  R  F   W  F  Q   L  Y  S   M  R  Y  F·
      V  A  I  L   I  S  F   L  V  S   A  V  F  H   E  V  L·
5401  GTAGCTATTC TAATCTCCTT TCTGGTTTCA GCTGTATTCC ATGAGGTACT
      L  S  S  S   E  A  F   F  M  I   G  S  I  S   V  F  P·
      · K  F  F   R  S  L   F  H  D  R   F  N  F   C  F  S
      ·*  V  L   Q  K  P  F   S  *  S   V  Q  F   L  F  F  L·
5451  TTAAGTTCTT CAGAAGCCTT TTTCATGATC GGTTCAATTT CTGTTTTTCC
      ·K  T  C   Y  C  S  N   S  T  Q   H  I  T   N  N  T  F·
      *  D  M  L   L  F  E   F  H  S   A  H  Y  *   Q  Y  V·
      · R  H  A   I  V  R   I  P  L  S   T  L  L   T  I  R
5501  TAAGACATGC TATTGTTCGA ATTCCACTCA GCACATTACT AACAATACGT
      · D  L  T   Y  Q  Y   I  I  T  T   S  L  F   T  L  *
      ·*  P  Y   V  P  I  Y   H  H  H   I  S  F   Y  I  V  N·
      L  T  L  R   T  N  I   S  S  P   H  L  F  L   H  C  E·
5551  TTGACCTTAC GTACCAATAT ATCATCACCA CATCTCTTTT TACATTGTGA
      I  H  R  Y   V  L  R   C  R  A   T  F  S  N   S  G  H·
      · S  Q  I   C  I  A   V  P  C  H   I  F  K   F  W  A
      ·F  T  D   M  Y  C  G   A  V  P   H  F  Q   I  L  G  I·
5601  ATTCACAGAT ATGTATTGCG GTGCCGTGCC ACATTTTCAA ATTCTGGGCA
      ·F  L  G   S  C  F  R   Y  R  N   N  T  N   I  *  L  L·
      F  S  G  I   M  F  Q   V  *  K   *  H  *  Y   I  T  T·
      · F  W  D   H  V  S   G  I  E  I   T  L  I   Y  N  Y
5651  TTTTCTGGGA TCATGTTTCA GGTATAGAAA TAACACTAAT ATATAACTAC
      · P  P  F   R  I  I   S  L  S  G   L  A  F   L  V  T
      ·T  S  I   P  N  Y  K   S  F  W   L  G  F   S  S  Y  I·
      Y  L  H  S   E  L  *   V  F  L   A  W  L  F   *  L  H·
5701  TACCTCCATT CCGAATTATA AGTCTTTCTG GCTTGGCTTT TCTAGTTACA
      L  Y  *  V   Y  I  *   I  I  I   V  I  Y  L   D  I  V·
      · I  L  G   I  Y  L   D  Y  N  S   Y  I  S   R  H  C
      ·Y  T  R   Y  I  S  R   L  *  *   L  Y  I   *  T  L  C·
5751  TTATACTAGG TATATATCTA GATTATAATA GTTATATATC TAGACATTGT
      ·Y  I  *   M  H  T  K   C  Y  L   S  R  K   *  D  H  G·
      V  Y  L  D   A  Y  Q   M  L  P   I  *  K  I   G  S  W·
      · I  S  R   C  I  P   N  V  T  Y   L  E  N   R  I  M
5801  GTATATCTAG ATGCATACCA AATGTTACCT ATCTAGAAAA TAGGATCATG
      · F  R  Y   R  S  S   N  N  I  I   T  T  T   S  I  S
      ·F  Q  V   *  K  *  *   *  Y  N   N  Y  Y   L  H  F  E·
      V  S  G  I   E  V  V   I  I  *   *  L  L  P   P  F  R·
5851  GTTTCAGGTA TAGAAGTAGT AATAATATAA TAACTACTAC CTCCATTTCG
      N  C  K  S   L  *  L   G  F  Y   R  *  C  *   E  L  Y·
      · L  *  V   I  M  T   W  L  L  *   I  M  L   R  V  I
      ·T  V  S   H  Y  D  L   A  F  I   D  N  A   K  S  Y  I·
5901  AACTGTAAGT CATTATGACT TGGCTTTTAT AGATAATGCT AAGAGTTATA
      ·I  W  T   L  S  R  C   V  A  T   N  L  G   K  L  E  R·
      Y  L  D  I   I  *  M   R  S  Y   E  S  R  K   T  R  T·
      · S  G  H   Y  L  D   A  *  L  R   I  *  E   N  *  N
5951  TATCTGGACA TTATCTAGAT GCGTAGCTAC GAATCTAGGA AAACTAGAAC
      · L  V  I   I  P  A   F  S  F  E   S  I  S   V  Y  S
      ·T  C  N   Y  P  C  L   F  F  *   V  H  Q   C  L  F  S·
      D  L  *  L   S  L  P   F  L  L   S  P  S  V   S  I  L·
6001  GACTTGTAAT TATCCCTGCC TTTTCTTTTG AGTCCATCAG TGTCTATTCT
      L  T  F  *   F  H  H   Y  I  H   K  N  N  T   T  S  W·
      · Y  V  L   I  P  S   L  H  P  *   E  Q  Y   Y  I  L
      ·L  R  F   D  S  I  I   T  S  I   R  T  I   L  H  L  G·
6051  CTTACGTTTT GATTCCATCA TTACATCCAT AAGAACAATA CTACATCTTG
      ·I  Q  C   T  F  H  C   F  H  I   G  *  H   W  L  M  S·
      D  T  M  Y   L  P  L   F  S  H   R  L  T  L   V  D  V·
      · Y  N  V   P  S  T   V  F  T  *   A  D  T   G  *  C
6101  GATACAATGT ACCTTCCACT GTTTTCACAT AGGCTGACAC TGGTTGATGT
      · D  S  Q   I  P  L   V  F  L  T   R  Y  L   H  A  T
      ·*  L  T   D  T  V  G   I  L  D   K  I  S   P  C  Y  V·
      L  T  H  R   Y  R  W   Y  S  *   Q  D  I  S   M  L  R·
6151  CTGACTCACA GATACCGTTG GTATTCTTGA CAAGATATCT CCATGCTACG
      F  K  H  V   M  V  R   C  V  N   Y  V  L  F   F  P  L·
      · Q  A  C   N  G  T   L  C  Q  L   C  P  F   F  P  I
      ·S  S  M   *  W  Y  A   V  S  I   M  S  F   F  S  H  Y·
6201  TTCAAGCATG TAATGGTACG CTGTGTCAAT TATGTCCTTT TTTTCCCATT
      ·P  L  A   T  T  *  P   S  S  S   Y  L  A   G  G  Q  H·
      T  S  C  H   Y  L  T   I  I  F   L  F  G  R   W  A  T·
      · L  L  P   L  P  N   H  H  L  L   I  W  Q   V  G  N
6251  ACCTCTTGCC ACTACCTAAC CATCATCTTC TTATTTGGCA GGTGGGCAAC
```

Figure 2 Cont.

```
      · D  I  L   V  L  Q   Y  S  R  T   A  D  V   C  P  S
      · *  Y  F   G  S  S  V   *  S  D   S  R  C   V  S  F  Y ·
       M  I  F  W   F  F  S   I  V  G   Q  P  M  C   V  L  L ·
6301  ATGATATTTT GGTTCTTCAG TATAGTCGGA CAGCCGATGT GTGTCCTTCT
       I  L  P  *   R  H  E   Q  A  G   P  G  K  *   I
      · T  T  M   T  S  *   T  G  R  P   R  Q  V   D
      · Y  Y  H   D  V  M  N   R  Q  A   Q  A  S   R  *
6351  ATACTACCAT GACGTCATGA ACAGGCAGGC CCAGGCAAGT AGATAG(SEQ ID NO:117)
```

Figure 3

```
      S S K A R S P R S S N G G L R R
      V V E G S * P * K L Q W R T P K T ·
      R R R L V A L E A P M A D S E D ·
1     TCGTCGAA GGCTCGTAGC CCTAGAAGCT CCAATGGCGG ACTCCGAAGA
      R A A S R A P P P T A P R S R C C ·
      · R R Q P C T A A H R A P L A V L
      · A P P A V H R R P P R P A R G A A ·
51    CGCGCCGCCA GCCGTGCACC GCCGCCCACC GCGGCCCGCT CGCGGTGCTG
      · C S P G L R G R V A P P A E I R R ·
      L Q P R A S R P R C A A G * D P A ·
      · A A Q G F A A A L R R R L R S G
101   CTGCAGCCCA GGGCTTCGCG GCCGCGTTGC GCCGCCGGCT GAGATCCGGC
      · C G G G T R Q L C R R L R G R V
      · L R W R H A P A L P Q T P G T S L ·
      A A V A A R A S F A A D S G D E S ·
151   GCTGCGGTGG CGGCACGCGC CAGCTTTGCC GCAGACTCCG GGGACGAGTC
      W P R R A L F V S P P R Q Q R G R ·
      · A P A S P L R L A A A T T A G A
      · G P G E P S S S R R R D N S G G A ·
201   TGGCCCCGGC GAGCCCTCTT CGTCTCGCCG CCGCGACAAC AGCGGGGGCG
      · L V R R R R P G R G R G L L R V H ·
      P R P P P A A G P G Q G T S P R S ·
      · S S A A G G R A G A G D F S A F
251   CCTCGTCCGC CGCCGGCGGC CGGGCCGGGG CAGGGGACTT CTCCGCGTTC
      · L P R R G A C P P E S Q G E P S
      · P S A P R R L S T G K P R R A L * ·
      T F R A A A P V H R K A K E S P L ·
301   ACCTTCCGCG CCGCGGCGCC TGTCCACCGG AAAGCCAAGG AGAGCCCTCT
      E L R R H L Q A G Q S R D L F D C ·
      · A P T P S S S R S E Q G P I * L
      · S S D A I F K Q V R A G T Y L I A ·
351   GAGCTCCGAC GCCATCTTCA AGCAGGTCAG AGCAGGGACC TATTTGATTG
      · R A R A T C S S R C Q L F C G R F ·
      P R P R D L F V E M S A I L R P I ·
      · A P A R P V R R D V S Y S A A D
401   CCGCGCCCGC GCGACCTGTT CGTCGAGATG TCAGCTATTC TGCGGCCGAT
      · * F L R H A C L V S S V T N L K
      · L I S P P C L F G F I S N E F E T ·
      F N F S A M L V W F H Q * R I * N ·
451   TTTAATTTCT CCGCCATGCT TGTTTGGTTT CATCAGTAAC GAATTTGAAA
      L M C N R L I V A G E F S R C I Y ·
      · D V * P I N R S R G I L E V H L
      · * C V T D * S * Q G N S R G A S T ·
501   CTGATGTGTA ACCGATTAAT CGTAGCAGGG GAATTCTCGA GGTGCATCTA
      · A C G I K A S P F I Q R I W E G N ·
      R M W D K G V A F Y S E N L G G E ·
      · H V G * R R R L L F R E S G R G
551   CGCATGTGGG ATAAAGGCGT CGCCTTTTAT TCAGAGAATC TGGGAGGGGA
      · L T F R A A Y A C E K L E R S K
      · F N F S C C I C V R E A R T * Q T ·
      I * L F V L H M R A R S S N V A N ·
601   ATTTAACTTT TCGTGCTGCA TATGCGTGCG AGAAGCTCGA ACGTAGCAAA
      Q R A A H S S F C F I S T P T V W ·
      · A C C P Q F I L F Y * H T N R L
      · S V L P T V H S V L L A H Q P F G ·
651   CAGCGTGCTG CCCACAGTTC ATTCTGTTTT ATTAGCACAC CAACCGTTTG
      · * Q L L S G M I C L D * C G * K E ·
      V T V T * W H D M S * L V W I K G ·
      · D S Y L V A * Y V L I S V D K R
701   GTGACAGTTA CTTAGTGGCA TGATATGTCT TGATTAGTGT GGATAAAAGG
      · L F Y * L G A V S S N H V I S F
      · T F L L V G S C E F K S R D L L Y ·
      N F F T S W E L * V Q I T * S P L ·
751   AACTTTTTTA CTAGTTGGGA GCTGTGAGTT CAAATCACGT GATCTCCTTT
      I G I V R D L P F Y K W I Q Y M I ·
      · W H R T * P A I L Q M D P V H D
      · L A S Y V T C H F T N G S S T * * ·
801   ATTGGCATCG TACGTGACCT GCCATTTTAC AAATGGATCC AGTACATGAT
```

Figure 3 Cont.

```
     · I  *  Y   V  C  F  S   S  H  G   K  V  I   V  R  S  L ·
      N  M  I  C   V  L  Q   L  T  W   *  G  H  S   E  V  T ·
     ·  Y  D  M   C  A  S   A  H  M  V   R  S  *   *  G  H
851  AATATGATAT GTGTGCTTCA GCTCACATGG TAAGGTCATA GTGAGGTCAC
     ·  R  N  *   E  N  F   P  V  S  C   V  F  Y   V  K  I
     · *  E  L   G  K  F  S   C  F  L   C  F  L   C  E  N  K ·
      L  G  T  R   K  I  F   L  F  P   V  F  F  M   *  K  * ·
901  TTAGGAACTA GGAAAATTTT CCTGTTTCCT GTGTTTTTTA TGTGAAAATA
      N  *  F  F   L  Y  D   S  *  A   I  H  V  A   M  L  F ·
     ·  L  I  L   P  V  R   F  L  S  N   S  C  G   Y  A  V
     · T  D  S   S  C  T  I   P  K  Q   F  M  W   L  C  C  F ·
951  AACTGATTCT TCCTGTACGA TTCCTAAGCA ATTCATGTGG CTATGCTGTT
     · S  L  K   I  L  L  H   Q  R  I   L  F  Y   H  E  I  E ·
      F  P  Q  N   F  A  S   S  E  N   I  V  L  P   *  D  * ·
     ·  P  S  K   F  C  F   I  R  E  Y   C  F  T   M  R  L
1001 TTCCCTCAAA ATTTTGCTTC ATCAGAGAAT ATTGTTTTAC CATGAGATTG
     ·  S  C  *   L  I  L   L  F  W  F   L  T  E   S  C  R
     · E  L  L   A  N  T  S   I  L  V   S  D  R   V  M  Q  A ·
      R  A  V  S   *  Y  F   Y  F  G   F  *  Q  S   H  A  G ·
1051 AGAGCTGTTA GCTAATACTT CTATTTTGGT TTCTGACAGA GTCATGCAGG
      P  F  Q  P   M  Y  C   C  S  G   C  G  E  *   Q  A  H ·
     ·  F  S  T   Y  V  L   L  F  W  L   R  *  I   A  G  S
     · L  F  N   L  C  I  V   V  L  V   A  V  N   S  R  L  I ·
1101 CCTTTTCAAC CTATGTATTG TTGTTCTGGT TGCGGTGAAT AGCAGGCTCA
     · Y  *  E   P  D  E  G   S  C  H   T  F  S   I  E  Q  I ·
      L  L  R  T   *  *  R   F  L  S   Y  F  F  D   *  A  N ·
     ·  I  E  N   L  M  K   V  L  V  I   L  F  R   L  S  K
1151 TTATTGAGAA CCTGATGAAG GTTCTTGTCA TACTTTTTCG ATTGAGCAAA
     ·  D  A  I   V  L  V   P  F  T  Q   H  I  *   A  V  L
     · *  C  H   C  S  C  A   F  H  S   T  Y  L   S  C  S  F ·
      L  M  P  L   F  L  C   L  S  L   N  I  F  E   L  F  F ·
1201 TTGATGCCAT TGTTCTTGTG CCTTTCACTC AACATATTTG AGCTGTTCTT
      F  *  C  L   L  Q  Y   G  L  L   I  R  S  G   F  W  F ·
     ·  L  M  P   F  A  V   W  L  I  N   K  I  W   L  L  V
     · S  D  A   F  C  S  M   A  Y  *   *  D  L   A  F  G  L ·
1251 TTCTGATGCC TTTTGCAGCA TGGCTTATTA ATAAGATCTG GCTTTTCGTT
     · N  A  T   S  L  R  D   W  P  L   L  M  C   W  *  *  S ·
      *  C  Y  I   I  A  R   L  A  T   A  N  V  L   V  I  V ·
     ·  M  L  H   H  C  E   T  G  H  C   *  C  V   G  N  S
1301 TAATGCTACA TCATTGCGAG ACTGGCCACT GCTAATGTGT TGGTAATAGT
     ·  I  L  L   Y  H  P   L  L  Q  W   L  L  N   S  E  T
     · N  T  A   L  S  S  T   S  S  M   A  S  *   L  *  N  L ·
      Q  Y  C  S   I  I  H   F  F  N   G  F  L  T   L  K  L ·
1351 CAATACTGCT CTATCATCCA CTTCTTCAAT GGCTTCTTAA CTCTGAAACT
      *  S  A  N   L  Y  F   Q  P  *   S  T  H  I   S  P  W ·
     ·  I  S  *   F  I  F   S  A  L  V   Y  P  Y   F  P  L
     · N  Q  L   I  Y  I  F   S  L  S   L  P  I   F  P  L  G ·
1401 TAATCAGCTA ATTTATATTT TCAGCCTTAG TCTACCCATA TTTCCCCTTG
     · C  I  C   S  R  K  V   G  I  Q   Q  S  H   *  *  S  C ·
      V  H  L  Q   S  K  S   W  H  S   T  I  S  L   V  I  L ·
     ·  A  F  A   V  E  K   L  A  F  N   N  L  I   S  D  P
1451 GTGCATTTGC AGTCGAAAAG TTGGCATTCA ACAATCTCAT TAGTGATCCT
     ·  K  R  T   P  P  S   Y  K  A  Y   F  F  W   C  P  G
     · *  A  H   T  S  F  L   *  S  L   L  F  L   V  S  R  F ·
      V  S  A  H   L  L  P   I  K  L   T  F  S  G   V  Q  V ·
1501 GTAAGCGCAC ACCTCCTTCC TATAAAGCTT ACTTTTTCTG GTGTCCAGGT
      S  H  *  Q   F  M  H   F  P  Y   C  G  W  T   A  N  Y ·
     ·  S  L  T   V  Y  A   F  S  I  L   W  M  D   G  E  L
     · L  I  N   S  L  C  I   F  H  I   V  D  G   R  R  T  I ·
1551 TCTCATTAAC AGTTTATGCA TTTTCCATAT TGTGGATGGA CGGCGAACTA
     · *  F  H   L  S  K  Q   L  *  D   T  F  C   L  Y  C  F ·
      L  V  S  F   I  K  T   V  V  R   H  L  L  F   V  L  F ·
     ·  S  F  I   Y  Q  N   S  C  E  T   P  F  V   C  I  V
1601 TTAGTTTCAT TTATCAAAAC AGTTGTGAGA CACCTTTTGT TTGTATTGTT
     ·  S  K  F   C  L  *   T  I  D  L   W  F  F   P  F  S
     · L  Q  I   L  L  I  N   H  R  F   M  V  L   S  F  F  R ·
      S  P  N  F   A  Y  K   P  S  I   Y  G  S  F   L  F  Q ·
1651 TCTCCAAATT TTGCTTATAA ACCATCGATT TATGGTTCTT TCCTTTTTCA
      G  Y  Y  L   F  S  H   P  F  Y   N  I  *  N   C  I  S ·
     ·  L  L  P   V  F  T   S  F  L  Q   H  L  K   L  Y  I
     · A  T  T   C  F  H  I   L  F  T   T  F  E   I  V  Y  P ·
1701 GGCTACTACC TGTTTTCACA TCCTTTTTAC AACATTTGAA ATTGTATATC
```

Figure 3 Cont.

```
     · S  A  R   D  S  *  V   S  I  C   N  N  L   *  I  Y  D ·
      Q  C  S  *   F  L  S   K  Y  M   *  *  P  L   N  I  * ·
     ·  V  L  V   I  L  K   *  V  Y  V   I  T  F   K  Y  M
1751 CAGTGCTCGT GATTCTTAAG TAAGTATATG TAATAACCTT TAAATATATG
     ·  *  L  C   T  S  L   C  V  K  I   L  P  C   C  L  S
     · L  I  M   H  F  P  L   R  Q  D   I  A  M   L  F  I  K ·
      I  D  Y  A   L  P  S   A  S  R   Y  C  H  V   V  Y  Q ·
1801 ATTGATTATG CACTTCCCTC TGCGTCAAGA TATTGCCATG TTGTTTATCA
      R  K  Q  I   *  E  *   N  T  C   A  S  M  L   F  S  S ·
     ·  K  A  N   L  R  I   K  H  M  C   Q  Y  A   V  *  F
     · E  S  K   F  E  N  K   T  H  V   P  V  C   C  L  V  H ·
1851 AGAAAGCAAA TTTGAGAATA AAACACATGT GCCAGTATGC TGTTTAGTTC
     · Y  E  S   T  K  I  F   F  E  C   *  I  A   F  V  T  F ·
      I  *  I  Y   Q  N  F   L  R  M   L  N  R  I   C  N  F ·
     ·  M  N  L   P  K  F   S  S  N  V   K  S  H   L  *  L
1901 ATATGAATCT ACCAAAATTT TCTTCGAATG TTAAATCGCA TTTGTAACTT
     ·  G  *  Y   R  F  R   T  N  I  T   P  F  C   L  V  L
     · W  I  I   P  F  S  Y   K  Y  H   A  I  L   P  C  V  N ·
      L  D  N  T   V  F  V   Q  I  S   R  H  F  A   L  C  * ·
1951 TTGGATAATA CCGTTTTCGT ACAAATATCA CGCCATTTTG CCTTGTGTTA
      T  P  S  S   V  T  G   F  R  C   D  S  A  V   L  S  G ·
     ·  T  K  F   C  N  W   V  Q  V  *   F  C  S   F  I  R
     · H  Q  V   L  *  L  G   S  G  V   I  L  Q   F  Y  Q  A ·
2001 ACACCAAGTT CTGTAACTGG GTTCAGGTGT GATTCTGCAG TTTTATCAGG
     · F  V  L   M  F  I  A   C  I  V   W  L  K   L  V  S  F ·
      L  C  V  D   V  Y  C   L  H  C   L  A  E  A   C  I  F ·
     ·  L  C  *   C  L  L   P  A  L  F   G  *  S   L  Y  L
2051 CTTTGTGTTG ATGTTTATTG CCTGCATTGT TTGGCTGAAG CTTGTATCTT
     ·  A  H  T   N  H  D   I  R  K  L   I  T  S   G  K  K
     · C  T  Y   K  P  *  Y   K  K  T   D  H  K   R  Q  E  G ·
      L  H  I  Q   T  M  I   *  E  N   *  S  Q  A   A  R  R ·
2101 TTGCACATAC AAACCATGAT ATAAGAAAAC TGATCACAAG CGGCAAGAAG
      V  H  C  V   L  Y  F   F  L  L   R  L  F  Y   I  C  F ·
     ·  T  L  C   A  I  F   F  P  S  P   F  V  L   Y  L  L
     · Y  I  V   C  Y  I  F   S  F  S   V  C  F   I  F  A  L ·
2151 GTACATTGTG TGCTATATTT TTTCCTTCTC CGTTTGTTTT ATATTTGCTT
     · K  A  L   I  P  I  M   *  L  V   D  Q  K   E  A  N  I ·
      *  S  S  Y   S  N  Y   V  I  S   *  S  E  G   S  K  Y ·
     ·  K  L  L   F  Q  L   C  N  *  L   I  R  R   K  Q  I
2201 TAAAGCTCTT ATTCCAATTA TGTAATTAGT TGATCAGAAG GAAGCAAATA
     ·  Q  S  S   F  F  F   C  Y  I  N   T  S  E   M  P  S
     · S  V  L   V  F  F  L   L  Y  K   Y  I  *   N  A  I  Y ·
      F  S  P  R   F  F  S   V  I  *   I  H  L  K   C  H  L ·
2251 TTCAGTCCTC GTTTTTTTTC TGTTATATAA ATACATCTGA AATGCCATCT
      M  G  I  R   I  L  L   I  C  L   N  R  S  Q   I  F  V ·
     ·  G  D  *   N  P  F   D  L  F  E   *  V  T   D  F  R
     · W  G  L   E  S  F  *   F  V  *   I  G  H   R  F  S  F ·
2301 ATGGGGATTA GAATCCTTTT GATTTGTTTG AATAGGTCAC AGATTTTCGT
     · C  K  S   P  Y  G  R   R  H  Q   H  L  S   F  W  L  S ·
      L  *  E  S   L  W  K   K  A  S   A  F  I  L   L  V  I ·
     ·  V  R  V   L  M  E   E  G  I  S   I  Y  P   F  G  Y
2351 TTGTAAGAGT CCTTATGGAA GAAGGCATCA GCATTTATCC TTTTGGTTAT
     ·  R  L  L   S  I  *   F  D  *  I   E  Q  A   L  R  Y
     · P  F  V   V  H  I  I   *  L  N   *  T  S   T  *  V  L ·
      P  V  C  C   P  Y  N   L  I  E   L  N  K  H   L  G  T ·
2401 CCCGTTTGTT GTCCATATAA TTTGATTGAA TTGAACAAGC ACTTAGGTAC
      L  G  P  R   A  C  L   E  A  P   S  F  *  E   T  G  L ·
     ·  R  A  *   G  L  F   G  S  T  *   F  L  R   N  W  F
     · *  G  L   G  P  V  W   K  H  L   V  F  K   K  L  V  Y ·
2451 TTAGGGCCTA GGGCCTGTTT GGAAGCACCT AGTTTTTAAG AAACTGGTTT
     · *  K  L   R  W  F  Q   T  Y  *   F  M  S   *  F  I  E ·
      M  K  T  E   V  V  P   N  I  L   V  Y  V  L   V  Y  R ·
     ·  E  N  *   G  G  S   K  H  T  S   L  C  P   S  L  *
2501 ATGAAAACTG AGGTGGTTCC AAACATACTA GTTTATGTCC TAGTTTATAG
     ·  T  G  F   S  I  S   *  K  P  R   S  *  P   P  L  A
     · N  W  I   L  N  F  L   K  T  K   K  L  A   S  P  S  * ·
      K  L  D  S   Q  F  L   K  N  Q   E  A  S  L   P  *  L ·
2551 AAACTGGATT CTCAATTTCT TAAAAACCAA GAAGCTAGCC TCCCCTAGCT
      K  A  S  L   *  K  Q   W  W  F   Q  T  T  L   T  S  F ·
     ·  S  Q  F   M  K  T   V  V  V  P   N  N  I   N  Q  F
     · K  P  V   Y  E  N  S   G  G  S   K  Q  H   *  P  V  F ·
2601 AAAGCCAGTT TATGAAAACA GTGGTGGTTC CAAACAACAT TAACCAGTTT
```

Figure 3 Cont.

```
      ·F  S  S   *  I  S  L   *  K  L   D  S  *   K  L  G  C·
       F  F  L  I   N  Q  S   L  E  T   G  F  L  K   T  R  L·
      ·  F  P  H   K  S  V   S  R  N  W   I  L  K   N  *  V
2651  TTTTTCCTCA TAAATCAGTC TCTAGAAACT GGATTCTTAA AAACTAGGTT
      ·  F  Q  T   G  P  *   Q  T  F  *   S  T  L   V  I  L
      ·L  P  N   R  A  L  A   N  V  L   I  Y  S   S  D  S  S·
       A  S  K  Q   G  L  S   K  R  F   N  L  L  *   *  F  F·
2701  GCTTCCAAAC AGGGCCTTAG CAAACGTTTT AATCTACTCT AGTGATTCTT
       L  L  L  C   Q  N  S   F  G  V   V  T  L  N   A  A  K·
      ·  L  T  L   S  E  F   F  R  S  C   D  T  *   C  S  K
      ·S  Y  S   V  R  I  L   S  E  L   *  H  L   M  Q  Q  R·
2751  CTCTTACTCT GTCAGAATTC TTTCGGAGTT GTGACACTTA ATGCAGCAAA
      ·G  F  *   H  N  K  Y   L  H  L   T  L  I   C  C  W  T·
       G  I  L  T   *  *  I   F  T  F   N  I  D  M   L  L  D·
      ·  D  F  N   I  I  N   I  Y  I  *   H  *  Y   V  A  G
2801  GGGATTTTAA CATAATAAAT ATTTACATTT AACATTGATA TGTTGCTGGA
      ·  C  C  F   S  S  L   G  F  P  P   S  P  D   L  T  L
      ·L  L  L   L  I  T  G   F  S  S   L  S  *   L  N  P  C·
       P  A  A  S   H  H  W   V  F  L   P  L  L  T   *  P  L·
2851  CCTGCTGCTT CTCATCACTG GGTTTTCCTC CCTCTCCTGA CTTAACCCTT
       V  L  Y  Y   F  *  R   C  S  *   *  S  S  L   L  W  P·
      ·  T  L  L   L  L  E   M  F  I  V   V  Q  P   S  L  A
      ·Y  S  I   T  F  R  D   V  H  S   S  P  A   F  S  G  P·
2901  GTACTCTATT ACTTTTAGAG ATGTTCATAG TAGTCCAGCC TTCTCTGGCC
      ·K  V  L   G  L  A  W   S  W  A   C  K  *   N  A  K  I·
       Q  G  A  G   L  S  L   V  V  G   L  *  M  K   C  K  N·
      ·  R  C  W   A  *  L   G  R  G  L   V  N  E   M  Q  K
2951  CAAGGTGCTG GGCTTAGCTT GGTCGTGGGC TTGTAAATGA AATGCAAAAA
      ·  C  R  Y   L  Y  M   L  C  L  R   L  L  L   L  K  M
      ·M  Q  V   S  V  Y  V   M  L  K   T  I  V   T  K  N  V·
       Y  A  G  I   C  I  C   Y  A  *   D  Y  C  Y   *  K  C·
3001  TATGCAGGTA TCTGTATATG TTATGCTTAA GACTATTGTT ACTAAAAATG
       *  Y  I  L   F  V  L   I  F  L   K  K  N  I   *  K  Y·
      ·  I  Y  P   I  R  V   N  I  F  K   E  K  Y   I  K  I
      ·N  I  S   Y  S  C  *   Y  F  *   R  K  I   Y  K  N  I·
3051  TAATATATCC TATTCGTGTT AATATTTTTA AAGAAAAATA TATAAAAATA
      ·*  Y  I   G  L  Q  V   R  S  *   E  F  T   G  P  T  W·
       L  I  Y  W   A  S  G   E  E  L   R  V  Y  G   S  N  L·
      ·  N  I  L   G  F  R   *  G  V  E   S  L  R   V  Q  P
3101  TTAATATATT GGGCTTCAGG TGAGGAGTTG AGAGTTTACG GGTCCAACCT
      ·  S  G  A   *  S  P   Q  L  L  P   F  M  F   Y  M  Y
      ·V  R  C   M  I  T  S   I  T  T   I  Y  V   L  Y  V  F·
       G  P  V  H   D  H  L   N  Y  Y   H  L  C  F   I  C  I·
3151  GGTCCGGTGC ATGATCACCT CAATTACTAC CATTTATGTT TTATATGTAT
       L  T  V  V   S  L  L   H  K  L   I  Y  R  L   Y  *  V·
      ·  N  C  C   *  F  V   T  *  V  N   I  P  F   I  L  G
      ·*  L  L   L  V  C  Y   I  S  *   Y  T  V   Y  I  R  L·
3201  TTAACTGTTG TTAGTTTGTT ACATAAGTTA ATATACCGTT TATATTAGGT
      ·D  N  E   L  T  A  A   G  I  D   N  L  Q   A  P  T  L·
       *  *  *  T   D  R  G   W  H  R   *  F  T  S   S  N  S·
      ·  I  M  N   *  P  R   L  A  *  I   I  Y  K   L  Q  L
3251  TGATAATGAA CTGACCGCGG CTGGCATAGA TAATTTACAA GCTCCAACTC
      ·  G  S  L   T  Y  F   M  M  A  P   T  L  C   Y  Q  V
      ·W  E  S   N  I  L  H   D  G  S   D  T  L   L  S  G  N·
       L  G  V  *   H  T  S   *  W  L   R  H  S  V   I  R  *·
3301  TTGGGAGTCT AACATACTTC ATGATGGCTC GGACACTCTG TTATCAGGTA
       I  F  R  S   C  M  L   I  *  S   R  Y  M  I   F  F  I·
      ·  F  P  I   M  Y  V   D  L  K  Q   I  Y  D   F  F  Y
      ·F  S  D   H  V  C  *   S  K  A   D  I  *   F  F  L  L·
3351  ATTTTCCGAT CATGTATGTT GATCTAAAGC AGATATATGA TTTTTTTTAT
      ·T  F  R   L  A  I  S   D  *  Q   Q  K  V   C  W  Q  G·
       Y  L  S  T   G  H  F   *  L  A   A  E  S  V   L  A  R·
      ·  P  F  D   W  P  F   L  I  S  S   R  K  C   A  G  K
3401  TACCTTTCGA CTGGCCATTT CTGATTAGCA GCAGAAAGTG TGCTGGCAAG
      ·  E  T  F   *  K  R   T  T  F  V   L  H  A   A  K  L
      ·*  N  I   L  E  T  Y   Y  F  C   F  A  C   S  Q  V  I·
       V  K  H  F   R  N  V   L  L  L   F  C  M  Q   P  S  Y·
3451  GTGAAACATT TTAGAAACGT ACTACTTTTG TTTTGCATGC AGCCAAGTTA
       S  S  N  T   L  C  *   K  R  L   A  G  P  S   S  Y  S·
      ·  L  E  H   L  M  L   E  K  V  G   W  S  V   K  L  F
      ·P  R  T   P  Y  V  R   K  G  W   L  V  R   Q  V  I  L·
3501  TCCTCGAACA CCTTATGTTA GAAAAGGTTG GCTGGTCCGT CAAGTTATTC
```

Figure 3 Cont.

```
      · I  L  D  I  Y  W  S  P  R  I  H  Y  *  A  S  K  L ·
       Y  T  *  Y  L  L  V  S  K  D  S  L  L  S  K  *  A ·
      · Y  L  I  F  T  G  L  Q  G  F  I  I  E  Q  V  S
3551  TATACTTGAT ATTTACTGGT CTCCAAGGAT TCATTATTGA GCAAGTAAGC
      · F  I  C  L  H  I  Y  I  L  *  N  I  L  I  H  F
      · V  Y  M  S  P  Y  I  Y  L  V  K  Y  P  H  T  F  L ·
       C  L  Y  V  S  I  Y  I  S  C  K  I  S  S  Y  I  S ·
3601  TGTTTATATG TCTCCATATA TATATCTTGT AAAATATCCT CATACATTTC
       L  T  F  Y  *  F  Y  N  L  A  V  H  K  S  Y  C  C ·
      · N  L  L  L  I  L  Q  S  C  S  T  *  I  L  L  L
      · *  P  F  I  D  F  T  I  L  Q  Y  I  N  P  I  V  V ·
3651  TTAACCTTTT ATTGATTTTA CAATCTTGCA GTACATAAAT CCTATTGTTG
      · E  L  S  T  S  I  D  G  R  I  T  E  C  C  R  D  C ·
       *  T  L  N  I  H  *  W  E  D  Y  *  M  L  *  R  L ·
      · N  S  Q  H  P  L  M  G  G  L  L  N  A  V  E  T
3701  TGAACTCTCA ACATCCATTG ATGGGAGGAT TACTGAATGC TGTAGAGACT
      · F  E  A  L  I  T  K  C  L  P  V  A  L  H  V  L
      · F  *  S  S  H  Y  Q  M  S  T  C  G  F  A  C  F  I ·
       V  L  K  L  S  L  P  N  V  Y  L  W  L  C  M  F  Y ·
3751  GTTTTGAAGC TCTCATTACC AAATGTCTAC CTGTGGCTTT GCATGTTTTA
       L  P  F  P  S  V  V  V  N  Y  I  F  Y  L  F  I  Q ·
      · A  F  S  I  C  G  S  K  L  Y  F  L  S  I  H  S
      · C  L  F  H  L  W  *  *  I  I  F  S  I  Y  S  F  K ·
3801  TTGCCTTTTC CATCTGTGGT AGTAAATTAT ATTTTCTATC TATTCATTCA
      · I  Q  I  H  D  R  S  *  Y  Y  S  N  I  S  H  R  C ·
       N  S  N  T  *  S  I  L  I  L  F  *  Y  Q  S  S  M ·
      · F  K  Y  M  I  D  P  D  I  I  L  I  S  V  I  D
3851  AATTCAAATA CATGATCGAT CCTGATATTA TTCTAATATC AGTCATCGAT
      · F  F  S  E  H  A  C  S  R  R  K  L  F  P  F  M
      · L  L  L  R  T  C  M  L  S  E  K  I  I  S  F  Y  A ·
       A  S  S  P  N  M  H  A  L  G  E  N  Y  F  L  L  C ·
3901  GCTTCTTCTC CGAACATGCA TGCTCTCGGA GAAAATTATT TCCTTTTATG
       L  F  Q  I  C  I  F  A  V  S  N  L  Y  S  S  I  Q ·
      · L  S  N  L  H  I  C  S  F  E  L  I  F  I  Y  T
      · S  F  K  F  A  Y  L  Q  F  R  T  Y  I  H  L  Y  R ·
3951  CTCTTTCAAA TTTGCATATT TGCAGTTTCG AACTTATATT CATCTATACA
      · V  K  H  T  C  *  D  S  S  I  W  *  P  R  I  L  Q ·
       G  *  T  Y  L  L  R  F  F  D  L  V  T  E  N  S  T ·
      · L  N  I  L  A  E  I  L  R  F  G  D  R  E  F  Y
4001  GGTTAAACAT ACTTGCTGAG ATTCTTCGAT TTGGTGACCG AGAATTCTAC
      · R  L  V  E  C  K  D  N  *  *  G  E  I  L  P  C
      · K  T  G  G  M  Q  R  Q  L  M  R  *  N  T  T  V  F ·
       K  D  W  W  N  A  K  T  I  D  E  V  K  Y  Y  R  V ·
4051  AAAGACTGGT GGAATGCAAA GACAATTGAT GAGGTGAAAT ACTACCGTGT
       L  L  Q  P  S  I  T  S  F  F  N  *  Q  K  E  S  R ·
      · V  A  T  *  Y  N  F  I  F  Q  L  T  K  G  I  *
      · C  C  N  L  V  *  L  H  F  S  T  N  K  R  N  L  G ·
4101  TTGTTGCAAC CTAGTATAAC TTCATTTTTC AACTAACAAA AGGAATCTAG
      · *  A  *  L  M  L  C  M  L  F  A  V  V  A  C  V  A ·
       V  S  I  A  D  V  V  Y  V  V  C  C  C  C  L  C  C ·
      · K  H  S  *  C  C  V  C  C  L  L  L  L  V  L
4151  GTAAGCATAG CTGATGTTGT GTATGTTGTT TGCTGTTGTT GCTTGTGTTG
      · V  L  G  W  D  Q  Y  W  R  K  W  N  M  V  C  L
      · C  A  W  M  G  S  V  L  E  K  M  E  H  G  M  P  F ·
       L  C  L  D  G  I  S  T  G  E  N  G  T  W  Y  A  F ·
4201  CTGTGCTTGG ATGGGATCAG TACTGGAGAA AATGGAACAT GGTATGCCTT
       F  F  L  G  N  N  N  S  S  K  N  V  L  P  D  M  V ·
      · L  S  W  Q  *  *  F  *  Q  E  C  T  A  R  H  G
      · S  F  L  A  I  I  I  L  A  R  M  Y  C  Q  T  W  Y ·
4251  TTCTTTCTTG GCAATAATAA TTCTAGCAAG AATGTACTGC CAGACATGGT
      · Y  A  V  V  V  R  C  N  H  L  K  A  T  A  *  *  K ·
       I  R  S  C  G  *  M  *  P  S  *  S  N  C  I  I  K ·
      · T  Q  L  W  L  D  V  T  I  L  K  Q  L  H  N  K
4301  ATACGCAGTT GTGGTTAGAT GTAACCATCT TAAAGCAACT GCATAATAAA
      · W  Q  V  T  V  R  L  L  R  T  M  K  S  G  L  L
      · M  A  S  H  C  K  I  V  E  N  Y  E  I  W  T  L  G ·
       N  G  K  S  L  *  D  C  *  E  L  *  N  L  D  S  W ·
4351  AATGGCAAGT CACTGTAAGA TTGTTGAGAA CTATGAAATC TGGACTCTTG
       V  H  R  T  I  L  I  C  M  F  Q  V  V  *  I  T  P ·
      · T  Q  N  Y  S  N  L  Y  V  P  S  S  L  N  N  T
      · Y  T  E  L  F  *  F  V  C  S  K  *  F  E  *  H  P ·
4401  GTACACAGAA CTATTCTAAT TTGTATGTTC CAAGTAGTTT GAATAACACC
```

Figure 3 Cont.

· R I * W I Y S S P M I F V G P Y * ·
Q N L M D L F F S N D L C W S I L ·
· E F D G F I L L Q * S L L V H I
4451 CAGAATTTGA TGGATTTATT CTTCTCCAAT GATCTTTGTT GGTCCATATT
· F H L L K Y Y D * * F A H F D S
· I S F A E I L * L I I C T F * Q P ·
N F I C * N I M T N N L H I L T A ·
4501 AATTTCATTT GCTGAAATAT TATGACTAAT AATTTGCACA TTTTGACAGG
L C I N G L F V I Y I S L A C E M ·
· V H K W I V R H I Y F P C M R N
· C A * M D C S S Y I F P L H A K W ·
4551 CTGTGCATAA ATGGATTGTT CGTCATATAT ATTTCCCTTG CATGCGAAAT
· V Y Q R * N N I C V D V M L R V A ·
G I S K V K * Y L C G C Y A Q G C ·
· Y I K G K I I F V W M L C S G L
4601 GGTATATCAA AGGTAAAATA ATATTTGTGT GGATGTTATG CTCAGGGTTG
· S S A Y K T K L Y L H Y S L C L
· F Q C I * D * T V P S L Q F V P C ·
L P V H I R L N C T F T T V C A L ·
4651 CTTCCAGTGC ATATAAGACT AAACTGTACC TTCACTACAG TTTGTGCCTT
V N P L T S Q C L L V I S N F S K ·
· K S L N Q S V L A C N F * F F K
· * I P * P V S A C L * F L I F Q S ·
4701 GTAAATCCCT TAACCAGTCA GTGCTTGCTT GTAATTTCTA ATTTTTCAAA
· * L * E L L P C C L G Q S N * F T ·
V T I R I T S M L F R A I * L V H ·
· N Y K N Y F H A V * G N L I S S
4751 GTAACTATAA GAATTACTTC CATGCTGTTT AGGGCAATCT AATTAGTTCA
· S E T K V H V L I K I C K F N S
· Q * N * S S C T H K N L * V Q Q * ·
P V K L K F M Y S * K S V S S T V ·
4801 CCAGTGAAAC TAAAGTTCAT GTACTCATAA AAATCTGTAA GTTCAACAGT
K S I L L S L L S N K N V F N F V ·
· K Y S F E F I E Q * E C V * F C
· K V F F * V Y * A I R M C L I L Y ·
4851 AAAAGTATTC TTTTGAGTTT ATTGAGCAAT AAGAATGTGT TTAATTTTGT
· W I Y C P P V * L L Y * R C Y I L ·
M D L L S S S L A P I L K V L Y F ·
· G S T V L Q S S S Y T E G A I F
4901 ATGGATCTAC TGTCCTCCAG TCTAGCTCCT ATACTGAAGG TGCTATATTT
· L S S L L C C Y Y Y C L K L F T
· V I Q S S V L L L L L F K V I H L ·
C Y P V F C A V I I T V * S Y S L ·
4951 TGTTATCCAG TCTTCTGTGC TGTTATTATT ACTGTTTAAA GTTATTCACT
Y L C * F V T G S C C F Y I V L C ·
· F V L V C Y R K L L F L Y R S L
· I C A S L L Q E V A V F I S F F V ·
5001 TATTTGTGCT AGTTTGTTAC AGGAAGTTGC TGTTTTTATA TCGTTCTTTG
· F C C T S * G N L F T F S L F I C ·
F L L Y F M R * L I Y L F T L H L ·
· S A V L H E V T Y L P F H S S S
5051 TTTCTGCTGT ACTTCATGAG GTAACTTATT TACCTTTTCA CTCTTCATCT
· Y I N Y I V L Y F Q M C P F E F
· L Y * L Y S S L F S N V S F R V S ·
A I L I I * F S I F K C V L S S F ·
5101 GCTATATTAA TTATATAGTT CTCTATTTTC AAATGTGTCC TTTCGAGTTT
R H A F V Q T Y Q L Q I T W M K C ·
· T C F C S N L P A A D Y L D E V
· D M L L F K L T S C R L L G * S A ·
5151 CGACATGCTT TTGTTCAAAC TTACCAGCTG CAGATTACTT GGATGAAGTG
· S I * N * I F H N P V P F E K I M ·
L Y I K L N I S * S S P F R E N Y ·
· L Y K I K Y F I I Q S L S R K L
5201 CTCTATATAA AATTAAATAT TTCATAATCC AGTCCCTTTC GAGAAAATTA
· I H F V C N C T P V M C C C S L
· D T F C L Q L Y T S Y V L L F P A ·
* Y I L F A I V H Q L C V A V P C ·
5251 TGATACATTT TGTTTGCAAT TGTACACCAG TTATGTGTTG CTGTTCCCTG
P H T Q V L G F L R N H A S G K Y ·
· T Y S S S G L S * E S C F R * I
· H I L K F W A F L G I M L Q V N I ·
5301 CCACATACTC AAGTTCTGGG CTTTCTTAGG AATCATGCTT CAGGTAAATA

Figure 3 Cont.

```
     · N  T  T   P  D  A  V   D  Q  Y   P  T  F   M  F  F  F ·
      *  Y  N  A   R  C  C   G  S  I   S  N  I  Y   V  F  L ·
     ·  I  Q  R   Q  M  L   W  I  N  I   Q  H  L   C  F  S
5351 TAATACAACG CCAGATGCTG TGGATCAATA TCCAACATTT ATGTTTTTCT
     ·  T  H  F   F  L  Y   *  F  F  F   H  S  L   *  S  E
     · Y  S  F   F  P  L  L   V  L  F   S  F  A   I  V  *  G ·
      L  L  I  F   S  F  I   S  S  F   F  I  R  Y   S  L  R ·
5401 TTACTCATTT TTTCCTTTAT TAGTTCTTTT TTCATTCGCT ATAGTCTGAG
      V  L  *  A   P  E  G   N  S  H   L  I  W  F   H  V  F ·
     ·  L  M  S   T  R  R   Q  Q  S  S   N  M  V   P  C  I
     · S  Y  E   H  Q  K  A   T  V  I   *  Y  G   S  M  Y  L ·
5451 GTCTTATGAG CACCAGAAGG CAACAGTCAT CTAATATGGT TCCATGTATT
     · M  L  S   P  K  Q  K   T  V  L   T  P  Y   F  F  S  S ·
      Y  V  V  S   *  T  E   N  C  S   D  T  I  F   L  F  L ·
     ·  C  C  L   L  N  R   K  L  F  *   H  H  I   S  F  P
5501 TATGTTGTCT CCTAAACAGA AAACTGTTCT GACACCATAT TTCTTTTCCT
     ·  F  Y  Q   I  P  L   I  I  L  T   S  Y  L   K  N  K
     · F  L  P   D  S  P  H   H  I  D   I  I  P   Q  K  *  I ·
      L  F  T  R   F  P  S   S  Y  *   H  H  T  S   K  I  N ·
5551 CTTTTTACCA GATTCCCCTC ATCATATTGA CATCATACCT CAAAAATAAA
      F  S  D  T   M  V  S   H  I  F   L  S  *  Y   L  L  G ·
     ·  Q  *  H   N  G  E   P  Y  F  S   *  L  I   L  A  R
     · S  V  T   Q  W  *  A   I  F  F   L  V  D   T  C  *  D ·
5601 TTCAGTGACA CAATGGTGAG CCATATTTTT CTTAGTTGAT ACTTGCTAGG
     · S  F  F   M  G  T  C   L  I  C   G  I  F   N  R  L  A ·
      I  V  F  Y   G  N  L   S  N  L   W  Y  I  Q   *  V  G ·
     ·  R  F  L   W  E  P   V  *  F  V   V  Y  S   I  G  W
5651 ATCGTTTTTT ATGGGAACCT GTCTAATTTG TGGTATATTC AATAGGTTGG
     ·  I  *  S   F  G  F   F  S  A  Y   T  G  S   Q  C  V
     · N  M  I   F  W  F  F   F  C  I   Y  G  Q   P  M  C  V ·
      Q  Y  D  L   L  V  F   F  L  H   I  R  A  A   N  V  C ·
5701 CAATATGATC TTTTGGTTTT TTTTCTGCAT ATACGGGCAG CCAATGTGTG
      F  Y  C  I   T  M  M   *  *  T   G  L  R  R   Q  N  N ·
     ·  L  L  Y   Y  H  D   V  M  N  R   T  E  K   A  K  *
     · S  I  V   L  P  *  C   D  E  P   D  *  E   G  K  I  T ·
5751 TTCTATTGTA TTACCATGAT GTGATGAACC GGACTGAGAA GGCAAAATAA
     · H  L  *   I  F  F  G   V  S  F   L  P  S   W  K  L  K ·
      P  S  V  D   L  F  W   C  F  I   S  S  I  M   E  T  E ·
     ·  I  C  R   S  F  L   V  F  H  F   F  H  H   G  N  *
5801 CCATCTGTAG ATCTTTTTTG GTGTTTCATT TCTTCCATCA TGGAAACTGA
     ·  A  I  I   C  A  H   S  K  P  A   S  C  L   P  V  F
     · S  N  N   L  C  T  Q   *  T  S   I  V  S   S  S  F
      K  Q  *  S   V  H  T   V  N  Q   H  R  V  F   Q  F
5851 AAGCAATAAT CTGTGCACAC AGTAAACCAG CATCGTGTCT TCCAGTTTTT (SEQ ID NO:118)
```

Figure 5
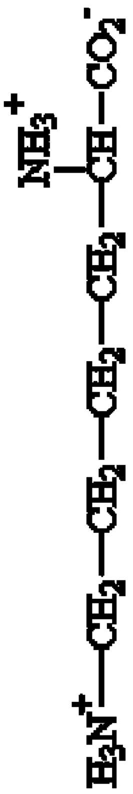
lysine (K)
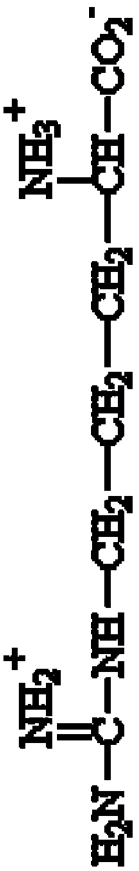
arginine (R)

SEQUENCE LISTING

<160> NUMBER OF SEQ ID NOS: 146

<210> SEQ ID NO 1
<211> LENGTH: 2074
<212> TYPE: DNA
<213> ORGANISM: Arabidopsis thaliana

<400> SEQUENCE: 1

```
tgaatccttt ttcctttctt cttcttcttc tcttcagaga aaactttgct tctctttcta     60
taaggaacca gacacgaatc ccattcccac cgatttctta gcttcttcct tcaatccgct    120
ctttccctct ccattagatt ctgtttcctc tttcaatttc ttctgcatgc ttctcgattc    180
tctctgacgc ctcttttctc ccgacgctgt ttcgtcaaac gcttttcgaa atggcgattt    240
tggattctgc tggcgttact acggtgacgg agaacggtgg cggagagttc gtcgatcttg    300
ataggcttcg tcgacggaaa tcgagatcgg attcttctaa cggacttctt ctctctggtt    360
ccgataataa ttctccttcg gatgatgttg gagctcccgc cgacgttagg gatcggattg    420
attccgttgt taacgatgac gctcagggaa cagccaattt ggccggagat aataacggtg    480
gtggcgataa taacggtggt ggaagaggcg gcggagaagg aagaggaaac gccgatgcta    540
cgtttacgta tcgaccgtcg gttccagctc atcggagggc gagagagagt ccacttagct    600
ccgacgcaat cttcaaacag agccatgccg gattattcaa cctctgtgta gtagttctta    660
ttgctgtaaa cagtagactc atcatcgaaa atcttatgaa gtatggttgg ttgatcagaa    720
cggatttctg gtttagttca agatcgctgc gagattggcc gcttttcatg tgttgtatat    780
ccctttcgat ctttcctttg gctgccttta cggttgagaa attggtactt cagaaataca    840
tatcagaacc tgttgtcatc tttcttcata ttattatcac catgacagag gttttgtatc    900
cagtttacgt caccctaagg tgtgattctg ctttttttatc aggtgtcact ttgatgctcc    960
tcacttgcat tgtgtggcta aagttggttt cttatgctca tactagctat gacataagat   1020
ccctagccaa tgcagctgat aaggccaatc ctgaagtctc ctactacgtt agcttgaaga   1080
gcttggcata tttcatggtc gctcccacat tgtgttatca gccaagttat ccacgttctg   1140
catgtatacg gaagggttgg gtggctcgtc aatttgcaaa actggtcata ttcaccggat   1200
tcatgggatt tataatagaa caatatataa atcctattgt caggaactca aagcatcctt   1260
tgaaaggcga tcttctatat gctattgaaa gagtgttgaa gctttcagtt ccaaatttat   1320
atgtgtggct ctgcatgttc tactgcttct tccacctttg gttaaacata ttggcagagc   1380
ttctctgctt cggggatcgt gaattctaca aagattggtg gaatgcaaaa agtgtgggag   1440
attactggag aatgtggaat atgcctgttc ataaatggat ggttcgacat atatacttcc   1500
cgtgcttgcg cagcaagata ccaaagacac tcgccattat cattgctttc ctagtctctg   1560
cagtctttca tgagctatgc atcgcagttc cttgtcgtct cttcaagcta tgggcttttc   1620
ttgggattat gtttcaggtg cctttggtct tcatcacaaa ctatctacag gaaaggtttg   1680
gctcaacggt ggggaacatg atcttctggt tcatcttctg cattttcgga caaccgatgt   1740
gtgtgcttct ttattaccac gacctgatga accgaaaagg atcgatgtca tgaaacaact   1800
gttcaaaaaa tgactttctt caaacatcta tggcctcgtt ggatctccgt tgatgttgtg   1860
gtggttctga tgctaaaacg acaaatagtg ttataaccat tgaagaagaa aagaaaatta   1920
gagttgttgt atctgcaaaa attttggtag agacacgcga acccgtttgg attttgttat   1980
ggtgtaaaga aatttcaatc aaaaaactgt tgtaataatt gttaccaaaa agaaatgctt   2040
ttctggaaac gaggggaaaa atagtagttt tgtt                               2074
```

<210> SEQ ID NO 2
<211> LENGTH: 1512
<212> TYPE: DNA
<213> ORGANISM: Brassica juncea

<400> SEQUENCE: 2
atggcgattt tggattctgg aggcgtcgct gtaccgccga cggagaacgg cgtcgcggat 60
ctcgacaggc tccaccgtcg taaatcgagt tcggattctt ccaacggact cctctccgat 120
acttccccgt cggacgatgt tggagctgcg gcggccgaaa gggatcgggt tgattccgct 180
gccgaggagg aggctcaggg aacagcgaat ttagctggcg gagatgccga aactagggaa 240
tccgccggag gcgatgtaag gtttacgtat cgaccgtcgg ttccagctca tcggaggacg 300
agggagagtc ctctcagctc cgacgctatc ttcaaacaaa gccatgcagg attgttcaac 360
ctctgtgtag ttgttcttgt tgctgttaac agtagactca tcatcgaaaa cctcatgaag 420
tatggttggt tgatcagaac tgatttttgg tttagttcta catccttacg agactggccg 480
cttttcatgt gttgtctttc actttcggtc tttcctttgg ctgccttcac ggtcgagaaa 540
atggtacttc agaaattcat atctgagcct gttgccatca ttcttcatgt cattataacc 600
atgacagagg tcttgtatcc agtctacgtc acactgaggt gtgattctgc cttcttgtca 660
ggtgtcacgt tgatgctgct cacttgcatt gtgtggctga agttggtttc ttacgctcat 720
actagctacg acataagaac cctggccaat tcagctgata aggtcgatcc tgaaatctcc 780
tactatgtta gcttgaagag cttggcgtat ttcatggttg ctcccacact gtgttatcag 840
ccaagctatc cacgttctcc atgtatccgg aagggttggg tggctcgtca acttgcaaaa 900
ctggtcatat tcactggact catgggattt ataatagagc aatatataaa tcctattgtt 960
aggaactcaa agcatcctct gaaaggggac cttctatatg ctattgaaag agtgttgaag 1020
ctttcagttc caaatctata tgtgtggctc tgcatgttct actgcttctt ccacctttgg 1080
ttaaacatat tggcagagct cctctgcttc ggggaccgtg aattctacaa agattggtgg 1140
aatgcaaaaa gcgttggaga ttattggaga atgtggaata tgcctgttca caaatggatg 1200
gttcgacatg tatactttcc gtgcctgcgc atcaagatac caaaagtacc cgccattatc 1260
attgctttct tagtctctgc agtctttcat gagttatgca tcgcagttcc ttgccgtctc 1320
ttcaatctat gggctttcat gggaattatg tttcaggtcc ctttggtctt tatcacaaac 1380
tttttacaag aaaggtttgg ctccatggtg ggaaacatga tctttggttc agcttcttgc 1440
attttcggac aaccgatgtg tgggcttctt tattaccatg acctgatgaa ccgcaaagga 1500
tccatgtcct ga 1512

<210> SEQ ID NO 3
<211> LENGTH: 1512
<212> TYPE: DNA
<213> ORGANISM: Brassica napus

<400> SEQUENCE: 3
atggcgattt tggattctgg aggcgtcgct gtaccgccga cggagaacgg cgtcgcggat 60
ctcgacaggc tccaccgtcg taaatcgagt tcggattctt ccaacggact cctctccgat 120
acttccccgt cggacgatgt tggagctgcg gcggccgaaa gggatcgggt tgattccgct 180
gccgaggagg aggctcaggg aacagcgaat ttagctggcg gagatgccga aactagggaa 240
tccgccggag gcgatgtaag gtttacgtat cgaccgtcgg ttccagctca tcggaggacg 300

-continued

```
agggagagtc ctctcagctc cgacgctatc ttcaaacaaa gccatgcagg attgttcaac    360
ctctgtgtag ttgttcttgt tgctgttaac agtagactca tcatcgaaaa cctcatgaag    420
tatggttggt tgatcagaac tgatttttgg tttagttcta catccttacg agactggccg    480
cttttcatgt gttgtctttc actttcggtc tttcctttgg ctgccttcac ggtcgagaaa    540
atggtacttc agaaattcat atctgagcct gttgccatca ttcttcatgt cattataacc    600
atgacagagg tcttgtatcc agtctacgtc acactgaggt gtgattctgc cttcttgtca    660
ggtgtcacgt tgatgctgct cacttgcatt gtgtggctga agttggtttc ttacgctcat    720
actagctacg acataagaac cctggccaat tcagctgata aggtcgatcc tgaaatctcc    780
tactatgtta gcttgaagag cttggcgtat ttcatggttg ctcccacact gtgttatcag    840
ccaagctatc cacgttctcc atgtatccgg aagggttggg tggctcgtca acttgcaaaa    900
ctggtcatat tcactggact catgggattt ataatagagc aatatataaa tcctattgtt    960
aggaactcaa agcatcctct gaaaggggac cttctatatg ctattgaaag agtgttgaag   1020
ctttcagttc caaatctata tgtgtggctc tgcatgttct actgcttctt ccacctttgg   1080
ttaaacatat tggcagagct cctctgcttc ggggaccgtg aattctacaa agattggtgg   1140
aatgcaaaaa gcgttggaga ttattggaga atgtggaata tgcctgttca caaatggatg   1200
gttcgacatg tatactttcc gtgcctgcgc atcaagatac caaaagtacc cgccattatc   1260
attgctttct tagtctctgc agtctttcat gagttatgca tcgcagttcc ttgccgtctc   1320
ttcaatctat gggctttcat gggaattatg tttcaggtcc ctttggtctt tatcacaaac   1380
tttttacaag aaaggtttgg ctccatggtg ggaaacatga tctttggttc agcttcttgc   1440
attttcggac aaccgatgtg tgggcttctt tattaccatg acctgatgaa ccgcaaagga   1500
tccatgtcct ga                                                       1512
```

<210> SEQ ID NO 4
<211> LENGTH: 1510
<212> TYPE: DNA
<213> ORGANISM: Brassica juncea

<400> SEQUENCE: 4

```
atggcgattt tggattctgg aactgtcacg atggcgacgg agaacggtgt cgcggatctc     60
gatatgcttc gtcgtcgtaa atcgagatcg gattcttcca acggacttct ctccgagact    120
tccccatcgg atgatgctgg agctccggcc gacgtggagg atcgggttga ttcagctgct    180
cagggaacag cgaatttagc tggagatacg gaaactaggg aatccggtgg aggaggagga    240
ggaggaaacg gcgaggtaag gtttacgtat cgaccgtcgg ttccagctca tcggaggacg    300
agggagagtc cactcagctc cgacgctatc ttcaaacaaa gccatgcagg attgttcaac    360
ctctgtgtag ttgttcttgt tgctgttaac agtagactca tcatcgaaaa tctcatgaag    420
tacggttggt tgatcagaac tgatttctgg tttagttcta catccctccg agattggccg    480
cttttcatgt gttgtctttc actttcaatc tttcctttgg ctgcctttac cgtcgagaaa    540
ttggtactcc agaaattcat atctgaacct gttgtcatca ttcttcatat tattatcacc    600
atgactgagg tcttgtatcc agtctacgtc accctaaggt gtgattcggc tttcttatca    660
ggtgtcacat tgatgctact cacttgcatt gtgtggctga agttggtttc ttacgctcat    720
actaattacg acataagaac cgtagctaat tcagctgata aggtcgatcc tgaagtctcc    780
tactatgtta gcttgaagag cttggcgtat ttcatggttg ctcccacatt gtgttatcag    840
ccaagctatc cacgttctcc gggtatccgg aagggttggg tggctcgtca atttgcgaaa    900
```

ctggtcatat tcactggact catgggtttt ataatagagc aatatataaa tcctattgtg 960
aggaactcaa agcatccttt gaaaggggat cttctatacg ctattgaaag agtgttgaag 1020
ctttcagttc caaatctata tgtgtggctc tgcatgttct actgcttctt ccacctttgg 1080
ttaaatatat tggcagagct cctttgcttc ggggatcgtg aattctacaa agattggtgg 1140
aatgcaaaaa gcgtaggaga ttattggaga atgtggaata tgcctgttca taaatggatg 1200
gttcgacatg tatactttcc atgcctgcgc ataaagatac cgaaagtacc cgccattatc 1260
attgctttct tagtctctgc agttttccat gagctgtgca ttgcagttcc ttgccgtctc 1320
tttaatttat gggctttcat aggaatcatg tttcaggtgc ctttggtctt tatcacaaac 1380
tatttacaag aaaggtttgg ctccatggtg ggaaacatga tcttctggtt cagcttctgc 1440
attttcggac aaccgatgtg tgtgcttctt tattaccatg acctcatgaa ccgcaaagga 1500
tccatgtcct 1510

<210> SEQ ID NO 5
<211> LENGTH: 2090
<212> TYPE: DNA
<213> ORGANISM: Tropaeolum majus

<400> SEQUENCE: 5
acgcggggag ttttcaaaat catattatgc tttttcttca ctactgcatg aactttcttt 60
ctacttcttg caactgattt gtaatcctta cacatgtttc tagttttctc catataaaaa 120
aaatattctc tgagcttctc gattctctag agagagaagg ccaaaaaaaa atggcggtgg 180
cagagtcgtc acagaacacg acaaccatga gtggtcacgg cgactcggat ctcaacaatt 240
tccgtagaag gaaaccgagt tcctccgtga ttgaaccttc gtcgtccggt tttacatcca 300
ccaatggcgt accggcgact ggccacgtgg ctgagaatcg tgaccaggat cgggtagggg 360
ctatggagaa cgcaacagga tcggtcaact taattggaaa tggtggaggc gtggttatcg 420
ggaatgaaga gaaacaggta ggggagactg atatacgatt cacttaccgg ccttcgtttc 480
cggctcatcg gagggtgagg gagagtcctc ttagctctga tgcaatcttc aaacagagcc 540
atgcgggttt attcaacttg tgtatagtag tgctcattgc agtaaacagt aggcttatca 600
tcgaaaatct tatgaagtat ggttggttga tcgatactgg tttctggttt agctcaagat 660
cactgggtga ttggtccatc tttatgtgct gtcttacact cccaattttc ccacttgctg 720
cttttattgt tgaaaagctg gtgcagcgaa atcatatatc tgaacttgtt gctgttctcc 780
ttcatgtaat cgtttctacc gctgcagttt tatatccagt tattgtgatc ttaacgtgtg 840
attcggtgta tatgtctggt gtggtattga tgctctttgg ttgcattatg tggttgaagc 900
tggtgtcata tgcacatact agttctgata ttagaacact ggccaaatct ggctataagg 960
gggatgcgca ccccaattca accattgtga gttgctcata tgatgttagc ttgaagagtt 1020
tggcatactt catggttgct ccgacattat gttaccagcc tagctatcct cgttcgtcgt 1080
gtatccgcaa gggttgggtt gttcgtcaat ttgtcaaact aatagttttc ataggactca 1140
tggggttcat tatagaacaa tatattaatc ctatcgttcg aaattccaaa cacccattga 1200
aaggagattt tttatatgca atagaaagag ttttgaagct ttcagttcca aatctatatg 1260
tttggctttg catgttctac tctttttcc acctctggtt gaacatactg gctgagcttc 1320
ttcgctttgg tgatcgtgaa ttctacaaag attggtggaa tgcaaaaact gttgcggagt 1380
attggaaaat gtggaatatg cctgttcata gatggatggt tcgtcatcta tattttccct 1440
gtttgaggaa tgggataccc aaggaaggtg ccattattat cgcgttctta gtttctggtg 1500
ctttccatga gctctgcatt gcagttcctt gccacgtatt caagttatgg gcctttatag 1560
gcattatgtt tcaggttccc ttggtattga ttacgaatta tctacaagaa aagttcagta 1620
attctatggt gggcaatatg atcttctggt tcatcttctg catacttggc caacctatgt 1680
gtgtccttct atattaccat gacctgataa atctaaagga aaagtgaaaa aatggaagtt 1740
gcctatgctc agagtattcc tatcccaatg cacacattat atggttctgt acaatctgtg 1800 ccccttcat cctttacacg tacccatgct ggttcctgca cgatgatttg ccttttgttt 1860
gtaagcaata tttggagaga gtccaattta ggaagtgact agtgtggctt atatcttgta 1920
tactaccttt agtcatgggg gggtttttat attactagta ccaaaagtca agttgtatat 1980
gatttacggt ttagtttctt tcatgttttt tgtttttgtg taaatatacg tttcatatat 2040
cactgttttt tcaaagtaaa atcaataata ccccatagat gttgaaactg 2090

<210> SEQ ID NO 6
<211> LENGTH: 1494
<212> TYPE: DNA
<213> ORGANISM: Echium pitardii

<400> SEQUENCE: 6
cacaaatgac aatatgggag tcgccggaga tcataagctc cgatgaagca gcagcggcgt 60
tgaggcggag aggcggcgcc aaggaggttg cggaacagag attggatagt gaagaagaga 120
agaagaagga ggaggaaaat ggaaaactga agtatactta tcgagcttcc gctccggctc 180
accggagaat caaggagagt cctcttagct ccgacgccat tttcaaacaa agtcatgcag 240
gcctcttcaa tctttgcatt gtggtgcttg ttgctgtaaa cagtcggctt atcattgaga 300
atttgatgaa gtatggttgg ctaattagct cagggttttg gttaagttca acatcattaa 360
gcgactggcc acttctaata tgttgtctca gtctgccgat attccctctg gcttcttttg 420
tggttgaaaa gttgtctcaa caggaattta tatctgagca agtggtgatc actcttcatg 480
cactcataac aacgactgtg attatgtatc cagtaattgt catcctcaga tgtgatcccg 540
ccgttctatc aggtgtgata ttgatgcttt tcacgtgtat tgtgtggttg aagctggtat 600
cttatgcaca tacaaactat gatatgcgag cactagcaaa ggactgtgat aagttacagg 660
cactatcagg ctcttcaatg gaagattgtt cttttgaagt caacttccaa gctttggtat 720
acttcatggt tgctccgaca ttatgttatc agctaaggta tccgcgtacc ccctgcattc 780
gttggggttg ggttacacgt catctcatca agttaatcat atttactgga ctgatgggat 840
tcattattga gcagtatatt aatccaattg tgaaaaattc acaacatcca ttgaagggga 900
acctgttgta tgctatagag agggtcttga agctttcagt tccaaatata tatgtctggc 960
tctgcatgtt ttattgtctc ttccatcttt ggttaaatat actagccgaa cttctgtgtt 1020
ttggggatcg tgagttctac aaagattggt ggaatgctca aacgatagag gagtattgga 1080
ggatgtggaa catgcctgta cataaatgga tggttcgtca tatatatttc ccttgcttgc 1140
ggaatgggat gcctaaggag ttggctattt tgattgcgtt cctaatatct gcaatcttcc 1200
atgagctgtg cattgctgtg ccgtgtcaca tctttaagtt ctgggctttt atcggaataa 1260
tgtttcaggt ccctttggtc cttctgacaa atgttttggt aaaaaagttc caaaattcaa 1320
tggttggcaa tatgatattc tggtgcttct tctgcattct tggtcaaccc atgagtctgc 1380
tgctctatta ccatgatgtc ttgaatagaa aagttaatgc aaactgatac tacagatatc 1440
ttgaaaatgt catcacaaag agtgtgaagg atcgataggt ttcgctcaac agga 1494

<210> SEQ ID NO 7
<211> LENGTH: 1828
<212> TYPE: DNA
<213> ORGANISM: Vernonia galamensis

<400> SEQUENCE: 7
tctgagctca aatcaaattt ctgcgactca tacaggattc aactcaatac tttcttgatc 60
ggttctgctg ttcatttact tgtaatttct acttctgctt tgctttcatt tcaagctttt 120
ttccttaata atggcgttat tagatacgcc tcagattgga gaaataacga ccaccgccac 180
cacaactata agacggcgga ccactgtcaa gcctgatgct ggaatcggag atggattgtt 240
tgattcttcg tcgtcttcca aaaccaactc atccttcgag gatggtgaca gtttgaatgg 300
tgatttcaat gacaaattta aggaacagat cggagctggt gatgaatcca aggacgactc 360
caaggggaac ggacagaaga tagatcacgg aggagttaaa aagggacgtg aaacgactgt 420
ggtgcattat gcttatcggc cttcttctcc ggctcatcgg agaattaaag aatctccgct 480
tagctctgac gccatcttca agcagagtca tgcaggcctc tttaaccttt gcatagtggt 540
gcttgttgca gtaaatggta ggctcatcat tgagaatctg atgaagtatg gactattgat 600
caattccaac ttttggttca gttcgagatc attgagagac tggccacttc tgatgtgctg 660
cctcactcct tctgactttc cacttgctgc ctacattgtt gagaaattgg catggaaaaa 720
acgtatatcc gaccctgttg taatcacact ccatgttata ataactacaa ctgcaattct 780
ttatccggtc ttcatgattc tgaggttcga ttcagttgtt ctatcaggcg tctcgttgat 840
gctgtgtgct tgcattaatt ggttgaagtt ggtatctttt gtgcatacaa attatgacat 900
gcggtcgctt ttgaactcaa ctgataaggg agaagtggaa cccatgtctt caaatatgga 960
ttatttttat gatgtcaact tcaaaagctt ggtttatttc atggttgctc caactttgtg 1020
ttaccagata agctatcctc gcactgcatt tattcgaaag ggttgggtgt tacggcaact 1080
gatcaagcta gtaatattta cagggttcat gggattcatc attgaacaat atatcaatcc 1140
gattgtcaaa aattctcgtc atccattgaa aggagacttt ttatatgcga ttgagcgggt 1200
tttaaagctt tcagttccga atttatatgt gtggctctgt atgttctact gcttttttca 1260
cctttggtta aatatacttg ctgagcttct ttgttttggg gatcgtgaat tttataaaga 1320
ttggtggaat gcacaaacta ttgaagagta ttggaggcta tggaatatgc ctgttcataa 1380
atggattgtt aggcaccttt attttccatg cttgcgtaat gggataccta agggtgctgc 1440
catattggtt gcatttttca tgtctgccgt gttccatgag ctttgtattg ctgttccctg 1500
ccacattttc aagttttggg cttttatcgg gatcatgttt caggtcccgt tggtcctact 1560
cacaaattac ttgcagcaca agtttcaaaa ctcgatggtg ggaaatatga tcttctggtg 1620
ctttttcagc atttttggtc aacccatgtg tgtattactt tactaccatg atgtcatgaa 1680
tcaaaagggg aaaagcaaat aaaaagatgt gattgtgttg ctccatttga tctcatagca 1740
tgactggact aaacaaaccc aagggacaca ttttagtcct taaaggaaaa tttttgtagg 1800
aaaaaaaaaa aaaaaaaaaa aaaaaaaa 1828

<210> SEQ ID NO 8
<211> LENGTH: 2099
<212> TYPE: DNA
<213> ORGANISM: Nicotiana tabacum

<400> SEQUENCE: 8

-continued

```
ggcacgagcg aaatcttacc caatcctccg ttgcttttct tttagatcct ctttttctgt     60
cattctcttt ttcccaataa caacaactca ttgcatgtga aggttgattt tgatttttgt    120
gtttattcaa actctctctt cacgattttc ttactctttc tagaagtatc cattactttt    180
tagtctgtga ttcggcgaaa gtaagcaatg gtgatcatgg aattgccgga gagcgtcgaa    240
atgacgacga cgacgacgac ttcgggtatt gagaacctca actccgatct taatcactcg    300
gttcggagga gacgtggcag taatggtttt gaggcggcta gtgcaattaa cagttcggat    360
gcgaatatga gcgaagatag aagagatgtg tgtggcagcg gtgctggatt ggaaacggtg    420
aatgagcgga gtaaatcggt tggtgagtcc agtgatgtaa ttcgaaagga ggacgacagg    480
aatgataatg ttgcgaatgg tgaggaaagc aaatcaacgg aaacaacaac gacgccgttt    540
aaatttgctt acagggcgtc ggcaccagct caccggcgaa tcaaggagag tcctctcagc    600
tccgacgcca ttttcaaaca gagtcacgca ggcctgttca atctctgtgt ggtggtgctg    660
attgctgtta acagcaggct gattatcgag aacttgatga agtatggcct tttaattagg    720
gctggctttt ggtttagctc gaagtcgttg agggattggc cgcttctaat gtgctgtctc    780
agtctccaaa ttttgccgct cgctgctttt cttgtggaga agttggcaca gcagaggcat    840
ttgactgagc gtgcggtggt tactcttcac ataactataa caacagctgc cattttgtat    900
ccagttctgg tcattcttgg gtgtgattct gcttttctgt ttggtgtcat attgatgctg    960
gttgcttgca ttgtgtggat gaagctggtt tcttacgcac atacaaatca tgatatgaga   1020
cagctcgcaa agtctacgga caaggatgaa acttcagatg ggatttctc ttatgatgtt   1080
agcttcaaga gtttggctta cttcatggtt gcgccaacat tatgttatca gcttagctat   1140
ccccacactc catgcattcg caaaggttgg gtggcacgcc aattcatcaa gctggtaata   1200
tttacaggat tgatgggatt tatcatagaa cagtacatta acccaattgt gcaaaactca   1260
caacatcctt tgaaaggaaa ccttttatat gccatcgaga gggtattgaa gctttcggtt   1320
ccaaatttat atgtctggct ctgcatgttt tactgcttct ttcatctttg gctaaatata   1380
cttgcggaac tactatgttt tggtgatcgt gagttctaca aggattggtg gaatgccaaa   1440
acaattgatg agtactggag gatgtggaat atgcctgttc ataagtggat ggttcgtcac   1500
atttatttcc cttgcttaag aaacggaatt ccaaaggggg tcgcaatact gattgctttc   1560
cttgtatctg ctgttttcca cgagctgtgt attgctgttc catgtcgcct tttcaagtgg   1620
tgggcattca tgggaattat gttccaggtt cctttggtca tactcacaaa cttcttacaa   1680
aacaagttcc aaagctcgat ggtgggcaat atgatgttct ggtgcttttt ctgcattctt   1740
ggtcagccaa tgtgtgtgct tctgtattac cacgatgtga tgaatagaaa aagcagtgca   1800
cgttaagctt catccaggga tgaattgttg tatgagcaag tattttaagt tttggatccc   1860
aagctctatt ctactgtttc tggcaaggca ttcctgctat ttccttcatc agttccaaca   1920
atattcagat gatacgaaat atctgtttgg aatgcacaac acaagccacg gccagagatg   1980
ctgatgtctc acattttatt gtgttcttca tgtcggagaa atgtaaaata ctatcttgag   2040
ataactctca tgttagtaaa taccttttg cctctaaaaa aaaaaaaaaa aaaaaaaaa   2099
```

<210> SEQ ID NO 9
<211> LENGTH: 1964
<212> TYPE: DNA
<213> ORGANISM: Perilla frutescens

<400> SEQUENCE: 9

```
tttagaacca aactattctc cgttaagttc tgagttcgat ttctttcttt tctcaaattt     60
```

```
tccgtgcgat ggcgatcttg gactcgccgg agatcctgga cacgacgtcg tccagtgccg    120
acaacggcgc cgcacatcac accactcttc gccggagaca aagtgcgcgc tccgttccgc    180
ctcttctcga ctccgattcc aactctctgg aggcagagag cgcaatcaat gattccgaaa    240
atgttcgaaa cgacgctaat ttgatcgaaa atctccgcgg cggagccgtg gaatccgaga    300
acgaaaaaca ggagagttat ggtaaggagg agggggcgaa agtgaaggag aatggagaaa    360
ctagtaatgg caacggaact gatgttatgg ccgtcaaatt cacattcagg ccggcggcgc    420
ctgctcaccg caaaaataag gagagtcctc ttagctccga cgccatcttc aaacagagcc    480
atgcaggcct cttcaacctt tgtatagtgg tgcttgttgc tgtaaatagc agactaataa    540
ttgagaattt aatgaagtat gggtggctga tcaaatcagg attttggttt agttcaacat    600
cgcttaggga ttggccactg ctaatgtgtt gtcttagtct tccagttttt gcactcgctt    660
catttcttgt cgagaagttg gtgaaactaa attatatacc tgagtgggtc gcagtctttc    720
ttcatgttac aatcacaaca gtggaaatct tgtttccagt tgttgtcatt cttaggtgtg    780
attctgctgt tctatcaggt gtcacgctaa tgctctttgc ttgcactgta tggttgaagc    840
tcgtttccta cgcacataca aactatgatt tgagagtact tgcaaaatca cttgataagt    900
gggaagctat gtccaggtac tggaacctcg actacgctta tgatgtaagc tttaagagtc    960
tggcatactt catggttgct cctacattgt gttaccagcc aagctaccct cggacagctt   1020
gcattcggaa gggttgggtg gtaaggcaac taattaagct ggtaatattc acaggactca   1080
tgggatttat tatagaacag tacataaacc cgatcgttca aaattctcaa catcctctga   1140
aaggaaacct tttatatgcc attgagaggg tcttgaagct ttctgttcca aatttatatg   1200
tgtggctctg catgttttat tgttttttcc acctctggct aaatatactt gctgaacttc   1260
tgtgctttgg ggaccgtgag ttttataagg attggtggaa tgcgaggaca gtggaggagt   1320
actggagaat gtggaatatg cctgtccata aatggatggt tcggcatata tactgtccat   1380
gcttacaaaa tggaatacca aagatagtgg cagttttgat cgcgtttctt gtgtctgcga   1440
tttttcatga gctgtgcgtt gcagtccctt gccaaatatt caagttttgg gcgttctcgg   1500
gtatcatgct tcaggttcct ctcgtaatcg tgactaatta cttgcaagaa aagttcaaaa   1560
actcaatggt gggcaatatg atgttctggt gcttcttctg tatctttggt caacctatgt   1620
gtgtgttgct gtactaccac gacttgatga atcgaaaagc tagtgcaagg tagggatgtg   1680
attcatcttc tgagtagaaa tctaaagctc accagcccca acccacccga aaaacaaaaa   1740
ggagcaagga tcctgattgt gagctggtag ataatttgct acaactatgt ttcttaaata   1800
gctgggagta gtttgttatc tgccttcacc taggacgacg ttatgatctg ttgtgatggg   1860
ggtaaggggg catgcaaatt ttgtctattt ttcaaggaat acagaaatgg tgaaaatttg   1920
atgaagcata cccctcgttt actgacaaaa aaaaaaaaaa aaaa                    1964
```

<210> SEQ ID NO 10
<211> LENGTH: 1539
<212> TYPE: DNA
<213> ORGANISM: Zea mays

<400> SEQUENCE: 10

```
atggcggact ccgaagacgc gccgccagcc gtgcaccgcc gcccaccgcg ccccgctcgc     60
ggtgctgctg cagcccaggg cttcgcggcc gcgttgcgcc gccggctgag atccggcgct    120
gcggtggcgg cacgcgccag ctttgccgca gactccgggg acgagtctgg ccccggcgag    180
```

```
ccctcttcgt ctcgccgccg cgacaacagc gggggcgcct cgtccgccgc cggcggccgg    240
gccggggcag ggacttctc cgcgttcacc ttccgcgccg cggcgcctgt ccaccggaaa    300
gccaaggaga gccctctgag ctccgacgcc atcttcaagc agagtcatgc aggccttttc    360
aacctatgta ttgttgttct ggttgcggtg aatagcaggc tcattattga gaacctgatg    420
aagtatggct tattaataag atctggcttt tggtttaatg ctacatcatt gcgagactgg    480
ccactgctaa tgtgttgcct tagtctaccc atatttcccc ttggtgcatt tgcagtcgaa    540
aagttggcat tcaacaatct cattagtgat cctgctacta cctgttttca catccttttt    600
acaacatttg aaattgtata tccagtgctc gtgattctta agtgtgattc tgcagtttta    660
tcaggctttg tgttgatgtt tattgcctgc attgtttggc tgaagcttgt atcttttgca    720
catacaaacc atgatataag aaaactgatc acaagcggca agaaggttga taatgaactg    780
accgcggctg gcatagataa tttacaagct ccaactcttg ggagtctaac atacttcatg    840
atggctccga cactctgtta tcagccaagt tatcctcgaa caccttatgt tagaaaaggt    900
tggctggtcc gtcaagttat tctatacttg atatttactg gtctccaagg attcattatt    960
gagcaataca taaatcctat tgttgtgaac tctcaacatc cattgatggg aggattactg   1020
aatgctgtag agactgtttt gaagctctca ttaccaaatg tctacctgtg gctttgcatg   1080
ttttattgcc ttttccatct gtggttaaac atacttgctg agattcttcg atttggtgac   1140
cgagaattct acaaagactg gtggaatgca aagacaattg atgagtactg gagaaaatgg   1200
aacatgcctg tgcataaatg gattgttcgt catatatatt tcccttgcat gcgaaatggt   1260
atatcaaagg aagttgctgt ttttatatcg ttctttgttt ctgctgtact tcatgagtta   1320
tgtgttgctg ttccctgcca catactcaag ttctgggctt tcttaggaat catgcttcag   1380
attcccctca tcatattgac atcatacctc aaaaataaat tcagtgacac aatggttggc   1440
aatatgatct tttggttttt tttctgcata tacgggcagc caatgtgtgt tctattgtat   1500
taccatgatg tgatgaaccg gactgagaag gcaaaataa                          1539
```

<210> SEQ ID NO 11
<211> LENGTH: 1548
<212> TYPE: DNA
<213> ORGANISM: Sorghum bicolor

<400> SEQUENCE: 11

```
atggcggaca ccgacgacgc gccgccggcc ccggccgtgc accgccgccc accgcgcccc     60
gcccgcggtg ctgccgctgc ccagggcttc gcggccaagt tgcgccgacg gctcagctcc    120
ggcgccgcgg cggcggcgcg cgccagcttc gcggcagact ccggggacga gtccggcccc    180
ggggagccct cttcgtcccg ccgccgcgac aacggcgggg acgcctcgtc cgccgccgac    240
ggcggccggg gcggggcagg ggacttctcc gctttcacgt tccgcgccgc ggcgcctgtc    300
caccggaaag ccaaggagag ccccctcagc tccgacgcta tcttcaagca gagtcatgca    360
ggccttttca acctatgtat tgttgttctg gttgcagtga atagcaggct cattattgag    420
aacctgatga agtatggctt attaataagg tctggctttt ggtttaatgc tacatcattg    480
cgagactggc cactgctaat gtgttgcctt agtctacctg tgtttcccct tggtgcattt    540
gcagttgaaa agttggcatt caacaatctc attactgatg ctgccgctac ctgttttcac    600
atctttctta caacacttga aattgtatat ccagtgcttg tgattcttaa gtgtgattct    660
gcagttttat caggctttgt gttgatgttt attgcctgca ttgtttggct gaagcttgta    720
tcttttgcac atacaaacca tgatataaga aaactgatca caagcggcaa gaaggttgat    780
```

aatgaactga ccgtggctga catagataat ttacaagctc caactcttgg gagtctaaca 840
tacttcatga tggctccgac actctgttat cagccaagtt atcctcgaac accttatgtt 900
agaaaaggtt ggctggttcg tcaagttatt ctatacttga tatttactgg tctccaagga 960
ttcattattg agcaatacat aaatcctatt gttgtgaact ctcaacatcc attgaaggga 1020
ggattactga atgctgtaga gactgttttg aagctctcat taccaaatgt ctacctgtgg 1080
ctttgcatgt tctattgcct tttccatcta tggttaaaca tacttgctga gattcttcga 1140
tttggtgacc gtgaattcta caaagactgg tggaatgcaa aaacaattga tgagtactgg 1200
agaaaatgga acatgcctgt gcataaatgg atgcttcgtc atatatattt tccttgcata 1260
cgaaatggta tatcaaagga agttgctgct tttatagcgt tctttgtttc tgctgtattt 1320
catgagttat gtgttgctgt tccctgccac atactcaagt tctgggcttt cttaggaatc 1380
atgcttcaga ttcccctcat catactgaca tcatacctca aaaataaatt caatgacaca 1440
atggttggca atatgatctt ttggttcttt ttctgcattt acgggcagcc aatgtgcgtt 1500
ctattgtatt accatgatgt gatgaaccgg actgagaaga caaaataa 1548

<210> SEQ ID NO 12
<211> LENGTH: 2103
<212> TYPE: DNA
<213> ORGANISM: Oryza sativa

<400> SEQUENCE: 12
gtcgtcccgc gtctctcctc acctctcgtc tccctcgcga cgtctcccct tctccctcca 60
cccctccaat ggtgggctcc gatggcgacg gcgacggcgg cggaggggaa gcacacgcgc 120
cggcggcgcc cgcgcaccac caccgccggc ccccgcgccc gcggggaggc agcggggcca 180
tcgtcgaggg cttcgcggcg gcgctccgtc gcaggatccg ctcgggggcc gcggcggccg 240
cgcgggccag cttcgggggc gactccgggg acgaggccgc ctccggggag ccctcctcgt 300
cctcgtcctc gtccccgtcc cgccgccgtg gcggcgactc caacggggcg gaggcgtcct 360
ccgccgccgg gggcggtggt ggccgtggcg gcggtgggga cttctccgcg ttcacgttcc 420
gcgcggcggc gccggtgcac cgcaaggcca aggagagccc cctcagctcc gacgccatct 480
tcaagcagag tcatgcaggc cttttcaacc tatgcattgt tgttctagtt gcagtgaaca 540
gcaggcttat tatcgagaac ttaatgaagt atggcttatt aataagagct gggttttggt 600
ttaatgataa atcattgcgg gactggccac ttctaatgtg ttgtcttagt ctgcctgctt 660 tcccccctggg tgcatttgca gttgaaaagt tggcatttaa caatgttatt actgatgctg 720
ttgctacctg cctccatatc ttcctttcaa caaccgaaat tgtatatcca gtgcttgtga 780
ttcttaagtg tgattctgca gttttgtctg gctttttgtt gatatttatt gcctgtattg 840
tttggctgaa gcttgtatct tttgcacata caaaccatga tataaggcaa ctgaccatgg 900
gcggcaagaa ggttgataat gaactaagca cagttgacat ggataattta caacctccaa 960
ctttagggaa tctaatatac ttcatgatgg ctcctacact ctgttatcag ccaagctatc 1020
cccgaacttc atgtgttaga aaaggttggc tgattcgtca aattattctg tacttgatct 1080
ttactggtct tcaaggcttc attattgagc aatacataaa tccaattgtt gtgaattctc 1140
agcatccatt gaaaggagga ctcctaaatg ctgtagagac tgttttgaaa ctctcattac 1200
caaatgttta cctgtggctt tgcatgttct atgctttttt ccatctctgg ttaagtatac 1260
ttgctgagat tcttcgattt ggtgaccgtg aattctacaa agattggtgg aatgcaaaaa 1320
caattgatga gtattggaga aaatggaata tgcctgtaca taaatgggtt gttcgccata 1380
tttactttcc ttgcatgcga aatggtatat caaaggaagt tgctgtcttg atatcattcc 1440
ttgtttctgc cgtactccat gagatatgtg tcgctgttcc ctgccgcatt ctcaagttct 1500
gggcattctt aggaataatg ctacagatcc cccttatcgt attgacagca tacctcaaaa 1560
gtaaattcag agatacaatg gttggcaaca tgatattttg gttctttttc tgcatctatg 1620
ggcagccaat gtgccttctc ctgtactatc atgatgtgat gaacaggatt gagaaggcaa 1680
gataaatgcg tgttgccatc tttttcctct gtttcatttt gtaccagcag aagcacaagc 1740
aataatccac atgctagcca taaaacagca tgattcccaa cggtgtggta cagccaacct 1800
tcctgttatt ctattttctt ggctgtggtg tagatttagt ttttaacttg tggctaaccg 1860
caggaatgcc tgtagataag catctgtcat tctgtctggc gacgttctcc ttattaatgt 1920
gtagatgtag aactgtttcc gaaaactata tatcttgaat ctgttatgcc tcgacgaaca 1980
taatcctttt gttaagctta gttggtacag tctagaaagg ataagagtcg tggatgtacg 2040
atttcgtctg ccatatatca cgctcatatt ggcacaggta actttgtcgc taccttctat 2100
ctc 2103

<210> SEQ ID NO 13
<211> LENGTH: 1473
<212> TYPE: DNA
<213> ORGANISM: Oryza sativa

<400> SEQUENCE: 13
atggccccgc ccccctcgct cgccccccgat cgcggcggcg gcgaacccga cgacgccctc 60
cgcctgcggg cccgcgccgc cgccgccgcc ggtgacgctc ccgctccgca gcagcagcag 120
gagcagaggc atcaggagca gcagcagcag ctgctctggt accgcgcgtc ggcgcccgcc 180
caccgccgcg tcagggagag ccccctcagc tccgacgcca tcttccgcca gagccatgca 240
ggccttctga acctatgcat tgttgtgctg gttgctgtga acagcagact tattattgag 300
aatttaatga agtatggcct actaattaga gctggatttt ggtttagtgg aacatcgctg 360
gcagattggc ctcttctcat gtgctgtctc actttaccaa ctttcccgct tgctgcactt 420
atggttgaga agttggctca aagaaaactt attagtaaac atgtggttat tcttctccat 480
atcgttatta caacatctgt ccttgtctat ccagttgttg tgattctaaa gtgtgattcg 540
gcagtattat ctggatttgt gttgatgttt cttgcaagca ttatttggtt gaagcttgtt 600
tcttttgctc atacaaatta tgatataaga atgctgtcca aaagtattga aaagggcgtg 660
acacatgaca tttctataga tccggagaac attaaatggc caacctttaa aaggctatcc 720
tacttcatgt tggccccaac actttgttac cagccaagtt atccccgaac tacatatatt 780
agaaaaggtt gggtggtccg acaactgata aaatgccttg tttttacagg cttgatgggt 840
tttataattg agcaatacat aaatccaatt gtgaagaatt cgaagcatcc attgaaaggg 900
aatttcttga atgctataga gagagtattg aaattatcag tgccaacatt atatgtctgg 960
ctttgcatgt tctactgttt tttccatctc tggttgaata ttcttgctga gctcctctgt 1020
tttggtgatc gtgaattcta caaggactgg tggaatgcca aaacagttga agagtattgg 1080
agaatgtgga atatgcctgt tcacaagtgg gtcattcgac atatatattt tccatgcata 1140
aggaatggtt tttcaaaggg tgttgctatc ctaatctcgt tcctggtttc agctgcattt 1200
catgagatat gtattattta tttcattgtc cttatcgatt tgcagctatg tgttgctgtt 1260
ccatgccaca tttttaaatt ctgggcattt attgggatca tgtttcagat tcccctggta 1320
ttcttgacga aataccttca agataaattc aataacacaa tggtgggcaa catgatattt 1380
tggttcttct tcagcatcct ggggcaacca atgtgtgttc tcttatacta ccatgatgtc 1440
atgaacaggc aacaagccca aacaaataga tag 1473

<210> SEQ ID NO 14
<211> LENGTH: 1590
<212> TYPE: DNA
<213> ORGANISM: Sorghum bicolor

<400> SEQUENCE: 14
atggccccgc ccccctccat ggccgccgcc tccgatcgcg ccgtccccgg cgccgacgcg 60
accgaggcgt cctccctccg cctccgccgc gccccctcag ccgacgccgg cgaccttgcc 120
gacgattcct caggagaccg gcgggagaac ggcgagccgc aaccgccgca ggagcagcag 180
cagcagcacg agatgctgta ctaccgcgcg tcggcgcccg cccaccgccg cgtcaaggag 240
agccccctca gctccgacgc catcttccgg cagagccatg ctggtcttct gaatctatgc 300
atcgttgttc tgattgcagt gaacagcaga ctcattattg agaatttaat gaagtatggc 360
ctattgataa gagctggatt ttggtttagt gcaagatcgc tgggtgactg gccccttcta 420
atgtgctgcc tcactttacc agttttccca cttgttgccc tcatggctga gaagctgatt 480
agaagaaagc tcattggtga acatgtggtt attctactcc atatcattat tacaacatct 540
gtcattgtct atccagttgt tgtgactctt aagtgcgact cagcagtgct atctggattc 600
ttgctaatgt ttcttgcgag catcatgtgg atgaagcttg tctcttatgc acatacaaat 660
tatgatataa gggcattgtc caaaagtact gaaaagggtg ctgcatatgg aaattatgtc 720
gatcctgaga gtatgaaaga tccaaccttt aaaagtctag tgtacttcat gttggcccca 780
acactttgtt accagccaac ttatccccga actacatgta ttaggaaggg ttgggtgacc 840
cgacaactta taaagtgcct ggtttttaca ggcttgatgg gcttcataat tgagcaatat 900
ataaacccaa ttgtgaagaa ttccaaacat ccactgaaag ggaatttctt gaatgctata 960
gaaagagtct taaaactctc agtgccaaca ttatatgtat ggctttgcat gttctattgc 1020
ttttttcatt tatggctgaa cattctagct gaactcctct gtttcggtga ccgtgaattc 1080
tacaaggact ggtggaatgc caaaactgtt gaagagtact ggaggatgtg gaacatgcct 1140
gttcataaat ggatcatcag acacatatat tttccatgta taaggaaagg cttttccagg 1200
ggtgtagcta ttctagtctc gtttctggtt tcagctgtat ttcatgagat atgtattgcg 1260
gtgccgtgcc acattttcaa attctgggca ttttctggga tcatgtttca gataccgttg 1320
gtattcttga caagatatct ccaggctacg ttcaagaata taatggtggg caacatgata 1380
ttttggttct tcttcagtat agtcgggcag ccgatgtgtg tccttttata ctaccatgat 1440
gtcatgaaca ggcaggccca gcaagtagat aattcggcag aaacatgtac tttaagacaa 1500
gttatcagaa gcagactgga gcgacgcagc aggaagcagc agcagcagca ggccagcagc 1560
ccccctttgc cattgttacc agctagctag 1590

<210> SEQ ID NO 15
<211> LENGTH: 1485
<212> TYPE: DNA
<213> ORGANISM: Zea mays

<400> SEQUENCE: 15
atggccccgc ccccctccat gcctgccgcc tccgatcgcg ccggccctgg ccgcgacgcg 60
ggcgactcgt cctcccttcg cctccgccgc gcccccctcag ccgacgccgg cgaccttgcc 120
ggcgattcct cgggaggctt gcgggagaac ggcgagccgc aatcgccgac gaatccgccg 180
ccgcaggagc agcagcagca cgagatgcta tactaccgcg cgtcggcgcc cgcccaccgc 240
cgcgtcaagg agagcccccct cagctctgac gccatcttcc ggcagagcca tgctggtctt 300
ctgaatctat gcattgttgt tctgatcgca gtgaacagca gactcattat tgagaattta 360
atgaagtatg gcctgttgat aagagctgga ttttggttta gtgcaagatc gctgggtgac 420 tggcccccttc taatgtgctg cctcactcta ccagttttcc cactagttgc actcatggct 480
gagaagctga tcacaagaaa gctcattggt gaacatgtgg ttattctact ccatatcatt 540
attacaacat ctgccattgt ctatccagtt gttgtgactc ttaagtgtga ctcagcagta 600
ctatctggat ttgtgctaat gtttcttgcg agcatcatgt ggatgaagct tgtctcttat 660
gcacatacaa attatgatat aagggtattg tccaaaagta ctgaaaaggg tgctgcatat 720
ggaaattatg tcgatcctga gaatatgaaa gatccaacct ttaaaagtct agtgtacttt 780
atgttggccc caacactttg ttaccagcca acttatcctc aaactacatg tattagaaag 840
ggttgggtga cccagcaact cataaagtgc gtggttttta caggcttgat gggcttcata 900
attgagcaat atataaaccc aattgtgaag aattccaaac atccactgaa agggaatttt 960
ttgaatgcta tagaaagagt cttaaaactc tcagtgccaa cattatatgt atggctttgc 1020
atgttctatt gctttttttca tttatggctg aacattgtag ctgaactcct ctgtttcggt 1080
gaccgtgaat tctataagga ctggtggaat gccaaaactg ttgaagagta ctggaggatg 1140
tggaacatgc ctgttcataa gtggatcatc agacacatat attttccatg tataaggaaa 1200
ggcttttcca ggggtgtagc tattctaatc tcgtttctgg tttcagctgt atttcatgag 1260
atatgtattg cggtgccttg ccacattttc aaattctggg cattttctgg gatcatgttt 1320
cagataccct tggtattctt gacaagatat ctccatgcta cgttcaagca tgtaatggtg 1380
ggcaacatga tattttggtt cttcttcagt atagtcggac agccgatgtg tgtccttcta 1440
tactaccatg acgtcatgaa caggcaggcc caggcaagta gatag 1485

<210> SEQ ID NO 16
<211> LENGTH: 1912
<212> TYPE: DNA
<213> ORGANISM: Physcomitrella patens

<400> SEQUENCE: 16
atgcctgtga agagtagcaa tctggcgggg gagagggctg ccaccagcca tattaatgcc 60
aacacgaaat tcgacctgcg ggggtgtacg cctgcgcatc gcgttaggag ggaaagcccg 120
cttagttcag acgcaatttt tcatcagagt catgctgggt tgttcaatct ctgtattgtt 180
gttttgatag ctgttaacag ccggcttatt attgagaact taatgaagta tggactactc 240
attagaactg gtttctggtt tagctccaag tctgcacgcg attggccact cttgatgtgc 300
ggtttgagtt taccgacttt tccctttgca gcgttactag tggaaaaact atgctggaaa 360
aatgaaaacg ggaaatggtt gattttcgta ctacacctca taatcagcac tgtagggata 420
ctgtatcctg gatatgttat acacagggtg caatccgcac tgctgcctgg tcttgtattg 480
atactcattg cagtgactgg gtggatgaag cttatatctt acgctcatgt caacaaggac 540
atgcgagaac ttttgagagc caaagaaaag ctacctgagg caccacagta cgcagataaa 600
atagaggttc cggaccacct tacgatccaa aatattgctt atttcatgct cgcgcccaca 660
ctttgctacc agttgagcta ccctcgttcg gacacaattc gaaaaagttg ggtgttacgg 720

```
caagccggga aattggttgt gttcttgggt ttagggggat tcatcattga gcagtacata    780

aatcccactg tgaagaattc acagcacccg ctcaggggca actatcttca agcactggag    840

agggttttaa agctttcgtt gccagttctt tatgtttggc tgtgcttgtt ctactgttta    900

tttcatcttt ggttgaatat tgtggcggag ctacttcgct ttggggacag ggaattttat    960

aaggactggt ggaatgctca aacagttgaa gagtattggc gaatgtggaa catgcctgtg   1020

cacaagtgga tggtgcggca tatttatttt ccctccattc gagctggctt atcaaagaaa   1080

gcagcagtac tactggtgtt tgcaatttca gctttgtttc atgaggttat cattggtgtt   1140

ccgtgtcata tgcttcgatg ctgggctttt cttggtatca tgatgcaggt tccgttggtg   1200

tacttgacaa acgtgataaa agagcggtac catagctcta tggttggaaa tatggtattt   1260

tggttcttct tttgcattgt cgggcaaccc atgtgcttgc ttctctacta ccacgacgtt   1320

ttcaacaact ttcccagtac ctgaactgag atcacccatt cgtgcagttg ttaatcttgt   1380

gaatagcact cctcatctgt accttgttat ggcttccact tctcgagaat cgactaaacc   1440

gcaactcata tgtttgtcaa taacgattca ttcgtaggcg ggttggtgtg agattacaag   1500

agaggaaact ttcgtcgtaa gccagcagtg tagatacagt ccaggtagga gtgtaacggg   1560

cacttgcttc aagggcagat ccttgtcaac gcaagctttt gttggagctt gttggagctt   1620

gtttcgcact tagtattctt ttctagctgt agttttaggt gacgttagtc tattcttggt   1680

cccatcatcc atcctgtaag atgctgggcg tgctcacgtg cagaagctgc ctcgaatcct   1740

acgttacaat ttcatgttgg ataccgcgtg gatgtccgct tcagaatctg cgtcatgatg   1800

atgcacacca tttttttcta ttggaaactg aacagagggt agtgatacgt aagaacattt   1860

tgggaaccgt gcctgaaaat cgtcggagca aataatgatg tggttttgca gc            1912
```

```
<210> SEQ ID NO 17
<211> LENGTH: 1278
<212> TYPE: DNA
<213> ORGANISM: Selaginella moellendorffii

<400> SEQUENCE: 17

atgcggccct cgctcccggc gcaccggcgg agcaaggaga gcccgctcag ctccgacgcc     60

atcttcacgc agagccacgc cggcctcttc aacctctgca tcgtcgtgct ggtggcggtg    120

aacagccggc tcatcatcga gaatctcatg aagtatggcc tcctcatcca ggccgaggtc    180

ctcttcagct ccaagtcgct caaggactgg ccgctcctca tgtgtggcct ctcgctgctg    240

atcttccccc tcgccgccta tgtcatcgag aagatcaagg cccgccgccc cgccaccgcc    300

gtggcgccgc tccacttgat caacctcgcc gccgcgctgc tctacccgat ctacgtgatc    360

gagatgttcc agtcggatct cctctcgggg ctggttctca tgctcatcgc cgtcaccggc    420

tggctcaagc tcgtctccta cgcgcacacc aacgccgaca tccgcgcggt gaagaaggac    480

ggtggcaaga tcgagctccc cgccgaggcg ccggcgatcg actacccgga caacatctcg    540

ctcaagaaca tcgcctactt catggcagcg ccgacgctgt gctaccagct gagctacccg    600

cgctcgccgc ggattagaac cgggtgggtg ctccggcagc tgggcaagtg gatcgtcttc    660

aacggattca tgggcttcat catcgggcag tacatgaatc cgatcatccg gaactcgacg    720

cacccgctca aggggaacta cctctacgcg atcgagcgcg tgctcaagct gtccatcccc    780

acgctctacg tctggctcgg cttcttctac tgcttcttcc acctgtggct caacatcgtg    840

gcggagatcc tgtgcttcgg cgaccgcgag ttctacaagg actggtggaa cgccaagtcg    900
```

-continued

```
gtggacgagt actggcggct gtggaacatg cccgtccacc gctggctcgt ccgccacgtc    960

tacttcccgt gcctccggct gggcctccac aagcagttcg ccattttggt ggtgttcgtc   1020

atctccggga tctttcacga gatttgcatc gcggtgccgt gccacatgct gcggggctgg   1080

gcgtttctgg ggatcatgtt ccaggtgccg ctggttctgg tgaccaacgt cctccagcgc   1140

aagttccaga gctccatggt cggcaacatg atcttctggt tcttcttttg catcgtcggg   1200

cagccgatgt gcgtgctgct ctactatcac gacgttgtca acaggcagca gctccagcta   1260

gctgggcggt ccaaataa                                                 1278
```

<210> SEQ ID NO 18
<211> LENGTH: 1524
<212> TYPE: DNA
<213> ORGANISM: Euonymus alatus

<400> SEQUENCE: 18

```
atggctgcta acttgaacga agcctcggat cttaattttt cgcttcggag gagaactggt     60

ggcatctcaa gtacgactgt gcctgattct agttccgaga caagttcgtc ggaggcggac    120

tatttggacg gaggcaaagg tgccgcggac gtcaaagatc gtggggatgg tgcggtggag    180

tttcagaatt cgatgaagaa cgtggagagg attgagaaac atgagagccg agtaggattg    240

gattcgagat tcacgtatag gccatcggtc ccggctcatc gcacaataaa ggagagcccg    300

cttagctcgg acgcaatatt caaacagagt cacgcaggtc tcttcaatct ctgtatagta    360

gttctggttg ctgtgaacag caggctgatc attgaaaatc taatgaagta tggatggtta    420

ataaggagtg ggttttggtt cagctcaaga tcattgagag actggcccct ttttatgtgt    480

tgtctcacac taccagtatt ccctcttgct gcttttctgt ttgagaagtt ggctcaaaaa    540

aatttaatat ctgaacctgt tgttgttttg cttcatatag taaacactac agctgccgtt    600

ttataccctg ttttggtgat tctaaggtgt gattctgcct ttatgtctgg ggttacgttg    660

atgctctttg cttgtattgt gtggttaaag ttggtatctt atgctcatac caactatgat    720

atgagagccc tcaccaagtc tgttgaaaag ggggacacgc cgttgagctc tcagaacatg    780

gattactcgt ttgatgtcaa tatcaagagt ttggcatatt ttatggttgc tcccacatta    840

tgttaccaga ttagctatcc tcgtacccca tatgttcgca agggttgggt ggttcgtcaa    900

tttgtcaagt taataatatt tactggactt atgggattta taattgaaca atatatcaat    960

cctattgtcc agaattcaca acaccctttg aaaggaaact tttgtatgc cattgagaga   1020

gttttgaagc tttcagtccc aaacctttat gtttggctct gcatgttcta ctgccttttt   1080

catctctggt taaacatact tgctgaactt ctttgttttg gtgatcgtga gttctacaag   1140

gattggtgga acgctaaaac tgttgaggag tactggagaa tgtggaacat gcctgttcat   1200

aagtggatgg ttcgtcatat ctacttccca tgcttgagga acgggatacc caagggtgtt   1260

gcttttgtca tttccttctt agtttctgcc gtcttccatg agctatgcat tgctgttccc   1320

tgccacatct tcaagttatg ggctttcttt ggaataatgc ttcaggttcc cttggtgttg   1380

atcacaagtt atctgcaaaa taagttcaga agctcaatgg tgggaaatat gatgttttgg   1440

ttctctttct gcatttttgg tcaacctatg tgcttacttc tatattacca tgatttgatg   1500

aatcgcaatg ggaagatgga gtag                                          1524
```

<210> SEQ ID NO 19
<211> LENGTH: 1557
<212> TYPE: DNA
<213> ORGANISM: Vitis vinifera

<400> SEQUENCE: 19
atggcgatct gcaactcgcc tgtcagtgtg accacgtcgt catcaagctc tcacgccgat 60
tcagatctcg acttttccat tcggaagagg ttcggcggga aggggaaggc cgtggcggat 120
tcgtcgctgg agacggagac ggaggcggcg gcggcggcgg tgctcgaagc agagaagtcg 180
gtgggcgagg tggggagtgg cggtgatcga ggggaatcgg ggagtcaggt ggtgaggaat 240
ggggagaacg gagtggctga ggttgccgcg aaattcgcgt accggccgtg tgcgccggct 300
caccggaaag tgaaggaaag tcctctcagt tctgacgcca ttttcagaca gagtcatgcg 360
ggtctcttca acctctgtat agtagtgctt gtagctgtaa acagccggct tatcattgag 420
aatcttatga agtatggttg gttaatcagg gctggttttt ggtttagttc aaaatcattg 480
agagattggc cactctttat gtgctgttta accctcccaa tctttccact tgctgctttt 540
gtggttgaaa agttggctca acaaaagtat atctctgagc aggttgttgt ctctcttcac 600
atcataatta ctacagctgc agttttgttt ccagttttgg tgattctaag gtgtgattca 660
gctgttctct ctggtgtcac actaatgctc tttgcttgca ttgtgtggtt aaaattggta 720
tcttttgcac atacaaatta tgacatgaga gcagttgcca agttaattga taagggggat 780
gacttgtcca cttcattgaa tatggattac ccttatgatg tcaacttcaa gagtttggca 840
tacttcatgg ttgcccccac gctatgttac cagccaagct atcctcgcag cacatgcatt 900
cggaagggtt gggtctttcg ccaatttgtc aagttggcaa tatttacagg tgttatggga 960
tttataatag aacagtatat taatccaatt gttcagaatt ctcagcaccc tttgaagggg 1020
aatttttttt atgcattgga gaggattttg aagctttctg ttccaaattt atatgtgtgg 1080
ctctgcatgt tctactgctt tttccacctc tggttaaata tacttgctga gcttcttcgt 1140
tttggggacc gtgagttcta taaagattgg tggaatgcaa aaacagttga ggagtattgg 1200
agaatgtgga atatgcctgt tcataaatgg atggttcgcc atctctattt tccatgtcta 1260
cggaatggga tatctaaggg agtttctgtg gtgattgcct ttgccatatc tgccatattc 1320
catgagctat gcattgctgt accttgtcac atgtttaagc tttgggcttt cattggaatt 1380
atgttccagg ttcccttggt tttggtcaca aattacttgc aaaataagtt cagaaattct 1440
atggtgggaa atatgatctt ctggctgttt ttcagcattc ttggtcagcc aatgtgtgtg 1500
cttctatatt accatgactt gatgaatcga aaagagacaa ctgaatcaag cctctga 1557

<210> SEQ ID NO 20
<211> LENGTH: 1880
<212> TYPE: DNA
<213> ORGANISM: Glycine max
<220> FEATURE:
<221> NAME/KEY: misc_feature
<222> LOCATION: (1798)..(1798)
<223> OTHER INFORMATION: n is a, c, g, or t

<400> SEQUENCE: 20
gaagagaaga ctgagttagt aaacacgctc gctcggtctt cttttccaat ggcgatttcc 60
gatgagcctg aaactgtagc cactgctctc aaccactctt ccctgcgccg ccgtcccacc 120
gccgctggcc tcttcaattc gcccgagacg accaccgaca gttccggtga tgacttggcc 180
aaggattccg gttccgacga ctccatcagc agcgacgccg ccaattcgca accgcaacaa 240
aaacaagaca ctgatttctc cgtcctcaaa ttcgcctacc gtccttccgt ccccgctcat 300
cgcaaagtga aggaaagtcc gctcagctcc gacaccattt tccgtcagag tcacgcgggc 360

```
ctcttcaacc tctgtatagt agtccttgtt gctgtgaata gccgactcat cattgagaat    420
ttaatgaagt atggttggtt gatcaaatct ggcttttggt ttagctcaaa gtcattgaga    480
gactggcccc tcttcatgtg ttgtctttct cttgtggtat ttccttttgc tgcatttata    540
gtggagaagt tggcacagca gaagtgtata cccgaaccag ttgttgttgt acttcatata    600
atcattacct cagcttcact tttctatcca gttttagtaa ttctcaggtg tgattctgct    660
tttctatcag gtgttacgtt aatgctattt gcttgtgttg tatggttaaa attggtgtct    720
tatgcacata caaactatga tatgagagca cttaccaaat cagttgaaaa gggagaagct    780
ctgcccgata ctctgaacat ggactatcct tacaatgtaa gcttcaagag cttagcatat    840
ttcctggttg cccctacatt atgttaccag ccaagctatc ctcgcacacc ttatattcga    900
aagggttggc tgtttcgcca acttgtcaag ctgataatat ttacaggagt tatgggattt    960
ataatagaac aatacattaa tcccattgta caaaattcac agcatcctct caagggaaac   1020
cttctttacg ccatcgagag agttctgaag ctttctgttc caaatttata tgtgtggctc   1080
tgcatgttct attgcttttt ccacctttgg ttaaatatat tggcagagct tcttcgattt   1140
ggtgatcgtg aattctacca ggattggtgg aatgccaaaa ctgttgaaga ttattggagg   1200
atgtggaata tgcctgttca caaatggatg atccgccacc tatattttcc atgtttaagg   1260
cacggtatac caaaggccgt tgctctttta attgccttcc tggtttctgc tttattccat   1320
gagctgtgca tcgctgttcc ttgccacata ttcaagttgt gggctttcgg tggaattatg   1380
tttcaggttc ctttggtctt catcactaat tatctgcaaa ataaattcag aaactcgatg   1440
gttggaaata tgatttttg gttcatattc agtattcttg gtcaacctat gtgcgtactg   1500
ctatattacc atgacttaat gaataggaaa ggcaaacttg actgaaggtg cacgtggata   1560
agcttttctg tttttggagt gtataattga tgtcgatatg ttgatcaata ttggtttcca   1620
cgagtacttt catctaccat ggcagtggct gctctgaagg atttccacct gatataccag   1680
gtcgcgaggc taattcatct tgatctatgt acttaatcaa ctctcctctg gcaattgtat   1740
cgatatatgc aattttgaga gccatacact ggcattgata actgccaagg aacagtgnta   1800
gctgtttttc tgttaaatgt taattagtag agagctagat gtaaataaat ttatgctcaa   1860
aaaaaaaaaa aaaaaaaaaa                                                1880
```

<210> SEQ ID NO 21
<211> LENGTH: 1960
<212> TYPE: DNA
<213> ORGANISM: Glycine max

<400> SEQUENCE: 21

```
acgcgggggg agaagagaag actgagttag aaaacacgct cggtcttctt ctccaatggc      60
gatttccgat gagcctgaaa gtgtagccac tgctctcaac cactcttccc tgcgccgccg     120
tccctccgcc acctccaccg ccggcctctt caattcgcct gagacaacca ccgacagttc     180
cggtgatgac ttggccaagg attctggttc cgacgactcc atcaacagcg acgacgccgc     240
cgtcaattcc caacagcaaa acgaaaaaca agacactgat ttctccgtcc tcaaattcgc     300
ctaccgtcct tccgtccccg ctcaccgcaa agtgaaggaa agtccgctca gctccgacac     360
tattttccgt cagagtcacg cgggcctctt caacctttgt atagtagtcc ttgttgctgt     420
gaatagccga ctcatcattg agaatttaat gaagtatggt tggttgatca aatctggctt     480
ttggtttagc tcaaagtcat tgagagactg gccccttttc atgtgttgtc tttctcttgt     540
ggtatttcct ttcgctgcct ttatagtgga gaagttggca caacggaagt gtatacccga     600
```

```
accagttgtt gttgtacttc atataatcat tacctcaact tcgcttttct atccagtttt    660

agttattctc aggtgtgatt ctgcttttgt atcaggtgtc acgttaatgc tgttttcttg    720

tgttgtatgg ttaaaattgg tgtcttatgc acatacaaac tatgatatga gagcacttac    780

caaattagtt gaaaagggag aagcactgct cgatactctg aacatggact atccttacaa    840

cgtaagcttc aagagcttgg catatttcct ggttgcccct acattatgtt accagccaag    900

ctatcctcgc acaccttata ttcgaaaggg ttggttgttt cgccaacttg tcaagctgat    960

aatatttaca ggagttatgg gatttataat agaacaatat attaatccca tagtacaaaa   1020

ttcacagcat cctctcaagg gaaaccttct ttacgccacc gagagagttc tgaagctttc   1080

tgttccaaat ttatatgtgt ggctctgcat gttctattgc tttttccacc tttggttaaa   1140

tatcctggca gagcttcttc gatttggtga tcgtgaattc tacaaggatt ggtggaatgc   1200

caaaactgtc gaagattatt ggaggatgtg gaatatgcct gttcacaaat ggatgatccg   1260

ccacctatat tatccatgtt taaggcacgg tctcccaaag gctgctgctc ttttaattgc   1320

cttcctggtt tctgctttat tccatgagct gtgcattgct gttccttgcc acatattcaa   1380

gttgtgggct ttcggtggaa ttatgtttca ggttcctttg gtcttgatca ctaattatct   1440

gcaaaataaa ttcagaaact caatggttgg aaatatgatt ttttggttca tattcagtat   1500

ccttggtcaa cctatgtgtg tactgctata ctaccatgac ttgatgaata ggaaaggcaa   1560

acttgactga agctacggcc attacatttt aaaggtgcac atggatgagc ttttcagttt   1620

tcagattgta aaattgatgt ggatatgttg gtcaatattg ttttctacga atgctttcat   1680

ctaccatggc attggctgct ctgaaggaat tccacgggat atgccagttc acgaggctaa   1740

ttcattatct tgatctatgt acttaccaac tctcctctgg caattgtatc aaaatatgca   1800

attttgagag ccatacactg gcattgataa ctgccaagga acactctaac tgttttctgt   1860

tagctgttaa ttagtagagg gctagatgta aatggtttat gctcaatata tttatttcct   1920

cctagtcttc aagttccaaa aaaaaaaaaa aaaaaaaaaa                         1960
```

```
<210> SEQ ID NO 22
<211> LENGTH: 1536
<212> TYPE: DNA
<213> ORGANISM: Lotus japonicus

<400> SEQUENCE: 22

atggcgattt ccgaagactc tgaatctcta ttcgccgccg ccgccgcttc ctccgtcatc     60

caaagcggct cttccgtacg ccgcaggccc agcgctatct ccgccgtcgc gacagtcgaa    120

gacgagagtt cgagtgaaga gccggtgccg gtgagggatt ctggttccga cgtcgacgac    180

tccgtaagca gcgagcaaca cgtctccccc gccaccgcca atcgagagaa gaatcaggtg    240

catgacatct cagccaccaa attcgcctac cgtccttccg cccccgctca tcgcagagtc    300

aaggagagcc ccctcagctc cgacaacatt ttccgtcatc atgcgggtct cttcaacctt    360

tgtatagttg tgcttgttgc agtgaatagc agacttatca ttgagaattt gatgaagtat    420

ggttggttga ttaggactgg cttttggttt agttcaaaat cattgaggga ttggccactc    480

ttcatgtgtt gtctcagtct tgcaatattt ccttttgccg cctttgtagt cgagaagttg    540

gtgcaacaga agtgtatttc tgaaccagtt gttgttcttc atatattcat ttcaacagct    600

gcagttgtct atccagtttt agtaatcctc aggactgatt ctgcttttcc atcaggcgtc    660

acattaatgt tatttgcttg cattgtatgg ctaaaactgg tgtcttatgc acatacgaac    720
```

```
tatgatatga gagaacttac caaatcaatt gaaaagggag aagcacttcc caatactctg    780
aatatggact attcttatga tgtgagcttc aagagcttgg catactttat gattgctcct    840
acattatgtt accagccaag atatcctcgc agtccttcta tccggaaagg ttgggtgctt    900
cgtcaacttg tcaagctgat aatatttaca ggagtaatgg gatttataat agaacaatat    960
attaatccta tagttcaaaa ttcacagcat cctttgaagg gaaacctact atatgccatt   1020
gaaagagttc tgaagctgtc tgttccaaac ttatatgtgt ggctctgcat gttctactgc   1080
tttttccacc tttggttaaa tattctcgca gagcttctta gatttggtga tcgcgagttc   1140
tacaaggatt ggtggaatgc caaaactttt gaagagtatt ggaggatgtg gaatatgcct   1200
gttcacaaat ggatgatccg acacctatat tttccatgtt taagaaatgg tatacccaag   1260
ggtgttgcta ttttaattgc cttcctggtt tctgcattgt tccatgagct gtgcattgct   1320
gttccttgcc acattttcaa gttgtgggct tttggtggaa ttatgtttca ggttcctttg   1380
atcttgataa caaattatct gcaaaataag ttcagaaact caatggttgg aaacatgatt   1440
ttttggttca tattcagtat tcttggtcaa ccaatggccg tactgctata ctaccacgat   1500
ttgatgaatc ggaaaagcaa acttgaccaa agctag                             1536
```

```
<210> SEQ ID NO 23
<211> LENGTH: 1620
<212> TYPE: DNA
<213> ORGANISM: Medicago truncatula

<400> SEQUENCE: 23

atggcaattt ccgatacacc ggaaaccact gcaaccgcca cagccaccgt aacaaccatc     60
gaaaccgaca cagatctcaa acgctcttca ctccgacgac gaccgagcgc cacatcaacc    120
gccggtggtc tcttcgacgc ggaaagtgca gctgcagatg ccgttcgaga ttcaggctcc    180
gatgattcgt tgaacggtaa gatcaacaac gaagaagagg ttaaagatcg aaaaacggat    240
catgcagaag gaattgttga cgatgatgat gataatgcgg ttaagaagaa tggtggtaat    300
gacgtcatca atgatcgtga aaatgttgct gtcgatttca aattcactta tcgtccttca    360
gttcccgctc accggagaag caaagaaagt cctcttagct ccggcaatat ttttagacag    420
agtcatgcag gactgttcaa tctctgtatt gtggtgcttg ttgcagtgaa tagtaggctt    480
attattgaaa atctgatgaa gtatggatgg ttgattcgat ctggcttttg gtttagttca    540
aaatcgctta gagattggcc cctcttcatg tgttgtctta gtcttgcaat atttccactt    600
gctgcctttg tagtcgaaaa gttggcccaa caaaaacgta tttctgaacc agttattgtt    660
ctccttcata ttgtaattac aactgttata tcttatggat ccatggcctt gctgtgcagg    720
tgcgattctg ctttttttatc tggttccacg ttaatgctat tgacttgcat agtgtggtta    780
aaattggtgt catatgcaca tacaacctat gatatgagag cgcttgctgt ttcaaatgaa    840
aagggagaaa caatgcccga tactttcaat atggaggagt acccacacaa tgtgagcttc    900
cagagtttag catacttcat ggttgctcct acattatgct accagccaag ctatcctcgc    960
acaccttcgg ttcgaaaggg ttgggtctgt cgacaacttc tcaagctggt catatttaca   1020
ggagttatgg gatttataat agaacaatat atgaatccta ttgtccagaa ttcacaacat   1080
ccattgaagg gaaaccttct atatgccatt gagagagttc tgaagctttc tgttccaaat   1140
gtttatgtgt ggctgtgcat gttctattgc tttttccatc tttggttaaa tatacttgcg   1200
gagcttctcc ggtttggtga tcgtgagttc tacaaagatt ggtggaatgc ccaaacggtt   1260
gaagagtatt ggaggatgtg gaatatgcct gtgcacaaat ggatggttcg tcacgtgtat   1320
```

```
tttccctgca taaggtttgg tatacccaag ggtgctgctg ctttgactgc tttcctggtt   1380

tctgctgtgt tccatgagtt atgcattgct gttccttgcc gcatgttcaa gttgtgggct   1440

tttattggaa ttatgttcca ggttcctttg gtcttgatca ccaattacct gaaaaataaa   1500

tacagaaact caatggttgg aaatatgatt ttttggttca tattttgtat tcttggtcaa   1560

cctatgtgtg tactactata ctatcatgac ttgatgaata ggaaaggtga aattgactga   1620
```

<210> SEQ ID NO 24
<211> LENGTH: 1566
<212> TYPE: DNA
<213> ORGANISM: Jatropha curcas

<400> SEQUENCE: 24

```
atgacgattt tggagaccac tactagcgga ggtgatggtg ttgctgagtc gtcttccgat     60

cttaacgtat cgcttcgacg gagacggaaa ggcaccagct cggatggagc tttgccggaa    120

ttgacttcga atattgttga attggaatct gaaagcggtg gccaggtgat gatggatcca    180

ggtatggtga cggaaccgga gacagagaaa attaatggaa aagattgcgg cggtgacaag    240

gataagattg acaatcgcga gaatcgtggg aggtcggata ttaaattcac gtaccggcca    300

tcggtgccgg ctcatcgagc gctcagggag agtccgctta gctctgatgc tatatttaaa    360

caaagtcatg caggtctgtt caacctctgt atagtagtgc ttgttgctgt taacagcagg    420

cttatcattg aaaatctaat gaagtatggt tggttaatta aaacggggtt ttggtttagt    480

tcaagatcgt tgagagattg gccccttctt atgtgctgtc ttaccctccc tatattctct    540

cttgccgcct atctagttga gaagttggca tatcgaaaat atatatctgc acctattgtt    600

attttctttc atatgctcat taccacaaca gcagttttgt acccagtttc tgtgattctc    660

agttgtgggt ctgctgttct gtctggtgtt gcattgatgc tctttgcttg tatcgtgtgg    720

ttgaaattag tatcttatgc acatacaaac tatgacatga gagccattgc caactcagct    780

gacaagggag atgcactatc cgatacttca ggtgcagatt cttcacgtga tgttagcttc    840

aagagtttgg tctacttcat ggttgctcct acgctatgtt accagccaag ttatcctcga    900

acagattcag ttagaaaggg ttgggtggtt cgtcaatttg tcaagttaat aatatttaca    960

ggattcatgg gatttatcat agaacaatat atcaatccta ttgtccagaa ttcacaacac   1020

cccttaaagg gggatctatt atatgccatt gaaagggttt tgaagctctc agttccaaac   1080

ttatatgtgt ggctctgcat gttctactgc ttttttcatc tatggttaaa tatacttgct   1140

gagctccttc ggtttggtga cagagagttc tataaagatt ggtggaatgc aaggacagtt   1200

gaggagtact ggagaatgtg gaatatgcct gttcataagt ggatggttcg ccatatctac   1260

tttccatgct tgcggcataa aataccaagg ggggtagcct tgttaattgc tttcttcgtt   1320

tcagctgtat ttcatgagtt gtgcattgct gttccttgcc acatgttcaa gctctgggct   1380

tttattggaa ttatgtttca gattccattg gtcgggatca ctaattacct ccagaacaag   1440

ttcagaagct ccatggtggg aaatatgatc ttttggttca ttttctgcat tcttggtcaa   1500

cccatgtgtg tgctattgta ttatcatgac ctaatgaatc ggaaaggcaa tgctgaatta   1560

agatga                                                              1566
```

<210> SEQ ID NO 25
<211> LENGTH: 2084
<212> TYPE: DNA
<213> ORGANISM: Vernicia fordii

<400> SEQUENCE: 25

```
tctctctctc tttgctttac gtgtacatcg accaccacca cagccatctt gcgactgttc     60
aattatccta taagtaccac cgcattcatc accgccaatc cttaactcta atttgctata    120
ctaaacactt gctttatatg cgcttttcta tttactcttc actgtaattt cttattggta    180
ttcaaagtgt tttcaatgac aatccctgaa acgccggata attccacgga tgctaccacc    240
agtggcggtg ctgagtcctc ttccgatctt aacctttctc ttcgacggag gaggactgct    300
tcaaactccg atggagctgt cgcggaattg gcttccaaga ttgatgagtt ggaatctgat    360
gccggaggag gccaggtgat taaggatccg ggagcagaaa tggattcggg gactttgaaa    420
agtaatggaa aagattgcgg aaccgttaag gataggattg aaaatcgtga gaatcgtgga    480
ggatcggatg ttaaattcac gtatcggccg tcggtgccgg ctcaccgggc gctcaaggag    540
agtccgctta gctctgataa tatatttaaa caaagtcatg caggtctctt caatctctgt    600
atagtagtgc ttgtagcggt taacagtcgg cttatcattg aaaacataat gaagtatggt    660
tggttaatta agactgggtt ttggtttagt tcaagatcgt tgagagactg gccacttctt    720
atgtgctgtc ttaccctccc aatattttct cttgctgcct atctagttga gaagttggcc    780
tgtcggaagt atatatctgc acccactgtt gtttttcttc atattctttt ctcctcaaca    840
gcagttttat accctgtttc tgtgattctc agttgtgaat ctgctgtttt gtccggtgtc    900
gcattgatgc tctttgcttg tatcgtgtgg ttgaaattgg tatcttatgc acatacaaac    960
tttgatatga gagcaattgc taactcagtt gataagggag atgcgctatc caatgcttcg   1020
agtgcagagt cctctcatga tgttagcttc aagagtttgg tttatttcat ggttgctccc   1080
acattgtgtt accagccaag ttatcctcga actgcatcca ttcgaaaggg ttgggtggtt   1140
cgtcaatttg ttaagttaat aatatttaca ggattcatgg gatttatcat agaacaatat   1200
atcaatccta tcgttcagaa ttcacaacat cctttaaaag gggatctctt atatgccatt   1260
gagagggttt tgaagctctc agttccgaat ttatatgtct ggctttgcat gttctactgc   1320
ttttttcacc tatggttaaa tatacttgct gagctccttc gctttggtga tagagagttc   1380
tataaagatt ggtggaatgc aaggacagtt gaggagtatt ggagaatgtg gaatatgcct   1440
gttcataagt ggatggttcg ccatatctac tttccatgct tgcggcataa aataccaagg   1500
ggggtggcct tattaattac tttcttcgtt tcagcagtat ttcatgagtt gtgcattgct   1560
gttccttgcc acatattcaa gctctgggct tttattggaa taatgtttca gattcctttg   1620
gtcgggatca caaattacct tcaaaacaag ttcagaagct caatggtggg gaacatgatc   1680
ttctggttca ttttctgcat tcttggtcaa ccaatgtgct tgctgttgta ttaccatgac   1740
ctaatgaatc gaaaagggac taccgaatca agatgacact aactcatcgt gtggtagact   1800
ctatatatat acatagactt accagagatg ggttgcttcc aacatattgt gcacaagagg   1860
caattgttgt tctcatcaga agagtgggtt aattaattaa ttaatgtaca agcaattttg   1920
aaagtataat cactggcagg gactagtgcc cgactgtagt actgagatta tagaggtatt   1980
atcaatcgtt agtggaaaat tgtaaatgta taaagttcaa tctttgtatt gtttcttttc   2040
taatatcata tttttttta ttgctcatca aaaaaaaaaa aaaa                    2084
```

<210> SEQ ID NO 26
<211> LENGTH: 1828
<212> TYPE: DNA
<213> ORGANISM: Vernonia galamensis

<400> SEQUENCE: 26

-continued

```
tctgagctca aatcaaattt ctgcgactca tacaggattc aactcaatac tttcttgatc     60
ggttctgctg ttcatttact tgtaatttct acttctgctt tgctttcatt tcaagctttt    120
ttccttaata atggcgttat tagatacgcc tcagattgga gaaataacga ccaccgccac    180
cacaactata agacggcgga ccactgtcaa gcctgatgct ggaatcggag atggattgtt    240
tgattcttcg tcgtcttcca aaaccaactc atccttcgag gatggtgaca gtttgaatgg    300
tgatttcaat gacaaattta aggaacagat cggagctggt gatgaatcca aggacgactc    360
caaggggaac ggacagaaga tagatcacgg aggagttaaa aagggacgtg aaacgactgt    420
ggtgcattat gcttatcggc cttcttctcc ggctcatcgg agaattaaag aatctccgct    480
tagctctgac gccatcttca agcagagtca tgcaggcctc tttaaccttt gcatagtggt    540
gcttgttgca gtaaatggta ggctcatcat tgagaatctg atgaagtatg gactattgat    600
caattccaac ttttggttca gttcgagatc attgagagac tggccacttc tgatgtgctg    660
cctcactcct tctgactttc cacttgctgc ctacattgtt gagaaattgg catggaaaaa    720
acgtatatcc gaccctgttg taatcacact ccatgttata ataactacaa ctgcaattct    780
ttatccggtc ttcatgattc tgaggttcga ttcagttgtt ctatcaggcg tctcgttgat    840
gctgtgtgct tgcattaatt ggttgaagtt ggtatctttt gtgcatacaa attatgacat    900
gcggtcgctt ttgaactcaa ctgataaggg agaagtggaa cccatgtctt caaatatgga    960
ttatttttat gatgtcaact tcaaaagctt ggtttatttc atggttgctc caactttgtg   1020
ttaccagata agctatcctc gcactgcatt tattcgaaag ggttgggtgt tacggcaact   1080
gatcaagcta gtaatattta cagggttcat gggattcatc attgaacaat atatcaatcc   1140
gattgtcaaa aattctcgtc atccattgaa aggagacttt ttatatgcga ttgagcgggt   1200
tttaaagctt tcagttccga atttatatgt gtggctctgt atgttctact gctttttca    1260
cctttggtta aatatacttg ctgagcttct ttgttttggg gatcgtgaat tttataaaga   1320
ttggtggaat gcacaaacta ttgaagagta ttggaggcta tggaatatgc ctgttcataa   1380
atggattgtt aggcaccttt attttccatg cttgcgtaat gggataccta agggtgctgc   1440
catattggtt gcatttttca tgtctgccgt gttccatgag ctttgtattg ctgttccctg   1500
ccacatttc aagttttggg cttttatcgg gatcatgttt caggtcccgt tggtcctact    1560
cacaaattac ttgcagcaca agtttcaaaa ctcgatggtg ggaaatatga tcttctggtg   1620
ctttttcagc atttttggtc aacccatgtg tgtattactt tactaccatg atgtcatgaa   1680
tcaaaagggg aaaagcaaat aaaaagatgt gattgtgttg ctccatttga tctcatagca   1740
tgactggact aaacaaaccc aagggacaca ttttagtcct taaaggaaaa tttttgtagg   1800
aaaaaaaaaa aaaaaaaaaa aaaaaaaa                                      1828
```

```
<210> SEQ ID NO 27
<211> LENGTH: 2020
<212> TYPE: DNA
<213> ORGANISM: Ricinus communis

<400> SEQUENCE: 27

cttcttcttc tgctgctgtt cctctctcct ccaccgccac gctcacctct ctttgcatga     60
cataatacta ttgttcttat tatcattttc actctttaaa tacaaacatc aattattcct    120
tttctatcaa acacatgtat tctattctct cgtcgtctag attctcatct tcattgaatc    180
ctccttctta gcgtgtcttt gtccacttct tttgggcacc gacgttttta atctccatga    240
```

```
cgattctcga aacgccagaa actcttggcg tcatctcctc ctccgccact tccgatctca    300

acctctctct ccgacgtaga cggacctcaa atgactccga tggtgcactt gctgatttgg    360

cttcgaagtt tgatgatgat gacgacgtaa gatcggaaga ttctgctgaa aatattatcg    420

aagatcctgt agcagcggtt actgaattgg cgacagcaaa gagtaacgga aaagactgtg    480

ttgccaatag taataaggat aaaattgata gccatggagg atcatcggat tttaaacttg    540

catataggcc ttcggttcca gctcaccggt cacttaagga gagtccgctt agctctgatt    600

taatatttaa acaaagtcat gcaggtctgt ttaacctttg tatagtagtg ctcgtagctg    660

ttaacagcag gctcatcatt gagaatttaa tgaagtatgg ctggttaatt aagacgggct    720

tttggtttag ttcaagatca ttgagagatt ggccgctttt tatgtgctgt ctttctctcc    780

cagtattccc ccttgctgcc tatctagttg agaaggccgc atatcgaaaa tatatatctc    840

cgcctattgt tattttcctt catgtgatca tcacctcagc agctgttttg tacccagctt    900

ctgtaattct cagttgtgaa tctgcttttt tatctggtgt cacattgatg gaacttgctt    960

gtatggtatg gttgaaattg gtatcctatg cacatacaaa ctatgatatg agagcgatcg   1020

ctgacaccat tcataaggaa gatgcatcca attcttctag tacagagtat tgtcatgatg   1080

tgagctttaa gactttggcg tacttcatgg tcgcacccac attatgttac cagccaagtt   1140

atcctcgcac agcatttatt agaaagggct gggtgttccg tcaatttgtc aaactaataa   1200

tttttacagg attcatggga tttatcatag aacaatacat caatcctatc gtccagaatt   1260

ctcaacaccc tttaaaaggg gatctcttat atgccattga gagggttctg aagctctcag   1320

ttccgaattt atatgtgtgg ctctgcttgt tctactgctt ttttcacctg tggttgaata   1380

tagttgctga gctccttcgc ttcggtgacc gggagttcta caaagattgg tggaatgcaa   1440

aaactgttga ggagtactgg aggatgtgga atatgcctgt tcacaagtgg atggttcgcc   1500

atatctactt cccatgccta cgtcgtaaaa taccaagggg ggtagcaata gttattgctt   1560

tcttcgtttc agctgtattt catgagttgt gcattgctgt tccttgccac atgttcaaac   1620

tttgggcttt ttttggaata atgtttcaga ttcctttagt tgtgatcact aattattttc   1680

aaaggaagtt cagaagctca atggtgggaa atatgatctt ctggttcttt ttctgcattc   1740

tcggccaacc tatgtgtgta ctgttgtatt accatgacct aatgaatcgc gatgggaact   1800

gaaccatggg ctcagtccag atatgggtac accttccaag atgttatttt cgtgagtgaa   1860

gactgcacca cagtgttgtt cttgttacac aatccccatt gacagagtag gttaatcgtc   1920

agtttcagga gataagacac aattttgaaa gtacagcaga ggctgctatt aatgtatcat   1980

gttgagtttc tgttatgtta tgttattctt ttttaatctc                         2020
```

<210> SEQ ID NO 28
<211> LENGTH: 1444
<212> TYPE: DNA
<213> ORGANISM: Populus trichocarpa

<400> SEQUENCE: 28

```
aaatcatggc ggcgttagag tctccggaga atcatatacg acgtcggatc ttaacttctc     60

cgttcgacgg aggtctacta ctgtcacgga ttcgccttcg acggagatga tggaatcgga    120

ggatttgaaa agtaatggta aagaatgcga taaggttacg aatgagaatc gatcggatat    180

taaattcaat tatcggcctt caatgcctgc tcatcgtggt gttagagaga gtcctcttag    240

ttctgatgct atttttaaac aaagtcatgc aggtctcttc aatctctgta tagttgtgct    300

tgtggctata aacagcaggc ttatcattga aaatataatc aagtatggtt ggttaattaa    360
```

cggtggattt tggtttagtt caaaatcatt aagagactgg cccctgttta tgtgctgtct 420
tagccttcca gcattccctt tcgcggccta tcttgttgag aagttggcat atcaaaatta 480
tttacctcaa cttgttgttg ttttccttca tacaatcatc accacaggat cacttttata 540
tccagtttta gtaattctca ggtgtgattc tgcttttcta tctggtgtca cgttgatgct 600
cttttcttgc attgtgtggc taaaattggt atcttatgct catacaaact ctgatttgag 660
agcaattgcc aagtcaatag atagggaaga tgtcccatcc atttctcctt atgtgggtaa 720
tccttatgat acttacttta agagtttggt ctacttcatg gtggctccca cattatgtta 780
ccagtcaagc tatcctcgca ctgaatctgt tcgaaaggga tgggtggttc aacaatttgt 840
caagttaata atatttactg gattcatggg atttatcata gaacaatata tcaatcctat 900
tgttaagaat tcacagcacc cttttaaagg aaatctcttg tatgccattg agagggtctt 960
gaagctctca gttcctaatt tatatgtatg gctttgcatg ttctactgct tttccacct 1020 gtggttaaat atacttgccg agctcctttg ctttggtgat cgggagttct acaaggattg 1080
gtggaatgca agaactgttg aagaatattg gagaatgtgg aatatgccag ttcataagtg 1140
gatggttcgc catatctatt ttccatgcct acggaataaa ataccgaagg ggttagctat 1200
acttattgcc ttcttagttt cagctgtatt tcacgagctg tgcattgctg ttccctgcca 1260
cgtgttcaag ctctgggcat ttattggaat tatgttacag gttcccttag tggtgatcac 1320
aaaatttctc caaaataagt tcagaagctc catggtggga aacatgatct tctggttgtt 1380
tttcagcatt cttggtcaac caatgtgtgt gcttctgtat taccatgact tgatgaatcg 1440
gaag 1444

<210> SEQ ID NO 29
<211> LENGTH: 1816
<212> TYPE: DNA
<213> ORGANISM: Populus trichocarpa

<400> SEQUENCE: 29
aacatattta aatcatggcg gagtcagagt caccggagaa tcgtatagcg gcaatggaaa 60
gtacatcttc ctcgacgtca gatctcaact tctctattcg acggaggtct acagtcatgg 120
actcggcttc gacggaaatg atgggatcgg agggtttgaa aagtagtggt aaagcatgcg 180
ataaggttaa gattgagaag caatcagata tgaaattcaa ttatcggcca tcaatgcccg 240
ctcatagtgg tgttagagag agtcctctta gttctgatgc tatttttaaa caaagtcatg 300
caggtctctt caatctctgt atagtagtgc ttgtggctgt aaacagcagg cttatcattg 360
aaaatttaat caagtacggc tggttaatca attcaggatt ttggtttagt tcaaaatcat 420
taagagactg gcccctgttt atgtgctgtc ttagtcttcc agcattccct ctcgcggcct 480
atctcgttga gaagttggca tatcgaaatt gtatatctga acttgttgtt gttttccttc 540
atataatcat caccacagca tcacttttgt atccagtttt agtaattctc aggtgtgatt 600
ctgctttact atctggtggc acattgatgc tctttgcttg cattgtgtgg ttgaaattgg 660
tatcttttgc acatacaagc tctgatatga gagcaattgc caagtcaatt gataaggaaa 720
ataccccatc catttcttcg aaagcagata attcttatga tgctaacttt aagagtttgg 780
tctacttcat ggtggctccc acattatgtt accagtcaag ctatcctcgt tctgcatctg 840
ttcgaaaggg ttgggtggtt cgacaatttg tcaagttaat aatatttact ggattcatgg 900
gatttatcat agaacaatat atcaatccta ttgttcagaa ctcgcagcac cctttgaaag 960

-continued

```
gaaatctctt gtatgccatt gagagggtct tgaagctctc agttcctaat ttatatgttt   1020

ggctctgcat gttctactgc tttttccact tgtggttaaa tatacttgcc gagctccttc   1080

gctttggtga tcgggagttc tacaaggatt ggtggaatgc aagaactgtt gaagagtact   1140

ggagaatgtg gaatatgcca gttcataagt ggatggttcg ccatatctat tttccatgtt   1200

tacggaataa aataccaaag tgggcagcct tacttattgc cttctttgtc tcagctgtat   1260

ttcatgagtt gtgtattgct gttccttgcc acatgttcaa gctctgggca tttattggaa   1320

ttatgtttca ggttccctta gtggtgatca caaaattcct tcaaaataag ttcaaaagct   1380

caatggtggg caatatgatc ttctggttat ttttcagcat tcttggtcaa cctatgtgtg   1440

tgcttctata ttaccatgac ttgatgaatc ggaaagggaa aactgaacga agatgacaaa   1500

tgcggtatgg tagagatcgt caagatgaac aaaatgcacg gttatgatag tagagcaggc   1560

attaggtgtg ccttttctta tgtattctgc aggagaaatt gactcgattt tgttgagtcg   1620

agagatggtc tcttcaggac ttttattttt atgtatctca attgacgtgc aagcaatttt   1680

ggaagtacaa gcactggcaa ttaaaatgcc aatgcaacag tggatctgtt gtgttggtta   1740

atcatttcca gaaatttgta aatgtttctt gttccgtctt ttgcttcaaa ggaaataaaa   1800

aaagaagaaa atttct                                                   1816


<210> SEQ ID NO 30
<211> LENGTH: 520
<212> TYPE: PRT
<213> ORGANISM: Arabidopsis thaliana

<400> SEQUENCE: 30

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220
```

Val Tyr Val Thr Leu Arg Cys Asp Ser Ala Phe Leu Ser Gly Val Thr
225 230 235 240

Leu Met Leu Leu Thr Cys Ile Val Trp Leu Lys Leu Val Ser Tyr Ala
245 250 255

His Thr Ser Tyr Asp Ile Arg Ser Leu Ala Asn Ala Ala Asp Lys Ala
260 265 270

Asn Pro Glu Val Ser Tyr Tyr Val Ser Leu Lys Ser Leu Ala Tyr Phe
275 280 285

Met Val Ala Pro Thr Leu Cys Tyr Gln Pro Ser Tyr Pro Arg Ser Ala
290 295 300

Cys Ile Arg Lys Gly Trp Val Ala Arg Gln Phe Ala Lys Leu Val Ile
305 310 315 320

Phe Thr Gly Phe Met Gly Phe Ile Ile Glu Gln Tyr Ile Asn Pro Ile
325 330 335

Val Arg Asn Ser Lys His Pro Leu Lys Gly Asp Leu Leu Tyr Ala Ile
340 345 350

Glu Arg Val Leu Lys Leu Ser Val Pro Asn Leu Tyr Val Trp Leu Cys
355 360 365

Met Phe Tyr Cys Phe Phe His Leu Trp Leu Asn Ile Leu Ala Glu Leu
370 375 380

Leu Cys Phe Gly Asp Arg Glu Phe Tyr Lys Asp Trp Trp Asn Ala Lys
385 390 395 400

Ser Val Gly Asp Tyr Trp Arg Met Trp Asn Met Pro Val His Lys Trp
405 410 415

Met Val Arg His Ile Tyr Phe Pro Cys Leu Arg Ser Lys Ile Pro Lys
420 425 430

Thr Leu Ala Ile Ile Ile Ala Phe Leu Val Ser Ala Val Phe His Glu
435 440 445

Leu Cys Ile Ala Val Pro Cys Arg Leu Phe Lys Leu Trp Ala Phe Leu
450 455 460

Gly Ile Met Phe Gln Val Pro Leu Val Phe Ile Thr Asn Tyr Leu Gln
465 470 475 480

Glu Arg Phe Gly Ser Thr Val Gly Asn Met Ile Phe Trp Phe Ile Phe
485 490 495

Cys Ile Phe Gly Gln Pro Met Cys Val Leu Leu Tyr Tyr His Asp Leu
500 505 510

Met Asn Arg Lys Gly Ser Met Ser
515 520

<210> SEQ ID NO 31
<211> LENGTH: 503
<212> TYPE: PRT
<213> ORGANISM: Brassica juncea

<400> SEQUENCE: 31

Met Ala Ile Leu Asp Ser Gly Gly Val Ala Val Pro Pro Thr Glu Asn
1 5 10 15

Gly Val Ala Asp Leu Asp Arg Leu His Arg Arg Lys Ser Arg Ser Asp
20 25 30

Ser Ser Asn Gly Leu Leu Ser Asp Thr Ser Pro Ser Asp Asp Val Gly
35 40 45

Ala Ala Ala Ala Glu Arg Asp Arg Val Asp Ser Ala Ala Glu Glu Glu
50 55 60

Ala Gln Gly Thr Ala Asn Leu Ala Gly Gly Asp Ala Glu Thr Arg Glu

-continued

```
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Pro Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Leu Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
        275                 280                 285

Ile Arg Lys Gly Trp Val Ala Arg Gln Phe Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
        435                 440                 445

Ile Met Phe Gln Val Pro Leu Val Phe Ile Thr Asn Phe Leu Gln Glu
    450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
                485                 490                 495
```

```
Asn Arg Lys Gly Ser Met Ser
            500


<210> SEQ ID NO 32
<211> LENGTH: 503
<212> TYPE: PRT
<213> ORGANISM: Brassica napus

<400> SEQUENCE: 32

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
        275                 280                 285

Ile Arg Lys Gly Trp Val Ala Arg Gln Leu Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
```

```
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
        435                 440                 445

Ile Met Phe Gln Val Pro Leu Val Phe Ile Thr Asn Phe Leu Gln Glu
    450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
                485                 490                 495

Asn Arg Lys Gly Ser Met Ser
            500


<210> SEQ ID NO 33
<211> LENGTH: 503
<212> TYPE: PRT
<213> ORGANISM: Brassica juncea

<400> SEQUENCE: 33

Met Ala Ile Leu Asp Ser Gly Thr Val Thr Met Ala Thr Glu Asn Gly
1               5                   10                  15

Val Ala Asp Leu Asp Met Leu Arg Arg Arg Lys Ser Arg Ser Asp Ser
            20                  25                  30

Ser Asn Gly Leu Leu Ser Glu Thr Ser Pro Ser Asp Asp Ala Gly Ala
        35                  40                  45

Pro Ala Asp Val Glu Asp Arg Val Asp Ser Ala Ala Gln Gly Thr Ala
    50                  55                  60

Asn Leu Ala Gly Asp Thr Glu Thr Arg Glu Ser Gly Gly Gly Gly Gly
65                  70                  75                  80

Gly Gly Asn Gly Glu Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Ile Phe Pro Leu Ala Ala Phe
                165                 170                 175

Thr Val Glu Lys Leu Val Leu Gln Lys Phe Ile Ser Glu Pro Val Val
            180                 185                 190

Ile Ile Leu His Ile Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220
```

```
Met Leu Leu Thr Cys Ile Val Trp Leu Lys Leu Val Ser Tyr Ala His
225                 230                 235                 240

Thr Asn Tyr Asp Ile Arg Thr Val Ala Asn Ser Ala Asp Lys Val Asp
                245                 250                 255

Pro Glu Val Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Gly
        275                 280                 285

Ile Arg Lys Gly Trp Val Ala Arg Gln Phe Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Ile Gly
        435                 440                 445

Ile Met Phe Gln Val Pro Leu Val Phe Ile Thr Asn Tyr Leu Gln Glu
    450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
                485                 490                 495

Asn Arg Lys Gly Ser Met Ser
            500


<210> SEQ ID NO 34
<211> LENGTH: 518
<212> TYPE: PRT
<213> ORGANISM: Tropaeolum majus

<400> SEQUENCE: 34

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95
```

-continued

```
Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510
```

Ile Asn Leu Lys Glu Lys
        515

<210> SEQ ID NO 35
<211> LENGTH: 473
<212> TYPE: PRT
<213> ORGANISM: Echium pitardii

<400> SEQUENCE: 35

```
Met Thr Ile Trp Glu Ser Pro Glu Ile Ile Ser Ser Asp Glu Ala Ala
1               5                   10                  15

Ala Ala Leu Arg Arg Arg Gly Gly Ala Lys Glu Val Ala Glu Gln Arg
            20                  25                  30

Leu Asp Ser Glu Glu Glu Lys Lys Lys Glu Glu Glu Asn Gly Lys Leu
        35                  40                  45

Lys Tyr Thr Tyr Arg Ala Ser Ala Pro Ala His Arg Arg Ile Lys Glu
    50                  55                  60

Ser Pro Leu Ser Ser Asp Ala Ile Phe Lys Gln Ser His Ala Gly Leu
65                  70                  75                  80

Phe Asn Leu Cys Ile Val Val Leu Val Ala Val Asn Ser Arg Leu Ile
                85                  90                  95

Ile Glu Asn Leu Met Lys Tyr Gly Trp Leu Ile Ser Ser Gly Phe Trp
            100                 105                 110

Leu Ser Ser Thr Ser Leu Ser Asp Trp Pro Leu Leu Ile Cys Cys Leu
        115                 120                 125

Ser Leu Pro Ile Phe Pro Leu Ala Ser Phe Val Val Glu Lys Leu Ser
    130                 135                 140

Gln Gln Glu Phe Ile Ser Glu Gln Val Val Ile Thr Leu His Ala Leu
145                 150                 155                 160

Ile Thr Thr Thr Val Ile Met Tyr Pro Val Ile Val Ile Leu Arg Cys
                165                 170                 175

Asp Pro Ala Val Leu Ser Gly Val Ile Leu Met Leu Phe Thr Cys Ile
            180                 185                 190

Val Trp Leu Lys Leu Val Ser Tyr Ala His Thr Asn Tyr Asp Met Arg
        195                 200                 205

Ala Leu Ala Lys Asp Cys Asp Lys Leu Gln Ala Leu Ser Gly Ser Ser
    210                 215                 220

Met Glu Asp Cys Ser Phe Glu Val Asn Phe Gln Ala Leu Val Tyr Phe
225                 230                 235                 240

Met Val Ala Pro Thr Leu Cys Tyr Gln Leu Arg Tyr Pro Arg Thr Pro
                245                 250                 255

Cys Ile Arg Trp Gly Trp Val Thr Arg His Leu Ile Lys Leu Ile Ile
            260                 265                 270

Phe Thr Gly Leu Met Gly Phe Ile Ile Glu Gln Tyr Ile Asn Pro Ile
        275                 280                 285

Val Lys Asn Ser Gln His Pro Leu Lys Gly Asn Leu Leu Tyr Ala Ile
    290                 295                 300

Glu Arg Val Leu Lys Leu Ser Val Pro Asn Ile Tyr Val Trp Leu Cys
305                 310                 315                 320

Met Phe Tyr Cys Phe Phe His Leu Trp Leu Asn Ile Leu Ala Glu Leu
                325                 330                 335

Leu Cys Phe Gly Asp Arg Glu Phe Tyr Lys Asp Trp Trp Asn Ala Gln
            340                 345                 350

Thr Ile Glu Glu Tyr Trp Arg Met Trp Asn Met Pro Val His Lys Trp
        355                 360                 365
```

```
Met Val Arg His Ile Tyr Phe Pro Cys Leu Arg Asn Gly Met Pro Lys
    370                 375                 380

Glu Leu Ala Ile Leu Ile Ala Phe Leu Ile Ser Ala Ile Phe His Glu
385                 390                 395                 400

Leu Cys Ile Ala Val Pro Cys His Ile Phe Lys Phe Trp Ala Phe Ile
                405                 410                 415

Gly Ile Met Phe Gln Val Pro Leu Val Leu Leu Thr Asn Val Leu Val
            420                 425                 430

Lys Lys Phe Gln Asn Ser Met Val Gly Asn Met Ile Phe Trp Cys Phe
        435                 440                 445

Phe Cys Ile Leu Gly Gln Pro Met Ser Leu Leu Leu Tyr Tyr His Asp
    450                 455                 460

Val Leu Asn Arg Lys Val Asn Ala Asn
465                 470


<210> SEQ ID NO 36
<211> LENGTH: 523
<212> TYPE: PRT
<213> ORGANISM: Vernonia galamensis

<400> SEQUENCE: 36

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
            20                  25                  30

Gly Asp Gly Leu Phe Asp Ser Ser Ser Ser Ser Lys Thr Asn Ser Ser
        35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
        115                 120                 125

Gly Leu Phe Asn Leu Cys Ile Val Val Leu Val Ala Val Asn Gly Arg
    130                 135                 140

Leu Ile Ile Glu Asn Leu Met Lys Tyr Gly Leu Leu Ile Asn Ser Asn
145                 150                 155                 160

Phe Trp Phe Ser Ser Arg Ser Leu Arg Asp Trp Pro Leu Leu Met Cys
                165                 170                 175

Cys Leu Thr Pro Ser Asp Phe Pro Leu Ala Ala Tyr Ile Val Glu Lys
            180                 185                 190

Leu Ala Trp Lys Lys Arg Ile Ser Asp Pro Val Val Ile Thr Leu His
        195                 200                 205

Val Ile Ile Thr Thr Thr Ala Ile Leu Tyr Pro Val Phe Met Ile Leu
    210                 215                 220

Arg Phe Asp Ser Val Val Leu Ser Gly Val Ser Leu Met Leu Cys Ala
225                 230                 235                 240

Cys Ile Asn Trp Leu Lys Leu Val Ser Phe Val His Thr Asn Tyr Asp
                245                 250                 255

Met Arg Ser Leu Leu Asn Ser Thr Asp Lys Gly Glu Val Glu Pro Met
```

260 265 270

Ser Ser Asn Met Asp Tyr Phe Tyr Asp Val Asn Phe Lys Ser Leu Val
275 280 285

Tyr Phe Met Val Ala Pro Thr Leu Cys Tyr Gln Ile Ser Tyr Pro Arg
290 295 300

Thr Ala Phe Ile Arg Lys Gly Trp Val Leu Arg Gln Leu Ile Lys Leu
305 310 315 320

Val Ile Phe Thr Gly Phe Met Gly Phe Ile Ile Glu Gln Tyr Ile Asn
325 330 335

Pro Ile Val Lys Asn Ser Arg His Pro Leu Lys Gly Asp Phe Leu Tyr
340 345 350

Ala Ile Glu Arg Val Leu Lys Leu Ser Val Pro Asn Leu Tyr Val Trp
355 360 365

Leu Cys Met Phe Tyr Cys Phe Phe His Leu Trp Leu Asn Ile Leu Ala
370 375 380

Glu Leu Leu Cys Phe Gly Asp Arg Glu Phe Tyr Lys Asp Trp Trp Asn
385 390 395 400

Ala Gln Thr Ile Glu Glu Tyr Trp Arg Leu Trp Asn Met Pro Val His
405 410 415

Lys Trp Ile Val Arg His Leu Tyr Phe Pro Cys Leu Arg Asn Gly Ile
420 425 430

Pro Lys Gly Ala Ala Ile Leu Val Ala Phe Phe Met Ser Ala Val Phe
435 440 445

His Glu Leu Cys Ile Ala Val Pro Cys His Ile Phe Lys Phe Trp Ala
450 455 460

Phe Ile Gly Ile Met Phe Gln Val Pro Leu Val Leu Leu Thr Asn Tyr
465 470 475 480

Leu Gln His Lys Phe Gln Asn Ser Met Val Gly Asn Met Ile Phe Trp
485 490 495

Cys Phe Phe Ser Ile Phe Gly Gln Pro Met Cys Val Leu Leu Tyr Tyr
500 505 510

His Asp Val Met Asn Gln Lys Gly Lys Ser Lys
515 520

<210> SEQ ID NO 37
<211> LENGTH: 532
<212> TYPE: PRT
<213> ORGANISM: Nicotiana tabacum

<400> SEQUENCE: 37

Met Val Ile Met Glu Leu Pro Glu Ser Val Glu Met Thr Thr Thr Thr
1 5 10 15

Thr Thr Ser Gly Ile Glu Asn Leu Asn Ser Asp Leu Asn His Ser Val
20 25 30

Arg Arg Arg Arg Gly Ser Asn Gly Phe Glu Ala Ala Ser Ala Ile Asn
35 40 45

Ser Ser Asp Ala Asn Met Ser Glu Asp Arg Arg Asp Val Cys Gly Ser
50 55 60

Gly Ala Gly Leu Glu Thr Val Asn Glu Arg Ser Lys Ser Val Gly Glu
65 70 75 80

Ser Ser Asp Val Ile Arg Lys Glu Asp Asp Arg Asn Asp Asn Val Ala
85 90 95

Asn Gly Glu Glu Ser Lys Ser Thr Glu Thr Thr Thr Thr Pro Phe Lys
100 105 110

-continued

```
Phe Ala Tyr Arg Ala Ser Ala Pro Ala His Arg Arg Ile Lys Glu Ser
        115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Met Lys Tyr Gly Leu Leu Ile Arg Ala Gly Phe Trp Phe
                165                 170                 175

Ser Ser Lys Ser Leu Arg Asp Trp Pro Leu Leu Met Cys Cys Leu Ser
            180                 185                 190

Leu Gln Ile Leu Pro Leu Ala Ala Phe Leu Val Glu Lys Leu Ala Gln
        195                 200                 205

Gln Arg His Leu Thr Glu Arg Ala Val Val Thr Leu His Ile Thr Ile
    210                 215                 220

Thr Thr Ala Ala Ile Leu Tyr Pro Val Leu Val Ile Leu Gly Cys Asp
225                 230                 235                 240

Ser Ala Phe Leu Phe Gly Val Ile Leu Met Leu Val Ala Cys Ile Val
                245                 250                 255

Trp Met Lys Leu Val Ser Tyr Ala His Thr Asn His Asp Met Arg Gln
            260                 265                 270

Leu Ala Lys Ser Thr Asp Lys Asp Glu Thr Ser Asp Gly Asp Phe Ser
        275                 280                 285

Tyr Asp Val Ser Phe Lys Ser Leu Ala Tyr Phe Met Val Ala Pro Thr
    290                 295                 300

Leu Cys Tyr Gln Leu Ser Tyr Pro His Thr Pro Cys Ile Arg Lys Gly
305                 310                 315                 320

Trp Val Ala Arg Gln Phe Ile Lys Leu Val Ile Phe Thr Gly Leu Met
                325                 330                 335

Gly Phe Ile Ile Glu Gln Tyr Ile Asn Pro Ile Val Gln Asn Ser Gln
            340                 345                 350

His Pro Leu Lys Gly Asn Leu Leu Tyr Ala Ile Glu Arg Val Leu Lys
        355                 360                 365

Leu Ser Val Pro Asn Leu Tyr Val Trp Leu Cys Met Phe Tyr Cys Phe
    370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Ile Asp Glu Tyr
                405                 410                 415

Trp Arg Met Trp Asn Met Pro Val His Lys Trp Met Val Arg His Ile
            420                 425                 430

Tyr Phe Pro Cys Leu Arg Asn Gly Ile Pro Lys Gly Val Ala Ile Leu
        435                 440                 445

Ile Ala Phe Leu Val Ser Ala Val Phe His Glu Leu Cys Ile Ala Val
    450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
            500                 505                 510

Gln Pro Met Cys Val Leu Leu Tyr Tyr His Asp Val Met Asn Arg Lys
        515                 520                 525

Ser Ser Ala Arg
```

530

<210> SEQ ID NO 38
<211> LENGTH: 534
<212> TYPE: PRT
<213> ORGANISM: Perilla frutescens

<400> SEQUENCE: 38

```
Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Gln Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
        275                 280                 285

Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335

Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
        355                 360                 365
```

Leu Lys Leu Ser Val Pro Asn Leu Tyr Val Trp Leu Cys Met Phe Tyr
    370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460

Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510

Phe Gly Gln Pro Met Cys Val Leu Leu Tyr Tyr His Asp Leu Met Asn
        515                 520                 525

Arg Lys Ala Ser Ala Arg
    530

<210> SEQ ID NO 39
<211> LENGTH: 512
<212> TYPE: PRT
<213> ORGANISM: Zea mays

<400> SEQUENCE: 39

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190

Thr Thr Cys Phe His Ile Leu Phe Thr Thr Phe Glu Ile Val Tyr Pro
        195                 200                 205

```
Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
            260                 265                 270

Leu Gly Ser Leu Thr Tyr Phe Met Met Ala Pro Thr Leu Cys Tyr Gln
        275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
        355                 360                 365

Leu Asn Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
            420                 425                 430

Val Ser Ala Val Leu His Glu Leu Cys Val Ala Val Pro Cys His Ile
        435                 440                 445

Leu Lys Phe Trp Ala Phe Leu Gly Ile Met Leu Gln Ile Pro Leu Ile
    450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510


<210> SEQ ID NO 40
<211> LENGTH: 515
<212> TYPE: PRT
<213> ORGANISM: Sorghum bicolor

<400> SEQUENCE: 40

Met Ala Asp Thr Asp Asp Ala Pro Pro Ala Pro Ala Val His Arg Arg
1               5                   10                  15

Pro Pro Arg Pro Ala Arg Gly Ala Ala Ala Ala Gln Gly Phe Ala Ala
            20                  25                  30

Lys Leu Arg Arg Arg Leu Ser Ser Gly Ala Ala Ala Ala Ala Arg Ala
        35                  40                  45

Ser Phe Ala Ala Asp Ser Gly Asp Glu Ser Gly Pro Gly Glu Pro Ser
    50                  55                  60

Ser Ser Arg Arg Arg Asp Asn Gly Gly Asp Ala Ser Ser Ala Ala Asp
```

-continued

```
65                  70                  75                  80

Gly Gly Arg Gly Gly Ala Gly Asp Phe Ser Ala Phe Thr Phe Arg Ala
                85                  90                  95

Ala Ala Pro Val His Arg Lys Ala Lys Glu Ser Pro Leu Ser Ser Asp
            100                 105                 110

Ala Ile Phe Lys Gln Ser His Ala Gly Leu Phe Asn Leu Cys Ile Val
        115                 120                 125

Val Leu Val Ala Val Asn Ser Arg Leu Ile Ile Glu Asn Leu Met Lys
    130                 135                 140

Tyr Gly Leu Leu Ile Arg Ser Gly Phe Trp Phe Asn Ala Thr Ser Leu
145                 150                 155                 160

Arg Asp Trp Pro Leu Leu Met Cys Cys Leu Ser Leu Pro Val Phe Pro
                165                 170                 175

Leu Gly Ala Phe Ala Val Glu Lys Leu Ala Phe Asn Asn Leu Ile Thr
            180                 185                 190

Asp Ala Ala Ala Thr Cys Phe His Ile Phe Leu Thr Thr Leu Glu Ile
        195                 200                 205

Val Tyr Pro Val Leu Val Ile Leu Lys Cys Asp Ser Ala Val Leu Ser
    210                 215                 220

Gly Phe Val Leu Met Phe Ile Ala Cys Ile Val Trp Leu Lys Leu Val
225                 230                 235                 240

Ser Phe Ala His Thr Asn His Asp Ile Arg Lys Leu Ile Thr Ser Gly
                245                 250                 255

Lys Lys Val Asp Asn Glu Leu Thr Val Ala Asp Ile Asp Asn Leu Gln
            260                 265                 270

Ala Pro Thr Leu Gly Ser Leu Thr Tyr Phe Met Met Ala Pro Thr Leu
        275                 280                 285

Cys Tyr Gln Pro Ser Tyr Pro Arg Thr Pro Tyr Val Arg Lys Gly Trp
    290                 295                 300

Leu Val Arg Gln Val Ile Leu Tyr Leu Ile Phe Thr Gly Leu Gln Gly
305                 310                 315                 320

Phe Ile Ile Glu Gln Tyr Ile Asn Pro Ile Val Val Asn Ser Gln His
                325                 330                 335

Pro Leu Lys Gly Gly Leu Leu Asn Ala Val Glu Thr Val Leu Lys Leu
            340                 345                 350

Ser Leu Pro Asn Val Tyr Leu Trp Leu Cys Met Phe Tyr Cys Leu Phe
        355                 360                 365

His Leu Trp Leu Asn Ile Leu Ala Glu Ile Leu Arg Phe Gly Asp Arg
    370                 375                 380

Glu Phe Tyr Lys Asp Trp Trp Asn Ala Lys Thr Ile Asp Glu Tyr Trp
385                 390                 395                 400

Arg Lys Trp Asn Met Pro Val His Lys Trp Met Leu Arg His Ile Tyr
                405                 410                 415

Phe Pro Cys Ile Arg Asn Gly Ile Ser Lys Glu Val Ala Ala Phe Ile
            420                 425                 430

Ala Phe Phe Val Ser Ala Val Phe His Glu Leu Cys Val Ala Val Pro
        435                 440                 445

Cys His Ile Leu Lys Phe Trp Ala Phe Leu Gly Ile Met Leu Gln Ile
    450                 455                 460

Pro Leu Ile Ile Leu Thr Ser Tyr Leu Lys Asn Lys Phe Asn Asp Thr
465                 470                 475                 480

Met Val Gly Asn Met Ile Phe Trp Phe Phe Phe Cys Ile Tyr Gly Gln
                485                 490                 495
```

```
Pro Met Cys Val Leu Leu Tyr Tyr His Asp Val Met Asn Arg Thr Glu
            500                 505                 510

Lys Thr Lys
        515


<210> SEQ ID NO 41
<211> LENGTH: 538
<212> TYPE: PRT
<213> ORGANISM: Oryza sativa

<400> SEQUENCE: 41

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Asn Asp Lys Ser Leu Arg Asp Trp Pro Leu Leu Met Cys Cys
            180                 185                 190

Leu Ser Leu Pro Ala Phe Pro Leu Gly Ala Phe Ala Val Glu Lys Leu
        195                 200                 205

Ala Phe Asn Asn Val Ile Thr Asp Ala Val Ala Thr Cys Leu His Ile
    210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255

Ile Val Trp Leu Lys Leu Val Ser Phe Ala His Thr Asn His Asp Ile
            260                 265                 270

Arg Gln Leu Thr Met Gly Gly Lys Lys Val Asp Asn Glu Leu Ser Thr
        275                 280                 285

Val Asp Met Asp Asn Leu Gln Pro Pro Thr Leu Gly Asn Leu Ile Tyr
    290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
```

```
            340                 345                 350

Ile Val Val Asn Ser Gln His Pro Leu Lys Gly Gly Leu Leu Asn Ala
        355                 360                 365

Val Glu Thr Val Leu Lys Leu Ser Leu Pro Asn Val Tyr Leu Trp Leu
    370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Val Val Arg His Ile Tyr Phe Pro Cys Met Arg Asn Gly Ile Ser
        435                 440                 445

Lys Glu Val Ala Val Leu Ile Ser Phe Leu Val Ser Ala Val Leu His
    450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
        515                 520                 525

Asp Val Met Asn Arg Ile Glu Lys Ala Arg
    530                 535


<210> SEQ ID NO 42
<211> LENGTH: 477
<212> TYPE: PRT
<213> ORGANISM: Oryza sativa

<400> SEQUENCE: 42

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
    130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Val Ile Leu
                165                 170                 175
```

```
Lys Cys Asp Ser Ala Val Leu Ser Gly Phe Val Leu Met Phe Leu Ala
            180                 185                 190

Ser Ile Ile Trp Leu Lys Leu Val Ser Phe Ala His Thr Asn Tyr Asp
        195                 200                 205

Ile Arg Met Leu Ser Lys Ser Ile Glu Lys Gly Val Thr His Asp Ile
    210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
            260                 265                 270

Leu Val Phe Thr Gly Leu Met Gly Phe Ile Ile Glu Gln Tyr Ile Asn
        275                 280                 285

Pro Ile Val Lys Asn Ser Lys His Pro Leu Lys Gly Asn Phe Leu Asn
    290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
        355                 360                 365

Lys Trp Val Ile Arg His Ile Tyr Phe Pro Cys Ile Arg Asn Gly Phe
    370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
            420                 425                 430

Leu Gln Asp Lys Phe Asn Asn Thr Met Val Gly Asn Met Ile Phe Trp
        435                 440                 445

Phe Phe Phe Ser Ile Leu Gly Gln Pro Met Cys Val Leu Leu Tyr Tyr
    450                 455                 460

His Asp Val Met Asn Arg Gln Gln Ala Gln Thr Asn Arg
465                 470                 475
```

<210> SEQ ID NO 43
<211> LENGTH: 529
<212> TYPE: PRT
<213> ORGANISM: Sorghum bicolor

<400> SEQUENCE: 43

```
Met Ala Pro Pro Pro Ser Met Ala Ala Ala Ser Asp Arg Ala Val Pro
1               5                   10                  15

Gly Ala Asp Ala Thr Glu Ala Ser Ser Leu Arg Leu Arg Arg Ala Pro
            20                  25                  30

Ser Ala Asp Ala Gly Asp Leu Ala Asp Asp Ser Ser Gly Asp Arg Arg
        35                  40                  45

Glu Asn Gly Glu Pro Gln Pro Pro Gln Glu Gln Gln Gln Gln His Glu
    50                  55                  60

Met Leu Tyr Tyr Arg Ala Ser Ala Pro Ala His Arg Arg Val Lys Glu
65                  70                  75                  80
```

-continued

```
Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
            100                 105                 110

Ile Glu Asn Leu Met Lys Tyr Gly Leu Leu Ile Arg Ala Gly Phe Trp
        115                 120                 125

Phe Ser Ala Arg Ser Leu Gly Asp Trp Pro Leu Leu Met Cys Cys Leu
    130                 135                 140

Thr Leu Pro Val Phe Pro Leu Val Ala Leu Met Ala Glu Lys Leu Ile
145                 150                 155                 160

Arg Arg Lys Leu Ile Gly Glu His Val Val Ile Leu Leu His Ile Ile
                165                 170                 175

Ile Thr Thr Ser Val Ile Val Tyr Pro Val Val Val Thr Leu Lys Cys
            180                 185                 190

Asp Ser Ala Val Leu Ser Gly Phe Leu Leu Met Phe Leu Ala Ser Ile
        195                 200                 205

Met Trp Met Lys Leu Val Ser Tyr Ala His Thr Asn Tyr Asp Ile Arg
    210                 215                 220

Ala Leu Ser Lys Ser Thr Glu Lys Gly Ala Ala Tyr Gly Asn Tyr Val
225                 230                 235                 240

Asp Pro Glu Ser Met Lys Asp Pro Thr Phe Lys Ser Leu Val Tyr Phe
                245                 250                 255

Met Leu Ala Pro Thr Leu Cys Tyr Gln Pro Thr Tyr Pro Arg Thr Thr
            260                 265                 270

Cys Ile Arg Lys Gly Trp Val Thr Arg Gln Leu Ile Lys Cys Leu Val
        275                 280                 285

Phe Thr Gly Leu Met Gly Phe Ile Ile Glu Gln Tyr Ile Asn Pro Ile
    290                 295                 300

Val Lys Asn Ser Lys His Pro Leu Lys Gly Asn Phe Leu Asn Ala Ile
305                 310                 315                 320

Glu Arg Val Leu Lys Leu Ser Val Pro Thr Leu Tyr Val Trp Leu Cys
                325                 330                 335

Met Phe Tyr Cys Phe Phe His Leu Trp Leu Asn Ile Leu Ala Glu Leu
            340                 345                 350

Leu Cys Phe Gly Asp Arg Glu Phe Tyr Lys Asp Trp Trp Asn Ala Lys
        355                 360                 365

Thr Val Glu Glu Tyr Trp Arg Met Trp Asn Met Pro Val His Lys Trp
    370                 375                 380

Ile Ile Arg His Ile Tyr Phe Pro Cys Ile Arg Lys Gly Phe Ser Arg
385                 390                 395                 400

Gly Val Ala Ile Leu Val Ser Phe Leu Val Ser Ala Val Phe His Glu
                405                 410                 415

Ile Cys Ile Ala Val Pro Cys His Ile Phe Lys Phe Trp Ala Phe Ser
            420                 425                 430

Gly Ile Met Phe Gln Ile Pro Leu Val Phe Leu Thr Arg Tyr Leu Gln
        435                 440                 445

Ala Thr Phe Lys Asn Ile Met Val Gly Asn Met Ile Phe Trp Phe Phe
    450                 455                 460

Phe Ser Ile Val Gly Gln Pro Met Cys Val Leu Leu Tyr Tyr His Asp
465                 470                 475                 480

Val Met Asn Arg Gln Ala Gln Gln Val Asp Asn Ser Ala Glu Thr Cys
                485                 490                 495
```

```
Thr Leu Arg Gln Val Ile Arg Ser Arg Leu Glu Arg Arg Ser Arg Lys
            500                 505                 510

Gln Gln Gln Gln Gln Ala Ser Ser Pro Pro Leu Pro Leu Leu Pro Ala
        515                 520                 525

Ser


<210> SEQ ID NO 44
<211> LENGTH: 494
<212> TYPE: PRT
<213> ORGANISM: Zea mays

<400> SEQUENCE: 44

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Ser Ala Arg Ser Leu Gly Asp Trp Pro Leu Leu
    130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
    210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
    290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335
```

```
Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
        435                 440                 445

Arg Tyr Leu His Ala Thr Phe Lys His Val Met Val Gly Asn Met Ile
    450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490


<210> SEQ ID NO 45
<211> LENGTH: 447
<212> TYPE: PRT
<213> ORGANISM: Physcomitrella patens

<400> SEQUENCE: 45

Met Pro Val Lys Ser Ser Asn Leu Ala Gly Glu Arg Ala Ala Thr Ser
1               5                   10                  15

His Ile Asn Ala Asn Thr Lys Phe Asp Leu Arg Gly Cys Thr Pro Ala
            20                  25                  30

His Arg Val Arg Arg Glu Ser Pro Leu Ser Ser Asp Ala Ile Phe His
        35                  40                  45

Gln Ser His Ala Gly Leu Phe Asn Leu Cys Ile Val Val Leu Ile Ala
    50                  55                  60

Val Asn Ser Arg Leu Ile Ile Glu Asn Leu Met Lys Tyr Gly Leu Leu
65                  70                  75                  80

Ile Arg Thr Gly Phe Trp Phe Ser Ser Lys Ser Ala Arg Asp Trp Pro
                85                  90                  95

Leu Leu Met Cys Gly Leu Ser Leu Pro Thr Phe Pro Phe Ala Ala Leu
            100                 105                 110

Leu Val Glu Lys Leu Cys Trp Lys Asn Glu Asn Gly Lys Trp Leu Ile
        115                 120                 125

Phe Val Leu His Leu Ile Ile Ser Thr Val Gly Ile Leu Tyr Pro Gly
    130                 135                 140

Tyr Val Ile His Arg Val Gln Ser Ala Leu Leu Pro Gly Leu Val Leu
145                 150                 155                 160

Ile Leu Ile Ala Val Thr Gly Trp Met Lys Leu Ile Ser Tyr Ala His
                165                 170                 175

Val Asn Lys Asp Met Arg Glu Leu Leu Arg Ala Lys Glu Lys Leu Pro
            180                 185                 190

Glu Ala Pro Gln Tyr Ala Asp Lys Ile Glu Val Pro Asp His Leu Thr
        195                 200                 205

Ile Gln Asn Ile Ala Tyr Phe Met Leu Ala Pro Thr Leu Cys Tyr Gln
    210                 215                 220
```

```
Leu Ser Tyr Pro Arg Ser Asp Thr Ile Arg Lys Ser Trp Val Leu Arg
225                 230                 235                 240

Gln Ala Gly Lys Leu Val Val Phe Leu Gly Leu Gly Gly Phe Ile Ile
                245                 250                 255

Glu Gln Tyr Ile Asn Pro Thr Val Lys Asn Ser Gln His Pro Leu Arg
            260                 265                 270

Gly Asn Tyr Leu Gln Ala Leu Glu Arg Val Leu Lys Leu Ser Leu Pro
        275                 280                 285

Val Leu Tyr Val Trp Leu Cys Leu Phe Tyr Cys Leu Phe His Leu Trp
    290                 295                 300

Leu Asn Ile Val Ala Glu Leu Leu Arg Phe Gly Asp Arg Glu Phe Tyr
305                 310                 315                 320

Lys Asp Trp Trp Asn Ala Gln Thr Val Glu Glu Tyr Trp Arg Met Trp
                325                 330                 335

Asn Met Pro Val His Lys Trp Met Val Arg His Ile Tyr Phe Pro Ser
            340                 345                 350

Ile Arg Ala Gly Leu Ser Lys Lys Ala Ala Val Leu Leu Val Phe Ala
        355                 360                 365

Ile Ser Ala Leu Phe His Glu Val Ile Ile Gly Val Pro Cys His Met
    370                 375                 380

Leu Arg Cys Trp Ala Phe Leu Gly Ile Met Met Gln Val Pro Leu Val
385                 390                 395                 400

Tyr Leu Thr Asn Val Ile Lys Glu Arg Tyr His Ser Ser Met Val Gly
                405                 410                 415

Asn Met Val Phe Trp Phe Phe Phe Cys Ile Val Gly Gln Pro Met Cys
            420                 425                 430

Leu Leu Leu Tyr Tyr His Asp Val Phe Asn Asn Phe Pro Ser Thr
        435                 440                 445


<210> SEQ ID NO 46
<211> LENGTH: 425
<212> TYPE: PRT
<213> ORGANISM: Selaginella moellendorffii

<400> SEQUENCE: 46

Met Arg Pro Ser Leu Pro Ala His Arg Arg Ser Lys Glu Ser Pro Leu
1               5                   10                  15

Ser Ser Asp Ala Ile Phe Thr Gln Ser His Ala Gly Leu Phe Asn Leu
            20                  25                  30

Cys Ile Val Val Leu Val Ala Val Asn Ser Arg Leu Ile Ile Glu Asn
        35                  40                  45

Leu Met Lys Tyr Gly Leu Leu Ile Gln Ala Glu Val Leu Phe Ser Ser
    50                  55                  60

Lys Ser Leu Lys Asp Trp Pro Leu Leu Met Cys Gly Leu Ser Leu Leu
65                  70                  75                  80

Ile Phe Pro Leu Ala Ala Tyr Val Ile Glu Lys Ile Lys Ala Arg Arg
                85                  90                  95

Pro Ala Thr Ala Val Ala Pro Leu His Leu Ile Asn Leu Ala Ala Ala
            100                 105                 110

Leu Leu Tyr Pro Ile Tyr Val Ile Glu Met Phe Gln Ser Asp Leu Leu
        115                 120                 125

Ser Gly Leu Val Leu Met Leu Ile Ala Val Thr Gly Trp Leu Lys Leu
    130                 135                 140

Val Ser Tyr Ala His Thr Asn Ala Asp Ile Arg Ala Val Lys Lys Asp
```

-continued

```
145                 150                 155                 160

Gly Gly Lys Ile Glu Leu Pro Ala Glu Ala Pro Ala Ile Asp Tyr Pro
                165                 170                 175

Asp Asn Ile Ser Leu Lys Asn Ile Ala Tyr Phe Met Ala Ala Pro Thr
            180                 185                 190

Leu Cys Tyr Gln Leu Ser Tyr Pro Arg Ser Pro Arg Ile Arg Thr Gly
        195                 200                 205

Trp Val Leu Arg Gln Leu Gly Lys Trp Ile Val Phe Asn Gly Phe Met
    210                 215                 220

Gly Phe Ile Ile Gly Gln Tyr Met Asn Pro Ile Ile Arg Asn Ser Thr
225                 230                 235                 240

His Pro Leu Lys Gly Asn Tyr Leu Tyr Ala Ile Glu Arg Val Leu Lys
                245                 250                 255

Leu Ser Ile Pro Thr Leu Tyr Val Trp Leu Gly Phe Phe Tyr Cys Phe
            260                 265                 270

Phe His Leu Trp Leu Asn Ile Val Ala Glu Ile Leu Cys Phe Gly Asp
        275                 280                 285

Arg Glu Phe Tyr Lys Asp Trp Trp Asn Ala Lys Ser Val Asp Glu Tyr
    290                 295                 300

Trp Arg Leu Trp Asn Met Pro Val His Arg Trp Leu Val Arg His Val
305                 310                 315                 320

Tyr Phe Pro Cys Leu Arg Leu Gly Leu His Lys Gln Phe Ala Ile Leu
                325                 330                 335

Val Val Phe Val Ile Ser Gly Ile Phe His Glu Ile Cys Ile Ala Val
            340                 345                 350

Pro Cys His Met Leu Arg Gly Trp Ala Phe Leu Gly Ile Met Phe Gln
        355                 360                 365

Val Pro Leu Val Leu Val Thr Asn Val Leu Gln Arg Lys Phe Gln Ser
    370                 375                 380

Ser Met Val Gly Asn Met Ile Phe Trp Phe Phe Phe Cys Ile Val Gly
385                 390                 395                 400

Gln Pro Met Cys Val Leu Leu Tyr Tyr His Asp Val Val Asn Arg Gln
                405                 410                 415

Gln Leu Gln Leu Ala Gly Arg Ser Lys
            420                 425


<210> SEQ ID NO 47
<211> LENGTH: 507
<212> TYPE: PRT
<213> ORGANISM: Euonymus alatus

<400> SEQUENCE: 47

Met Ala Ala Asn Leu Asn Glu Ala Ser Asp Leu Asn Phe Ser Leu Arg
1               5                   10                  15

Arg Arg Thr Gly Gly Ile Ser Ser Thr Thr Val Pro Asp Ser Ser Ser
            20                  25                  30

Glu Thr Ser Ser Ser Glu Ala Asp Tyr Leu Asp Gly Gly Lys Gly Ala
        35                  40                  45

Ala Asp Val Lys Asp Arg Gly Asp Gly Ala Val Glu Phe Gln Asn Ser
    50                  55                  60

Met Lys Asn Val Glu Arg Ile Glu Lys His Glu Ser Arg Val Gly Leu
65                  70                  75                  80

Asp Ser Arg Phe Thr Tyr Arg Pro Ser Val Pro Ala His Arg Thr Ile
                85                  90                  95
```

-continued

```
Lys Glu Ser Pro Leu Ser Ser Asp Ala Ile Phe Lys Gln Ser His Ala
            100                 105                 110

Gly Leu Phe Asn Leu Cys Ile Val Val Leu Val Ala Val Asn Ser Arg
        115                 120                 125

Leu Ile Ile Glu Asn Leu Met Lys Tyr Gly Trp Leu Ile Arg Ser Gly
    130                 135                 140

Phe Trp Phe Ser Ser Arg Ser Leu Arg Asp Trp Pro Leu Phe Met Cys
145                 150                 155                 160

Cys Leu Thr Leu Pro Val Phe Pro Leu Ala Ala Phe Leu Phe Glu Lys
                165                 170                 175

Leu Ala Gln Lys Asn Leu Ile Ser Glu Pro Val Val Val Leu Leu His
            180                 185                 190

Ile Val Asn Thr Thr Ala Ala Val Leu Tyr Pro Val Leu Val Ile Leu
        195                 200                 205

Arg Cys Asp Ser Ala Phe Met Ser Gly Val Thr Leu Met Leu Phe Ala
    210                 215                 220

Cys Ile Val Trp Leu Lys Leu Val Ser Tyr Ala His Thr Asn Tyr Asp
225                 230                 235                 240

Met Arg Ala Leu Thr Lys Ser Val Glu Lys Gly Asp Thr Pro Leu Ser
                245                 250                 255

Ser Gln Asn Met Asp Tyr Ser Phe Asp Val Asn Ile Lys Ser Leu Ala
            260                 265                 270

Tyr Phe Met Val Ala Pro Thr Leu Cys Tyr Gln Ile Ser Tyr Pro Arg
        275                 280                 285

Thr Pro Tyr Val Arg Lys Gly Trp Val Val Arg Gln Phe Val Lys Leu
    290                 295                 300

Ile Ile Phe Thr Gly Leu Met Gly Phe Ile Ile Glu Gln Tyr Ile Asn
305                 310                 315                 320

Pro Ile Val Gln Asn Ser Gln His Pro Leu Lys Gly Asn Phe Leu Tyr
                325                 330                 335

Ala Ile Glu Arg Val Leu Lys Leu Ser Val Pro Asn Leu Tyr Val Trp
            340                 345                 350

Leu Cys Met Phe Tyr Cys Leu Phe His Leu Trp Leu Asn Ile Leu Ala
        355                 360                 365

Glu Leu Leu Cys Phe Gly Asp Arg Glu Phe Tyr Lys Asp Trp Trp Asn
    370                 375                 380

Ala Lys Thr Val Glu Glu Tyr Trp Arg Met Trp Asn Met Pro Val His
385                 390                 395                 400

Lys Trp Met Val Arg His Ile Tyr Phe Pro Cys Leu Arg Asn Gly Ile
                405                 410                 415

Pro Lys Gly Val Ala Phe Val Ile Ser Phe Leu Val Ser Ala Val Phe
            420                 425                 430

His Glu Leu Cys Ile Ala Val Pro Cys His Ile Phe Lys Leu Trp Ala
        435                 440                 445

Phe Phe Gly Ile Met Leu Gln Val Pro Leu Val Leu Ile Thr Ser Tyr
    450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Leu Tyr Tyr
                485                 490                 495

His Asp Leu Met Asn Arg Asn Gly Lys Met Glu
            500                 505
```

```
<210> SEQ ID NO 48
<211> LENGTH: 518
<212> TYPE: PRT
<213> ORGANISM: Vitis vinifera

<400> SEQUENCE: 48

Met Ala Ile Cys Asn Ser Pro Val Ser Val Thr Thr Ser Ser Ser Ser
1               5                   10                  15

Ser His Ala Asp Ser Asp Leu Asp Phe Ser Ile Arg Lys Arg Phe Gly
            20                  25                  30

Gly Lys Gly Lys Ala Val Ala Asp Ser Ser Leu Glu Thr Glu Thr Glu
        35                  40                  45

Ala Ala Ala Ala Ala Val Leu Glu Ala Glu Lys Ser Val Gly Glu Val
    50                  55                  60

Gly Ser Gly Gly Asp Arg Gly Glu Ser Gly Ser Gln Val Val Arg Asn
65                  70                  75                  80

Gly Glu Asn Gly Val Ala Glu Val Ala Ala Lys Phe Ala Tyr Arg Pro
                85                  90                  95

Cys Ala Pro Ala His Arg Lys Val Lys Glu Ser Pro Leu Ser Ser Asp
            100                 105                 110

Ala Ile Phe Arg Gln Ser His Ala Gly Leu Phe Asn Leu Cys Ile Val
        115                 120                 125

Val Leu Val Ala Val Asn Ser Arg Leu Ile Ile Glu Asn Leu Met Lys
    130                 135                 140

Tyr Gly Trp Leu Ile Arg Ala Gly Phe Trp Phe Ser Ser Lys Ser Leu
145                 150                 155                 160

Arg Asp Trp Pro Leu Phe Met Cys Cys Leu Thr Leu Pro Ile Phe Pro
                165                 170                 175

Leu Ala Ala Phe Val Val Glu Lys Leu Ala Gln Gln Lys Tyr Ile Ser
            180                 185                 190

Glu Gln Val Val Val Ser Leu His Ile Ile Ile Thr Thr Ala Ala Val
        195                 200                 205

Leu Phe Pro Val Leu Val Ile Leu Arg Cys Asp Ser Ala Val Leu Ser
    210                 215                 220

Gly Val Thr Leu Met Leu Phe Ala Cys Ile Val Trp Leu Lys Leu Val
225                 230                 235                 240

Ser Phe Ala His Thr Asn Tyr Asp Met Arg Ala Val Ala Lys Leu Ile
                245                 250                 255

Asp Lys Gly Asp Asp Leu Ser Thr Ser Leu Asn Met Asp Tyr Pro Tyr
            260                 265                 270

Asp Val Asn Phe Lys Ser Leu Ala Tyr Phe Met Val Ala Pro Thr Leu
        275                 280                 285

Cys Tyr Gln Pro Ser Tyr Pro Arg Ser Thr Cys Ile Arg Lys Gly Trp
    290                 295                 300

Val Phe Arg Gln Phe Val Lys Leu Ala Ile Phe Thr Gly Val Met Gly
305                 310                 315                 320

Phe Ile Ile Glu Gln Tyr Ile Asn Pro Ile Val Gln Asn Ser Gln His
                325                 330                 335

Pro Leu Lys Gly Asn Phe Phe Tyr Ala Leu Glu Arg Ile Leu Lys Leu
            340                 345                 350

Ser Val Pro Asn Leu Tyr Val Trp Leu Cys Met Phe Tyr Cys Phe Phe
        355                 360                 365

His Leu Trp Leu Asn Ile Leu Ala Glu Leu Leu Arg Phe Gly Asp Arg
    370                 375                 380
```

Glu Phe Tyr Lys Asp Trp Trp Asn Ala Lys Thr Val Glu Glu Tyr Trp
385 390 395 400

Arg Met Trp Asn Met Pro Val His Lys Trp Met Val Arg His Leu Tyr
405 410 415

Phe Pro Cys Leu Arg Asn Gly Ile Ser Lys Gly Val Ser Val Val Ile
420 425 430

Ala Phe Ala Ile Ser Ala Ile Phe His Glu Leu Cys Ile Ala Val Pro
435 440 445

Cys His Met Phe Lys Leu Trp Ala Phe Ile Gly Ile Met Phe Gln Val
450 455 460

Pro Leu Val Leu Val Thr Asn Tyr Leu Gln Asn Lys Phe Arg Asn Ser
465 470 475 480

Met Val Gly Asn Met Ile Phe Trp Leu Phe Phe Ser Ile Leu Gly Gln
485 490 495

Pro Met Cys Val Leu Leu Tyr Tyr His Asp Leu Met Asn Arg Lys Glu
500 505 510

Thr Thr Glu Ser Ser Leu
515

<210> SEQ ID NO 49
<211> LENGTH: 498
<212> TYPE: PRT
<213> ORGANISM: Glycine max

<400> SEQUENCE: 49

Met Ala Ile Ser Asp Glu Pro Glu Thr Val Ala Thr Ala Leu Asn His
1 5 10 15

Ser Ser Leu Arg Arg Arg Pro Thr Ala Ala Gly Leu Phe Asn Ser Pro
20 25 30

Glu Thr Thr Thr Asp Ser Ser Gly Asp Asp Leu Ala Lys Asp Ser Gly
35 40 45

Ser Asp Asp Ser Ile Ser Ser Asp Ala Ala Asn Ser Gln Pro Gln Gln
50 55 60

Lys Gln Asp Thr Asp Phe Ser Val Leu Lys Phe Ala Tyr Arg Pro Ser
65 70 75 80

Val Pro Ala His Arg Lys Val Lys Glu Ser Pro Leu Ser Ser Asp Thr
85 90 95

Ile Phe Arg Gln Ser His Ala Gly Leu Phe Asn Leu Cys Ile Val Val
100 105 110

Leu Val Ala Val Asn Ser Arg Leu Ile Ile Glu Asn Leu Met Lys Tyr
115 120 125

Gly Trp Leu Ile Lys Ser Gly Phe Trp Phe Ser Ser Lys Ser Leu Arg
130 135 140

Asp Trp Pro Leu Phe Met Cys Cys Leu Ser Leu Val Val Phe Pro Phe
145 150 155 160

Ala Ala Phe Ile Val Glu Lys Leu Ala Gln Gln Lys Cys Ile Pro Glu
165 170 175

Pro Val Val Val Val Leu His Ile Ile Ile Thr Ser Ala Ser Leu Phe
180 185 190

Tyr Pro Val Leu Val Ile Leu Arg Cys Asp Ser Ala Phe Leu Ser Gly
195 200 205

Val Thr Leu Met Leu Phe Ala Cys Val Val Trp Leu Lys Leu Val Ser
210 215 220

Tyr Ala His Thr Asn Tyr Asp Met Arg Ala Leu Thr Lys Ser Val Glu
225 230 235 240

```
Lys Gly Glu Ala Leu Pro Asp Thr Leu Asn Met Asp Tyr Pro Tyr Asn
            245                 250                 255

Val Ser Phe Lys Ser Leu Ala Tyr Phe Leu Val Ala Pro Thr Leu Cys
            260                 265                 270

Tyr Gln Pro Ser Tyr Pro Arg Thr Pro Tyr Ile Arg Lys Gly Trp Leu
        275                 280                 285

Phe Arg Gln Leu Val Lys Leu Ile Ile Phe Thr Gly Val Met Gly Phe
    290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
                325                 330                 335

Val Pro Asn Leu Tyr Val Trp Leu Cys Met Phe Tyr Cys Phe Phe His
            340                 345                 350

Leu Trp Leu Asn Ile Leu Ala Glu Leu Leu Arg Phe Gly Asp Arg Glu
        355                 360                 365

Phe Tyr Gln Asp Trp Trp Asn Ala Lys Thr Val Glu Asp Tyr Trp Arg
    370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ala
                405                 410                 415

Phe Leu Val Ser Ala Leu Phe His Glu Leu Cys Ile Ala Val Pro Cys
            420                 425                 430

His Ile Phe Lys Leu Trp Ala Phe Gly Gly Ile Met Phe Gln Val Pro
        435                 440                 445

Leu Val Phe Ile Thr Asn Tyr Leu Gln Asn Lys Phe Arg Asn Ser Met
    450                 455                 460

Val Gly Asn Met Ile Phe Trp Phe Ile Phe Ser Ile Leu Gly Gln Pro
465                 470                 475                 480

Met Cys Val Leu Leu Tyr Tyr His Asp Leu Met Asn Arg Lys Gly Lys
                485                 490                 495

Leu Asp


<210> SEQ ID NO 50
<211> LENGTH: 504
<212> TYPE: PRT
<213> ORGANISM: Glycine max

<400> SEQUENCE: 50

Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Ser Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110
```

```
Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Val Leu His Ile Ile Ile
            180                 185                 190

Thr Ser Thr Ser Leu Phe Tyr Pro Val Leu Val Ile Leu Arg Cys Asp
        195                 200                 205

Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Ile Phe
    290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Arg Phe Gly Asp Arg Glu Phe Tyr Lys Asp Trp Trp Asn Ala Lys Thr
    370                 375                 380

Val Glu Asp Tyr Trp Arg Met Trp Asn Met Pro Val His Lys Trp Met
385                 390                 395                 400

Ile Arg His Leu Tyr Tyr Pro Cys Leu Arg His Gly Leu Pro Lys Ala
                405                 410                 415

Ala Ala Leu Leu Ile Ala Phe Leu Val Ser Ala Leu Phe His Glu Leu
            420                 425                 430

Cys Ile Ala Val Pro Cys His Ile Phe Lys Leu Trp Ala Phe Gly Gly
        435                 440                 445

Ile Met Phe Gln Val Pro Leu Val Leu Ile Thr Asn Tyr Leu Gln Asn
    450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
            500
```

<210> SEQ ID NO 51
<211> LENGTH: 511

<212> TYPE: PRT
<213> ORGANISM: Lotus japonicus

<400> SEQUENCE: 51

```
Met Ala Ile Ser Glu Asp Ser Glu Ser Leu Phe Ala Ala Ala Ala Ala
1               5                   10                  15

Ser Ser Val Ile Gln Ser Gly Ser Ser Val Arg Arg Arg Pro Ser Ala
            20                  25                  30

Ile Ser Ala Val Ala Thr Val Glu Asp Glu Ser Ser Ser Glu Glu Pro
        35                  40                  45

Val Pro Val Arg Asp Ser Gly Ser Asp Val Asp Asp Ser Val Ser Ser
    50                  55                  60

Glu Gln His Val Ser Pro Ala Thr Ala Asn Arg Glu Lys Asn Gln Val
65                  70                  75                  80

His Asp Ile Ser Ala Thr Lys Phe Ala Tyr Arg Pro Ser Ala Pro Ala
                85                  90                  95

His Arg Arg Val Lys Glu Ser Pro Leu Ser Ser Asp Asn Ile Phe Arg
            100                 105                 110

His His Ala Gly Leu Phe Asn Leu Cys Ile Val Val Leu Val Ala Val
        115                 120                 125

Asn Ser Arg Leu Ile Ile Glu Asn Leu Met Lys Tyr Gly Trp Leu Ile
    130                 135                 140

Arg Thr Gly Phe Trp Phe Ser Ser Lys Ser Leu Arg Asp Trp Pro Leu
145                 150                 155                 160

Phe Met Cys Cys Leu Ser Leu Ala Ile Phe Pro Phe Ala Ala Phe Val
                165                 170                 175

Val Glu Lys Leu Val Gln Gln Lys Cys Ile Ser Glu Pro Val Val Val
            180                 185                 190

Leu His Ile Phe Ile Ser Thr Ala Ala Val Val Tyr Pro Val Leu Val
        195                 200                 205

Ile Leu Arg Thr Asp Ser Ala Phe Pro Ser Gly Val Thr Leu Met Leu
    210                 215                 220

Phe Ala Cys Ile Val Trp Leu Lys Leu Val Ser Tyr Ala His Thr Asn
225                 230                 235                 240

Tyr Asp Met Arg Glu Leu Thr Lys Ser Ile Glu Lys Gly Glu Ala Leu
                245                 250                 255

Pro Asn Thr Leu Asn Met Asp Tyr Ser Tyr Asp Val Ser Phe Lys Ser
            260                 265                 270

Leu Ala Tyr Phe Met Ile Ala Pro Thr Leu Cys Tyr Gln Pro Arg Tyr
        275                 280                 285

Pro Arg Ser Pro Ser Ile Arg Lys Gly Trp Val Leu Arg Gln Leu Val
    290                 295                 300

Lys Leu Ile Ile Phe Thr Gly Val Met Gly Phe Ile Ile Glu Gln Tyr
305                 310                 315                 320

Ile Asn Pro Ile Val Gln Asn Ser Gln His Pro Leu Lys Gly Asn Leu
                325                 330                 335

Leu Tyr Ala Ile Glu Arg Val Leu Lys Leu Ser Val Pro Asn Leu Tyr
            340                 345                 350

Val Trp Leu Cys Met Phe Tyr Cys Phe Phe His Leu Trp Leu Asn Ile
        355                 360                 365

Leu Ala Glu Leu Leu Arg Phe Gly Asp Arg Glu Phe Tyr Lys Asp Trp
    370                 375                 380

Trp Asn Ala Lys Thr Phe Glu Glu Tyr Trp Arg Met Trp Asn Met Pro
385                 390                 395                 400
```

```
Val His Lys Trp Met Ile Arg His Leu Tyr Phe Pro Cys Leu Arg Asn
                405                 410                 415

Gly Ile Pro Lys Gly Val Ala Ile Leu Ile Ala Phe Leu Val Ser Ala
            420                 425                 430

Leu Phe His Glu Leu Cys Ile Ala Val Pro Cys His Ile Phe Lys Leu
        435                 440                 445

Trp Ala Phe Gly Gly Ile Met Phe Gln Val Pro Leu Ile Leu Ile Thr
    450                 455                 460

Asn Tyr Leu Gln Asn Lys Phe Arg Asn Ser Met Val Gly Asn Met Ile
465                 470                 475                 480

Phe Trp Phe Ile Phe Ser Ile Leu Gly Gln Pro Met Ala Val Leu Leu
                485                 490                 495

Tyr Tyr His Asp Leu Met Asn Arg Lys Ser Lys Leu Asp Gln Ser
            500                 505                 510


<210> SEQ ID NO 52
<211> LENGTH: 539
<212> TYPE: PRT
<213> ORGANISM: Medicago truncatula

<400> SEQUENCE: 52

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
            20                  25                  30

Arg Arg Pro Ser Ala Thr Ser Thr Ala Gly Gly Leu Phe Asp Ala Glu
        35                  40                  45

Ser Ala Ala Ala Asp Ala Val Arg Asp Ser Gly Ser Asp Asp Ser Leu
    50                  55                  60

Asn Gly Lys Ile Asn Asn Glu Glu Glu Val Lys Asp Arg Lys Thr Asp
65                  70                  75                  80

His Ala Glu Gly Ile Val Asp Asp Asp Asp Asp Asn Ala Val Lys Lys
                85                  90                  95

Asn Gly Gly Asn Asp Val Ile Asn Asp Arg Glu Asn Val Ala Val Asp
            100                 105                 110

Phe Lys Phe Thr Tyr Arg Pro Ser Val Pro Ala His Arg Arg Ser Lys
        115                 120                 125

Glu Ser Pro Leu Ser Ser Gly Asn Ile Phe Arg Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Trp Leu Ile Arg Ser Gly Phe
                165                 170                 175

Trp Phe Ser Ser Lys Ser Leu Arg Asp Trp Pro Leu Phe Met Cys Cys
            180                 185                 190

Leu Ser Leu Ala Ile Phe Pro Leu Ala Ala Phe Val Val Glu Lys Leu
        195                 200                 205

Ala Gln Gln Lys Arg Ile Ser Glu Pro Val Ile Val Leu Leu His Ile
    210                 215                 220

Val Ile Thr Thr Val Ala Ile Ile Tyr Pro Val Leu Val Ile Leu Trp
225                 230                 235                 240

Cys Asp Ser Ala Phe Leu Ser Gly Ser Thr Leu Met Leu Leu Thr Cys
                245                 250                 255

Ile Val Trp Leu Lys Leu Val Ser Tyr Ala His Thr Thr Tyr Asp Met
```

```
            260                 265                 270

Arg Ala Leu Ala Val Ser Asn Glu Lys Gly Glu Thr Met Pro Asp Thr
        275                 280                 285

Phe Asn Met Glu Glu Tyr Pro His Asn Val Ser Phe Gln Ser Leu Ala
    290                 295                 300

Tyr Phe Met Val Ala Pro Thr Leu Cys Tyr Gln Pro Ser Tyr Pro Arg
305                 310                 315                 320

Thr Pro Ser Val Arg Lys Gly Trp Val Cys Arg Gln Leu Leu Lys Leu
                325                 330                 335

Val Ile Phe Thr Gly Val Met Gly Phe Ile Ile Glu Gln Tyr Met Asn
            340                 345                 350

Pro Ile Val Gln Asn Ser Gln His Pro Leu Lys Gly Asn Leu Leu Tyr
        355                 360                 365

Ala Ile Glu Arg Val Leu Lys Leu Ser Val Pro Asn Val Tyr Val Trp
    370                 375                 380

Leu Cys Met Phe Tyr Cys Phe Phe His Leu Trp Leu Asn Ile Leu Ala
385                 390                 395                 400

Glu Leu Leu Arg Phe Gly Asp Arg Glu Phe Tyr Lys Asp Trp Trp Asn
                405                 410                 415

Ala Gln Thr Val Glu Glu Tyr Trp Arg Met Trp Asn Met Pro Val His
            420                 425                 430

Lys Trp Met Val Arg His Val Tyr Phe Pro Cys Ile Arg Phe Gly Ile
        435                 440                 445

Pro Lys Gly Ala Ala Ala Leu Thr Ala Phe Leu Val Ser Ala Val Phe
    450                 455                 460

His Glu Leu Cys Ile Ala Val Pro Cys Arg Met Phe Lys Leu Trp Ala
465                 470                 475                 480

Phe Ile Gly Ile Met Phe Gln Val Pro Leu Val Leu Ile Thr Asn Tyr
                485                 490                 495

Leu Lys Asn Lys Tyr Arg Asn Ser Met Val Gly Asn Met Ile Phe Trp
            500                 505                 510

Phe Ile Phe Cys Ile Leu Gly Gln Pro Met Cys Val Leu Leu Tyr Tyr
        515                 520                 525

His Asp Leu Met Asn Arg Lys Gly Glu Ile Asp
    530                 535


<210> SEQ ID NO 53
<211> LENGTH: 521
<212> TYPE: PRT
<213> ORGANISM: Jatropha curcas

<400> SEQUENCE: 53

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
    50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95
```

-continued

```
Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125

Leu Cys Ile Val Val Leu Val Ala Val Asn Ser Arg Leu Ile Ile Glu
    130                 135                 140

Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
                165                 170                 175

Pro Ile Phe Ser Leu Ala Ala Tyr Leu Val Glu Lys Leu Ala Tyr Arg
            180                 185                 190

Lys Tyr Ile Ser Ala Pro Ile Val Ile Phe Phe His Met Leu Ile Thr
        195                 200                 205

Thr Thr Ala Val Leu Tyr Pro Val Ser Val Ile Leu Ser Cys Gly Ser
    210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
                245                 250                 255

Ala Asn Ser Ala Asp Lys Gly Asp Ala Leu Ser Asp Thr Ser Gly Ala
            260                 265                 270

Asp Ser Ser Arg Asp Val Ser Phe Lys Ser Leu Val Tyr Phe Met Val
        275                 280                 285

Ala Pro Thr Leu Cys Tyr Gln Pro Ser Tyr Pro Arg Thr Asp Ser Val
    290                 295                 300

Arg Lys Gly Trp Val Val Arg Gln Phe Val Lys Leu Ile Ile Phe Thr
305                 310                 315                 320

Gly Phe Met Gly Phe Ile Ile Glu Gln Tyr Ile Asn Pro Ile Val Gln
                325                 330                 335

Asn Ser Gln His Pro Leu Lys Gly Asp Leu Leu Tyr Ala Ile Glu Arg
            340                 345                 350

Val Leu Lys Leu Ser Val Pro Asn Leu Tyr Val Trp Leu Cys Met Phe
        355                 360                 365

Tyr Cys Phe Phe His Leu Trp Leu Asn Ile Leu Ala Glu Leu Leu Arg
    370                 375                 380

Phe Gly Asp Arg Glu Phe Tyr Lys Asp Trp Trp Asn Ala Arg Thr Val
385                 390                 395                 400

Glu Glu Tyr Trp Arg Met Trp Asn Met Pro Val His Lys Trp Met Val
                405                 410                 415

Arg His Ile Tyr Phe Pro Cys Leu Arg His Lys Ile Pro Arg Gly Val
            420                 425                 430

Ala Leu Leu Ile Ala Phe Phe Val Ser Ala Val Phe His Glu Leu Cys
        435                 440                 445

Ile Ala Val Pro Cys His Met Phe Lys Leu Trp Ala Phe Ile Gly Ile
    450                 455                 460

Met Phe Gln Ile Pro Leu Val Gly Ile Thr Asn Tyr Leu Gln Asn Lys
465                 470                 475                 480

Phe Arg Ser Ser Met Val Gly Asn Met Ile Phe Trp Phe Ile Phe Cys
                485                 490                 495

Ile Leu Gly Gln Pro Met Cys Val Leu Leu Tyr Tyr His Asp Leu Met
            500                 505                 510

Asn Arg Lys Gly Asn Ala Glu Leu Arg
```

515 520

<210> SEQ ID NO 54
<211> LENGTH: 526
<212> TYPE: PRT
<213> ORGANISM: Vernicia fordii

<400> SEQUENCE: 54

Met Thr Ile Pro Glu Thr Pro Asp Asn Ser Thr Asp Ala Thr Thr Ser
1 5 10 15

Gly Gly Ala Glu Ser Ser Ser Asp Leu Asn Leu Ser Leu Arg Arg Arg
20 25 30

Arg Thr Ala Ser Asn Ser Asp Gly Ala Val Ala Glu Leu Ala Ser Lys
35 40 45

Ile Asp Glu Leu Glu Ser Asp Ala Gly Gly Gly Gln Val Ile Lys Asp
50 55 60

Pro Gly Ala Glu Met Asp Ser Gly Thr Leu Lys Ser Asn Gly Lys Asp
65 70 75 80

Cys Gly Thr Val Lys Asp Arg Ile Glu Asn Arg Glu Asn Arg Gly Gly
85 90 95

Ser Asp Val Lys Phe Thr Tyr Arg Pro Ser Val Pro Ala His Arg Ala
100 105 110

Leu Lys Glu Ser Pro Leu Ser Ser Asp Asn Ile Phe Lys Gln Ser His
115 120 125

Ala Gly Leu Phe Asn Leu Cys Ile Val Val Leu Val Ala Val Asn Ser
130 135 140

Arg Leu Ile Ile Glu Asn Ile Met Lys Tyr Gly Trp Leu Ile Lys Thr
145 150 155 160

Gly Phe Trp Phe Ser Ser Arg Ser Leu Arg Asp Trp Pro Leu Leu Met
165 170 175

Cys Cys Leu Thr Leu Pro Ile Phe Ser Leu Ala Ala Tyr Leu Val Glu
180 185 190

Lys Leu Ala Cys Arg Lys Tyr Ile Ser Ala Pro Thr Val Val Phe Leu
195 200 205

His Ile Leu Phe Ser Ser Thr Ala Val Leu Tyr Pro Val Ser Val Ile
210 215 220

Leu Ser Cys Glu Ser Ala Val Leu Ser Gly Val Ala Leu Met Leu Phe
225 230 235 240

Ala Cys Ile Val Trp Leu Lys Leu Val Ser Tyr Ala His Thr Asn Phe
245 250 255

Asp Met Arg Ala Ile Ala Asn Ser Val Asp Lys Gly Asp Ala Leu Ser
260 265 270

Asn Ala Ser Ser Ala Glu Ser Ser His Asp Val Ser Phe Lys Ser Leu
275 280 285

Val Tyr Phe Met Val Ala Pro Thr Leu Cys Tyr Gln Pro Ser Tyr Pro
290 295 300

Arg Thr Ala Ser Ile Arg Lys Gly Trp Val Val Arg Gln Phe Val Lys
305 310 315 320

Leu Ile Ile Phe Thr Gly Phe Met Gly Phe Ile Ile Glu Gln Tyr Ile
325 330 335

Asn Pro Ile Val Gln Asn Ser Gln His Pro Leu Lys Gly Asp Leu Leu
340 345 350

Tyr Ala Ile Glu Arg Val Leu Lys Leu Ser Val Pro Asn Leu Tyr Val
355 360 365

```
Trp Leu Cys Met Phe Tyr Cys Phe Phe His Leu Trp Leu Asn Ile Leu
    370                 375                 380

Ala Glu Leu Leu Arg Phe Gly Asp Arg Glu Phe Tyr Lys Asp Trp Trp
385                 390                 395                 400

Asn Ala Arg Thr Val Glu Glu Tyr Trp Arg Met Trp Asn Met Pro Val
                405                 410                 415

His Lys Trp Met Val Arg His Ile Tyr Phe Pro Cys Leu Arg His Lys
            420                 425                 430

Ile Pro Arg Gly Val Ala Leu Leu Ile Thr Phe Phe Val Ser Ala Val
        435                 440                 445

Phe His Glu Leu Cys Ile Ala Val Pro Cys His Ile Phe Lys Leu Trp
    450                 455                 460

Ala Phe Ile Gly Ile Met Phe Gln Ile Pro Leu Val Gly Ile Thr Asn
465                 470                 475                 480

Tyr Leu Gln Asn Lys Phe Arg Ser Ser Met Val Gly Asn Met Ile Phe
                485                 490                 495

Trp Phe Ile Phe Cys Ile Leu Gly Gln Pro Met Cys Leu Leu Leu Tyr
            500                 505                 510

Tyr His Asp Leu Met Asn Arg Lys Gly Thr Thr Glu Ser Arg
        515                 520                 525


<210> SEQ ID NO 55
<211> LENGTH: 523
<212> TYPE: PRT
<213> ORGANISM: Vernonia galamensis

<400> SEQUENCE: 55

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
            20                  25                  30

Gly Asp Gly Leu Phe Asp Ser Ser Ser Ser Ser Lys Thr Asn Ser Ser
        35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
        115                 120                 125

Gly Leu Phe Asn Leu Cys Ile Val Val Leu Val Ala Val Asn Gly Arg
    130                 135                 140

Leu Ile Ile Glu Asn Leu Met Lys Tyr Gly Leu Leu Ile Asn Ser Asn
145                 150                 155                 160

Phe Trp Phe Ser Ser Arg Ser Leu Arg Asp Trp Pro Leu Leu Met Cys
                165                 170                 175

Cys Leu Thr Pro Ser Asp Phe Pro Leu Ala Ala Tyr Ile Val Glu Lys
            180                 185                 190

Leu Ala Trp Lys Lys Arg Ile Ser Asp Pro Val Val Ile Thr Leu His
        195                 200                 205

Val Ile Ile Thr Thr Thr Ala Ile Leu Tyr Pro Val Phe Met Ile Leu
    210                 215                 220
```

```
Arg Phe Asp Ser Val Val Leu Ser Gly Val Ser Leu Met Leu Cys Ala
225                 230                 235                 240

Cys Ile Asn Trp Leu Lys Leu Val Ser Phe Val His Thr Asn Tyr Asp
                245                 250                 255

Met Arg Ser Leu Leu Asn Ser Thr Asp Lys Gly Glu Val Glu Pro Met
            260                 265                 270

Ser Ser Asn Met Asp Tyr Phe Tyr Asp Val Asn Phe Lys Ser Leu Val
        275                 280                 285

Tyr Phe Met Val Ala Pro Thr Leu Cys Tyr Gln Ile Ser Tyr Pro Arg
    290                 295                 300

Thr Ala Phe Ile Arg Lys Gly Trp Val Leu Arg Gln Leu Ile Lys Leu
305                 310                 315                 320

Val Ile Phe Thr Gly Phe Met Gly Phe Ile Ile Glu Gln Tyr Ile Asn
                325                 330                 335

Pro Ile Val Lys Asn Ser Arg His Pro Leu Lys Gly Asp Phe Leu Tyr
            340                 345                 350

Ala Ile Glu Arg Val Leu Lys Leu Ser Val Pro Asn Leu Tyr Val Trp
        355                 360                 365

Leu Cys Met Phe Tyr Cys Phe Phe His Leu Trp Leu Asn Ile Leu Ala
    370                 375                 380

Glu Leu Leu Cys Phe Gly Asp Arg Glu Phe Tyr Lys Asp Trp Trp Asn
385                 390                 395                 400

Ala Gln Thr Ile Glu Glu Tyr Trp Arg Leu Trp Asn Met Pro Val His
                405                 410                 415

Lys Trp Ile Val Arg His Leu Tyr Phe Pro Cys Leu Arg Asn Gly Ile
            420                 425                 430

Pro Lys Gly Ala Ala Ile Leu Val Ala Phe Phe Met Ser Ala Val Phe
        435                 440                 445

His Glu Leu Cys Ile Ala Val Pro Cys His Ile Phe Lys Phe Trp Ala
    450                 455                 460

Phe Ile Gly Ile Met Phe Gln Val Pro Leu Val Leu Leu Thr Asn Tyr
465                 470                 475                 480

Leu Gln His Lys Phe Gln Asn Ser Met Val Gly Asn Met Ile Phe Trp
                485                 490                 495

Cys Phe Phe Ser Ile Phe Gly Gln Pro Met Cys Val Leu Leu Tyr Tyr
            500                 505                 510

His Asp Val Met Asn Gln Lys Gly Lys Ser Lys
        515                 520


<210> SEQ ID NO 56
<211> LENGTH: 521
<212> TYPE: PRT
<213> ORGANISM: Ricinus communis

<400> SEQUENCE: 56

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Arg Thr Ser Asn
            20                  25                  30

Asp Ser Asp Gly Ala Leu Ala Asp Leu Ala Ser Lys Phe Asp Asp Asp
        35                  40                  45

Asp Asp Val Arg Ser Glu Asp Ser Ala Glu Asn Ile Ile Glu Asp Pro
    50                  55                  60

Val Ala Ala Val Thr Glu Leu Ala Thr Ala Lys Ser Asn Gly Lys Asp
```

-continued

```
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
            180                 185                 190

Lys Ala Ala Tyr Arg Lys Tyr Ile Ser Pro Pro Ile Val Ile Phe Leu
        195                 200                 205

His Val Ile Ile Thr Ser Ala Ala Val Leu Tyr Pro Ala Ser Val Ile
    210                 215                 220

Leu Ser Cys Glu Ser Ala Phe Leu Ser Gly Val Thr Leu Met Glu Leu
225                 230                 235                 240

Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
            260                 265                 270

Ser Ser Ser Thr Glu Tyr Cys His Asp Val Ser Phe Lys Thr Leu Ala
        275                 280                 285

Tyr Phe Met Val Ala Pro Thr Leu Cys Tyr Gln Pro Ser Tyr Pro Arg
    290                 295                 300

Thr Ala Phe Ile Arg Lys Gly Trp Val Phe Arg Gln Phe Val Lys Leu
305                 310                 315                 320

Ile Ile Phe Thr Gly Phe Met Gly Phe Ile Ile Glu Gln Tyr Ile Asn
                325                 330                 335

Pro Ile Val Gln Asn Ser Gln His Pro Leu Lys Gly Asp Leu Leu Tyr
            340                 345                 350

Ala Ile Glu Arg Val Leu Lys Leu Ser Val Pro Asn Leu Tyr Val Trp
        355                 360                 365

Leu Cys Leu Phe Tyr Cys Phe Phe His Leu Trp Leu Asn Ile Val Ala
    370                 375                 380

Glu Leu Leu Arg Phe Gly Asp Arg Glu Phe Tyr Lys Asp Trp Trp Asn
385                 390                 395                 400

Ala Lys Thr Val Glu Glu Tyr Trp Arg Met Trp Asn Met Pro Val His
                405                 410                 415

Lys Trp Met Val Arg His Ile Tyr Phe Pro Cys Leu Arg Arg Lys Ile
            420                 425                 430

Pro Arg Gly Val Ala Ile Val Ile Ala Phe Phe Val Ser Ala Val Phe
        435                 440                 445

His Glu Leu Cys Ile Ala Val Pro Cys His Met Phe Lys Leu Trp Ala
    450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
                485                 490                 495
```

Phe Phe Phe Cys Ile Leu Gly Gln Pro Met Cys Val Leu Leu Tyr Tyr
500 505 510

His Asp Leu Met Asn Arg Asp Gly Asn
515 520

<210> SEQ ID NO 57
<211> LENGTH: 446
<212> TYPE: PRT
<213> ORGANISM: Populus trichocarpa

<400> SEQUENCE: 57

Met Met Glu Ser Glu Asp Leu Lys Ser Asn Gly Lys Glu Cys Asp Lys
1 5 10 15

Val Thr Asn Glu Asn Arg Ser Asp Ile Lys Phe Asn Tyr Arg Pro Ser
20 25 30

Met Pro Ala His Arg Gly Val Arg Glu Ser Pro Leu Ser Ser Asp Ala
35 40 45

Ile Phe Lys Gln Ser His Ala Gly Leu Phe Asn Leu Cys Ile Val Val
50 55 60

Leu Val Ala Ile Asn Ser Arg Leu Ile Ile Glu Asn Ile Ile Lys Tyr
65 70 75 80

Gly Trp Leu Ile Asn Gly Gly Phe Trp Phe Ser Ser Lys Ser Leu Arg
85 90 95

Asp Trp Pro Leu Phe Met Cys Cys Leu Ser Leu Pro Ala Phe Pro Phe
100 105 110

Ala Ala Tyr Leu Val Glu Lys Leu Ala Tyr Gln Asn Tyr Leu Pro Gln
115 120 125

Leu Val Val Val Phe Leu His Thr Ile Ile Thr Thr Gly Ser Leu Leu
130 135 140

Tyr Pro Val Leu Val Ile Leu Arg Cys Asp Ser Ala Phe Leu Ser Gly
145 150 155 160

Val Thr Leu Met Leu Phe Ser Cys Ile Val Trp Leu Lys Leu Val Ser
165 170 175

Tyr Ala His Thr Asn Ser Asp Leu Arg Ala Ile Ala Lys Ser Ile Asp
180 185 190

Arg Glu Asp Val Pro Ser Ile Ser Pro Tyr Val Gly Asn Pro Tyr Asp
195 200 205

Thr Tyr Phe Lys Ser Leu Val Tyr Phe Met Val Ala Pro Thr Leu Cys
210 215 220

Tyr Gln Ser Ser Tyr Pro Arg Thr Glu Ser Val Arg Lys Gly Trp Val
225 230 235 240

Val Gln Gln Phe Val Lys Leu Ile Ile Phe Thr Gly Phe Met Gly Phe
245 250 255

Ile Ile Glu Gln Tyr Ile Asn Pro Ile Val Lys Asn Ser Gln His Pro
260 265 270

Phe Lys Gly Asn Leu Leu Tyr Ala Ile Glu Arg Val Leu Lys Leu Ser
275 280 285

Val Pro Asn Leu Tyr Val Trp Leu Cys Met Phe Tyr Cys Phe Phe His
290 295 300

Leu Trp Leu Asn Ile Leu Ala Glu Leu Leu Cys Phe Gly Asp Arg Glu
305 310 315 320

Phe Tyr Lys Asp Trp Trp Asn Ala Arg Thr Val Glu Glu Tyr Trp Arg
325 330 335

Met Trp Asn Met Pro Val His Lys Trp Met Val Arg His Ile Tyr Phe

```
            340                 345                 350

Pro Cys Leu Arg Asn Lys Ile Pro Lys Gly Leu Ala Ile Leu Ile Ala
        355                 360                 365

Phe Leu Val Ser Ala Val Phe His Glu Leu Cys Ile Ala Val Pro Cys
    370                 375                 380

His Val Phe Lys Leu Trp Ala Phe Ile Gly Ile Met Leu Gln Val Pro
385                 390                 395                 400

Leu Val Val Ile Thr Lys Phe Leu Gln Asn Lys Phe Arg Ser Ser Met
                405                 410                 415

Val Gly Asn Met Ile Phe Trp Leu Phe Phe Ser Ile Leu Gly Gln Pro
            420                 425                 430

Met Cys Val Leu Leu Tyr Tyr His Asp Leu Met Asn Arg Lys
        435                 440                 445


<210> SEQ ID NO 58
<211> LENGTH: 493
<212> TYPE: PRT
<213> ORGANISM: Populus trichocarpa

<400> SEQUENCE: 58

Met Ala Glu Ser Glu Ser Pro Glu Asn Arg Ile Ala Ala Met Glu Ser
1               5                   10                  15

Thr Ser Ser Ser Thr Ser Asp Leu Asn Phe Ser Ile Arg Arg Arg Ser
            20                  25                  30

Thr Val Met Asp Ser Ala Ser Thr Glu Met Met Gly Ser Glu Gly Leu
        35                  40                  45

Lys Ser Ser Gly Lys Ala Cys Asp Lys Val Lys Ile Glu Lys Gln Ser
    50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
                85                  90                  95

Gly Leu Phe Asn Leu Cys Ile Val Val Leu Val Ala Val Asn Ser Arg
            100                 105                 110

Leu Ile Ile Glu Asn Leu Ile Lys Tyr Gly Trp Leu Ile Asn Ser Gly
        115                 120                 125

Phe Trp Phe Ser Ser Lys Ser Leu Arg Asp Trp Pro Leu Phe Met Cys
    130                 135                 140

Cys Leu Ser Leu Pro Ala Phe Pro Leu Ala Ala Tyr Leu Val Glu Lys
145                 150                 155                 160

Leu Ala Tyr Arg Asn Cys Ile Ser Glu Leu Val Val Val Phe Leu His
                165                 170                 175

Ile Ile Ile Thr Thr Ala Ser Leu Leu Tyr Pro Val Leu Val Ile Leu
            180                 185                 190

Arg Cys Asp Ser Ala Leu Leu Ser Gly Gly Thr Leu Met Leu Phe Ala
        195                 200                 205

Cys Ile Val Trp Leu Lys Leu Val Ser Phe Ala His Thr Ser Ser Asp
    210                 215                 220

Met Arg Ala Ile Ala Lys Ser Ile Asp Lys Glu Asn Thr Pro Ser Ile
225                 230                 235                 240

Ser Ser Lys Ala Asp Asn Ser Tyr Asp Ala Asn Phe Lys Ser Leu Val
                245                 250                 255

Tyr Phe Met Val Ala Pro Thr Leu Cys Tyr Gln Ser Ser Tyr Pro Arg
            260                 265                 270
```

Ser Ala Ser Val Arg Lys Gly Trp Val Val Arg Gln Phe Val Lys Leu
275 280 285

Ile Ile Phe Thr Gly Phe Met Gly Phe Ile Ile Glu Gln Tyr Ile Asn
290 295 300

Pro Ile Val Gln Asn Ser Gln His Pro Leu Lys Gly Asn Leu Leu Tyr
305 310 315 320

Ala Ile Glu Arg Val Leu Lys Leu Ser Val Pro Asn Leu Tyr Val Trp
325 330 335

Leu Cys Met Phe Tyr Cys Phe Phe His Leu Trp Leu Asn Ile Leu Ala
340 345 350

Glu Leu Leu Arg Phe Gly Asp Arg Glu Phe Tyr Lys Asp Trp Trp Asn
355 360 365

Ala Arg Thr Val Glu Glu Tyr Trp Arg Met Trp Asn Met Pro Val His
370 375 380

Lys Trp Met Val Arg His Ile Tyr Phe Pro Cys Leu Arg Asn Lys Ile
385 390 395 400

Pro Lys Trp Ala Ala Leu Leu Ile Ala Phe Phe Val Ser Ala Val Phe
405 410 415

His Glu Leu Cys Ile Ala Val Pro Cys His Met Phe Lys Leu Trp Ala
420 425 430

Phe Ile Gly Ile Met Phe Gln Val Pro Leu Val Val Ile Thr Lys Phe
435 440 445

Leu Gln Asn Lys Phe Lys Ser Ser Met Val Gly Asn Met Ile Phe Trp
450 455 460

Leu Phe Phe Ser Ile Leu Gly Gln Pro Met Cys Val Leu Leu Tyr Tyr
465 470 475 480

His Asp Leu Met Asn Arg Lys Gly Lys Thr Glu Arg Arg
485 490

<210> SEQ ID NO 59
<211> LENGTH: 554
<212> TYPE: PRT
<213> ORGANISM: Artificial Sequence
<220> FEATURE:
<223> OTHER INFORMATION: A. thaliana

<400> SEQUENCE: 59

Met Ala Ile Leu Asp Ser Ala Gly Val Thr Thr Val Thr Glu Asn Gly
1 5 10 15

Gly Gly Glu Phe Val Asp Leu Asp Arg Leu Arg Arg Arg Lys Ser Arg
20 25 30

Ser Asp Ser Ser Asn Gly Leu Leu Leu Ser Gly Ser Asp Asn Asn Ser
35 40 45

Pro Ser Asp Asp Val Gly Ala Pro Ala Asp Val Arg Asp Arg Ile Asp
50 55 60

Ser Val Val Asn Asp Asp Ala Gln Gly Thr Ala Asn Leu Ala Gly Asp
65 70 75 80

Asn Asn Gly Gly Gly Asp Asn Asn Gly Gly Gly Arg Gly Gly Gly Glu
85 90 95

Gly Arg Gly Asn Ala Asp Ala Thr Phe Thr Tyr Arg Pro Ser Val Pro
100 105 110

Ala His Arg Arg Ala Arg Glu Ser Pro Leu Ser Ser Asp Ala Ile Phe
115 120 125

Lys Gln Ser His Ala Gly Leu Phe Asn Leu Cys Val Val Val Leu Ile
130 135 140

```
Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser Ala Lys Gly Glu Leu Arg Gly His
        515                 520                 525

Pro Phe Glu Gly Lys Pro Ile Pro Asn Pro Leu Leu Gly Leu Asp Ser
    530                 535                 540

Thr Arg Thr Gly His His His His His His
545                 550
```

<210> SEQ ID NO 60
<211> LENGTH: 564
<212> TYPE: PRT
<213> ORGANISM: Artificial Sequence
<220> FEATURE:
<223> OTHER INFORMATION: Artificial

<400> SEQUENCE: 60

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Arg Gln Ser His Ala Gly Leu Leu Asn Leu Cys Ile Val Val Leu Val
    130                 135                 140

Ala Val Asn Ser Arg Leu Ile Ile Glu Asn Leu Met Lys Tyr Gly Leu
145                 150                 155                 160

Leu Ile Arg Ala Gly Phe Trp Phe Ser Gly Thr Ser Leu Ala Asp Trp
                165                 170                 175

Pro Leu Leu Met Cys Cys Leu Thr Leu Pro Thr Phe Pro Leu Ala Ala
            180                 185                 190

Leu Met Val Glu Lys Leu Ala Gln Arg Lys Leu Ile Ser Lys His Val
        195                 200                 205

Val Ile Leu Leu His Ile Val Ile Thr Thr Ser Val Leu Val Tyr Pro
    210                 215                 220

Val Val Val Ile Leu Lys Cys Asp Ser Ala Val Leu Ser Gly Phe Val
225                 230                 235                 240

Leu Met Phe Leu Ala Ser Ile Ile Trp Leu Lys Leu Val Ser Phe Ala
                245                 250                 255

His Thr Asn Tyr Asp Ile Arg Met Leu Ser Lys Ser Ile Glu Lys Gly
            260                 265                 270

Val Thr His Asp Ile Ser Ile Asp Pro Glu Asn Ile Lys Trp Pro Thr
        275                 280                 285

Phe Lys Arg Leu Ser Tyr Phe Met Leu Ala Pro Thr Leu Cys Tyr Gln
    290                 295                 300

Pro Ser Tyr Pro Arg Thr Thr Tyr Ile Arg Lys Gly Trp Val Val Arg
305                 310                 315                 320

Gln Leu Ile Lys Cys Leu Val Phe Thr Gly Leu Met Gly Phe Ile Ile
                325                 330                 335

Glu Gln Tyr Ile Asn Pro Ile Val Lys Asn Ser Lys His Pro Leu Lys
            340                 345                 350

Gly Asn Phe Leu Asn Ala Ile Glu Arg Val Leu Lys Leu Ser Val Pro
        355                 360                 365

Thr Leu Tyr Val Trp Leu Cys Met Phe Tyr Cys Phe Phe His Leu Trp
```

```
    370                 375                 380

Leu Asn Ile Leu Ala Glu Leu Leu Cys Phe Gly Asp Arg Glu Phe Tyr
385                 390                 395                 400

Lys Asp Trp Trp Asn Ala Lys Thr Val Glu Glu Tyr Trp Arg Met Trp
                405                 410                 415

Asn Met Pro Val His Lys Trp Val Ile Arg His Ile Tyr Phe Pro Cys
            420                 425                 430

Ile Arg Asn Gly Phe Ser Lys Gly Val Ala Ile Leu Ile Ser Phe Leu
        435                 440                 445

Val Ser Ala Ala Phe His Glu Leu Cys Val Ala Val Pro Cys His Ile
    450                 455                 460

Phe Lys Phe Trp Ala Phe Ile Gly Ile Met Phe Gln Ile Pro Leu Val
465                 470                 475                 480

Phe Leu Thr Lys Tyr Leu Gln Asp Lys Phe Asn Asn Thr Met Val Gly
                485                 490                 495

Asn Met Ile Phe Trp Phe Phe Phe Ser Ile Leu Gly Gln Pro Met Cys
            500                 505                 510

Val Leu Leu Tyr Tyr His Asp Val Met Asn Arg Gln Gln Ala Gln Thr
        515                 520                 525

Asn Arg Ala Lys Gly Glu Leu Arg Gly His Pro Phe Glu Gly Lys Pro
    530                 535                 540

Ile Pro Asn Pro Leu Leu Gly Leu Asp Ser Thr Arg Thr Gly His His
545                 550                 555                 560

His His His His


<210> SEQ ID NO 61
<211> LENGTH: 562
<212> TYPE: PRT
<213> ORGANISM: Artificial Sequence
<220> FEATURE:
<223> OTHER INFORMATION: Artifical

<400> SEQUENCE: 61

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Ile Val Val Leu Val
    130                 135                 140

Ala Val Asn Ser Arg Leu Ile Ile Glu Asn Leu Met Lys Tyr Gly Leu
145                 150                 155                 160

Leu Ile Arg Ala Gly Phe Trp Phe Asn Asp Lys Ser Leu Arg Asp Trp
                165                 170                 175
```

```
Pro Leu Leu Met Cys Cys Leu Ser Leu Pro Ala Phe Pro Leu Gly Ala
            180                 185                 190

Phe Ala Val Glu Lys Leu Ala Phe Asn Asn Val Ile Thr Asp Ala Val
        195                 200                 205

Ala Thr Cys Leu His Ile Phe Leu Ser Thr Thr Glu Ile Val Tyr Pro
    210                 215                 220

Val Leu Val Ile Leu Lys Cys Asp Ser Ala Val Leu Ser Gly Phe Leu
225                 230                 235                 240

Leu Ile Phe Ile Ala Cys Ile Val Trp Leu Lys Leu Val Ser Phe Ala
                245                 250                 255

His Thr Asn His Asp Ile Arg Gln Leu Thr Met Gly Gly Lys Lys Val
            260                 265                 270

Asp Asn Glu Leu Ser Thr Val Asp Met Asp Asn Leu Gln Pro Pro Thr
        275                 280                 285

Leu Gly Asn Leu Ile Tyr Phe Met Met Ala Pro Thr Leu Cys Tyr Gln
    290                 295                 300

Pro Ser Tyr Pro Arg Thr Ser Cys Val Arg Lys Gly Trp Leu Ile Arg
305                 310                 315                 320

Gln Ile Ile Leu Tyr Leu Ile Phe Thr Gly Leu Gln Gly Phe Ile Ile
                325                 330                 335

Glu Gln Tyr Ile Asn Pro Ile Val Val Asn Ser Gln His Pro Leu Lys
            340                 345                 350

Gly Gly Leu Leu Asn Ala Val Glu Thr Val Leu Lys Leu Ser Leu Pro
        355                 360                 365

Asn Val Tyr Leu Trp Leu Cys Met Phe Tyr Ala Phe Phe His Leu Trp
    370                 375                 380

Leu Ser Ile Leu Ala Glu Ile Leu Arg Phe Gly Asp Arg Glu Phe Tyr
385                 390                 395                 400

Lys Asp Trp Trp Asn Ala Lys Thr Ile Asp Glu Tyr Trp Arg Lys Trp
                405                 410                 415

Asn Met Pro Val His Lys Trp Val Val Arg His Ile Tyr Phe Pro Cys
            420                 425                 430

Met Arg Asn Gly Ile Ser Lys Glu Val Ala Val Leu Ile Ser Phe Leu
        435                 440                 445

Val Ser Ala Val Leu His Glu Ile Cys Val Ala Val Pro Cys Arg Ile
    450                 455                 460

Leu Lys Phe Trp Ala Phe Leu Gly Ile Met Leu Gln Ile Pro Leu Ile
465                 470                 475                 480

Val Leu Thr Ala Tyr Leu Lys Ser Lys Phe Arg Asp Thr Met Val Gly
                485                 490                 495

Asn Met Ile Phe Trp Phe Phe Phe Cys Ile Tyr Gly Gln Pro Met Cys
            500                 505                 510

Leu Leu Leu Tyr Tyr His Asp Val Met Asn Arg Ile Glu Lys Ala Arg
        515                 520                 525

Ala Lys Gly Glu Leu Arg Gly His Pro Phe Glu Gly Lys Pro Ile Pro
    530                 535                 540

Asn Pro Leu Leu Gly Leu Asp Ser Thr Arg Thr Gly His His His His
545                 550                 555                 560

His His
```

<210> SEQ ID NO 62
<211> LENGTH: 563
<212> TYPE: PRT

<213> ORGANISM: Artificial Sequence
<220> FEATURE:
<223> OTHER INFORMATION: Artifical

<400> SEQUENCE: 62

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Arg Gln Ser His Ala Gly Leu Leu Asn Leu Cys Ile Val Val Leu Ile
    130                 135                 140

Ala Val Asn Ser Arg Leu Ile Ile Glu Asn Leu Met Lys Tyr Gly Leu
145                 150                 155                 160

Leu Ile Arg Ala Gly Phe Trp Phe Ser Ala Arg Ser Leu Gly Asp Trp
                165                 170                 175

Pro Leu Leu Met Cys Cys Leu Thr Leu Pro Val Phe Pro Leu Val Ala
            180                 185                 190

Leu Met Ala Glu Lys Leu Ile Thr Arg Lys Leu Ile Gly Glu His Val
        195                 200                 205

Val Ile Leu Leu His Ile Ile Ile Thr Thr Ser Ala Ile Val Tyr Pro
    210                 215                 220

Val Val Val Thr Leu Lys Cys Asp Ser Ala Val Leu Ser Gly Phe Val
225                 230                 235                 240

Leu Met Phe Leu Ala Ser Ile Met Trp Met Lys Leu Val Ser Tyr Ala
                245                 250                 255

His Thr Asn Tyr Asp Ile Arg Val Leu Ser Lys Ser Thr Glu Lys Gly
            260                 265                 270

Ala Ala Tyr Gly Asn Tyr Val Asp Pro Glu Asn Met Lys Asp Pro Thr
        275                 280                 285

Phe Lys Ser Leu Val Tyr Phe Met Leu Ala Pro Thr Leu Cys Tyr Gln
    290                 295                 300

Pro Thr Tyr Pro Gln Thr Thr Cys Ile Arg Lys Gly Trp Val Thr Gln
305                 310                 315                 320

Gln Leu Ile Lys Cys Val Val Phe Thr Gly Leu Met Gly Phe Ile Ile
                325                 330                 335

Glu Gln Tyr Ile Asn Pro Ile Val Lys Asn Ser Lys His Pro Leu Lys
            340                 345                 350

Gly Asn Phe Leu Asn Ala Ile Glu Arg Val Leu Lys Leu Ser Val Pro
        355                 360                 365

Thr Leu Tyr Val Trp Leu Cys Met Phe Tyr Cys Phe Phe His Leu Trp
    370                 375                 380

Leu Asn Ile Val Ala Glu Leu Leu Cys Phe Gly Asp Arg Glu Phe Tyr
```

```
385                 390                 395                 400

Lys Asp Trp Trp Asn Ala Lys Thr Val Glu Glu Tyr Trp Arg Met Trp
                405                 410                 415

Asn Met Pro Val His Lys Trp Ile Ile Arg His Ile Tyr Phe Pro Cys
            420                 425                 430

Ile Arg Lys Gly Phe Ser Arg Gly Val Ala Ile Leu Ile Ser Phe Leu
        435                 440                 445

Val Ser Ala Val Phe His Glu Ile Cys Ile Ala Val Pro Cys His Ile
    450                 455                 460

Phe Lys Phe Trp Ala Phe Ser Gly Ile Met Phe Gln Ile Pro Leu Val
465                 470                 475                 480

Phe Leu Thr Arg Tyr Leu His Ala Thr Phe Lys His Val Met Val Gly
                485                 490                 495

Asn Met Ile Phe Trp Phe Phe Phe Ser Ile Val Gly Gln Pro Met Cys
            500                 505                 510

Val Leu Leu Tyr Tyr His Asp Val Met Asn Arg Gln Ala Gln Ala Ser
        515                 520                 525

Arg Ala Lys Gly Glu Leu Arg Gly His Pro Phe Glu Gly Lys Pro Ile
    530                 535                 540

Pro Asn Pro Leu Leu Gly Leu Asp Ser Thr Arg Thr Gly His His His
545                 550                 555                 560

His His His


<210> SEQ ID NO 63
<211> LENGTH: 562
<212> TYPE: PRT
<213> ORGANISM: Artificial Sequence
<220> FEATURE:
<223> OTHER INFORMATION: Artifical

<400> SEQUENCE: 63

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Ile Val Val Leu Val
    130                 135                 140

Ala Val Asn Ser Arg Leu Ile Ile Glu Asn Leu Met Lys Tyr Gly Leu
145                 150                 155                 160

Leu Ile Arg Ser Gly Phe Trp Phe Asn Ala Thr Ser Leu Arg Asp Trp
                165                 170                 175

Pro Leu Leu Met Cys Cys Leu Ser Leu Pro Ile Phe Pro Leu Gly Ala
            180                 185                 190
```

Phe Ala Val Glu Lys Leu Ala Phe Asn Asn Leu Ile Ser Asp Pro Ala
195 200 205

Thr Thr Cys Phe His Ile Leu Phe Thr Thr Phe Glu Ile Val Tyr Pro
210 215 220

Val Leu Val Ile Leu Lys Cys Asp Ser Ala Val Leu Ser Gly Phe Val
225 230 235 240

Leu Met Phe Ile Ala Cys Ile Val Trp Leu Lys Leu Val Ser Phe Ala
245 250 255

His Thr Asn His Asp Ile Arg Lys Leu Ile Thr Ser Gly Lys Lys Val
260 265 270

Asp Asn Glu Leu Thr Ala Ala Gly Ile Asp Asn Leu Gln Ala Pro Thr
275 280 285

Leu Gly Ser Leu Thr Tyr Phe Met Met Ala Pro Thr Leu Cys Tyr Gln
290 295 300

Pro Ser Tyr Pro Arg Thr Pro Tyr Val Arg Lys Gly Trp Leu Val Arg
305 310 315 320

Gln Val Ile Leu Tyr Leu Ile Phe Thr Gly Leu Gln Gly Phe Ile Ile
325 330 335

Glu Gln Tyr Ile Asn Pro Ile Val Val Asn Ser Gln His Pro Leu Met
340 345 350

Gly Gly Leu Leu Asn Ala Val Glu Thr Val Leu Lys Leu Ser Leu Pro
355 360 365

Asn Val Tyr Leu Trp Leu Cys Met Phe Tyr Cys Leu Phe His Leu Trp
370 375 380

Leu Asn Ile Leu Ala Glu Ile Leu Arg Phe Gly Asp Arg Glu Phe Tyr
385 390 395 400

Lys Asp Trp Trp Asn Ala Lys Thr Ile Asp Glu Tyr Trp Arg Lys Trp
405 410 415

Asn Met Pro Val His Lys Trp Ile Val Arg His Ile Tyr Phe Pro Cys
420 425 430

Met Arg Asn Gly Ile Ser Lys Glu Val Ala Val Phe Ile Ser Phe Phe
435 440 445

Val Ser Ala Val Leu His Glu Leu Cys Val Ala Val Pro Cys His Ile
450 455 460

Leu Lys Phe Trp Ala Phe Leu Gly Ile Met Leu Gln Ile Pro Leu Ile
465 470 475 480

Ile Leu Thr Ser Tyr Leu Lys Asn Lys Phe Ser Asp Thr Met Val Gly
485 490 495

Asn Met Ile Phe Trp Phe Phe Phe Cys Ile Tyr Gly Gln Pro Met Cys
500 505 510

Val Leu Leu Tyr Tyr His Asp Val Met Asn Arg Thr Glu Lys Ala Lys
515 520 525

Ala Lys Gly Glu Leu Arg Gly His Pro Phe Glu Gly Lys Pro Ile Pro
530 535 540

Asn Pro Leu Leu Gly Leu Asp Ser Thr Arg Thr Gly His His His His
545 550 555 560

His His

<210> SEQ ID NO 64
<211> LENGTH: 560
<212> TYPE: PRT
<213> ORGANISM: Artificial Sequence
<220> FEATURE:
<223> OTHER INFORMATION: Artifical

<400> SEQUENCE: 64

Met Ala Ile Leu Asp Ser Ala Gly Val Thr Thr Val Thr Glu Asn Gly
1 5 10 15

Gly Gly Glu Phe Val Asp Leu Asp Arg Leu Arg Arg Arg Lys Ser Arg
20 25 30

Ser Asp Ser Ser Asn Gly Leu Leu Leu Ser Gly Ser Asp Asn Asn Ser
35 40 45

Pro Ser Asp Asp Val Gly Ala Pro Ala Asp Val Arg Asp Arg Ile Asp
50 55 60

Ser Val Val Asn Asp Asp Ala Gln Gly Thr Ala Asn Leu Ala Gly Asp
65 70 75 80

Asn Asn Gly Gly Gly Asp Asn Asn Gly Gly Gly Arg Gly Gly Gly Glu
85 90 95

Gly Arg Gly Asn Ala Asp Ala Thr Phe Thr Tyr Arg Pro Ser Val Pro
100 105 110

Ala His Arg Arg Ala Arg Glu Ser Pro Leu Ser Ser Asp Ala Ile Phe
115 120 125

Lys Gln Ser His Ala Gly Leu Phe Asn Leu Cys Ile Val Val Leu Ile
130 135 140

Ala Val Asn Ser Arg Leu Ile Ile Glu Asn Leu Met Lys Tyr Gly Trp
145 150 155 160

Leu Ile Asp Thr Gly Phe Trp Phe Ser Ser Arg Ser Leu Gly Asp Trp
165 170 175

Ser Ile Phe Met Cys Cys Leu Thr Leu Pro Ile Phe Pro Leu Ala Ala
180 185 190

Phe Ile Val Glu Lys Leu Val Gln Arg Asn His Ile Ser Glu Leu Val
195 200 205

Ala Val Leu Leu His Val Ile Val Ser Thr Ala Ala Val Leu Tyr Pro
210 215 220

Val Ile Val Ile Leu Thr Cys Asp Ser Val Tyr Met Ser Gly Val Val
225 230 235 240

Leu Met Leu Phe Gly Cys Ile Met Trp Leu Lys Leu Val Ser Tyr Ala
245 250 255

His Thr Ser Ser Asp Ile Arg Thr Leu Ala Lys Ser Gly Tyr Lys Gly
260 265 270

Asp Ala His Pro Asn Ser Thr Ile Val Ser Cys Ser Tyr Asp Val Ser
275 280 285

Leu Lys Ser Leu Ala Tyr Phe Met Val Ala Pro Thr Leu Cys Tyr Gln
290 295 300

Pro Ser Tyr Pro Arg Ser Ser Cys Ile Arg Lys Gly Trp Val Val Arg
305 310 315 320

Gln Phe Val Lys Leu Ile Val Phe Ile Gly Leu Met Gly Phe Ile Ile
325 330 335

Glu Gln Tyr Ile Asn Pro Ile Val Arg Asn Ser Lys His Pro Leu Lys
340 345 350

Gly Asp Phe Leu Tyr Ala Ile Glu Arg Val Leu Lys Leu Ser Val Pro
355 360 365

Asn Leu Tyr Val Trp Leu Cys Met Phe Tyr Ser Phe Phe His Leu Trp
370 375 380

Leu Asn Ile Leu Ala Glu Leu Leu Arg Phe Gly Asp Arg Glu Phe Tyr
385 390 395 400

Lys Asp Trp Trp Asn Ala Lys Thr Val Ala Glu Tyr Trp Lys Met Trp

```
                405                 410                 415

Asn Met Pro Val His Arg Trp Met Val Arg His Leu Tyr Phe Pro Cys
            420                 425                 430

Leu Arg Asn Gly Ile Pro Lys Glu Gly Ala Ile Ile Ile Ala Phe Leu
        435                 440                 445

Val Ser Gly Ala Phe His Glu Leu Cys Ile Ala Val Pro Cys His Val
    450                 455                 460

Phe Lys Leu Trp Ala Phe Ile Gly Ile Met Phe Gln Val Pro Leu Val
465                 470                 475                 480

Leu Ile Thr Asn Tyr Leu Gln Glu Lys Phe Ser Asn Ser Met Val Gly
                485                 490                 495

Asn Met Ile Phe Trp Phe Ile Phe Cys Ile Leu Gly Gln Pro Met Cys
            500                 505                 510

Val Leu Leu Tyr Tyr His Asp Leu Ile Asn Leu Lys Glu Lys Ala Lys
        515                 520                 525

Gly Glu Leu Arg Gly His Pro Phe Glu Gly Lys Pro Ile Pro Asn Pro
    530                 535                 540

Leu Leu Gly Leu Asp Ser Thr Arg Thr Gly His His His His His His
545                 550                 555                 560


<210> SEQ ID NO 65
<211> LENGTH: 511
<212> TYPE: PRT
<213> ORGANISM: Artificial Sequence
<220> FEATURE:
<223> OTHER INFORMATION: Artifical

<400> SEQUENCE: 65

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
    130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Val Ile Leu
                165                 170                 175

Lys Cys Asp Ser Ala Val Leu Ser Gly Phe Val Leu Met Phe Leu Ala
            180                 185                 190

Ser Ile Ile Trp Leu Lys Leu Val Ser Phe Ala His Thr Asn Tyr Asp
        195                 200                 205

Ile Arg Met Leu Ser Lys Ser Ile Glu Lys Gly Val Thr His Asp Ile
```

```
    210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
            260                 265                 270

Leu Val Phe Thr Gly Leu Met Gly Phe Ile Ile Glu Gln Tyr Ile Asn
        275                 280                 285

Pro Ile Val Lys Asn Ser Lys His Pro Leu Lys Gly Asn Phe Leu Asn
    290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
        355                 360                 365

Lys Trp Val Ile Arg His Ile Tyr Phe Pro Cys Ile Arg Asn Gly Phe
    370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
            420                 425                 430

Leu Gln Asp Lys Phe Asn Asn Thr Met Val Gly Asn Met Ile Phe Trp
        435                 440                 445

Phe Phe Phe Ser Ile Leu Gly Gln Pro Met Cys Val Leu Leu Tyr Tyr
    450                 455                 460

His Asp Val Met Asn Arg Gln Gln Ala Gln Thr Asn Arg Ala Lys Gly
465                 470                 475                 480

Glu Leu Arg Gly His Pro Phe Glu Gly Lys Pro Ile Pro Asn Pro Leu
                485                 490                 495

Leu Gly Leu Asp Ser Thr Arg Thr Gly His His His His His His
            500                 505                 510


<210> SEQ ID NO 66
<211> LENGTH: 501
<212> TYPE: PRT
<213> ORGANISM: Artificial Sequence
<220> FEATURE:
<223> OTHER INFORMATION: Artifical

<400> SEQUENCE: 66

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Lys Gln Ser His Ala
```

-continued

```
65                  70                  75                  80

Gly Leu Phe Asn Leu Cys Val Val Val Leu Ile Ala Val Asn Ser Arg
                85                  90                  95

Leu Ile Ile Glu Asn Leu Met Lys Tyr Gly Trp Leu Ile Arg Thr Asp
            100                 105                 110

Phe Trp Phe Ser Ser Arg Ser Leu Arg Asp Trp Pro Leu Phe Met Cys
        115                 120                 125

Cys Ile Ser Leu Ser Ile Phe Pro Leu Ala Ala Phe Thr Val Glu Lys
    130                 135                 140

Leu Val Leu Gln Lys Tyr Ile Ser Glu Pro Val Val Ile Phe Leu His
145                 150                 155                 160

Ile Ile Ile Thr Met Thr Glu Val Leu Tyr Pro Val Tyr Val Thr Leu
                165                 170                 175

Arg Cys Asp Ser Ala Phe Leu Ser Gly Val Thr Leu Met Leu Leu Thr
            180                 185                 190

Cys Ile Val Trp Leu Lys Leu Val Ser Tyr Ala His Thr Ser Tyr Asp
        195                 200                 205

Ile Arg Ser Leu Ala Asn Ala Ala Asp Lys Ala Asn Pro Glu Val Ser
    210                 215                 220

Tyr Tyr Val Ser Leu Lys Ser Leu Ala Tyr Phe Met Val Ala Pro Thr
225                 230                 235                 240

Leu Cys Tyr Gln Pro Ser Tyr Pro Arg Ser Ala Cys Ile Arg Lys Gly
                245                 250                 255

Trp Val Ala Arg Gln Phe Ala Lys Leu Val Ile Phe Thr Gly Phe Met
            260                 265                 270

Gly Phe Ile Ile Glu Gln Tyr Ile Asn Pro Ile Val Arg Asn Ser Lys
        275                 280                 285

His Pro Leu Lys Gly Asp Leu Leu Tyr Ala Ile Glu Arg Val Leu Lys
    290                 295                 300

Leu Ser Val Pro Asn Leu Tyr Val Trp Leu Cys Met Phe Tyr Cys Phe
305                 310                 315                 320

Phe His Leu Trp Leu Asn Ile Leu Ala Glu Leu Leu Cys Phe Gly Asp
                325                 330                 335

Arg Glu Phe Tyr Lys Asp Trp Trp Asn Ala Lys Ser Val Gly Asp Tyr
            340                 345                 350

Trp Arg Met Trp Asn Met Pro Val His Lys Trp Met Val Arg His Ile
        355                 360                 365

Tyr Phe Pro Cys Leu Arg Ser Lys Ile Pro Lys Thr Leu Ala Ile Ile
    370                 375                 380

Ile Ala Phe Leu Val Ser Ala Val Phe His Glu Leu Cys Ile Ala Val
385                 390                 395                 400

Pro Cys Arg Leu Phe Lys Leu Trp Ala Phe Leu Gly Ile Met Phe Gln
                405                 410                 415

Val Pro Leu Val Phe Ile Thr Asn Tyr Leu Gln Glu Arg Phe Gly Ser
            420                 425                 430

Thr Val Gly Asn Met Ile Phe Trp Phe Ile Phe Cys Ile Phe Gly Gln
        435                 440                 445

Pro Met Cys Val Leu Leu Tyr Tyr His Asp Leu Met Asn Arg Lys Gly
    450                 455                 460

Ser Met Ser Ala Lys Gly Glu Leu Arg Gly His Pro Phe Glu Gly Lys
465                 470                 475                 480

Pro Ile Pro Asn Pro Leu Leu Gly Leu Asp Ser Thr Arg Thr Gly His
                485                 490                 495
```

His His His His His
500

<210> SEQ ID NO 67
<211> LENGTH: 509
<212> TYPE: PRT
<213> ORGANISM: Artificial Sequence
<220> FEATURE:
<223> OTHER INFORMATION: Artifical

<400> SEQUENCE: 67

Met Ala Pro Pro Pro Ser Leu Ala Pro Asp Arg Gly Gly Gly Glu Pro
1 5 10 15

Asp Asp Ala Leu Arg Leu Arg Ala Arg Ala Ala Ala Ala Ala Gly Asp
20 25 30

Ala Pro Ala Pro Gln Gln Gln Gln Glu Gln Arg His Gln Glu Gln Gln
35 40 45

Gln Gln Leu Leu Trp Tyr Arg Ala Ser Ala Pro Ala His Arg Arg Val
50 55 60

Arg Glu Ser Pro Leu Ser Ser Asp Ala Ile Phe Lys Gln Ser His Ala
65 70 75 80

Gly Leu Phe Asn Leu Cys Ile Val Val Leu Val Ala Val Asn Ser Arg
85 90 95

Leu Ile Ile Glu Asn Leu Met Lys Tyr Gly Leu Leu Ile Arg Ala Gly
100 105 110

Phe Trp Phe Asn Asp Lys Ser Leu Arg Asp Trp Pro Leu Leu Met Cys
115 120 125

Cys Leu Ser Leu Pro Ala Phe Pro Leu Gly Ala Phe Ala Val Glu Lys
130 135 140

Leu Ala Phe Asn Asn Val Ile Thr Asp Ala Val Ala Thr Cys Leu His
145 150 155 160

Ile Phe Leu Ser Thr Thr Glu Ile Val Tyr Pro Val Leu Val Ile Leu
165 170 175

Lys Cys Asp Ser Ala Val Leu Ser Gly Phe Leu Leu Ile Phe Ile Ala
180 185 190

Cys Ile Val Trp Leu Lys Leu Val Ser Phe Ala His Thr Asn His Asp
195 200 205

Ile Arg Gln Leu Thr Met Gly Gly Lys Lys Val Asp Asn Glu Leu Ser
210 215 220

Thr Val Asp Met Asp Asn Leu Gln Pro Pro Thr Leu Gly Asn Leu Ile
225 230 235 240

Tyr Phe Met Met Ala Pro Thr Leu Cys Tyr Gln Pro Ser Tyr Pro Arg
245 250 255

Thr Ser Cys Val Arg Lys Gly Trp Leu Ile Arg Gln Ile Ile Leu Tyr
260 265 270

Leu Ile Phe Thr Gly Leu Gln Gly Phe Ile Ile Glu Gln Tyr Ile Asn
275 280 285

Pro Ile Val Val Asn Ser Gln His Pro Leu Lys Gly Gly Leu Leu Asn
290 295 300

Ala Val Glu Thr Val Leu Lys Leu Ser Leu Pro Asn Val Tyr Leu Trp
305 310 315 320

Leu Cys Met Phe Tyr Ala Phe Phe His Leu Trp Leu Ser Ile Leu Ala
325 330 335

Glu Ile Leu Arg Phe Gly Asp Arg Glu Phe Tyr Lys Asp Trp Trp Asn
340 345 350

```
Ala Lys Thr Ile Asp Glu Tyr Trp Arg Lys Trp Asn Met Pro Val His
        355                 360                 365

Lys Trp Val Val Arg His Ile Tyr Phe Pro Cys Met Arg Asn Gly Ile
    370                 375                 380

Ser Lys Glu Val Ala Val Leu Ile Ser Phe Leu Val Ser Ala Val Leu
385                 390                 395                 400

His Glu Ile Cys Val Ala Val Pro Cys Arg Ile Leu Lys Phe Trp Ala
                405                 410                 415

Phe Leu Gly Ile Met Leu Gln Ile Pro Leu Ile Val Leu Thr Ala Tyr
            420                 425                 430

Leu Lys Ser Lys Phe Arg Asp Thr Met Val Gly Asn Met Ile Phe Trp
        435                 440                 445

Phe Phe Phe Cys Ile Tyr Gly Gln Pro Met Cys Leu Leu Leu Tyr Tyr
    450                 455                 460

His Asp Val Met Asn Arg Ile Glu Lys Ala Arg Ala Lys Gly Glu Leu
465                 470                 475                 480

Arg Gly His Pro Phe Glu Gly Lys Pro Ile Pro Asn Pro Leu Leu Gly
                485                 490                 495

Leu Asp Ser Thr Arg Thr Gly His His His His His His
            500                 505
```

<210> SEQ ID NO 68
<211> LENGTH: 510
<212> TYPE: PRT
<213> ORGANISM: Artificial Sequence
<220> FEATURE:
<223> OTHER INFORMATION: Artifical

<400> SEQUENCE: 68

```
Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Ile Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Ala Arg Ser Leu Gly Asp Trp Pro Leu Leu Met Cys
        115                 120                 125

Cys Leu Thr Leu Pro Val Phe Pro Leu Val Ala Leu Met Ala Glu Lys
    130                 135                 140

Leu Ile Thr Arg Lys Leu Ile Gly Glu His Val Val Ile Leu Leu His
145                 150                 155                 160

Ile Ile Ile Thr Thr Ser Ala Ile Val Tyr Pro Val Val Val Thr Leu
                165                 170                 175

Lys Cys Asp Ser Ala Val Leu Ser Gly Phe Val Leu Met Phe Leu Ala
            180                 185                 190

Ser Ile Met Trp Met Lys Leu Val Ser Tyr Ala His Thr Asn Tyr Asp
        195                 200                 205
```

```
Ile Arg Val Leu Ser Lys Ser Thr Glu Lys Gly Ala Ala Tyr Gly Asn
    210                 215                 220

Tyr Val Asp Pro Glu Asn Met Lys Asp Pro Thr Phe Lys Ser Leu Val
225                 230                 235                 240

Tyr Phe Met Leu Ala Pro Thr Leu Cys Tyr Gln Pro Thr Tyr Pro Gln
                245                 250                 255

Thr Thr Cys Ile Arg Lys Gly Trp Val Thr Gln Gln Leu Ile Lys Cys
            260                 265                 270

Val Val Phe Thr Gly Leu Met Gly Phe Ile Ile Glu Gln Tyr Ile Asn
        275                 280                 285

Pro Ile Val Lys Asn Ser Lys His Pro Leu Lys Gly Asn Phe Leu Asn
    290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Val Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
        355                 360                 365

Lys Trp Ile Ile Arg His Ile Tyr Phe Pro Cys Ile Arg Lys Gly Phe
    370                 375                 380

Ser Arg Gly Val Ala Ile Leu Ile Ser Phe Leu Val Ser Ala Val Phe
385                 390                 395                 400

His Glu Ile Cys Ile Ala Val Pro Cys His Ile Phe Lys Phe Trp Ala
                405                 410                 415

Phe Ser Gly Ile Met Phe Gln Ile Pro Leu Val Phe Leu Thr Arg Tyr
            420                 425                 430

Leu His Ala Thr Phe Lys His Val Met Val Gly Asn Met Ile Phe Trp
        435                 440                 445

Phe Phe Phe Ser Ile Val Gly Gln Pro Met Cys Val Leu Leu Tyr Tyr
    450                 455                 460

His Asp Val Met Asn Arg Gln Ala Gln Ala Ser Arg Ala Lys Gly Glu
465                 470                 475                 480

Leu Arg Gly His Pro Phe Glu Gly Lys Pro Ile Pro Asn Pro Leu Leu
                485                 490                 495

Gly Leu Asp Ser Thr Arg Thr Gly His His His His His His
            500                 505                 510
```

<210> SEQ ID NO 69
<211> LENGTH: 509
<212> TYPE: PRT
<213> ORGANISM: Artificial Sequence
<220> FEATURE:
<223> OTHER INFORMATION: Artifical

<400> SEQUENCE: 69

```
Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60
```

```
Arg Glu Ser Pro Leu Ser Ser Asp Ala Ile Phe Lys Gln Ser His Ala
65                  70                  75                  80

Gly Leu Phe Asn Leu Cys Ile Val Val Leu Val Ala Val Asn Ser Arg
                85                  90                  95

Leu Ile Ile Glu Asn Leu Met Lys Tyr Gly Leu Leu Ile Arg Ser Gly
            100                 105                 110

Phe Trp Phe Asn Ala Thr Ser Leu Arg Asp Trp Pro Leu Leu Met Cys
        115                 120                 125

Cys Leu Ser Leu Pro Ile Phe Pro Leu Gly Ala Phe Ala Val Glu Lys
    130                 135                 140

Leu Ala Phe Asn Asn Leu Ile Ser Asp Pro Ala Thr Thr Cys Phe His
145                 150                 155                 160

Ile Leu Phe Thr Thr Phe Glu Ile Val Tyr Pro Val Leu Val Ile Leu
                165                 170                 175

Lys Cys Asp Ser Ala Val Leu Ser Gly Phe Val Leu Met Phe Ile Ala
            180                 185                 190

Cys Ile Val Trp Leu Lys Leu Val Ser Phe Ala His Thr Asn His Asp
        195                 200                 205

Ile Arg Lys Leu Ile Thr Ser Gly Lys Lys Val Asp Asn Glu Leu Thr
    210                 215                 220

Ala Ala Gly Ile Asp Asn Leu Gln Ala Pro Thr Leu Gly Ser Leu Thr
225                 230                 235                 240

Tyr Phe Met Met Ala Pro Thr Leu Cys Tyr Gln Pro Ser Tyr Pro Arg
                245                 250                 255

Thr Pro Tyr Val Arg Lys Gly Trp Leu Val Arg Gln Val Ile Leu Tyr
            260                 265                 270

Leu Ile Phe Thr Gly Leu Gln Gly Phe Ile Ile Glu Gln Tyr Ile Asn
        275                 280                 285

Pro Ile Val Val Asn Ser Gln His Pro Leu Met Gly Gly Leu Leu Asn
    290                 295                 300

Ala Val Glu Thr Val Leu Lys Leu Ser Leu Pro Asn Val Tyr Leu Trp
305                 310                 315                 320

Leu Cys Met Phe Tyr Cys Leu Phe His Leu Trp Leu Asn Ile Leu Ala
                325                 330                 335

Glu Ile Leu Arg Phe Gly Asp Arg Glu Phe Tyr Lys Asp Trp Trp Asn
            340                 345                 350

Ala Lys Thr Ile Asp Glu Tyr Trp Arg Lys Trp Asn Met Pro Val His
        355                 360                 365

Lys Trp Ile Val Arg His Ile Tyr Phe Pro Cys Met Arg Asn Gly Ile
    370                 375                 380

Ser Lys Glu Val Ala Val Phe Ile Ser Phe Phe Val Ser Ala Val Leu
385                 390                 395                 400

His Glu Leu Cys Val Ala Val Pro Cys His Ile Leu Lys Phe Trp Ala
                405                 410                 415

Phe Leu Gly Ile Met Leu Gln Ile Pro Leu Ile Ile Leu Thr Ser Tyr
            420                 425                 430

Leu Lys Asn Lys Phe Ser Asp Thr Met Val Gly Asn Met Ile Phe Trp
        435                 440                 445

Phe Phe Phe Cys Ile Tyr Gly Gln Pro Met Cys Val Leu Leu Tyr Tyr
    450                 455                 460

His Asp Val Met Asn Arg Thr Glu Lys Ala Lys Ala Lys Gly Glu Leu
465                 470                 475                 480
```

```
Arg Gly His Pro Phe Glu Gly Lys Pro Ile Pro Asn Pro Leu Leu Gly
                485                 490                 495

Leu Asp Ser Thr Arg Thr Gly His His His His His His
            500                 505


<210> SEQ ID NO 70
<211> LENGTH: 507
<212> TYPE: PRT
<213> ORGANISM: Artificial Sequence
<220> FEATURE:
<223> OTHER INFORMATION: Artifical

<400> SEQUENCE: 70

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Lys Gln Ser His Ala
65                  70                  75                  80

Gly Leu Phe Asn Leu Cys Ile Val Val Leu Ile Ala Val Asn Ser Arg
                85                  90                  95

Leu Ile Ile Glu Asn Leu Met Lys Tyr Gly Trp Leu Ile Asp Thr Gly
            100                 105                 110

Phe Trp Phe Ser Ser Arg Ser Leu Gly Asp Trp Ser Ile Phe Met Cys
        115                 120                 125

Cys Leu Thr Leu Pro Ile Phe Pro Leu Ala Ala Phe Ile Val Glu Lys
    130                 135                 140

Leu Val Gln Arg Asn His Ile Ser Glu Leu Val Ala Val Leu Leu His
145                 150                 155                 160

Val Ile Val Ser Thr Ala Ala Val Leu Tyr Pro Val Ile Val Ile Leu
                165                 170                 175

Thr Cys Asp Ser Val Tyr Met Ser Gly Val Val Leu Met Leu Phe Gly
            180                 185                 190

Cys Ile Met Trp Leu Lys Leu Val Ser Tyr Ala His Thr Ser Ser Asp
        195                 200                 205

Ile Arg Thr Leu Ala Lys Ser Gly Tyr Lys Gly Asp Ala His Pro Asn
    210                 215                 220

Ser Thr Ile Val Ser Cys Ser Tyr Asp Val Ser Leu Lys Ser Leu Ala
225                 230                 235                 240

Tyr Phe Met Val Ala Pro Thr Leu Cys Tyr Gln Pro Ser Tyr Pro Arg
                245                 250                 255

Ser Ser Cys Ile Arg Lys Gly Trp Val Val Arg Gln Phe Val Lys Leu
            260                 265                 270

Ile Val Phe Ile Gly Leu Met Gly Phe Ile Ile Glu Gln Tyr Ile Asn
        275                 280                 285

Pro Ile Val Arg Asn Ser Lys His Pro Leu Lys Gly Asp Phe Leu Tyr
    290                 295                 300

Ala Ile Glu Arg Val Leu Lys Leu Ser Val Pro Asn Leu Tyr Val Trp
305                 310                 315                 320

Leu Cys Met Phe Tyr Ser Phe Phe His Leu Trp Leu Asn Ile Leu Ala
                325                 330                 335
```

-continued

```
Glu Leu Leu Arg Phe Gly Asp Arg Glu Phe Tyr Lys Asp Trp Trp Asn
            340                 345                 350

Ala Lys Thr Val Ala Glu Tyr Trp Lys Met Trp Asn Met Pro Val His
        355                 360                 365

Arg Trp Met Val Arg His Leu Tyr Phe Pro Cys Leu Arg Asn Gly Ile
    370                 375                 380

Pro Lys Glu Gly Ala Ile Ile Ile Ala Phe Leu Val Ser Gly Ala Phe
385                 390                 395                 400

His Glu Leu Cys Ile Ala Val Pro Cys His Val Phe Lys Leu Trp Ala
                405                 410                 415

Phe Ile Gly Ile Met Phe Gln Val Pro Leu Val Leu Ile Thr Asn Tyr
            420                 425                 430

Leu Gln Glu Lys Phe Ser Asn Ser Met Val Gly Asn Met Ile Phe Trp
        435                 440                 445

Phe Ile Phe Cys Ile Leu Gly Gln Pro Met Cys Val Leu Leu Tyr Tyr
    450                 455                 460

His Asp Leu Ile Asn Leu Lys Glu Lys Ala Lys Gly Glu Leu Arg Gly
465                 470                 475                 480

His Pro Phe Glu Gly Lys Pro Ile Pro Asn Pro Leu Leu Gly Leu Asp
                485                 490                 495

Ser Thr Arg Thr Gly His His His His His His
            500                 505


<210> SEQ ID NO 71
<211> LENGTH: 572
<212> TYPE: PRT
<213> ORGANISM: Artificial Sequence
<220> FEATURE:
<223> OTHER INFORMATION: Artifical

<400> SEQUENCE: 71

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Asn Asp Lys Ser Leu Arg Asp Trp Pro Leu Leu Met Cys Cys
            180                 185                 190
```

```
Leu Ser Leu Pro Ala Phe Pro Leu Gly Ala Phe Ala Val Glu Lys Leu
        195                 200                 205

Ala Phe Asn Asn Val Ile Thr Asp Ala Val Ala Thr Cys Leu His Ile
    210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255

Ile Val Trp Leu Lys Leu Val Ser Phe Ala His Thr Asn His Asp Ile
            260                 265                 270

Arg Gln Leu Thr Met Gly Gly Lys Lys Val Asp Asn Glu Leu Ser Thr
        275                 280                 285

Val Asp Met Asp Asn Leu Gln Pro Pro Thr Leu Gly Asn Leu Ile Tyr
    290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Lys Gly Gly Leu Leu Asn Ala
        355                 360                 365

Val Glu Thr Val Leu Lys Leu Ser Leu Pro Asn Val Tyr Leu Trp Leu
    370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Val Val Arg His Ile Tyr Phe Pro Cys Met Arg Asn Gly Ile Ser
        435                 440                 445

Lys Glu Val Ala Val Leu Ile Ser Phe Leu Val Ser Ala Val Leu His
    450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
        515                 520                 525

Asp Val Met Asn Arg Ile Glu Lys Ala Arg Ala Lys Gly Glu Leu Arg
    530                 535                 540

Gly His Pro Phe Glu Gly Lys Pro Ile Pro Asn Pro Leu Leu Gly Leu
545                 550                 555                 560

Asp Ser Thr Arg Thr Gly His His His His His His
                565                 570
```

<210> SEQ ID NO 72
<211> LENGTH: 564
<212> TYPE: PRT
<213> ORGANISM: Artificial Sequence
<220> FEATURE:
<223> OTHER INFORMATION: Artifical

<400> SEQUENCE: 72

```
Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Val Val Val Leu Ile Ala Val Asn Ser Arg Leu
145                 150                 155                 160

Ile Ile Glu Asn Leu Met Lys Tyr Gly Trp Leu Ile Arg Thr Asp Phe
                165                 170                 175

Trp Phe Ser Ser Arg Ser Leu Arg Asp Trp Pro Leu Phe Met Cys Cys
            180                 185                 190

Ile Ser Leu Ser Ile Phe Pro Leu Ala Ala Phe Thr Val Glu Lys Leu
        195                 200                 205

Val Leu Gln Lys Tyr Ile Ser Glu Pro Val Val Ile Phe Leu His Ile
    210                 215                 220

Ile Ile Thr Met Thr Glu Val Leu Tyr Pro Val Tyr Val Thr Leu Arg
225                 230                 235                 240

Cys Asp Ser Ala Phe Leu Ser Gly Val Thr Leu Met Leu Leu Thr Cys
                245                 250                 255

Ile Val Trp Leu Lys Leu Val Ser Tyr Ala His Thr Ser Tyr Asp Ile
            260                 265                 270

Arg Ser Leu Ala Asn Ala Ala Asp Lys Ala Asn Pro Glu Val Ser Tyr
        275                 280                 285

Tyr Val Ser Leu Lys Ser Leu Ala Tyr Phe Met Val Ala Pro Thr Leu
    290                 295                 300

Cys Tyr Gln Pro Ser Tyr Pro Arg Ser Ala Cys Ile Arg Lys Gly Trp
305                 310                 315                 320

Val Ala Arg Gln Phe Ala Lys Leu Val Ile Phe Thr Gly Phe Met Gly
                325                 330                 335

Phe Ile Ile Glu Gln Tyr Ile Asn Pro Ile Val Arg Asn Ser Lys His
            340                 345                 350

Pro Leu Lys Gly Asp Leu Leu Tyr Ala Ile Glu Arg Val Leu Lys Leu
        355                 360                 365

Ser Val Pro Asn Leu Tyr Val Trp Leu Cys Met Phe Tyr Cys Phe Phe
    370                 375                 380

His Leu Trp Leu Asn Ile Leu Ala Glu Leu Leu Cys Phe Gly Asp Arg
385                 390                 395                 400

Glu Phe Tyr Lys Asp Trp Trp Asn Ala Lys Ser Val Gly Asp Tyr Trp
```

-continued

```
                405                 410                 415

Arg Met Trp Asn Met Pro Val His Lys Trp Met Val Arg His Ile Tyr
            420                 425                 430

Phe Pro Cys Leu Arg Ser Lys Ile Pro Lys Thr Leu Ala Ile Ile Ile
        435                 440                 445

Ala Phe Leu Val Ser Ala Val Phe His Glu Leu Cys Ile Ala Val Pro
    450                 455                 460

Cys Arg Leu Phe Lys Leu Trp Ala Phe Leu Gly Ile Met Phe Gln Val
465                 470                 475                 480

Pro Leu Val Phe Ile Thr Asn Tyr Leu Gln Glu Arg Phe Gly Ser Thr
                485                 490                 495

Val Gly Asn Met Ile Phe Trp Phe Ile Phe Cys Ile Phe Gly Gln Pro
            500                 505                 510

Met Cys Val Leu Leu Tyr Tyr His Asp Leu Met Asn Arg Lys Gly Ser
        515                 520                 525

Met Ser Ala Lys Gly Glu Leu Arg Gly His Pro Phe Glu Gly Lys Pro
    530                 535                 540

Ile Pro Asn Pro Leu Leu Gly Leu Asp Ser Thr Arg Thr Gly His His
545                 550                 555                 560

His His His His


<210> SEQ ID NO 73
<211> LENGTH: 574
<212> TYPE: PRT
<213> ORGANISM: Artificial Sequence
<220> FEATURE:
<223> OTHER INFORMATION: Artifical

<400> SEQUENCE: 73

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Arg Gln Ser His Ala Gly
    130                 135                 140

Leu Leu Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Ser Gly Thr Ser Leu Ala Asp Trp Pro Leu Leu Met Cys Cys
            180                 185                 190

Leu Thr Leu Pro Thr Phe Pro Leu Ala Ala Leu Met Val Glu Lys Leu
        195                 200                 205
```

Ala Gln Arg Lys Leu Ile Ser Lys His Val Val Ile Leu Leu His Ile
    210                 215                 220

Val Ile Thr Thr Ser Val Leu Val Tyr Pro Val Val Val Ile Leu Lys
225                 230                 235                 240

Cys Asp Ser Ala Val Leu Ser Gly Phe Val Leu Met Phe Leu Ala Ser
                245                 250                 255

Ile Ile Trp Leu Lys Leu Val Ser Phe Ala His Thr Asn Tyr Asp Ile
            260                 265                 270

Arg Met Leu Ser Lys Ser Ile Glu Lys Gly Val Thr His Asp Ile Ser
        275                 280                 285

Ile Asp Pro Glu Asn Ile Lys Trp Pro Thr Phe Lys Arg Leu Ser Tyr
    290                 295                 300

Phe Met Leu Ala Pro Thr Leu Cys Tyr Gln Pro Ser Tyr Pro Arg Thr
305                 310                 315                 320

Thr Tyr Ile Arg Lys Gly Trp Val Val Arg Gln Leu Ile Lys Cys Leu
                325                 330                 335

Val Phe Thr Gly Leu Met Gly Phe Ile Ile Glu Gln Tyr Ile Asn Pro
            340                 345                 350

Ile Val Lys Asn Ser Lys His Pro Leu Lys Gly Asn Phe Leu Asn Ala
        355                 360                 365

Ile Glu Arg Val Leu Lys Leu Ser Val Pro Thr Leu Tyr Val Trp Leu
    370                 375                 380

Cys Met Phe Tyr Cys Phe Phe His Leu Trp Leu Asn Ile Leu Ala Glu
385                 390                 395                 400

Leu Leu Cys Phe Gly Asp Arg Glu Phe Tyr Lys Asp Trp Trp Asn Ala
                405                 410                 415

Lys Thr Val Glu Glu Tyr Trp Arg Met Trp Asn Met Pro Val His Lys
            420                 425                 430

Trp Val Ile Arg His Ile Tyr Phe Pro Cys Ile Arg Asn Gly Phe Ser
        435                 440                 445

Lys Gly Val Ala Ile Leu Ile Ser Phe Leu Val Ser Ala Ala Phe His
    450                 455                 460

Glu Leu Cys Val Ala Val Pro Cys His Ile Phe Lys Phe Trp Ala Phe
465                 470                 475                 480

Ile Gly Ile Met Phe Gln Ile Pro Leu Val Phe Leu Thr Lys Tyr Leu
                485                 490                 495

Gln Asp Lys Phe Asn Asn Thr Met Val Gly Asn Met Ile Phe Trp Phe
            500                 505                 510

Phe Phe Ser Ile Leu Gly Gln Pro Met Cys Val Leu Leu Tyr Tyr His
        515                 520                 525

Asp Val Met Asn Arg Gln Gln Ala Gln Thr Asn Arg Ala Lys Gly Glu
    530                 535                 540

Leu Arg Gly His Pro Phe Glu Gly Lys Pro Ile Pro Asn Pro Leu Leu
545                 550                 555                 560

Gly Leu Asp Ser Thr Arg Thr Gly His His His His His His
                565                 570

<210> SEQ ID NO 74
<211> LENGTH: 573
<212> TYPE: PRT
<213> ORGANISM: Artificial Sequence
<220> FEATURE:
<223> OTHER INFORMATION: Artifical

<400> SEQUENCE: 74

```
Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Arg Gln Ser His Ala Gly
    130                 135                 140

Leu Leu Asn Leu Cys Ile Val Val Leu Ile Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Ser Ala Arg Ser Leu Gly Asp Trp Pro Leu Leu Met Cys Cys
            180                 185                 190

Leu Thr Leu Pro Val Phe Pro Leu Val Ala Leu Met Ala Glu Lys Leu
        195                 200                 205

Ile Thr Arg Lys Leu Ile Gly Glu His Val Val Ile Leu Leu His Ile
    210                 215                 220

Ile Ile Thr Thr Ser Ala Ile Val Tyr Pro Val Val Val Thr Leu Lys
225                 230                 235                 240

Cys Asp Ser Ala Val Leu Ser Gly Phe Val Leu Met Phe Leu Ala Ser
                245                 250                 255

Ile Met Trp Met Lys Leu Val Ser Tyr Ala His Thr Asn Tyr Asp Ile
            260                 265                 270

Arg Val Leu Ser Lys Ser Thr Glu Lys Gly Ala Ala Tyr Gly Asn Tyr
        275                 280                 285

Val Asp Pro Glu Asn Met Lys Asp Pro Thr Phe Lys Ser Leu Val Tyr
    290                 295                 300

Phe Met Leu Ala Pro Thr Leu Cys Tyr Gln Pro Thr Tyr Pro Gln Thr
305                 310                 315                 320

Thr Cys Ile Arg Lys Gly Trp Val Thr Gln Gln Leu Ile Lys Cys Val
                325                 330                 335

Val Phe Thr Gly Leu Met Gly Phe Ile Ile Glu Gln Tyr Ile Asn Pro
            340                 345                 350

Ile Val Lys Asn Ser Lys His Pro Leu Lys Gly Asn Phe Leu Asn Ala
        355                 360                 365

Ile Glu Arg Val Leu Lys Leu Ser Val Pro Thr Leu Tyr Val Trp Leu
    370                 375                 380

Cys Met Phe Tyr Cys Phe Phe His Leu Trp Leu Asn Ile Val Ala Glu
385                 390                 395                 400

Leu Leu Cys Phe Gly Asp Arg Glu Phe Tyr Lys Asp Trp Trp Asn Ala
                405                 410                 415
```

```
Lys Thr Val Glu Glu Tyr Trp Arg Met Trp Asn Met Pro Val His Lys
            420                 425                 430

Trp Ile Ile Arg His Ile Tyr Phe Pro Cys Ile Arg Lys Gly Phe Ser
        435                 440                 445

Arg Gly Val Ala Ile Leu Ile Ser Phe Leu Val Ser Ala Val Phe His
    450                 455                 460

Glu Ile Cys Ile Ala Val Pro Cys His Ile Phe Lys Phe Trp Ala Phe
465                 470                 475                 480

Ser Gly Ile Met Phe Gln Ile Pro Leu Val Phe Leu Thr Arg Tyr Leu
                485                 490                 495

His Ala Thr Phe Lys His Val Met Val Gly Asn Met Ile Phe Trp Phe
            500                 505                 510

Phe Phe Ser Ile Val Gly Gln Pro Met Cys Val Leu Leu Tyr Tyr His
        515                 520                 525

Asp Val Met Asn Arg Gln Ala Gln Ala Ser Arg Ala Lys Gly Glu Leu
    530                 535                 540

Arg Gly His Pro Phe Glu Gly Lys Pro Ile Pro Asn Pro Leu Leu Gly
545                 550                 555                 560

Leu Asp Ser Thr Arg Thr Gly His His His His His His
                565                 570


<210> SEQ ID NO 75
<211> LENGTH: 572
<212> TYPE: PRT
<213> ORGANISM: Artificial Sequence
<220> FEATURE:
<223> OTHER INFORMATION: Artifical

<400> SEQUENCE: 75

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ser Gly Phe
                165                 170                 175

Trp Phe Asn Ala Thr Ser Leu Arg Asp Trp Pro Leu Leu Met Cys Cys
            180                 185                 190

Leu Ser Leu Pro Ile Phe Pro Leu Gly Ala Phe Ala Val Glu Lys Leu
        195                 200                 205
```

```
Ala Phe Asn Asn Leu Ile Ser Asp Pro Ala Thr Thr Cys Phe His Ile
    210                 215                 220

Leu Phe Thr Thr Phe Glu Ile Val Tyr Pro Val Leu Val Ile Leu Lys
225                 230                 235                 240

Cys Asp Ser Ala Val Leu Ser Gly Phe Val Leu Met Phe Ile Ala Cys
                245                 250                 255

Ile Val Trp Leu Lys Leu Val Ser Phe Ala His Thr Asn His Asp Ile
            260                 265                 270

Arg Lys Leu Ile Thr Ser Gly Lys Lys Val Asp Asn Glu Leu Thr Ala
        275                 280                 285

Ala Gly Ile Asp Asn Leu Gln Ala Pro Thr Leu Gly Ser Leu Thr Tyr
    290                 295                 300

Phe Met Met Ala Pro Thr Leu Cys Tyr Gln Pro Ser Tyr Pro Arg Thr
305                 310                 315                 320

Pro Tyr Val Arg Lys Gly Trp Leu Val Arg Gln Val Ile Leu Tyr Leu
                325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Met Gly Gly Leu Leu Asn Ala
        355                 360                 365

Val Glu Thr Val Leu Lys Leu Ser Leu Pro Asn Val Tyr Leu Trp Leu
    370                 375                 380

Cys Met Phe Tyr Cys Leu Phe His Leu Trp Leu Asn Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Ile Val Arg His Ile Tyr Phe Pro Cys Met Arg Asn Gly Ile Ser
        435                 440                 445

Lys Glu Val Ala Val Phe Ile Ser Phe Phe Val Ser Ala Val Leu His
    450                 455                 460

Glu Leu Cys Val Ala Val Pro Cys His Ile Leu Lys Phe Trp Ala Phe
465                 470                 475                 480

Leu Gly Ile Met Leu Gln Ile Pro Leu Ile Ile Leu Thr Ser Tyr Leu
                485                 490                 495

Lys Asn Lys Phe Ser Asp Thr Met Val Gly Asn Met Ile Phe Trp Phe
            500                 505                 510

Phe Phe Cys Ile Tyr Gly Gln Pro Met Cys Val Leu Leu Tyr Tyr His
        515                 520                 525

Asp Val Met Asn Arg Thr Glu Lys Ala Lys Ala Lys Gly Glu Leu Arg
    530                 535                 540

Gly His Pro Phe Glu Gly Lys Pro Ile Pro Asn Pro Leu Leu Gly Leu
545                 550                 555                 560

Asp Ser Thr Arg Thr Gly His His His His His His
                565                 570
```

<210> SEQ ID NO 76
<211> LENGTH: 570
<212> TYPE: PRT
<213> ORGANISM: Artificial Sequence
<220> FEATURE:
<223> OTHER INFORMATION: Artifical

<400> SEQUENCE: 76

-continued

```
Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Ile Ala Val Asn Ser Arg Leu
145                 150                 155                 160

Ile Ile Glu Asn Leu Met Lys Tyr Gly Trp Leu Ile Asp Thr Gly Phe
                165                 170                 175

Trp Phe Ser Ser Arg Ser Leu Gly Asp Trp Ser Ile Phe Met Cys Cys
            180                 185                 190

Leu Thr Leu Pro Ile Phe Pro Leu Ala Ala Phe Ile Val Glu Lys Leu
        195                 200                 205

Val Gln Arg Asn His Ile Ser Glu Leu Val Ala Val Leu Leu His Val
    210                 215                 220

Ile Val Ser Thr Ala Ala Val Leu Tyr Pro Val Ile Val Ile Leu Thr
225                 230                 235                 240

Cys Asp Ser Val Tyr Met Ser Gly Val Val Leu Met Leu Phe Gly Cys
                245                 250                 255

Ile Met Trp Leu Lys Leu Val Ser Tyr Ala His Thr Ser Ser Asp Ile
            260                 265                 270

Arg Thr Leu Ala Lys Ser Gly Tyr Lys Gly Asp Ala His Pro Asn Ser
        275                 280                 285

Thr Ile Val Ser Cys Ser Tyr Asp Val Ser Leu Lys Ser Leu Ala Tyr
    290                 295                 300

Phe Met Val Ala Pro Thr Leu Cys Tyr Gln Pro Ser Tyr Pro Arg Ser
305                 310                 315                 320

Ser Cys Ile Arg Lys Gly Trp Val Val Arg Gln Phe Val Lys Leu Ile
                325                 330                 335

Val Phe Ile Gly Leu Met Gly Phe Ile Ile Glu Gln Tyr Ile Asn Pro
            340                 345                 350

Ile Val Arg Asn Ser Lys His Pro Leu Lys Gly Asp Phe Leu Tyr Ala
        355                 360                 365

Ile Glu Arg Val Leu Lys Leu Ser Val Pro Asn Leu Tyr Val Trp Leu
    370                 375                 380

Cys Met Phe Tyr Ser Phe Phe His Leu Trp Leu Asn Ile Leu Ala Glu
385                 390                 395                 400

Leu Leu Arg Phe Gly Asp Arg Glu Phe Tyr Lys Asp Trp Trp Asn Ala
                405                 410                 415

Lys Thr Val Ala Glu Tyr Trp Lys Met Trp Asn Met Pro Val His Arg
```

```
            420                 425                 430

Trp Met Val Arg His Leu Tyr Phe Pro Cys Leu Arg Asn Gly Ile Pro
        435                 440                 445

Lys Glu Gly Ala Ile Ile Ile Ala Phe Leu Val Ser Gly Ala Phe His
    450                 455                 460

Glu Leu Cys Ile Ala Val Pro Cys His Val Phe Lys Leu Trp Ala Phe
465                 470                 475                 480

Ile Gly Ile Met Phe Gln Val Pro Leu Val Leu Ile Thr Asn Tyr Leu
                485                 490                 495

Gln Glu Lys Phe Ser Asn Ser Met Val Gly Asn Met Ile Phe Trp Phe
            500                 505                 510

Ile Phe Cys Ile Leu Gly Gln Pro Met Cys Val Leu Leu Tyr Tyr His
        515                 520                 525

Asp Leu Ile Asn Leu Lys Glu Lys Ala Lys Gly Glu Leu Arg Gly His
    530                 535                 540

Pro Phe Glu Gly Lys Pro Ile Pro Asn Pro Leu Leu Gly Leu Asp Ser
545                 550                 555                 560

Thr Arg Thr Gly His His His His His His
                565                 570


<210> SEQ ID NO 77
<211> LENGTH: 528
<212> TYPE: PRT
<213> ORGANISM: Artificial Sequence
<220> FEATURE:
<223> OTHER INFORMATION: Artifical

<400> SEQUENCE: 77

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Ser Ala Arg Ser Leu Gly Asp Trp Pro Leu Leu
    130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
```

```
    210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
    290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
        435                 440                 445

Arg Tyr Leu His Ala Thr Phe Lys His Val Met Val Gly Asn Met Ile
    450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg Ala Lys
                485                 490                 495

Gly Glu Leu Arg Gly His Pro Phe Glu Gly Lys Pro Ile Pro Asn Pro
            500                 505                 510

Leu Leu Gly Leu Asp Ser Thr Arg Thr Gly His His His His His His
        515                 520                 525


<210> SEQ ID NO 78
<211> LENGTH: 519
<212> TYPE: PRT
<213> ORGANISM: Artificial Sequence
<220> FEATURE:
<223> OTHER INFORMATION: Artifical

<400> SEQUENCE: 78

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
```

```
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Val Val Val Leu Ile Ala Val Asn
            100                 105                 110

Ser Arg Leu Ile Ile Glu Asn Leu Met Lys Tyr Gly Trp Leu Ile Arg
        115                 120                 125

Thr Asp Phe Trp Phe Ser Ser Arg Ser Leu Arg Asp Trp Pro Leu Phe
    130                 135                 140

Met Cys Cys Ile Ser Leu Ser Ile Phe Pro Leu Ala Ala Phe Thr Val
145                 150                 155                 160

Glu Lys Leu Val Leu Gln Lys Tyr Ile Ser Glu Pro Val Val Ile Phe
                165                 170                 175

Leu His Ile Ile Ile Thr Met Thr Glu Val Leu Tyr Pro Val Tyr Val
            180                 185                 190

Thr Leu Arg Cys Asp Ser Ala Phe Leu Ser Gly Val Thr Leu Met Leu
        195                 200                 205

Leu Thr Cys Ile Val Trp Leu Lys Leu Val Ser Tyr Ala His Thr Ser
    210                 215                 220

Tyr Asp Ile Arg Ser Leu Ala Asn Ala Ala Asp Lys Ala Asn Pro Glu
225                 230                 235                 240

Val Ser Tyr Tyr Val Ser Leu Lys Ser Leu Ala Tyr Phe Met Val Ala
                245                 250                 255

Pro Thr Leu Cys Tyr Gln Pro Ser Tyr Pro Arg Ser Ala Cys Ile Arg
            260                 265                 270

Lys Gly Trp Val Ala Arg Gln Phe Ala Lys Leu Val Ile Phe Thr Gly
        275                 280                 285

Phe Met Gly Phe Ile Ile Glu Gln Tyr Ile Asn Pro Ile Val Arg Asn
    290                 295                 300

Ser Lys His Pro Leu Lys Gly Asp Leu Leu Tyr Ala Ile Glu Arg Val
305                 310                 315                 320

Leu Lys Leu Ser Val Pro Asn Leu Tyr Val Trp Leu Cys Met Phe Tyr
                325                 330                 335

Cys Phe Phe His Leu Trp Leu Asn Ile Leu Ala Glu Leu Leu Cys Phe
            340                 345                 350

Gly Asp Arg Glu Phe Tyr Lys Asp Trp Trp Asn Ala Lys Ser Val Gly
        355                 360                 365

Asp Tyr Trp Arg Met Trp Asn Met Pro Val His Lys Trp Met Val Arg
    370                 375                 380

His Ile Tyr Phe Pro Cys Leu Arg Ser Lys Ile Pro Lys Thr Leu Ala
385                 390                 395                 400

Ile Ile Ile Ala Phe Leu Val Ser Ala Val Phe His Glu Leu Cys Ile
                405                 410                 415

Ala Val Pro Cys Arg Leu Phe Lys Leu Trp Ala Phe Leu Gly Ile Met
            420                 425                 430

Phe Gln Val Pro Leu Val Phe Ile Thr Asn Tyr Leu Gln Glu Arg Phe
        435                 440                 445

Gly Ser Thr Val Gly Asn Met Ile Phe Trp Phe Ile Phe Cys Ile Phe
    450                 455                 460

Gly Gln Pro Met Cys Val Leu Leu Tyr Tyr His Asp Leu Met Asn Arg
465                 470                 475                 480
```

Lys Gly Ser Met Ser Ala Lys Gly Glu Leu Arg Gly His Pro Phe Glu
485 490 495

Gly Lys Pro Ile Pro Asn Pro Leu Leu Gly Leu Asp Ser Thr Arg Thr
500 505 510

Gly His His His His His His
515

<210> SEQ ID NO 79
<211> LENGTH: 529
<212> TYPE: PRT
<213> ORGANISM: Artificial Sequence
<220> FEATURE:
<223> OTHER INFORMATION: Artifical

<400> SEQUENCE: 79

Met Ala Pro Pro Pro Ser Met Pro Ala Ala Ser Asp Arg Ala Gly Pro
1 5 10 15

Gly Arg Asp Ala Gly Asp Ser Ser Ser Leu Arg Leu Arg Arg Ala Pro
20 25 30

Ser Ala Asp Ala Gly Asp Leu Ala Gly Asp Ser Ser Gly Gly Leu Arg
35 40 45

Glu Asn Gly Glu Pro Gln Ser Pro Thr Asn Pro Pro Pro Gln Glu Gln
50 55 60

Gln Gln His Glu Met Leu Tyr Tyr Arg Ala Ser Ala Pro Ala His Arg
65 70 75 80

Arg Val Lys Glu Ser Pro Leu Ser Ser Asp Ala Ile Phe Arg Gln Ser
85 90 95

His Ala Gly Leu Leu Asn Leu Cys Ile Val Val Leu Val Ala Val Asn
100 105 110

Ser Arg Leu Ile Ile Glu Asn Leu Met Lys Tyr Gly Leu Leu Ile Arg
115 120 125

Ala Gly Phe Trp Phe Ser Gly Thr Ser Leu Ala Asp Trp Pro Leu Leu
130 135 140

Met Cys Cys Leu Thr Leu Pro Thr Phe Pro Leu Ala Ala Leu Met Val
145 150 155 160

Glu Lys Leu Ala Gln Arg Lys Leu Ile Ser Lys His Val Val Ile Leu
165 170 175

Leu His Ile Val Ile Thr Thr Ser Val Leu Val Tyr Pro Val Val Val
180 185 190

Ile Leu Lys Cys Asp Ser Ala Val Leu Ser Gly Phe Val Leu Met Phe
195 200 205

Leu Ala Ser Ile Ile Trp Leu Lys Leu Val Ser Phe Ala His Thr Asn
210 215 220

Tyr Asp Ile Arg Met Leu Ser Lys Ser Ile Glu Lys Gly Val Thr His
225 230 235 240

Asp Ile Ser Ile Asp Pro Glu Asn Ile Lys Trp Pro Thr Phe Lys Arg
245 250 255

Leu Ser Tyr Phe Met Leu Ala Pro Thr Leu Cys Tyr Gln Pro Ser Tyr
260 265 270

Pro Arg Thr Thr Tyr Ile Arg Lys Gly Trp Val Val Arg Gln Leu Ile
275 280 285

Lys Cys Leu Val Phe Thr Gly Leu Met Gly Phe Ile Ile Glu Gln Tyr
290 295 300

Ile Asn Pro Ile Val Lys Asn Ser Lys His Pro Leu Lys Gly Asn Phe
305 310 315 320

```
Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Leu Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
    370                 375                 380

Val His Lys Trp Val Ile Arg His Ile Tyr Phe Pro Cys Ile Arg Asn
385                 390                 395                 400

Gly Phe Ser Lys Gly Val Ala Ile Leu Ile Ser Phe Leu Val Ser Ala
                405                 410                 415

Ala Phe His Glu Leu Cys Val Ala Val Pro Cys His Ile Phe Lys Phe
            420                 425                 430

Trp Ala Phe Ile Gly Ile Met Phe Gln Ile Pro Leu Val Phe Leu Thr
        435                 440                 445

Lys Tyr Leu Gln Asp Lys Phe Asn Asn Thr Met Val Gly Asn Met Ile
    450                 455                 460

Phe Trp Phe Phe Phe Ser Ile Leu Gly Gln Pro Met Cys Val Leu Leu
465                 470                 475                 480

Tyr Tyr His Asp Val Met Asn Arg Gln Gln Ala Gln Thr Asn Arg Ala
                485                 490                 495

Lys Gly Glu Leu Arg Gly His Pro Phe Glu Gly Lys Pro Ile Pro Asn
            500                 505                 510

Pro Leu Leu Gly Leu Asp Ser Thr Arg Thr Gly His His His His His
        515                 520                 525

His


<210> SEQ ID NO 80
<211> LENGTH: 527
<212> TYPE: PRT
<213> ORGANISM: Artificial Sequence
<220> FEATURE:
<223> OTHER INFORMATION: Artifical

<400> SEQUENCE: 80

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Val Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Asn Asp Lys Ser Leu Arg Asp Trp Pro Leu Leu
    130                 135                 140
```

```
Met Cys Cys Leu Ser Leu Pro Ala Phe Pro Leu Gly Ala Phe Ala Val
145                 150                 155                 160

Glu Lys Leu Ala Phe Asn Asn Val Ile Thr Asp Ala Val Ala Thr Cys
                165                 170                 175

Leu His Ile Phe Leu Ser Thr Thr Glu Ile Val Tyr Pro Val Leu Val
            180                 185                 190

Ile Leu Lys Cys Asp Ser Ala Val Leu Ser Gly Phe Leu Leu Ile Phe
        195                 200                 205

Ile Ala Cys Ile Val Trp Leu Lys Leu Val Ser Phe Ala His Thr Asn
    210                 215                 220

His Asp Ile Arg Gln Leu Thr Met Gly Gly Lys Lys Val Asp Asn Glu
225                 230                 235                 240

Leu Ser Thr Val Asp Met Asp Asn Leu Gln Pro Pro Thr Leu Gly Asn
                245                 250                 255

Leu Ile Tyr Phe Met Met Ala Pro Thr Leu Cys Tyr Gln Pro Ser Tyr
            260                 265                 270

Pro Arg Thr Ser Cys Val Arg Lys Gly Trp Leu Ile Arg Gln Ile Ile
        275                 280                 285

Leu Tyr Leu Ile Phe Thr Gly Leu Gln Gly Phe Ile Ile Glu Gln Tyr
    290                 295                 300

Ile Asn Pro Ile Val Val Asn Ser Gln His Pro Leu Lys Gly Gly Leu
305                 310                 315                 320

Leu Asn Ala Val Glu Thr Val Leu Lys Leu Ser Leu Pro Asn Val Tyr
                325                 330                 335

Leu Trp Leu Cys Met Phe Tyr Ala Phe Phe His Leu Trp Leu Ser Ile
            340                 345                 350

Leu Ala Glu Ile Leu Arg Phe Gly Asp Arg Glu Phe Tyr Lys Asp Trp
        355                 360                 365

Trp Asn Ala Lys Thr Ile Asp Glu Tyr Trp Arg Lys Trp Asn Met Pro
    370                 375                 380

Val His Lys Trp Val Val Arg His Ile Tyr Phe Pro Cys Met Arg Asn
385                 390                 395                 400

Gly Ile Ser Lys Glu Val Ala Val Leu Ile Ser Phe Leu Val Ser Ala
                405                 410                 415

Val Leu His Glu Ile Cys Val Ala Val Pro Cys Arg Ile Leu Lys Phe
            420                 425                 430

Trp Ala Phe Leu Gly Ile Met Leu Gln Ile Pro Leu Ile Val Leu Thr
        435                 440                 445

Ala Tyr Leu Lys Ser Lys Phe Arg Asp Thr Met Val Gly Asn Met Ile
    450                 455                 460

Phe Trp Phe Phe Phe Cys Ile Tyr Gly Gln Pro Met Cys Leu Leu Leu
465                 470                 475                 480

Tyr Tyr His Asp Val Met Asn Arg Ile Glu Lys Ala Arg Ala Lys Gly
                485                 490                 495

Glu Leu Arg Gly His Pro Phe Glu Gly Lys Pro Ile Pro Asn Pro Leu
            500                 505                 510

Leu Gly Leu Asp Ser Thr Arg Thr Gly His His His His His His
        515                 520                 525
```

<210> SEQ ID NO 81
<211> LENGTH: 527
<212> TYPE: PRT
<213> ORGANISM: Artificial Sequence
<220> FEATURE:
<223> OTHER INFORMATION: Artifical

<400> SEQUENCE: 81

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Val Ala Val Asn
            100                 105                 110

Ser Arg Leu Ile Ile Glu Asn Leu Met Lys Tyr Gly Leu Leu Ile Arg
        115                 120                 125

Ser Gly Phe Trp Phe Asn Ala Thr Ser Leu Arg Asp Trp Pro Leu Leu
    130                 135                 140

Met Cys Cys Leu Ser Leu Pro Ile Phe Pro Leu Gly Ala Phe Ala Val
145                 150                 155                 160

Glu Lys Leu Ala Phe Asn Asn Leu Ile Ser Asp Pro Ala Thr Thr Cys
                165                 170                 175

Phe His Ile Leu Phe Thr Thr Phe Glu Ile Val Tyr Pro Val Leu Val
            180                 185                 190

Ile Leu Lys Cys Asp Ser Ala Val Leu Ser Gly Phe Val Leu Met Phe
        195                 200                 205

Ile Ala Cys Ile Val Trp Leu Lys Leu Val Ser Phe Ala His Thr Asn
    210                 215                 220

His Asp Ile Arg Lys Leu Ile Thr Ser Gly Lys Lys Val Asp Asn Glu
225                 230                 235                 240

Leu Thr Ala Ala Gly Ile Asp Asn Leu Gln Ala Pro Thr Leu Gly Ser
                245                 250                 255

Leu Thr Tyr Phe Met Met Ala Pro Thr Leu Cys Tyr Gln Pro Ser Tyr
            260                 265                 270

Pro Arg Thr Pro Tyr Val Arg Lys Gly Trp Leu Val Arg Gln Val Ile
        275                 280                 285

Leu Tyr Leu Ile Phe Thr Gly Leu Gln Gly Phe Ile Ile Glu Gln Tyr
    290                 295                 300

Ile Asn Pro Ile Val Val Asn Ser Gln His Pro Leu Met Gly Gly Leu
305                 310                 315                 320

Leu Asn Ala Val Glu Thr Val Leu Lys Leu Ser Leu Pro Asn Val Tyr
                325                 330                 335

Leu Trp Leu Cys Met Phe Tyr Cys Leu Phe His Leu Trp Leu Asn Ile
            340                 345                 350

Leu Ala Glu Ile Leu Arg Phe Gly Asp Arg Glu Phe Tyr Lys Asp Trp
        355                 360                 365

Trp Asn Ala Lys Thr Ile Asp Glu Tyr Trp Arg Lys Trp Asn Met Pro
    370                 375                 380

Val His Lys Trp Ile Val Arg His Ile Tyr Phe Pro Cys Met Arg Asn
385                 390                 395                 400

Gly Ile Ser Lys Glu Val Ala Val Phe Ile Ser Phe Phe Val Ser Ala

```
                405                 410                 415

Val Leu His Glu Leu Cys Val Ala Val Pro Cys His Ile Leu Lys Phe
            420                 425                 430

Trp Ala Phe Leu Gly Ile Met Leu Gln Ile Pro Leu Ile Ile Leu Thr
        435                 440                 445

Ser Tyr Leu Lys Asn Lys Phe Ser Asp Thr Met Val Gly Asn Met Ile
    450                 455                 460

Phe Trp Phe Phe Phe Cys Ile Tyr Gly Gln Pro Met Cys Val Leu Leu
465                 470                 475                 480

Tyr Tyr His Asp Val Met Asn Arg Thr Glu Lys Ala Lys Ala Lys Gly
                485                 490                 495

Glu Leu Arg Gly His Pro Phe Glu Gly Lys Pro Ile Pro Asn Pro Leu
            500                 505                 510

Leu Gly Leu Asp Ser Thr Arg Thr Gly His His His His His His
        515                 520                 525


<210> SEQ ID NO 82
<211> LENGTH: 524
<212> TYPE: PRT
<213> ORGANISM: Artificial Sequence
<220> FEATURE:
<223> OTHER INFORMATION: Artifical

<400> SEQUENCE: 82

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Ile Ala Val Asn
            100                 105                 110

Ser Arg Leu Ile Ile Glu Asn Leu Met Lys Tyr Gly Trp Leu Ile Asp
        115                 120                 125

Thr Gly Phe Trp Phe Ser Ser Arg Ser Leu Gly Asp Trp Ser Ile Phe
    130                 135                 140

Met Cys Cys Leu Thr Leu Pro Ile Phe Pro Leu Ala Ala Phe Ile Val
145                 150                 155                 160

Glu Lys Leu Val Gln Arg Asn His Ile Ser Glu Leu Val Ala Val Leu
                165                 170                 175

Leu His Val Ile Val Ser Thr Ala Ala Val Leu Tyr Pro Val Ile Val
            180                 185                 190

Ile Leu Thr Cys Asp Ser Val Tyr Met Ser Gly Val Val Leu Met Leu
        195                 200                 205

Phe Gly Cys Ile Met Trp Leu Lys Leu Val Ser Tyr Ala His Thr Ser
    210                 215                 220

Ser Asp Ile Arg Thr Leu Ala Lys Ser Gly Tyr Lys Gly Asp Ala His
225                 230                 235                 240

Pro Asn Ser Thr Ile Val Ser Cys Ser Tyr Asp Val Ser Leu Lys Ser
```

```
                245                 250                 255

Leu Ala Tyr Phe Met Val Ala Pro Thr Leu Cys Tyr Gln Pro Ser Tyr
            260                 265                 270

Pro Arg Ser Ser Cys Ile Arg Lys Gly Trp Val Val Arg Gln Phe Val
        275                 280                 285

Lys Leu Ile Val Phe Ile Gly Leu Met Gly Phe Ile Ile Glu Gln Tyr
    290                 295                 300

Ile Asn Pro Ile Val Arg Asn Ser Lys His Pro Leu Lys Gly Asp Phe
305                 310                 315                 320

Leu Tyr Ala Ile Glu Arg Val Leu Lys Leu Ser Val Pro Asn Leu Tyr
                325                 330                 335

Val Trp Leu Cys Met Phe Tyr Ser Phe Phe His Leu Trp Leu Asn Ile
            340                 345                 350

Leu Ala Glu Leu Leu Arg Phe Gly Asp Arg Glu Phe Tyr Lys Asp Trp
        355                 360                 365

Trp Asn Ala Lys Thr Val Ala Glu Tyr Trp Lys Met Trp Asn Met Pro
    370                 375                 380

Val His Arg Trp Met Val Arg His Leu Tyr Phe Pro Cys Leu Arg Asn
385                 390                 395                 400

Gly Ile Pro Lys Glu Gly Ala Ile Ile Ile Ala Phe Leu Val Ser Gly
                405                 410                 415

Ala Phe His Glu Leu Cys Ile Ala Val Pro Cys His Val Phe Lys Leu
            420                 425                 430

Trp Ala Phe Ile Gly Ile Met Phe Gln Val Pro Leu Val Leu Ile Thr
        435                 440                 445

Asn Tyr Leu Gln Glu Lys Phe Ser Asn Ser Met Val Gly Asn Met Ile
    450                 455                 460

Phe Trp Phe Ile Phe Cys Ile Leu Gly Gln Pro Met Cys Val Leu Leu
465                 470                 475                 480

Tyr Tyr His Asp Leu Ile Asn Leu Lys Glu Lys Ala Lys Gly Glu Leu
                485                 490                 495

Arg Gly His Pro Phe Glu Gly Lys Pro Ile Pro Asn Pro Leu Leu Gly
            500                 505                 510

Leu Asp Ser Thr Arg Thr Gly His His His His His
        515                 520
```

<210> SEQ ID NO 83
<211> LENGTH: 546
<212> TYPE: PRT
<213> ORGANISM: Artificial Sequence
<220> FEATURE:
<223> OTHER INFORMATION: Artifical

<400> SEQUENCE: 83

```
Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
```

-continued

```
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190

Thr Thr Cys Phe His Ile Leu Phe Thr Thr Phe Glu Ile Val Tyr Pro
        195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
            260                 265                 270

Leu Gly Ser Leu Thr Tyr Phe Met Met Ala Pro Thr Leu Cys Tyr Gln
        275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
        355                 360                 365

Leu Asn Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
            420                 425                 430

Val Ser Ala Val Leu His Glu Leu Cys Val Ala Val Pro Cys His Ile
        435                 440                 445

Leu Lys Phe Trp Ala Phe Leu Gly Ile Met Leu Gln Ile Pro Leu Ile
    450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510
```

Ala Lys Gly Glu Leu Arg Gly His Pro Phe Glu Gly Lys Pro Ile Pro
515 520 525

Asn Pro Leu Leu Gly Leu Asp Ser Thr Arg Thr Gly His His His His
530 535 540

His His
545

<210> SEQ ID NO 84
<211> LENGTH: 538
<212> TYPE: PRT
<213> ORGANISM: Artificial Sequence
<220> FEATURE:
<223> OTHER INFORMATION: Artifical

<400> SEQUENCE: 84

Met Ala Asp Ser Glu Asp Ala Pro Pro Ala Val His Arg Arg Pro Pro
1 5 10 15

Arg Pro Ala Arg Gly Ala Ala Ala Ala Gln Gly Phe Ala Ala Ala Leu
20 25 30

Arg Arg Arg Leu Arg Ser Gly Ala Ala Val Ala Ala Arg Ala Ser Phe
35 40 45

Ala Ala Asp Ser Gly Asp Glu Ser Gly Pro Gly Glu Pro Ser Ser Ser
50 55 60

Arg Arg Arg Asp Asn Ser Gly Gly Ala Ser Ser Ala Ala Gly Gly Arg
65 70 75 80

Ala Gly Ala Gly Asp Phe Ser Ala Phe Thr Phe Arg Ala Ala Ala Pro
85 90 95

Val His Arg Lys Ala Lys Glu Ser Pro Leu Ser Ser Asp Ala Ile Phe
100 105 110

Lys Gln Ser His Ala Gly Leu Phe Asn Leu Cys Val Val Val Leu Ile
115 120 125

Ala Val Asn Ser Arg Leu Ile Ile Glu Asn Leu Met Lys Tyr Gly Trp
130 135 140

Leu Ile Arg Thr Asp Phe Trp Phe Ser Ser Arg Ser Leu Arg Asp Trp
145 150 155 160

Pro Leu Phe Met Cys Cys Ile Ser Leu Ser Ile Phe Pro Leu Ala Ala
165 170 175

Phe Thr Val Glu Lys Leu Val Leu Gln Lys Tyr Ile Ser Glu Pro Val
180 185 190

Val Ile Phe Leu His Ile Ile Ile Thr Met Thr Glu Val Leu Tyr Pro
195 200 205

Val Tyr Val Thr Leu Arg Cys Asp Ser Ala Phe Leu Ser Gly Val Thr
210 215 220

Leu Met Leu Leu Thr Cys Ile Val Trp Leu Lys Leu Val Ser Tyr Ala
225 230 235 240

His Thr Ser Tyr Asp Ile Arg Ser Leu Ala Asn Ala Ala Asp Lys Ala
245 250 255

Asn Pro Glu Val Ser Tyr Tyr Val Ser Leu Lys Ser Leu Ala Tyr Phe
260 265 270

Met Val Ala Pro Thr Leu Cys Tyr Gln Pro Ser Tyr Pro Arg Ser Ala
275 280 285

Cys Ile Arg Lys Gly Trp Val Ala Arg Gln Phe Ala Lys Leu Val Ile
290 295 300

Phe Thr Gly Phe Met Gly Phe Ile Ile Glu Gln Tyr Ile Asn Pro Ile
305 310 315 320

```
Val Arg Asn Ser Lys His Pro Leu Lys Gly Asp Leu Leu Tyr Ala Ile
                325                 330                 335

Glu Arg Val Leu Lys Leu Ser Val Pro Asn Leu Tyr Val Trp Leu Cys
            340                 345                 350

Met Phe Tyr Cys Phe Phe His Leu Trp Leu Asn Ile Leu Ala Glu Leu
        355                 360                 365

Leu Cys Phe Gly Asp Arg Glu Phe Tyr Lys Asp Trp Trp Asn Ala Lys
    370                 375                 380

Ser Val Gly Asp Tyr Trp Arg Met Trp Asn Met Pro Val His Lys Trp
385                 390                 395                 400

Met Val Arg His Ile Tyr Phe Pro Cys Leu Arg Ser Lys Ile Pro Lys
                405                 410                 415

Thr Leu Ala Ile Ile Ile Ala Phe Leu Val Ser Ala Val Phe His Glu
            420                 425                 430

Leu Cys Ile Ala Val Pro Cys Arg Leu Phe Lys Leu Trp Ala Phe Leu
        435                 440                 445

Gly Ile Met Phe Gln Val Pro Leu Val Phe Ile Thr Asn Tyr Leu Gln
    450                 455                 460

Glu Arg Phe Gly Ser Thr Val Gly Asn Met Ile Phe Trp Phe Ile Phe
465                 470                 475                 480

Cys Ile Phe Gly Gln Pro Met Cys Val Leu Leu Tyr Tyr His Asp Leu
                485                 490                 495

Met Asn Arg Lys Gly Ser Met Ser Ala Lys Gly Glu Leu Arg Gly His
            500                 505                 510

Pro Phe Glu Gly Lys Pro Ile Pro Asn Pro Leu Leu Gly Leu Asp Ser
        515                 520                 525

Thr Arg Thr Gly His His His His His His
    530                 535
```

<210> SEQ ID NO 85
<211> LENGTH: 548
<212> TYPE: PRT
<213> ORGANISM: Artificial Sequence
<220> FEATURE:
<223> OTHER INFORMATION: Artifical

<400> SEQUENCE: 85

```
Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Arg Gln Ser His Ala Gly Leu Leu Asn Leu Cys Ile Val Val Leu Val
        115                 120                 125

Ala Val Asn Ser Arg Leu Ile Ile Glu Asn Leu Met Lys Tyr Gly Leu
    130                 135                 140
```

```
Leu Ile Arg Ala Gly Phe Trp Phe Ser Gly Thr Ser Leu Ala Asp Trp
145                 150                 155                 160

Pro Leu Leu Met Cys Cys Leu Thr Leu Pro Thr Phe Pro Leu Ala Ala
                165                 170                 175

Leu Met Val Glu Lys Leu Ala Gln Arg Lys Leu Ile Ser Lys His Val
            180                 185                 190

Val Ile Leu Leu His Ile Val Ile Thr Thr Ser Val Leu Val Tyr Pro
        195                 200                 205

Val Val Val Ile Leu Lys Cys Asp Ser Ala Val Leu Ser Gly Phe Val
    210                 215                 220

Leu Met Phe Leu Ala Ser Ile Ile Trp Leu Lys Leu Val Ser Phe Ala
225                 230                 235                 240

His Thr Asn Tyr Asp Ile Arg Met Leu Ser Lys Ser Ile Glu Lys Gly
                245                 250                 255

Val Thr His Asp Ile Ser Ile Asp Pro Glu Asn Ile Lys Trp Pro Thr
            260                 265                 270

Phe Lys Arg Leu Ser Tyr Phe Met Leu Ala Pro Thr Leu Cys Tyr Gln
        275                 280                 285

Pro Ser Tyr Pro Arg Thr Thr Tyr Ile Arg Lys Gly Trp Val Val Arg
    290                 295                 300

Gln Leu Ile Lys Cys Leu Val Phe Thr Gly Leu Met Gly Phe Ile Ile
305                 310                 315                 320

Glu Gln Tyr Ile Asn Pro Ile Val Lys Asn Ser Lys His Pro Leu Lys
                325                 330                 335

Gly Asn Phe Leu Asn Ala Ile Glu Arg Val Leu Lys Leu Ser Val Pro
            340                 345                 350

Thr Leu Tyr Val Trp Leu Cys Met Phe Tyr Cys Phe Phe His Leu Trp
        355                 360                 365

Leu Asn Ile Leu Ala Glu Leu Leu Cys Phe Gly Asp Arg Glu Phe Tyr
    370                 375                 380

Lys Asp Trp Trp Asn Ala Lys Thr Val Glu Glu Tyr Trp Arg Met Trp
385                 390                 395                 400

Asn Met Pro Val His Lys Trp Val Ile Arg His Ile Tyr Phe Pro Cys
                405                 410                 415

Ile Arg Asn Gly Phe Ser Lys Gly Val Ala Ile Leu Ile Ser Phe Leu
            420                 425                 430

Val Ser Ala Ala Phe His Glu Leu Cys Val Ala Val Pro Cys His Ile
        435                 440                 445

Phe Lys Phe Trp Ala Phe Ile Gly Ile Met Phe Gln Ile Pro Leu Val
    450                 455                 460

Phe Leu Thr Lys Tyr Leu Gln Asp Lys Phe Asn Asn Thr Met Val Gly
465                 470                 475                 480

Asn Met Ile Phe Trp Phe Phe Phe Ser Ile Leu Gly Gln Pro Met Cys
                485                 490                 495

Val Leu Leu Tyr Tyr His Asp Val Met Asn Arg Gln Gln Ala Gln Thr
            500                 505                 510

Asn Arg Ala Lys Gly Glu Leu Arg Gly His Pro Phe Glu Gly Lys Pro
        515                 520                 525

Ile Pro Asn Pro Leu Leu Gly Leu Asp Ser Thr Arg Thr Gly His His
    530                 535                 540

His His His His
545
```

<210> SEQ ID NO 86
<211> LENGTH: 546
<212> TYPE: PRT
<213> ORGANISM: Artificial Sequence
<220> FEATURE:
<223> OTHER INFORMATION: Artifical

<400> SEQUENCE: 86

```
Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ala Gly Phe Trp Phe Asn Asp Lys Ser Leu Arg Asp Trp
145                 150                 155                 160

Pro Leu Leu Met Cys Cys Leu Ser Leu Pro Ala Phe Pro Leu Gly Ala
                165                 170                 175

Phe Ala Val Glu Lys Leu Ala Phe Asn Asn Val Ile Thr Asp Ala Val
            180                 185                 190

Ala Thr Cys Leu His Ile Phe Leu Ser Thr Thr Glu Ile Val Tyr Pro
        195                 200                 205

Val Leu Val Ile Leu Lys Cys Asp Ser Ala Val Leu Ser Gly Phe Leu
    210                 215                 220

Leu Ile Phe Ile Ala Cys Ile Val Trp Leu Lys Leu Val Ser Phe Ala
225                 230                 235                 240

His Thr Asn His Asp Ile Arg Gln Leu Thr Met Gly Gly Lys Lys Val
                245                 250                 255

Asp Asn Glu Leu Ser Thr Val Asp Met Asp Asn Leu Gln Pro Pro Thr
            260                 265                 270

Leu Gly Asn Leu Ile Tyr Phe Met Met Ala Pro Thr Leu Cys Tyr Gln
        275                 280                 285

Pro Ser Tyr Pro Arg Thr Ser Cys Val Arg Lys Gly Trp Leu Ile Arg
    290                 295                 300

Gln Ile Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Lys
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Ala Phe Phe His Leu Trp
        355                 360                 365
```

Leu Ser Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Val Val Arg His Ile Tyr Phe Pro Cys
                405                 410                 415

Met Arg Asn Gly Ile Ser Lys Glu Val Ala Val Leu Ile Ser Phe Leu
            420                 425                 430

Val Ser Ala Val Leu His Glu Ile Cys Val Ala Val Pro Cys Arg Ile
        435                 440                 445

Leu Lys Phe Trp Ala Phe Leu Gly Ile Met Leu Gln Ile Pro Leu Ile
    450                 455                 460

Val Leu Thr Ala Tyr Leu Lys Ser Lys Phe Arg Asp Thr Met Val Gly
465                 470                 475                 480

Asn Met Ile Phe Trp Phe Phe Phe Cys Ile Tyr Gly Gln Pro Met Cys
                485                 490                 495

Leu Leu Leu Tyr Tyr His Asp Val Met Asn Arg Ile Glu Lys Ala Arg
            500                 505                 510

Ala Lys Gly Glu Leu Arg Gly His Pro Phe Glu Gly Lys Pro Ile Pro
        515                 520                 525

Asn Pro Leu Leu Gly Leu Asp Ser Thr Arg Thr Gly His His His His
    530                 535                 540

His His
545

<210> SEQ ID NO 87
<211> LENGTH: 547
<212> TYPE: PRT
<213> ORGANISM: Artificial Sequence
<220> FEATURE:
<223> OTHER INFORMATION: Artifical

<400> SEQUENCE: 87

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Arg Gln Ser His Ala Gly Leu Leu Asn Leu Cys Ile Val Val Leu Ile
        115                 120                 125

Ala Val Asn Ser Arg Leu Ile Ile Glu Asn Leu Met Lys Tyr Gly Leu
    130                 135                 140

Leu Ile Arg Ala Gly Phe Trp Phe Ser Ala Arg Ser Leu Gly Asp Trp
145                 150                 155                 160

Pro Leu Leu Met Cys Cys Leu Thr Leu Pro Val Phe Pro Leu Val Ala
                165                 170                 175

```
Leu Met Ala Glu Lys Leu Ile Thr Arg Lys Leu Ile Gly Glu His Val
            180                 185                 190

Val Ile Leu Leu His Ile Ile Ile Thr Thr Ser Ala Ile Val Tyr Pro
        195                 200                 205

Val Val Val Thr Leu Lys Cys Asp Ser Ala Val Leu Ser Gly Phe Val
    210                 215                 220

Leu Met Phe Leu Ala Ser Ile Met Trp Met Lys Leu Val Ser Tyr Ala
225                 230                 235                 240

His Thr Asn Tyr Asp Ile Arg Val Leu Ser Lys Ser Thr Glu Lys Gly
                245                 250                 255

Ala Ala Tyr Gly Asn Tyr Val Asp Pro Glu Asn Met Lys Asp Pro Thr
            260                 265                 270

Phe Lys Ser Leu Val Tyr Phe Met Leu Ala Pro Thr Leu Cys Tyr Gln
        275                 280                 285

Pro Thr Tyr Pro Gln Thr Thr Cys Ile Arg Lys Gly Trp Val Thr Gln
    290                 295                 300

Gln Leu Ile Lys Cys Val Val Phe Thr Gly Leu Met Gly Phe Ile Ile
305                 310                 315                 320

Glu Gln Tyr Ile Asn Pro Ile Val Lys Asn Ser Lys His Pro Leu Lys
                325                 330                 335

Gly Asn Phe Leu Asn Ala Ile Glu Arg Val Leu Lys Leu Ser Val Pro
            340                 345                 350

Thr Leu Tyr Val Trp Leu Cys Met Phe Tyr Cys Phe Phe His Leu Trp
        355                 360                 365

Leu Asn Ile Val Ala Glu Leu Leu Cys Phe Gly Asp Arg Glu Phe Tyr
    370                 375                 380

Lys Asp Trp Trp Asn Ala Lys Thr Val Glu Glu Tyr Trp Arg Met Trp
385                 390                 395                 400

Asn Met Pro Val His Lys Trp Ile Ile Arg His Ile Tyr Phe Pro Cys
                405                 410                 415

Ile Arg Lys Gly Phe Ser Arg Gly Val Ala Ile Leu Ile Ser Phe Leu
            420                 425                 430

Val Ser Ala Val Phe His Glu Ile Cys Ile Ala Val Pro Cys His Ile
        435                 440                 445

Phe Lys Phe Trp Ala Phe Ser Gly Ile Met Phe Gln Ile Pro Leu Val
    450                 455                 460

Phe Leu Thr Arg Tyr Leu His Ala Thr Phe Lys His Val Met Val Gly
465                 470                 475                 480

Asn Met Ile Phe Trp Phe Phe Phe Ser Ile Val Gly Gln Pro Met Cys
                485                 490                 495

Val Leu Leu Tyr Tyr His Asp Val Met Asn Arg Gln Ala Gln Ala Ser
            500                 505                 510

Arg Ala Lys Gly Glu Leu Arg Gly His Pro Phe Glu Gly Lys Pro Ile
        515                 520                 525

Pro Asn Pro Leu Leu Gly Leu Asp Ser Thr Arg Thr Gly His His His
    530                 535                 540

His His His
545
```

<210> SEQ ID NO 88
<211> LENGTH: 544
<212> TYPE: PRT
<213> ORGANISM: Artificial Sequence
<220> FEATURE:
<223> OTHER INFORMATION: Artifical

<400> SEQUENCE: 88

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Ile
        115                 120                 125

Ala Val Asn Ser Arg Leu Ile Ile Glu Asn Leu Met Lys Tyr Gly Trp
    130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ser Glu Leu Val
            180                 185                 190

Ala Val Leu Leu His Val Ile Val Ser Thr Ala Ala Val Leu Tyr Pro
        195                 200                 205

Val Ile Val Ile Leu Thr Cys Asp Ser Val Tyr Met Ser Gly Val Val
    210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
            260                 265                 270

Leu Lys Ser Leu Ala Tyr Phe Met Val Ala Pro Thr Leu Cys Tyr Gln
        275                 280                 285

Pro Ser Tyr Pro Arg Ser Ser Cys Ile Arg Lys Gly Trp Val Val Arg
    290                 295                 300

Gln Phe Val Lys Leu Ile Val Phe Ile Gly Leu Met Gly Phe Ile Ile
305                 310                 315                 320

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
        355                 360                 365

Leu Asn Ile Leu Ala Glu Leu Leu Arg Phe Gly Asp Arg Glu Phe Tyr
    370                 375                 380

Lys Asp Trp Trp Asn Ala Lys Thr Val Ala Glu Tyr Trp Lys Met Trp
385                 390                 395                 400

Asn Met Pro Val His Arg Trp Met Val Arg His Leu Tyr Phe Pro Cys

```
                405                 410                 415

Leu Arg Asn Gly Ile Pro Lys Glu Gly Ala Ile Ile Ile Ala Phe Leu
            420                 425                 430

Val Ser Gly Ala Phe His Glu Leu Cys Ile Ala Val Pro Cys His Val
        435                 440                 445

Phe Lys Leu Trp Ala Phe Ile Gly Ile Met Phe Gln Val Pro Leu Val
    450                 455                 460

Leu Ile Thr Asn Tyr Leu Gln Glu Lys Phe Ser Asn Ser Met Val Gly
465                 470                 475                 480

Asn Met Ile Phe Trp Phe Ile Phe Cys Ile Leu Gly Gln Pro Met Cys
                485                 490                 495

Val Leu Leu Tyr Tyr His Asp Leu Ile Asn Leu Lys Glu Lys Ala Lys
            500                 505                 510

Gly Glu Leu Arg Gly His Pro Phe Glu Gly Lys Pro Ile Pro Asn Pro
        515                 520                 525

Leu Leu Gly Leu Asp Ser Thr Arg Thr Gly His His His His His His
    530                 535                 540


<210> SEQ ID NO 89
<211> LENGTH: 552
<212> TYPE: PRT
<213> ORGANISM: Artificial Sequence
<220> FEATURE:
<223> OTHER INFORMATION: Artifical

<400> SEQUENCE: 89

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
```

-continued

```
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys Ala Lys Gly Glu Leu Arg Gly His Pro Phe
        515                 520                 525

Glu Gly Lys Pro Ile Pro Asn Pro Leu Leu Gly Leu Asp Ser Thr Arg
    530                 535                 540

Thr Gly His His His His His His
545                 550


<210> SEQ ID NO 90
<211> LENGTH: 546
<212> TYPE: PRT
<213> ORGANISM: Artificial Sequence
<220> FEATURE:
<223> OTHER INFORMATION: Artifical

<400> SEQUENCE: 90

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
```

```
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Val Val Val Leu Ile Ala Val Asn Ser Arg Leu Ile Ile
    130                 135                 140

Glu Asn Leu Met Lys Tyr Gly Trp Leu Ile Arg Thr Asp Phe Trp Phe
145                 150                 155                 160

Ser Ser Arg Ser Leu Arg Asp Trp Pro Leu Phe Met Cys Cys Ile Ser
                165                 170                 175

Leu Ser Ile Phe Pro Leu Ala Ala Phe Thr Val Glu Lys Leu Val Leu
            180                 185                 190

Gln Lys Tyr Ile Ser Glu Pro Val Val Ile Phe Leu His Ile Ile Ile
        195                 200                 205

Thr Met Thr Glu Val Leu Tyr Pro Val Tyr Val Thr Leu Arg Cys Asp
    210                 215                 220

Ser Ala Phe Leu Ser Gly Val Thr Leu Met Leu Leu Thr Cys Ile Val
225                 230                 235                 240

Trp Leu Lys Leu Val Ser Tyr Ala His Thr Ser Tyr Asp Ile Arg Ser
                245                 250                 255

Leu Ala Asn Ala Ala Asp Lys Ala Asn Pro Glu Val Ser Tyr Tyr Val
            260                 265                 270

Ser Leu Lys Ser Leu Ala Tyr Phe Met Val Ala Pro Thr Leu Cys Tyr
        275                 280                 285

Gln Pro Ser Tyr Pro Arg Ser Ala Cys Ile Arg Lys Gly Trp Val Ala
    290                 295                 300

Arg Gln Phe Ala Lys Leu Val Ile Phe Thr Gly Phe Met Gly Phe Ile
305                 310                 315                 320

Ile Glu Gln Tyr Ile Asn Pro Ile Val Arg Asn Ser Lys His Pro Leu
                325                 330                 335

Lys Gly Asp Leu Leu Tyr Ala Ile Glu Arg Val Leu Lys Leu Ser Val
            340                 345                 350

Pro Asn Leu Tyr Val Trp Leu Cys Met Phe Tyr Cys Phe Phe His Leu
        355                 360                 365

Trp Leu Asn Ile Leu Ala Glu Leu Leu Cys Phe Gly Asp Arg Glu Phe
    370                 375                 380

Tyr Lys Asp Trp Trp Asn Ala Lys Ser Val Gly Asp Tyr Trp Arg Met
385                 390                 395                 400

Trp Asn Met Pro Val His Lys Trp Met Val Arg His Ile Tyr Phe Pro
                405                 410                 415

Cys Leu Arg Ser Lys Ile Pro Lys Thr Leu Ala Ile Ile Ile Ala Phe
            420                 425                 430

Leu Val Ser Ala Val Phe His Glu Leu Cys Ile Ala Val Pro Cys Arg
        435                 440                 445

Leu Phe Lys Leu Trp Ala Phe Leu Gly Ile Met Phe Gln Val Pro Leu
    450                 455                 460
```

Val Phe Ile Thr Asn Tyr Leu Gln Glu Arg Phe Gly Ser Thr Val Gly
465 470 475 480

Asn Met Ile Phe Trp Phe Ile Phe Cys Ile Phe Gly Gln Pro Met Cys
485 490 495

Val Leu Leu Tyr Tyr His Asp Leu Met Asn Arg Lys Gly Ser Met Ser
500 505 510

Ala Lys Gly Glu Leu Arg Gly His Pro Phe Glu Gly Lys Pro Ile Pro
515 520 525

Asn Pro Leu Leu Gly Leu Asp Ser Thr Arg Thr Gly His His His His
530 535 540

His His
545

<210> SEQ ID NO 91
<211> LENGTH: 556
<212> TYPE: PRT
<213> ORGANISM: Artificial Sequence
<220> FEATURE:
<223> OTHER INFORMATION: Artifical

<400> SEQUENCE: 91

Met Ala Val Ala Glu Ser Ser Gln Asn Thr Thr Thr Met Ser Gly His
1 5 10 15

Gly Asp Ser Asp Leu Asn Asn Phe Arg Arg Arg Lys Pro Ser Ser Ser
20 25 30

Val Ile Glu Pro Ser Ser Ser Gly Phe Thr Ser Thr Asn Gly Val Pro
35 40 45

Ala Thr Gly His Val Ala Glu Asn Arg Asp Gln Asp Arg Val Gly Ala
50 55 60

Met Glu Asn Ala Thr Gly Ser Val Asn Leu Ile Gly Asn Gly Gly Gly
65 70 75 80

Val Val Ile Gly Asn Glu Glu Lys Gln Val Gly Glu Thr Asp Ile Arg
85 90 95

Phe Thr Tyr Arg Pro Ser Phe Pro Ala His Arg Arg Val Arg Glu Ser
100 105 110

Pro Leu Ser Ser Asp Ala Ile Phe Arg Gln Ser His Ala Gly Leu Leu
115 120 125

Asn Leu Cys Ile Val Val Leu Val Ala Val Asn Ser Arg Leu Ile Ile
130 135 140

Glu Asn Leu Met Lys Tyr Gly Leu Leu Ile Arg Ala Gly Phe Trp Phe
145 150 155 160

Ser Gly Thr Ser Leu Ala Asp Trp Pro Leu Leu Met Cys Cys Leu Thr
165 170 175

Leu Pro Thr Phe Pro Leu Ala Ala Leu Met Val Glu Lys Leu Ala Gln
180 185 190

Arg Lys Leu Ile Ser Lys His Val Val Ile Leu Leu His Ile Val Ile
195 200 205

Thr Thr Ser Val Leu Val Tyr Pro Val Val Val Ile Leu Lys Cys Asp
210 215 220

Ser Ala Val Leu Ser Gly Phe Val Leu Met Phe Leu Ala Ser Ile Ile
225 230 235 240

Trp Leu Lys Leu Val Ser Phe Ala His Thr Asn Tyr Asp Ile Arg Met
245 250 255

Leu Ser Lys Ser Ile Glu Lys Gly Val Thr His Asp Ile Ser Ile Asp
260 265 270

Pro Glu Asn Ile Lys Trp Pro Thr Phe Lys Arg Leu Ser Tyr Phe Met
275 280 285

Leu Ala Pro Thr Leu Cys Tyr Gln Pro Ser Tyr Pro Arg Thr Thr Tyr
290 295 300

Ile Arg Lys Gly Trp Val Val Arg Gln Leu Ile Lys Cys Leu Val Phe
305 310 315 320

Thr Gly Leu Met Gly Phe Ile Ile Glu Gln Tyr Ile Asn Pro Ile Val
325 330 335

Lys Asn Ser Lys His Pro Leu Lys Gly Asn Phe Leu Asn Ala Ile Glu
340 345 350

Arg Val Leu Lys Leu Ser Val Pro Thr Leu Tyr Val Trp Leu Cys Met
355 360 365

Phe Tyr Cys Phe Phe His Leu Trp Leu Asn Ile Leu Ala Glu Leu Leu
370 375 380

Cys Phe Gly Asp Arg Glu Phe Tyr Lys Asp Trp Trp Asn Ala Lys Thr
385 390 395 400

Val Glu Glu Tyr Trp Arg Met Trp Asn Met Pro Val His Lys Trp Val
405 410 415

Ile Arg His Ile Tyr Phe Pro Cys Ile Arg Asn Gly Phe Ser Lys Gly
420 425 430

Val Ala Ile Leu Ile Ser Phe Leu Val Ser Ala Ala Phe His Glu Leu
435 440 445

Cys Val Ala Val Pro Cys His Ile Phe Lys Phe Trp Ala Phe Ile Gly
450 455 460

Ile Met Phe Gln Ile Pro Leu Val Phe Leu Thr Lys Tyr Leu Gln Asp
465 470 475 480

Lys Phe Asn Asn Thr Met Val Gly Asn Met Ile Phe Trp Phe Phe Phe
485 490 495

Ser Ile Leu Gly Gln Pro Met Cys Val Leu Leu Tyr Tyr His Asp Val
500 505 510

Met Asn Arg Gln Gln Ala Gln Thr Asn Arg Ala Lys Gly Glu Leu Arg
515 520 525

Gly His Pro Phe Glu Gly Lys Pro Ile Pro Asn Pro Leu Leu Gly Leu
530 535 540

Asp Ser Thr Arg Thr Gly His His His His His His
545 550 555

<210> SEQ ID NO 92
<211> LENGTH: 554
<212> TYPE: PRT
<213> ORGANISM: Artificial Sequence
<220> FEATURE:
<223> OTHER INFORMATION: Artifical

<400> SEQUENCE: 92

Met Ala Val Ala Glu Ser Ser Gln Asn Thr Thr Thr Met Ser Gly His
1 5 10 15

Gly Asp Ser Asp Leu Asn Asn Phe Arg Arg Arg Lys Pro Ser Ser Ser
20 25 30

Val Ile Glu Pro Ser Ser Ser Gly Phe Thr Ser Thr Asn Gly Val Pro
35 40 45

Ala Thr Gly His Val Ala Glu Asn Arg Asp Gln Asp Arg Val Gly Ala
50 55 60

Met Glu Asn Ala Thr Gly Ser Val Asn Leu Ile Gly Asn Gly Gly Gly
65 70 75 80

```
Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
    130                 135                 140

Glu Asn Leu Met Lys Tyr Gly Leu Leu Ile Arg Ala Gly Phe Trp Phe
145                 150                 155                 160

Asn Asp Lys Ser Leu Arg Asp Trp Pro Leu Leu Met Cys Cys Leu Ser
                165                 170                 175

Leu Pro Ala Phe Pro Leu Gly Ala Phe Ala Val Glu Lys Leu Ala Phe
            180                 185                 190

Asn Asn Val Ile Thr Asp Ala Val Ala Thr Cys Leu His Ile Phe Leu
        195                 200                 205

Ser Thr Thr Glu Ile Val Tyr Pro Val Leu Val Ile Leu Lys Cys Asp
    210                 215                 220

Ser Ala Val Leu Ser Gly Phe Leu Leu Ile Phe Ile Ala Cys Ile Val
225                 230                 235                 240

Trp Leu Lys Leu Val Ser Phe Ala His Thr Asn His Asp Ile Arg Gln
                245                 250                 255

Leu Thr Met Gly Gly Lys Lys Val Asp Asn Glu Leu Ser Thr Val Asp
            260                 265                 270

Met Asp Asn Leu Gln Pro Pro Thr Leu Gly Asn Leu Ile Tyr Phe Met
        275                 280                 285

Met Ala Pro Thr Leu Cys Tyr Gln Pro Ser Tyr Pro Arg Thr Ser Cys
    290                 295                 300

Val Arg Lys Gly Trp Leu Ile Arg Gln Ile Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Lys Gly Gly Leu Leu Asn Ala Val Glu
            340                 345                 350

Thr Val Leu Lys Leu Ser Leu Pro Asn Val Tyr Leu Trp Leu Cys Met
        355                 360                 365

Phe Tyr Ala Phe Phe His Leu Trp Leu Ser Ile Leu Ala Glu Ile Leu
    370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Val
                405                 410                 415

Val Arg His Ile Tyr Phe Pro Cys Met Arg Asn Gly Ile Ser Lys Glu
            420                 425                 430

Val Ala Val Leu Ile Ser Phe Leu Val Ser Ala Val Leu His Glu Ile
        435                 440                 445

Cys Val Ala Val Pro Cys Arg Ile Leu Lys Phe Trp Ala Phe Leu Gly
    450                 455                 460

Ile Met Leu Gln Ile Pro Leu Ile Val Leu Thr Ala Tyr Leu Lys Ser
465                 470                 475                 480

Lys Phe Arg Asp Thr Met Val Gly Asn Met Ile Phe Trp Phe Phe Phe
                485                 490                 495
```

```
Cys Ile Tyr Gly Gln Pro Met Cys Leu Leu Leu Tyr Tyr His Asp Val
            500                 505                 510

Met Asn Arg Ile Glu Lys Ala Arg Ala Lys Gly Glu Leu Arg Gly His
        515                 520                 525

Pro Phe Glu Gly Lys Pro Ile Pro Asn Pro Leu Leu Gly Leu Asp Ser
    530                 535                 540

Thr Arg Thr Gly His His His His His His
545                 550
```

<210> SEQ ID NO 93
<211> LENGTH: 555
<212> TYPE: PRT
<213> ORGANISM: Artificial Sequence
<220> FEATURE:
<223> OTHER INFORMATION: Artifical

<400> SEQUENCE: 93

```
Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Arg Gln Ser His Ala Gly Leu Leu
        115                 120                 125

Asn Leu Cys Ile Val Val Leu Ile Ala Val Asn Ser Arg Leu Ile Ile
    130                 135                 140

Glu Asn Leu Met Lys Tyr Gly Leu Leu Ile Arg Ala Gly Phe Trp Phe
145                 150                 155                 160

Ser Ala Arg Ser Leu Gly Asp Trp Pro Leu Leu Met Cys Cys Leu Thr
                165                 170                 175

Leu Pro Val Phe Pro Leu Val Ala Leu Met Ala Glu Lys Leu Ile Thr
            180                 185                 190

Arg Lys Leu Ile Gly Glu His Val Val Ile Leu Leu His Ile Ile Ile
        195                 200                 205

Thr Thr Ser Ala Ile Val Tyr Pro Val Val Val Thr Leu Lys Cys Asp
    210                 215                 220

Ser Ala Val Leu Ser Gly Phe Val Leu Met Phe Leu Ala Ser Ile Met
225                 230                 235                 240

Trp Met Lys Leu Val Ser Tyr Ala His Thr Asn Tyr Asp Ile Arg Val
                245                 250                 255

Leu Ser Lys Ser Thr Glu Lys Gly Ala Ala Tyr Gly Asn Tyr Val Asp
            260                 265                 270

Pro Glu Asn Met Lys Asp Pro Thr Phe Lys Ser Leu Val Tyr Phe Met
        275                 280                 285

Leu Ala Pro Thr Leu Cys Tyr Gln Pro Thr Tyr Pro Gln Thr Thr Cys
    290                 295                 300
```

```
Ile Arg Lys Gly Trp Val Thr Gln Gln Leu Ile Lys Cys Val Val Phe
305                 310                 315                 320

Thr Gly Leu Met Gly Phe Ile Ile Glu Gln Tyr Ile Asn Pro Ile Val
                325                 330                 335

Lys Asn Ser Lys His Pro Leu Lys Gly Asn Phe Leu Asn Ala Ile Glu
            340                 345                 350

Arg Val Leu Lys Leu Ser Val Pro Thr Leu Tyr Val Trp Leu Cys Met
        355                 360                 365

Phe Tyr Cys Phe Phe His Leu Trp Leu Asn Ile Val Ala Glu Leu Leu
    370                 375                 380

Cys Phe Gly Asp Arg Glu Phe Tyr Lys Asp Trp Trp Asn Ala Lys Thr
385                 390                 395                 400

Val Glu Glu Tyr Trp Arg Met Trp Asn Met Pro Val His Lys Trp Ile
                405                 410                 415

Ile Arg His Ile Tyr Phe Pro Cys Ile Arg Lys Gly Phe Ser Arg Gly
            420                 425                 430

Val Ala Ile Leu Ile Ser Phe Leu Val Ser Ala Val Phe His Glu Ile
        435                 440                 445

Cys Ile Ala Val Pro Cys His Ile Phe Lys Phe Trp Ala Phe Ser Gly
    450                 455                 460

Ile Met Phe Gln Ile Pro Leu Val Phe Leu Thr Arg Tyr Leu His Ala
465                 470                 475                 480

Thr Phe Lys His Val Met Val Gly Asn Met Ile Phe Trp Phe Phe Phe
                485                 490                 495

Ser Ile Val Gly Gln Pro Met Cys Val Leu Leu Tyr Tyr His Asp Val
            500                 505                 510

Met Asn Arg Gln Ala Gln Ala Ser Arg Ala Lys Gly Glu Leu Arg Gly
        515                 520                 525

His Pro Phe Glu Gly Lys Pro Ile Pro Asn Pro Leu Leu Gly Leu Asp
    530                 535                 540

Ser Thr Arg Thr Gly His His His His His His
545                 550                 555


<210> SEQ ID NO 94
<211> LENGTH: 554
<212> TYPE: PRT
<213> ORGANISM: Artificial Sequence
<220> FEATURE:
<223> OTHER INFORMATION: Artifical

<400> SEQUENCE: 94

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110
```

-continued

```
Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
    130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
            180                 185                 190

Asn Asn Leu Ile Ser Asp Pro Ala Thr Thr Cys Phe His Ile Leu Phe
        195                 200                 205

Thr Thr Phe Glu Ile Val Tyr Pro Val Leu Val Ile Leu Lys Cys Asp
    210                 215                 220

Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
                245                 250                 255

Leu Ile Thr Ser Gly Lys Lys Val Asp Asn Glu Leu Thr Ala Ala Gly
            260                 265                 270

Ile Asp Asn Leu Gln Ala Pro Thr Leu Gly Ser Leu Thr Tyr Phe Met
        275                 280                 285

Met Ala Pro Thr Leu Cys Tyr Gln Pro Ser Tyr Pro Arg Thr Pro Tyr
    290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Met Gly Gly Leu Leu Asn Ala Val Glu
            340                 345                 350

Thr Val Leu Lys Leu Ser Leu Pro Asn Val Tyr Leu Trp Leu Cys Met
        355                 360                 365

Phe Tyr Cys Leu Phe His Leu Trp Leu Asn Ile Leu Ala Glu Ile Leu
    370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
                405                 410                 415

Val Arg His Ile Tyr Phe Pro Cys Met Arg Asn Gly Ile Ser Lys Glu
            420                 425                 430

Val Ala Val Phe Ile Ser Phe Phe Val Ser Ala Val Leu His Glu Leu
        435                 440                 445

Cys Val Ala Val Pro Cys His Ile Leu Lys Phe Trp Ala Phe Leu Gly
    450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe Phe
                485                 490                 495

Cys Ile Tyr Gly Gln Pro Met Cys Val Leu Leu Tyr Tyr His Asp Val
            500                 505                 510

Met Asn Arg Thr Glu Lys Ala Lys Ala Lys Gly Glu Leu Arg Gly His
        515                 520                 525

Pro Phe Glu Gly Lys Pro Ile Pro Asn Pro Leu Leu Gly Leu Asp Ser
```

530 535 540

Thr Arg Thr Gly His His His His His His
545 550

<210> SEQ ID NO 95
<211> LENGTH: 1812
<212> TYPE: DNA
<213> ORGANISM: Artificial Sequence
<220> FEATURE:
<223> OTHER INFORMATION: Artifical

<400> SEQUENCE: 95
ggatccacaa gtttgtacaa aaaagcaggc ttctagattt ctagttttct ccatataaaa 60
aaaatattct ctgagcttct cgattctcta aaaagacaag gccaaaaaaa acaccatggc 120
tgttgctgaa tcttctcaga acaccactac tatgtctgga cacggtgatt ctgacctcaa 180
cgtaaaagaa gatgtttttt atttccagca atgttacatt gttatacgta taatgatgag 240
tttagtgatc aagttcctct ttgattcttc tttcttgttg cagaacttca gacgtagaaa 300
gccttctagc tctgttatcg agccttcttc ttctggattc acctctacta acggtgttcc 360
tgctactgga catgttgctg agaacagaga tcaggataga gttggagcta tggaaaacgc 420
taccggatct gttaacctta tcggaaacgg tggaggtgtt gttatcggta acgaggaaaa 480
gcaagttgga gagactgata tcagattcac ctacagacca tctttcccag ctcacagaag 540
agttagggag tctccactct cgagtgatgc tatcttcaag cagtctcacg ctggactttt 600
caacctctgc atcgttgttc ttatcgctgt taatagcaga cttatcatcg agaacctcat 660
gaagtacgga tggcttatcg atactggatt ctggttctct tctcgttctc ttggtgactg 720
gtctatcttc atgtgctgtc ttactctccc tatcttccct cttgctgctt tcatcgttga 780
gaagcttgtt cagaggaacc atatcgctga gcttgttgct gttcttctcc acgttatcgt 840
ttctactgct gctgttctct accctgttat cgttatcctt acctgcgatt ctgtttacat 900
gtctggtgtt gtgcttatgc ttttcggatg catcatgtgg cttaagctcg tttcttacgc 960
tcacacctct tcagatatca gaaccctcgc taagtctgga tacaaaggtg atgctcaccc 1020
taactctact atcgtgtctt gctcttacga tgtgtctctt aagtctctcg cttacttcat 1080
ggttgctcct accctttgtt accaaccttc ttaccctaga tctagctgca tcagaaaggg 1140
atgggttgtg agacaattcg ttaagctcat cgtgttcatc ggacttatgg gattcatcat 1200
cgagcagtac atcaacccta tcgtgagaaa ctctaagcac cctctcaagg gagatttcct 1260
ttacgctatc gagagagtgc ttaagctttc tgtgcctaac ctttacgttt ggctctgcat 1320
gttctactca ttcttccacc tttggcttaa catccttgct gagttgctta gattcggaga 1380
cagagagttc tacaaggatt ggtggaacgc taagactgtt gctgagtact ggaagatgtg 1440
gaacatgcct gttcatagat ggatggttag gcacctttac ttcccttgtc tcagaaacgg 1500
aatccctaaa gagggtgcta tcatcattgc tttcttggtg tctggtgctt tccatgagtt 1560
gtgtatcgct gttccttgtc acgttttcaa gctctgggct ttcatcggaa tcatgttcca 1620
agttcctctc gttcttatca ctaactacct ccaagagaag ttctctaaca gcatggtggg 1680
aaacatgatt ttctggttca ttttctgcat ccttggacag cctatgtgtg ttcttctcta 1740
ctaccacgat ctcatcaacc tcaaagagaa gtgaaggtac cacccagctt tcttgtacaa 1800
agtggtgagc tc 1812

<210> SEQ ID NO 96

<211> LENGTH: 1740
<212> TYPE: DNA
<213> ORGANISM: Artificial Sequence
<220> FEATURE:
<223> OTHER INFORMATION: Artifical

<400> SEQUENCE: 96
gaattcacaa gtttgtacaa aaaagcaggc ttctagattt ctagttttct ccatataaaa 60
aaaatattct ctgagcttct cgattctcta aaaagacaag gccaaaaaaa acaccatggc 120
tcctccacct tctatgcctg ctgcttctga tagagctgga cctggaagag atgctggcga 180
ttctgtaaaa gaagatgttt tttatttcca gcaatgttac attgttatac gtataatgat 240
gagtttagtg atcaagttcc tctttgattc ttctttcttg ttgcagtcat ctctcagact 300
tagaagggct ccatctgctg acgctggtga ccttgctggt gatagctctg gtggacttag 360
agaaaacggt gagcctcaat ctcctactaa ccctccacct caagagcaac aacagcacga 420
gatgctttac tacagagctt ctgctcctgc tcatagaaga gtgaaagaat ctccactctc 480
gagtgatgct atcttcagac agtctcatgc tggacttctc aacctctgca tcgttgttct 540
tatcgctgtg aacagcagac ttatcatcga gaacctcatg aagtacggac ttctcatcag 600
agctggattc tggttctctg ctagatctct tggagattgg cctcttctta tgtgctgtct 660
tacccttcct gttttccctc ttgttgctct tatggccgag aagcttatca ctagaaagct 720
catcggagag catgttgtta tccttctcca catcatcatc actacctctg ctatcgttta 780
ccctgttgtt gttaccctta agtgcgattc tgctgttctt tctggattcg tgcttatgtt 840
cctcgcttct atcatgtgga tgaagctcgt ttcttacgct cacaccaact acgatatcag 900
agtgctctct aagtctactg agaagggtgc tgcttacgga aactatgtgg accctgagaa 960
catgaaggat cctaccttca agtctctcgt gtacttcatg cttgctccta ccctttgtta 1020
ccaacctact taccctcaga ctacctgtat cagaaaggga tgggttaccc aacaactcat 1080
caagtgcgtt gtgttcactg gacttatggg attcatcatc gagcagtaca tcaaccctat 1140
cgtgaagaac tctaagcacc ctcttaaggg aaacttcctc aacgctatcg agagagttct 1200
caagctttct gttcctactc tttacgtttg gctctgcatg ttctactgtt tcttccacct 1260
ttggctcaac atcgttgctg agcttctctg tttcggagat cgtgagttct acaaggattg 1320
gtggaacgct aagactgttg aggaatactg gcgtatgtgg aacatgcctg ttcataagtg 1380
gatcatcagg cacatctact tcccttgcat caggaaggga ttctctaggg gagttgctat 1440
ccttatctct ttcctcgttt ctgctgtttt ccatgagatc tgtatcgctg ttccttgtca 1500
catcttcaag ttctgggctt tctctggtat catgttccag atccctcttg ttttccttac 1560
cagatacctt cacgctactt tcaagcacgt tatggtggga aacatgattt tctggttctt 1620
tttcagcatc gttggacagc ctatgtgtgt tcttctctac taccacgatg ttatgaacag 1680
acaagctcag gcttctaggt gaaggtacca cccagctttc ttgtacaaag tggtgagctc 1740

<210> SEQ ID NO 97
<211> LENGTH: 1794
<212> TYPE: DNA
<213> ORGANISM: Artificial Sequence
<220> FEATURE:
<223> OTHER INFORMATION: Artifical

<400> SEQUENCE: 97
ggatccacaa gtttgtacaa aaaagcaggc ttctagattt ctagttttct ccatataaaa 60
aaaatattct ctgagcttct cgattctcta aaaagacaag gccaaaaaaa acaccatggc 120

```
tgattctgag gatgctcctc ctgctgttca tagaaggcct ccaagacctg ctagaggtgc    180
tgctgctgct gtaaaagaag atgtttttta tttccagcaa tgttacattg ttatacgtat    240
aatgatgagt ttagtgatca agttcctctt tgattcttct ttcttgttgc agcaaggatt    300
cgctgctgct cttagaagaa ggcttagaag cggagctgct gttgctgcta gagcttcttt    360
cgctgctgat tctggtgatg agtctggacc tggtgagcct tcttcatcta ggcgtagaga    420
taactctggt ggagcttctt ctgctgctgg tggtagagct ggtgctggtg atttctctgc    480
tttcaccttc agagctgctg ctcctgttca cagaaaggct aaagaatctc cactctcgag    540
tgatgctatc ttcaagcagt ctcacgctgg acttttcaac ctctgcatcg ttgttcttgt    600
tgctgtgaac agcagactca tcatcgagaa cctcatgaag tacggacttc tcatcagatc    660
tggattctgg ttcaacgcta cctctcttag agattggcct cttcttatgt gctgtctctc    720
tcttccaatc ttccctcttg gtgctttcgc tgttgagaag cttgctttca acaacctcat    780
ctctgatcct gctactactt gcttccacat ccttttcact accttcgaga tcgtttaccc    840
tgttctcgtt atccttaaat gcgattctgc tgttctttct ggattcgtgc tcatgttcat    900
tgcttgcatc gtttggctta agctcgtttc tttcgctcac actaaccacg atatcagaaa    960
gctcatcacc tctggaaaga aggttgacaa cgagcttact gctgctggaa tcgataacct   1020
tcaggctcct actcttggat ctctcaccta cttcatgatg gctcctaccc tttgttacca   1080
accttcttac cctagaaccc cttacgttag aaagggatgg cttgttagac aggttatcct   1140
ctaccttatc ttcactggac ttcagggatt catcatcgag cagtacatca accctatcgt   1200
tgttaactct cagcatcctc ttatgggagg acttcttaac gctgttgaga ctgtgcttaa   1260
gctttctctc cctaacgttt acctttggct ctgtatgttc tactgccttt tccacctttg   1320
gcttaacatc cttgctgaga tccttagatt cggagacaga gagttctaca aggattggtg   1380
gaacgctaag actatcgatg agtactggcg taagtggaac atgcctgttc ataagtggat   1440
cgtgaggcat atctacttcc cttgcatgag aaacggaatc tctaaagagg ttgccgtttt   1500
catctctttc ttcgtgtctg ctgttctcca tgagctttgt gttgctgttc cttgccacat   1560
ccttaagttc tgggctttcc ttggaatcat gcttcagatc cctcttatca tccttaccag   1620
ctacctcaag aacaagttct ctgataccat ggtgggaaac atgattttct ggttcttttt   1680
ctgcatctac ggacaaccta tgtgtgttct tctctactac cacgatgtta tgaacagaac   1740
cgagaaggcc aagtgaaggt accacccagc tttcttgtac aaagtggtga gctc         1794
```

<210> SEQ ID NO 98
<211> LENGTH: 518
<212> TYPE: PRT
<213> ORGANISM: Artificial Sequence
<220> FEATURE:
<223> OTHER INFORMATION: Artifical

<400> SEQUENCE: 98

```
Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60
```

-continued

```
Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ala Glu Leu Val Ala Val Leu Leu His Val Ile Val
        195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
```

```
                485                 490                 495

Cys Ile Leu Gly Gln Pro Met Cys Val Leu Leu Tyr Tyr His Asp Leu
            500                 505                 510

Ile Asn Leu Lys Glu Lys
        515


<210> SEQ ID NO 99
<211> LENGTH: 512
<212> TYPE: PRT
<213> ORGANISM: Artificial Sequence
<220> FEATURE:
<223> OTHER INFORMATION: Artifical

<400> SEQUENCE: 99

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190

Thr Thr Cys Phe His Ile Leu Phe Thr Thr Phe Glu Ile Val Tyr Pro
        195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
            260                 265                 270

Leu Gly Ser Leu Thr Tyr Phe Met Met Ala Pro Thr Leu Cys Tyr Gln
        275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
```

```
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
        355                 360                 365

Leu Asn Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
            420                 425                 430

Val Ser Ala Val Leu His Glu Leu Cys Val Ala Val Pro Cys His Ile
        435                 440                 445

Leu Lys Phe Trp Ala Phe Leu Gly Ile Met Leu Gln Ile Pro Leu Ile
    450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510


<210> SEQ ID NO 100
<211> LENGTH: 520
<212> TYPE: PRT
<213> ORGANISM: Artificial Sequence
<220> FEATURE:
<223> OTHER INFORMATION: Artifical

<400> SEQUENCE: 100

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
    130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
```

```
            180                 185                 190

Asn Asn Leu Ile Ser Asp Pro Ala Thr Thr Cys Phe His Ile Leu Phe
        195                 200                 205

Thr Thr Phe Glu Ile Val Tyr Pro Val Leu Val Ile Leu Lys Cys Asp
    210                 215                 220

Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
                245                 250                 255

Leu Ile Thr Ser Gly Lys Lys Val Asp Asn Glu Leu Thr Ala Ala Gly
            260                 265                 270

Ile Asp Asn Leu Gln Ala Pro Thr Leu Gly Ser Leu Thr Tyr Phe Met
        275                 280                 285

Met Ala Pro Thr Leu Cys Tyr Gln Pro Ser Tyr Pro Arg Thr Pro Tyr
    290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Met Gly Gly Leu Leu Asn Ala Val Glu
            340                 345                 350

Thr Val Leu Lys Leu Ser Leu Pro Asn Val Tyr Leu Trp Leu Cys Met
        355                 360                 365

Phe Tyr Cys Leu Phe His Leu Trp Leu Asn Ile Leu Ala Glu Ile Leu
    370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
                405                 410                 415

Val Arg His Ile Tyr Phe Pro Cys Met Arg Asn Gly Ile Ser Lys Glu
            420                 425                 430

Val Ala Val Phe Ile Ser Phe Phe Val Ser Ala Val Leu His Glu Leu
        435                 440                 445

Cys Val Ala Val Pro Cys His Ile Leu Lys Phe Trp Ala Phe Leu Gly
    450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe Phe
                485                 490                 495

Cys Ile Tyr Gly Gln Pro Met Cys Val Leu Leu Tyr Tyr His Asp Val
            500                 505                 510

Met Asn Arg Thr Glu Lys Ala Lys
        515                 520


<210> SEQ ID NO 101
<211> LENGTH: 510
<212> TYPE: PRT
<213> ORGANISM: Artificial Sequence
<220> FEATURE:
<223> OTHER INFORMATION: Artifical

<400> SEQUENCE: 101

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
```

-continued

```
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Ile
        115                 120                 125

Ala Val Asn Ser Arg Leu Ile Ile Glu Asn Leu Met Lys Tyr Gly Trp
    130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ala Glu Leu Val
            180                 185                 190

Ala Val Leu Leu His Val Ile Val Ser Thr Ala Ala Val Leu Tyr Pro
        195                 200                 205

Val Ile Val Ile Leu Thr Cys Asp Ser Val Tyr Met Ser Gly Val Val
    210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
            260                 265                 270

Leu Lys Ser Leu Ala Tyr Phe Met Val Ala Pro Thr Leu Cys Tyr Gln
        275                 280                 285

Pro Ser Tyr Pro Arg Ser Ser Cys Ile Arg Lys Gly Trp Val Val Arg
    290                 295                 300

Gln Phe Val Lys Leu Ile Val Phe Ile Gly Leu Met Gly Phe Ile Ile
305                 310                 315                 320

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
        355                 360                 365

Leu Asn Ile Leu Ala Glu Leu Leu Arg Phe Gly Asp Arg Glu Phe Tyr
    370                 375                 380

Lys Asp Trp Trp Asn Ala Lys Thr Val Ala Glu Tyr Trp Lys Met Trp
385                 390                 395                 400

Asn Met Pro Val His Arg Trp Met Val Arg His Leu Tyr Phe Pro Cys
                405                 410                 415

Leu Arg Asn Gly Ile Pro Lys Glu Gly Ala Ile Ile Ile Ala Phe Leu
            420                 425                 430

Val Ser Gly Ala Phe His Glu Leu Cys Ile Ala Val Pro Cys His Val
        435                 440                 445
```

```
Phe Lys Leu Trp Ala Phe Ile Gly Ile Met Phe Gln Val Pro Leu Val
    450                 455                 460

Leu Ile Thr Asn Tyr Leu Gln Glu Lys Phe Ser Asn Ser Met Val Gly
465                 470                 475                 480

Asn Met Ile Phe Trp Phe Ile Phe Cys Ile Leu Gly Gln Pro Met Cys
                485                 490                 495

Val Leu Leu Tyr Tyr His Asp Leu Ile Asn Leu Lys Glu Lys
            500                 505                 510


<210> SEQ ID NO 102
<211> LENGTH: 102
<212> TYPE: DNA
<213> ORGANISM: Artificial Sequence
<220> FEATURE:
<223> OTHER INFORMATION: Arabidopsis thaliana

<400> SEQUENCE: 102

gtaaaagaag atgtttttta tttccagcaa tgttacattg ttatacgtat aatgatgagt     60

ttagtgatca agttcctctt tgattcttct ttcttgttgc ag                       102


<210> SEQ ID NO 103
<211> LENGTH: 1761
<212> TYPE: DNA
<213> ORGANISM: Artificial Sequence
<220> FEATURE:
<223> OTHER INFORMATION: Brassica optimised

<400> SEQUENCE: 103

atggctgttg ctgaatcttc tcagaacacc actactatgt ctggacacgg tgattctgac     60

ctcaacgtaa aagaagatgt tttttatttc cagcaatgtt acattgttat acgtataatg    120

atgagtttag tgatcaagtt cctctttgat tcttctttct tgttgcagaa cttcagacgt    180

agaaagcctt ctagctctgt tatcgagcct tcttcttctg gattcacctc tactaacggt    240

gttcctgcta ctggacatgt tgctgagaac agagatcagg atagagttgg agctatggaa    300

aacgctaccg gatctgttaa ccttatcgga aacggtggag gtgttgttat cggtaacgag    360

gaaaagcaag ttggagagac tgatatcaga ttcacctaca gaccatcttt cccagctcac    420

agaagagtta gggagtctcc actctcgagt gatgctatct tcaagcagtc tcacgctgga    480

cttttcaacc tctgcatcgt tgttcttatc gctgttaata gcagacttat catcgagaac    540

ctcatgaagt acggatggct tatcgatact ggattctggt tctcttctcg ttctcttggt    600

gactggtcta tcttcatgtg ctgtcttact ctccctatct tccctcttgc tgctttcatc    660

gttgagaagc ttgttcagag gaaccatatc gctgagcttg ttgctgttct tctccacgtt    720

atcgtttcta ctgctgctgt tctctaccct gttatcgtta tccttacctg cgattctgtt    780

tacatgtctg gtgttgtgct tatgcttttc ggatgcatca tgtggcttaa gctcgtttct    840

tacgctcaca cctcttcaga tatcagaacc ctcgctaagt ctggatacaa aggtgatgct    900

caccctaact ctactatcgt gtcttgctct tacgatgtgt ctcttaagtc tctcgcttac    960

ttcatggttg ctcctaccct ttgttaccaa ccttcttacc ctagatctag ctgcatcaga   1020

aagggatggg ttgtgagaca attcgttaag ctcatcgtgt tcatcggact tatgggattc   1080

atcatcgagc agtacatcaa ccctatcgtg agaaactcta agcaccctct caagggagat   1140

ttcctttacg ctatcgagag agtgcttaag ctttctgtgc ctaaccttta cgtttggctc   1200

tgcatgttct actcattctt ccacctttgg cttaacatcc ttgctgagtt gcttagattc   1260
```

ggagacagag agttctacaa ggattggtgg aacgctaaga ctgttgctga gtactggaag 1320
atgtggaaca tgcctgttca tagatggatg gttaggcacc tttacttccc ttgtctcaga 1380
aacggaatcc ctaaagaggg tgctatcatc attgctttct tggtgtctgg tgctttccat 1440
gagttgtgta tcgctgttcc ttgtcacgtt ttcaagctct gggctttcat cggaatcatg 1500
ttccaagttc ctctcgttct tatcactaac tacctccaag agaagttctc taacagcatg 1560
gtgggaaaca tgattttctg gttcattttc tgcatccttg gacagcctat gtgtgttctt 1620
ctctactacc acgatctcat caacctcaaa gagaaggcta agggtgagct tagaggtcat 1680
cctttcgagg gtaagcctat ccctaaccct cttctcggtc tcgattctac tagaactggt 1740
catcatcatc accatcactg a 1761

<210> SEQ ID NO 104
<211> LENGTH: 1659
<212> TYPE: DNA
<213> ORGANISM: Artificial Sequence
<220> FEATURE:
<223> OTHER INFORMATION: Brassica optimised

<400> SEQUENCE: 104
atggctgttg ctgaatcttc tcagaacacc actactatgt ctggacacgg tgattctgac 60
ctcaacaact tcagacgtag aaagccttct agctctgtta tcgagccttc ttcttctgga 120
ttcacctcta ctaacggtgt tcctgctact ggacatgttg ctgagaacag agatcaggat 180
agagttggag ctatggaaaa cgctaccgga tctgttaacc ttatcggaaa cggtggaggt 240
gttgttatcg gtaacgagga aaagcaagtt ggagagactg atatcagatt cacctacaga 300
ccatctttcc cagctcacag aagagttagg gagtctccac tctcgagtga tgctatcttc 360
aagcagtctc acgctggact tttcaacctc tgcatcgttg ttcttatcgc tgttaatagc 420
agacttatca tcgagaacct catgaagtac ggatggctta tcgatactgg attctggttc 480
tcttctcgtt ctcttggtga ctggtctatc ttcatgtgct gtcttactct ccctatcttc 540
cctcttgctg ctttcatcgt tgagaagctt gttcagagga accatatcgc tgagcttgtt 600
gctgttcttc tccacgttat cgtttctact gctgctgttc tctaccctgt tatcgttatc 660
cttacctgcg attctgttta catgtctggt gttgtgctta tgcttttcgg atgcatcatg 720
tggcttaagc tcgtttctta cgctcacacc tcttcagata tcagaaccct cgctaagtct 780
ggatacaaag gtgatgctca ccctaactct actatcgtgt cttgctctta cgatgtgtct 840
cttaagtctc tcgcttactt catggttgct cctacccttt gttaccaacc ttcttaccct 900
agatctagct gcatcagaaa gggatgggtt gtgagacaat tcgttaagct catcgtgttc 960
atcggactta tgggattcat catcgagcag tacatcaacc ctatcgtgag aaactctaag 1020
caccctctca agggagattt cctttacgct atcgagagag tgcttaagct ttctgtgcct 1080
aacctttacg tttggctctg catgttctac tcattcttcc acctttggct taacatcctt 1140
gctgagttgc ttagattcgg agacagagag ttctacaagg attggtggaa cgctaagact 1200
gttgctgagt actggaagat gtggaacatg cctgttcata gatggatggt taggcacctt 1260
tacttccctt gtctcagaaa cggaatccct aaagagggtg ctatcatcat tgctttcttg 1320
gtgtctggtg ctttccatga gttgtgtatc gctgttcctt gtcacgtttt caagctctgg 1380
gctttcatcg gaatcatgtt ccaagttcct ctcgttctta tcactaacta cctccaagag 1440
aagttctcta acagcatggt gggaaacatg attttctggt tcattttctg catccttgga 1500
cagcctatgt gtgttcttct ctactaccac gatctcatca acctcaaaga gaaggctaag 1560
ggtgagctta gaggtcatcc tttcgagggt aagcctatcc ctaaccctct tctcggtctc 1620
gattctacta gaactggtca tcatcatcac catcactga 1659

<210> SEQ ID NO 105
<211> LENGTH: 552
<212> TYPE: PRT
<213> ORGANISM: Artificial Sequence
<220> FEATURE:
<223> OTHER INFORMATION: Brassica optimised

<400> SEQUENCE: 105

Met Ala Val Ala Glu Ser Ser Gln Asn Thr Thr Thr Met Ser Gly His
1 5 10 15

Gly Asp Ser Asp Leu Asn Asn Phe Arg Arg Arg Lys Pro Ser Ser Ser
20 25 30

Val Ile Glu Pro Ser Ser Ser Gly Phe Thr Ser Thr Asn Gly Val Pro
35 40 45

Ala Thr Gly His Val Ala Glu Asn Arg Asp Gln Asp Arg Val Gly Ala
50 55 60

Met Glu Asn Ala Thr Gly Ser Val Asn Leu Ile Gly Asn Gly Gly Gly
65 70 75 80

Val Val Ile Gly Asn Glu Glu Lys Gln Val Gly Glu Thr Asp Ile Arg
85 90 95

Phe Thr Tyr Arg Pro Ser Phe Pro Ala His Arg Arg Val Arg Glu Ser
100 105 110

Pro Leu Ser Ser Asp Ala Ile Phe Lys Gln Ser His Ala Gly Leu Phe
115 120 125

Asn Leu Cys Ile Val Val Leu Ile Ala Val Asn Ser Arg Leu Ile Ile
130 135 140

Glu Asn Leu Met Lys Tyr Gly Trp Leu Ile Asp Thr Gly Phe Trp Phe
145 150 155 160

Ser Ser Arg Ser Leu Gly Asp Trp Ser Ile Phe Met Cys Cys Leu Thr
165 170 175

Leu Pro Ile Phe Pro Leu Ala Ala Phe Ile Val Glu Lys Leu Val Gln
180 185 190

Arg Asn His Ile Ala Glu Leu Val Ala Val Leu Leu His Val Ile Val
195 200 205

Ser Thr Ala Ala Val Leu Tyr Pro Val Ile Val Ile Leu Thr Cys Asp
210 215 220

Ser Val Tyr Met Ser Gly Val Val Leu Met Leu Phe Gly Cys Ile Met
225 230 235 240

Trp Leu Lys Leu Val Ser Tyr Ala His Thr Ser Ser Asp Ile Arg Thr
245 250 255

Leu Ala Lys Ser Gly Tyr Lys Gly Asp Ala His Pro Asn Ser Thr Ile
260 265 270

Val Ser Cys Ser Tyr Asp Val Ser Leu Lys Ser Leu Ala Tyr Phe Met
275 280 285

Val Ala Pro Thr Leu Cys Tyr Gln Pro Ser Tyr Pro Arg Ser Ser Cys
290 295 300

Ile Arg Lys Gly Trp Val Val Arg Gln Phe Val Lys Leu Ile Val Phe
305 310 315 320

Ile Gly Leu Met Gly Phe Ile Ile Glu Gln Tyr Ile Asn Pro Ile Val
325 330 335

Arg Asn Ser Lys His Pro Leu Lys Gly Asp Phe Leu Tyr Ala Ile Glu

```
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys Ala Lys Gly Glu Leu Arg Gly His Pro Phe
        515                 520                 525

Glu Gly Lys Pro Ile Pro Asn Pro Leu Leu Gly Leu Asp Ser Thr Arg
    530                 535                 540

Thr Gly His His His His His His
545                 550
```

<210> SEQ ID NO 106
<211> LENGTH: 1743
<212> TYPE: DNA
<213> ORGANISM: Artificial Sequence
<220> FEATURE:
<223> OTHER INFORMATION: Brassica optimised

<400> SEQUENCE: 106

```
atggctgatt ctgaggatgc tcctcctgct gttcatagaa ggcctccaag acctgctaga     60

ggtgctgctg ctgctgtaaa agaagatgtt ttttatttcc agcaatgtta cattgttata    120

cgtataatga tgagtttagt gatcaagttc ctctttgatt cttctttctt gttgcagcaa    180

ggattcgctg ctgctcttag aagaaggctt agaagcggag ctgctgttgc tgctagagct    240

tctttcgctg ctgattctgg tgatgagtct ggacctggtg agccttcttc atctaggcgt    300

agagataact ctggtggagc ttcttctgct gctggtggta gagctggtgc tggtgatttc    360

tctgctttca ccttcagagc tgctgctcct gttcacagaa aggctaaaga atctccactc    420

tcgagtgatg ctatcttcaa gcagtctcac gctggacttt tcaacctctg catcgttgtt    480

cttgttgctg tgaacagcag actcatcatc gagaacctca tgaagtacgg acttctcatc    540

agatctggat tctggttcaa cgctacctct cttagagatt ggcctcttct tatgtgctgt    600

ctctctcttc caatcttccc tcttggtgct ttcgctgttg agaagcttgc tttcaacaac    660

ctcatctctg atcctgctac tacttgcttc cacatccttt tcactacctt cgagatcgtt    720

taccctgttc tcgttatcct taaatgcgat tctgctgttc tttctggatt cgtgctcatg    780

ttcattgctt gcatcgtttg gcttaagctc gtttctttcg ctcacactaa ccacgatatc    840
```

-continued

```
agaaagctca tcacctctgg aaagaaggtt gacaacgagc ttactgctgc tggaatcgat    900
aaccttcagg ctcctactct tggatctctc acctacttca tgatggctcc taccctttgt    960
taccaacctt cttaccctag aaccccttac gttagaaagg gatggcttgt tagacaggtt   1020
atcctctacc ttatcttcac tggacttcag ggattcatca tcgagcagta catcaaccct   1080
atcgttgtta actctcagca tcctcttatg ggaggacttc ttaacgctgt tgagactgtg   1140
cttaagcttt ctctccctaa cgtttacctt tggctctgta tgttctactg ccttttccac   1200
ctttggctta acatccttgc tgagatcctt agattcggag acagagagtt ctacaaggat   1260
tggtggaacg ctaagactat cgatgagtac tggcgtaagt ggaacatgcc tgttcataag   1320
tggatcgtga ggcatatcta cttcccttgc atgagaaacg gaatctctaa agaggttgcc   1380
gttttcatct ctttcttcgt gtctgctgtt ctccatgagc tttgtgttgc tgttccttgc   1440
cacatcctta agttctgggc tttccttgga atcatgcttc agatccctct tatcatcctt   1500
accagctacc tcaagaacaa gttctctgat accatggtgg gaaacatgat tttctggttc   1560
tttttctgca tctacggaca acctatgtgt gttcttctct actaccacga tgttatgaac   1620
agaaccgaga aggccaaggc taagggtgag cttagaggtc atcctttcga gggtaagcct   1680
atccctaacc ctcttctcgg tctcgattct actagaactg gtcatcatca tcaccatcac   1740
tga                                                                 1743
```

```
<210> SEQ ID NO 107
<211> LENGTH: 1641
<212> TYPE: DNA
<213> ORGANISM: Artificial Sequence
<220> FEATURE:
<223> OTHER INFORMATION: Brassica optimised

<400> SEQUENCE: 107

atggctgatt ctgaggatgc tcctcctgct gttcatagaa ggcctccaag acctgctaga     60
ggtgctgctg ctgctcaagg attcgctgct gctcttagaa gaaggcttag aagcggagct    120
gctgttgctg ctagagcttc tttcgctgct gattctggtg atgagtctgg acctggtgag    180
ccttcttcat ctaggcgtag agataactct ggtggagctt cttctgctgc tggtggtaga    240
gctggtgctg gtgatttctc tgctttcacc ttcagagctg ctgctcctgt tcacagaaag    300
gctaaagaat ctccactctc gagtgatgct atcttcaagc agtctcacgc tggacttttc    360
aacctctgca tcgttgttct tgttgctgtg aacagcagac tcatcatcga gaacctcatg    420
aagtacggac ttctcatcag atctggattc tggttcaacg ctacctctct tagagattgg    480
cctcttctta tgtgctgtct ctctcttcca atcttccctc ttggtgcttt cgctgttgag    540
aagcttgctt tcaacaacct catctctgat cctgctacta cttgcttcca catccttttc    600
actaccttcg agatcgttta ccctgttctc gttatcctta aatgcgattc tgctgttctt    660
tctggattcg tgctcatgtt cattgcttgc atcgtttggc ttaagctcgt ttctttcgct    720
cacactaacc acgatatcag aaagctcatc acctctggaa agaaggttga caacgagctt    780
actgctgctg gaatcgataa ccttcaggct cctactcttg gatctctcac ctacttcatg    840
atggctccta ccctttgtta ccaaccttct taccctagaa ccccttacgt tagaaaggga    900
tggcttgtta gacaggttat cctctacctt atcttcactg gacttcaggg attcatcatc    960
gagcagtaca tcaaccctat cgttgttaac tctcagcatc ctcttatggg aggacttctt   1020
aacgctgttg agactgtgct taagctttct ctccctaacg tttacctttg gctctgtatg   1080
ttctactgcc ttttccacct ttggcttaac atccttgctg agatccttag attcggagac   1140
```

```
agagagttct acaaggattg gtggaacgct aagactatcg atgagtactg gcgtaagtgg   1200

aacatgcctg ttcataagtg gatcgtgagg catatctact tcccttgcat gagaaacgga   1260

atctctaaag aggttgccgt tttcatctct ttcttcgtgt ctgctgttct ccatgagctt   1320

tgtgttgctg ttccttgcca catccttaag ttctgggctt tccttggaat catgcttcag   1380

atccctctta tcatccttac cagctacctc aagaacaagt tctctgatac catggtggga   1440

aacatgattt tctggttctt tttctgcatc tacggacaac ctatgtgtgt tcttctctac   1500

taccacgatg ttatgaacag aaccgagaag gccaaggcta agggtgagct tagaggtcat   1560

cctttcgagg gtaagcctat ccctaaccct cttctcggtc tcgattctac tagaactggt   1620

catcatcatc accatcactg a                                              1641
```

<210> SEQ ID NO 108
<211> LENGTH: 546
<212> TYPE: PRT
<213> ORGANISM: Artificial Sequence
<220> FEATURE:
<223> OTHER INFORMATION: Brassica optimised

<400> SEQUENCE: 108

```
Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190

Thr Thr Cys Phe His Ile Leu Phe Thr Thr Phe Glu Ile Val Tyr Pro
        195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
            260                 265                 270
```

```
Leu Gly Ser Leu Thr Tyr Phe Met Met Ala Pro Thr Leu Cys Tyr Gln
        275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
        355                 360                 365

Leu Asn Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
            420                 425                 430

Val Ser Ala Val Leu His Glu Leu Cys Val Ala Val Pro Cys His Ile
        435                 440                 445

Leu Lys Phe Trp Ala Phe Leu Gly Ile Met Leu Gln Ile Pro Leu Ile
    450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510

Ala Lys Gly Glu Leu Arg Gly His Pro Phe Glu Gly Lys Pro Ile Pro
        515                 520                 525

Asn Pro Leu Leu Gly Leu Asp Ser Thr Arg Thr Gly His His His His
    530                 535                 540

His His
545
```

<210> SEQ ID NO 109
<211> LENGTH: 1767
<212> TYPE: DNA
<213> ORGANISM: Artificial Sequence
<220> FEATURE:
<223> OTHER INFORMATION: Brassica optimised

<400> SEQUENCE: 109

```
atggctgttg ctgaatcttc tcagaacacc actactatgt ctggacacgg tgattctgac      60

ctcaacgtaa aagaagatgt tttttatttc cagcaatgtt acattgttat acgtataatg     120

atgagtttag tgatcaagtt cctctttgat tcttctttct tgttgcagaa cttcagacgt     180

agaaagcctt ctagctctgt tatcgagcct tcttcttctg gattcacctc tactaacggt     240

gttcctgcta ctggacatgt tgctgagaac agagatcagg atagagttgg agctatggaa     300

aacgctaccg gatctgttaa ccttatcgga aacggtggag gtgttgttat cggtaacgag     360

gaaaagcaag ttggagagac tgatatcaga ttcacctaca gaccatcttt cccagctcac     420
```

agaagagtta gggagtctcc actctcgagt gatgctatct tcaagcagtc tcacgctgga 480
cttttcaacc tctgcatcgt tgttcttgtt gctgtgaaca gcagactcat catcgagaac 540
ctcatgaagt acggacttct catcagatct ggattctggt tcaacgctac ctctcttaga 600
gattggcctc ttcttatgtg ctgtctctct cttccaatct tccctcttgg tgctttcgct 660
gttgagaagc ttgctttcaa caacctcatc tctgatcctg ctactacttg cttccacatc 720
cttttcacta ccttcgagat cgtttaccct gttctcgtta tccttaaatg cgattctgct 780
gttctttctg gattcgtgct catgttcatt gcttgcatcg tttggcttaa gctcgtttct 840
ttcgctcaca ctaaccacga tatcagaaag ctcatcacct ctggaaagaa ggttgacaac 900
gagcttactg ctgctggaat cgataacctt caggctccta ctcttggatc tctcacctac 960
ttcatgatgg ctcctaccct ttgttaccaa ccttcttacc ctagaacccc ttacgttaga 1020
aagggatggc ttgttagaca ggttatcctc taccttatct tcactggact tcagggattc 1080
atcatcgagc agtacatcaa ccctatcgtt gttaactctc agcatcctct tatgggagga 1140
cttcttaacg ctgttgagac tgtgcttaag ctttctctcc ctaacgttta cctttggctc 1200
tgtatgttct actgcctttt ccacctttgg cttaacatcc ttgctgagat ccttagattc 1260
ggagacagag agttctacaa ggattggtgg aacgctaaga ctatcgatga gtactggcgt 1320
aagtggaaca tgcctgttca taagtggatc gtgaggcata tctacttccc ttgcatgaga 1380
aacggaatct ctaaagaggt tgccgttttc atctctttct tcgtgtctgc tgttctccat 1440
gagctttgtg ttgctgttcc ttgccacatc cttaagttct gggctttcct tggaatcatg 1500
cttcagatcc ctcttatcat ccttaccagc tacctcaaga acaagttctc tgataccatg 1560
gtgggaaaca tgattttctg gttctttttc tgcatctacg gacaacctat gtgtgttctt 1620
ctctactacc acgatgttat gaacagaacc gagaaggcca aggctaaggg tgagcttaga 1680
ggtcatcctt tcgagggtaa gcctatccct aaccctcttc tcggtctcga ttctactaga 1740
actggtcatc atcatcacca tcactga 1767

<210> SEQ ID NO 110
<211> LENGTH: 1665
<212> TYPE: DNA
<213> ORGANISM: Artificial Sequence
<220> FEATURE:
<223> OTHER INFORMATION: Brassica optimised

<400> SEQUENCE: 110
atggctgttg ctgaatcttc tcagaacacc actactatgt ctggacacgg tgattctgac 60
ctcaacaact tcagacgtag aaagccttct agctctgtta tcgagccttc ttcttctgga 120
ttcacctcta ctaacggtgt tcctgctact ggacatgttg ctgagaacag agatcaggat 180
agagttggag ctatggaaaa cgctaccgga tctgttaacc ttatcggaaa cggtggaggt 240
gttgttatcg gtaacgagga aaagcaagtt ggagagactg atatcagatt cacctacaga 300
ccatctttcc cagctcacag aagagttagg gagtctccac tctcgagtga tgctatcttc 360
aagcagtctc acgctggact tttcaacctc tgcatcgttg ttcttgttgc tgtgaacagc 420
agactcatca tcgagaacct catgaagtac ggacttctca tcagatctgg attctggttc 480
aacgctacct ctcttagaga ttggcctctt cttatgtgct gtctctctct tccaatcttc 540
cctcttggtg ctttcgctgt tgagaagctt gctttcaaca acctcatctc tgatcctgct 600
actacttgct tccacatcct tttcactacc ttcgagatcg tttaccctgt tctcgttatc 660
cttaaatgcg attctgctgt tctttctgga ttcgtgctca tgttcattgc ttgcatcgtt 720

```
tggcttaagc tcgtttcttt cgctcacact aaccacgata tcagaaagct catcacctct    780

ggaaagaagg ttgacaacga gcttactgct gctggaatcg ataaccttca ggctcctact    840

cttggatctc tcacctactt catgatggct cctacccttt gttaccaacc ttcttaccct    900

agaacccctt acgttagaaa gggatggctt gttagacagg ttatcctcta ccttatcttc    960

actggacttc agggattcat catcgagcag tacatcaacc ctatcgttgt taactctcag   1020

catcctctta tgggaggact tcttaacgct gttgagactg tgcttaagct ttctctccct   1080

aacgtttacc tttggctctg tatgttctac tgcctttttcc acctttggct taacatcctt   1140

gctgagatcc ttagattcgg agacagagag ttctacaagg attggtggaa cgctaagact   1200

atcgatgagt actggcgtaa gtggaacatg cctgttcata agtggatcgt gaggcatatc   1260

tacttccctt gcatgagaaa cggaatctct aaagaggttg ccgttttcat ctctttcttc   1320

gtgtctgctg ttctccatga gctttgtgtt gctgttcctt gccacatcct taagttctgg   1380

gctttccttg gaatcatgct tcagatccct cttatcatcc ttaccagcta cctcaagaac   1440

aagttctctg ataccatggt gggaaacatg attttctggt tctttttctg catctacgga   1500

caacctatgt gtgttcttct ctactaccac gatgttatga acagaaccga gaaggccaag   1560

gctaagggtg agcttagagg tcatcctttc gagggtaagc ctatccctaa ccctcttctc   1620

ggtctcgatt ctactagaac tggtcatcat catcaccatc actga                   1665
```

<210> SEQ ID NO 111
<211> LENGTH: 554
<212> TYPE: PRT
<213> ORGANISM: Artificial Sequence
<220> FEATURE:
<223> OTHER INFORMATION: Brassica optimised

<400> SEQUENCE: 111

```
Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
    130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
            180                 185                 190
```

```
Asn Asn Leu Ile Ser Asp Pro Ala Thr Thr Cys Phe His Ile Leu Phe
        195                 200                 205

Thr Thr Phe Glu Ile Val Tyr Pro Val Leu Val Ile Leu Lys Cys Asp
    210                 215                 220

Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
                245                 250                 255

Leu Ile Thr Ser Gly Lys Lys Val Asp Asn Glu Leu Thr Ala Ala Gly
            260                 265                 270

Ile Asp Asn Leu Gln Ala Pro Thr Leu Gly Ser Leu Thr Tyr Phe Met
        275                 280                 285

Met Ala Pro Thr Leu Cys Tyr Gln Pro Ser Tyr Pro Arg Thr Pro Tyr
    290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Met Gly Gly Leu Leu Asn Ala Val Glu
            340                 345                 350

Thr Val Leu Lys Leu Ser Leu Pro Asn Val Tyr Leu Trp Leu Cys Met
        355                 360                 365

Phe Tyr Cys Leu Phe His Leu Trp Leu Asn Ile Leu Ala Glu Ile Leu
    370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
                405                 410                 415

Val Arg His Ile Tyr Phe Pro Cys Met Arg Asn Gly Ile Ser Lys Glu
            420                 425                 430

Val Ala Val Phe Ile Ser Phe Phe Val Ser Ala Val Leu His Glu Leu
        435                 440                 445

Cys Val Ala Val Pro Cys His Ile Leu Lys Phe Trp Ala Phe Leu Gly
    450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe Phe
                485                 490                 495

Cys Ile Tyr Gly Gln Pro Met Cys Val Leu Leu Tyr Tyr His Asp Val
            500                 505                 510

Met Asn Arg Thr Glu Lys Ala Lys Ala Lys Gly Glu Leu Arg Gly His
        515                 520                 525

Pro Phe Glu Gly Lys Pro Ile Pro Asn Pro Leu Leu Gly Leu Asp Ser
    530                 535                 540

Thr Arg Thr Gly His His His His His His
545                 550
```

<210> SEQ ID NO 112
<211> LENGTH: 1737
<212> TYPE: DNA
<213> ORGANISM: Artificial Sequence
<220> FEATURE:
<223> OTHER INFORMATION: Brassica optimised

<400> SEQUENCE: 112
atggctgatt ctgaggatgc tcctcctgct gttcatagaa ggcctccaag acctgctaga 60
ggtgctgctg ctgctgtaaa agaagatgtt ttttatttcc agcaatgtta cattgttata 120
cgtataatga tgagtttagt gatcaagttc ctctttgatt cttctttctt gttgcagcaa 180
ggattcgctg ctgctcttag aagaaggctt agaagcggag ctgctgttgc tgctagagct 240
tctttcgctg ctgattctgg tgatgagtct ggacctggtg agccttcttc atctaggcgt 300
agagataact ctggtggagc ttcttctgct gctggtggta gagctggtgc tggtgatttc 360
tctgctttca ccttcagagc tgctgctcct gttcacagaa aggctaaaga atctccactc 420
tcgagtgatg ctatcttcaa gcagtctcac gctggacttt tcaacctctg catcgttgtt 480
cttatcgctg ttaatagcag acttatcatc gagaacctca tgaagtacgg atggcttatc 540
gatactggat tctggttctc ttctcgttct cttggtgact ggtctatctt catgtgctgt 600
cttactctcc ctatcttccc tcttgctgct ttcatcgttg agaagcttgt tcagaggaac 660
catatcgctg agcttgttgc tgttcttctc cacgttatcg tttctactgc tgctgttctc 720
taccctgtta tcgttatcct tacctgcgat tctgtttaca tgtctggtgt tgtgcttatg 780
cttttcggat gcatcatgtg gcttaagctc gtttcttacg ctcacacctc ttcagatatc 840
agaaccctcg ctaagtctgg atacaaaggt gatgctcacc ctaactctac tatcgtgtct 900
tgctcttacg atgtgtctct taagtctctc gcttacttca tggttgctcc taccctttgt 960
taccaacctt cttaccctag atctagctgc atcagaaagg gatgggttgt gagacaattc 1020
gttaagctca tcgtgttcat cggacttatg ggattcatca tcgagcagta catcaaccct 1080
atcgtgagaa actctaagca ccctctcaag ggagatttcc tttacgctat cgagagagtg 1140
cttaagcttt ctgtgcctaa cctttacgtt tggctctgca tgttctactc attcttccac 1200
ctttggctta acatccttgc tgagttgctt agattcggag acagagagtt ctacaaggat 1260
tggtggaacg ctaagactgt tgctgagtac tggaagatgt ggaacatgcc tgttcataga 1320
tggatggtta ggcaccttta cttcccttgt ctcagaaacg gaatccctaa agagggtgct 1380
atcatcattg ctttcttggt gtctggtgct ttccatgagt tgtgtatcgc tgttccttgt 1440
cacgttttca agctctgggc tttcatcgga atcatgttcc aagttcctct cgttcttatc 1500
actaactacc tccaagagaa gttctctaac agcatggtgg gaaacatgat tttctggttc 1560
attttctgca tccttggaca gcctatgtgt gttcttctct actaccacga tctcatcaac 1620
ctcaaagaga aggctaaggg tgagcttaga ggtcatcctt tcgagggtaa gcctatccct 1680
aaccctcttc tcggtctcga ttctactaga actggtcatc atcatcacca tcactga 1737

<210> SEQ ID NO 113
<211> LENGTH: 1635
<212> TYPE: DNA
<213> ORGANISM: Artificial Sequence
<220> FEATURE:
<223> OTHER INFORMATION: Brassica optimised

<400> SEQUENCE: 113
atggctgatt ctgaggatgc tcctcctgct gttcatagaa ggcctccaag acctgctaga 60
ggtgctgctg ctgctcaagg attcgctgct gctcttagaa gaaggcttag aagcggagct 120
gctgttgctg ctagagcttc tttcgctgct gattctggtg atgagtctgg acctggtgag 180
ccttcttcat ctaggcgtag agataactct ggtggagctt cttctgctgc tggtggtaga 240
gctggtgctg gtgatttctc tgctttcacc ttcagagctg ctgctcctgt tcacagaaag 300
gctaaagaat ctccactctc gagtgatgct atcttcaagc agtctcacgc tggacttttc 360

```
aacctctgca tcgttgttct tatcgctgtt aatagcagac ttatcatcga gaacctcatg    420

aagtacggat ggcttatcga tactggattc tggttctctt ctcgttctct tggtgactgg    480

tctatcttca tgtgctgtct tactctccct atcttccctc ttgctgcttt catcgttgag    540

aagcttgttc agaggaacca tatcgctgag cttgttgctg ttcttctcca cgttatcgtt    600

tctactgctg ctgttctcta ccctgttatc gttatcctta cctgcgattc tgtttacatg    660

tctggtgttg tgcttatgct tttcggatgc atcatgtggc ttaagctcgt ttcttacgct    720

cacacctctt cagatatcag aaccctcgct aagtctggat acaaaggtga tgctcaccct    780

aactctacta tcgtgtcttg ctcttacgat gtgtctctta agtctctcgc ttacttcatg    840

gttgctccta ccctttgtta ccaaccttct taccctagat ctagctgcat cagaaaggga    900

tgggttgtga gacaattcgt taagctcatc gtgttcatcg gacttatggg attcatcatc    960

gagcagtaca tcaaccctat cgtgagaaac tctaagcacc ctctcaaggg agatttcctt   1020

tacgctatcg agagagtgct taagctttct gtgcctaacc tttacgtttg gctctgcatg   1080

ttctactcat tcttccacct ttggcttaac atccttgctg agttgcttag attcggagac   1140

agagagttct acaaggattg gtggaacgct aagactgttg ctgagtactg gaagatgtgg   1200

aacatgcctg ttcatagatg gatggttagg cacctttact tcccttgtct cagaaacgga   1260

atccctaaag agggtgctat catcattgct ttcttggtgt ctggtgcttt ccatgagttg   1320

tgtatcgctg ttccttgtca cgttttcaag ctctgggctt tcatcggaat catgttccaa   1380

gttcctctcg ttcttatcac taactacctc caagagaagt tctctaacag catggtggga   1440

aacatgattt tctggttcat tttctgcatc cttggacagc ctatgtgtgt tcttctctac   1500

taccacgatc tcatcaacct caaagagaag gctaagggtg agcttagagg tcatcctttc   1560

gagggtaagc ctatccctaa ccctcttctc ggtctcgatt ctactagaac tggtcatcat   1620

catcaccatc actga                                                    1635
```

```
<210> SEQ ID NO 114
<211> LENGTH: 544
<212> TYPE: PRT
<213> ORGANISM: Artificial Sequence
<220> FEATURE:
<223> OTHER INFORMATION: Brassica optimised

<400> SEQUENCE: 114

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Ile
        115                 120                 125
```

```
Ala Val Asn Ser Arg Leu Ile Ile Glu Asn Leu Met Lys Tyr Gly Trp
    130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ala Glu Leu Val
            180                 185                 190

Ala Val Leu Leu His Val Ile Val Ser Thr Ala Ala Val Leu Tyr Pro
        195                 200                 205

Val Ile Val Ile Leu Thr Cys Asp Ser Val Tyr Met Ser Gly Val Val
    210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
            260                 265                 270

Leu Lys Ser Leu Ala Tyr Phe Met Val Ala Pro Thr Leu Cys Tyr Gln
        275                 280                 285

Pro Ser Tyr Pro Arg Ser Ser Cys Ile Arg Lys Gly Trp Val Val Arg
    290                 295                 300

Gln Phe Val Lys Leu Ile Val Phe Ile Gly Leu Met Gly Phe Ile Ile
305                 310                 315                 320

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
        355                 360                 365

Leu Asn Ile Leu Ala Glu Leu Leu Arg Phe Gly Asp Arg Glu Phe Tyr
    370                 375                 380

Lys Asp Trp Trp Asn Ala Lys Thr Val Ala Glu Tyr Trp Lys Met Trp
385                 390                 395                 400

Asn Met Pro Val His Arg Trp Met Val Arg His Leu Tyr Phe Pro Cys
                405                 410                 415

Leu Arg Asn Gly Ile Pro Lys Glu Gly Ala Ile Ile Ile Ala Phe Leu
            420                 425                 430

Val Ser Gly Ala Phe His Glu Leu Cys Ile Ala Val Pro Cys His Val
        435                 440                 445

Phe Lys Leu Trp Ala Phe Ile Gly Ile Met Phe Gln Val Pro Leu Val
    450                 455                 460

Leu Ile Thr Asn Tyr Leu Gln Glu Lys Phe Ser Asn Ser Met Val Gly
465                 470                 475                 480

Asn Met Ile Phe Trp Phe Ile Phe Cys Ile Leu Gly Gln Pro Met Cys
                485                 490                 495

Val Leu Leu Tyr Tyr His Asp Leu Ile Asn Leu Lys Glu Lys Ala Lys
            500                 505                 510

Gly Glu Leu Arg Gly His Pro Phe Glu Gly Lys Pro Ile Pro Asn Pro
        515                 520                 525

Leu Leu Gly Leu Asp Ser Thr Arg Thr Gly His His His His His His
    530                 535                 540
```

<210> SEQ ID NO 115
<211> LENGTH: 1148
<212> TYPE: DNA
<213> ORGANISM: Artificial Sequence
<220> FEATURE:
<223> OTHER INFORMATION: Brassica napus

<400> SEQUENCE: 115
tttcttcatc ggtgattgat tcctttaaag acttatgttt cttatcttgc ttctgaggca 60
agtattcagt taccagttac cacttatatt ctggactttc tgactgcatc ctcatttttc 120
caacatttta aatttcacta ttggctgaat gcttcttctt tgaggaagaa acaattcaga 180
tggcagaaat gtatcaacca atgcatatat acaaatgtac ctcttgttct caaaacatct 240
atcggatggt tccatttgct ttgtcatcca attagtgact actttatatt attcactcct 300
ctttattact attttcatgc gaggttgcca tgtacattat atttgtaagg attgacgcta 360
ttgagcgttt ttcttcaatt ttctttattt tagacatggg tatgaaatgt gtgttagagt 420
tgggttgaat gagatatacg ttcaagtgaa gtggcatacc gttctcgagt aaggatgacc 480
tacccattct tgagacaaat gttacatttt agtatcagag taaaatgtgt acctataact 540
caaattcgat tgacatgtat ccattcaaca taaaattaaa ccagcctgca cctgcatcca 600
catttcaagt attttcaaac cgttcggctc ctatccaccg ggtgtaacaa gacggattcc 660
gaatttggaa gattttgact caaattccca atttatattg accgtgacta aatcaacttt 720
aacttctata attctgatta agctcccaat ttatattccc aacggcacta cctccaaaat 780
ttatagactc tcatcccctt ttaaaccaac ttagtaaacg ttttttttt taattttatg 840 aagttaagtt tttaccttgt ttttaaaaag aatcgttcat aagatgccat gccagaacat 900
tagctacacg ttacacatag catgcagccg cggagaattg tttttcttcg ccacttgtca 960
ctcccttcaa acacctaaga gcttctctct cacagcacac acatacaatc acatgcgtgc 1020
atgcattatt acacgtgatc gccatgcaaa tctcctttat agcctataaa ttaactcatc 1080
cgcttcactc tttactcaaa ccaaaactca tcaatacaaa caagattaaa aacatacacg 1140
gactctag 1148

<210> SEQ ID NO 116
<211> LENGTH: 3531
<212> TYPE: DNA
<213> ORGANISM: Arabidopsis thaliana

<400> SEQUENCE: 116
tgaatccttt ttcctttctt cttcttcttc tcttcagaga aaactttgct tctctttcta 60
taaggaacca gacacgaatc ccattcccac cgatttctta gcttcttcct tcaatccgct 120
ctttccctct ccattagatt ctgtttcctc tttcaatttc ttctgcatgc ttctcgattc 180
tctctgacgc ctcttttctc ccgacgctgt ttcgtcaaac gcttttcgaa atggcgattt 240
tggattctgc tggcgttact acggtgacgg agaacggtgg cggagagttc gtcgatcttg 300
ataggcttcg tcgacggaaa tcgagatcgg attcttctaa cggacttctt ctctctggtt 360
ccgataataa ttctccttcg gatgatgttg gagctcccgc cgacgttagg gatcggattg 420
attccgttgt taacgatgac gctcagggaa cagccaattt ggccggagat aataacggtg 480
gtggcgataa taacggtggt ggaagaggcg gcggagaagg aagaggaaac gccgatgcta 540
cgtttacgta tcgaccgtcg gttccagctc atcggagggc gagagagagt ccacttagct 600
ccgacgcaat cttcaaacag gtttaaaatc tcagaaatct tcgaatttgg tgtttgcttg 660

```
ttgttttata tggaattgag tttggtgatt gttttgcatt gcagagccat gccggattat    720
tcaacctctg tgtagtagtt cttattgctg taaacagtag actcatcatc gaaaatctta    780
tgaaggtttg ctgttacttg tttctccttt taggaattga attgcttgaa aatttatcag    840
agacgaataa ctttgttgtt gctatcattc atgtagtatg gttggttgat cagaacggat    900
ttctggttta gttcaagatc gctgcgagat tggccgcttt tcatgtgttg gtaaaagaag    960
atgtttttta tttccagcaa tgttacattg ttatacgtat aatgatgagt ttagtgatca   1020
agttcctctt tgattcttct ttcttgttgc agtatatccc tttcgatctt tcctttggct   1080
gcctttacgg ttgagaaatt ggtacttcag aaatacatat cagaacctgt gagtaattac   1140
tattctccag ccattactgt aatttttatt gaagacaagt ttgtatcatg aagaacttac   1200
aagttctgtt ttgaaaatgc tcaaggttgt catctttctt catattatta tcaccatgac   1260
agaggttttg tatccagttt acgtcaccct aaggtgatac tgtttttctg gtctcagttt   1320
gtgatactgt ttttaagttt agttgtctga cccggtgatc ttgaaaatgg acaggtgtga   1380
ttctgctttt ttatcaggtg tcactttgat gctcctcact tgcattgtgt ggctaaagtt   1440
ggtttcttat gctcatacta gctatgacat aagatcccta gccaatgcag ctgataaggt   1500
aaaatacgaa aaagaagcgt atgtattagt cacttgcact gtgttactgt tttaaccaaa   1560
cactgttatg aactttaggc caatcctgaa gtctcctact acgttagctt gaagagcttg   1620
gcatatttca tggtcgctcc cacattgtgt tatcaggtaa ctgcaaagtg catcaaccat   1680
tcttatactt gcaagagttt cttgtctaaa cctcggatct ttgcttttcc ccagccaagt   1740
tatccacgtt ctgcatgtat acggaagggt tgggtggctc gtcaatttgc aaaactggtc   1800
atattcaccg gattcatggg atttataata gaacaagtac gttttcacat cttgctttat   1860
tagttttcct tggtgaaaat catcatccct gcgttgtcac cacttgactt catgttcttt   1920
tgttacattt tggcagtata taaatcctat tgtcaggaac tcaaagcatc ctttgaaagg   1980
cgatcttcta tatgctattg aaagagtgtt gaagctttca gttccaaatt tatatgtgtg   2040
gctctgcatg ttctactgct tcttccacct ttggtatgct gtgatcccat ctctttcaaa   2100
ataatttgca aattcgaaaa accgaaaaag gctaaatctc atacgaattt gatattttta   2160
gtttcttaga gtcggtgatg taatttcagt tactgaacgc aaatctcttg tccaaaggtt   2220
aaacatattg gcagagcttc tctgcttcgg ggatcgtgaa ttctacaaag attggtggaa   2280
tgcaaaaagt gtgggagatg tgagctattt tactcaaaag aaaacttatg atttttaatg   2340
ttgtcgttgt ttttgggtca tctaactaac caaattcatg tattcactgt cttcctttat   2400
cagtactgga gaatgtggaa tatggtatgg ttctcttcct aaacatcacc ttcttttgta   2460
cacaaaatag aagaagagag ctaattaaga tcttgttttc cttgacagcc tgttcataaa   2520
tggatggttc gacatatata cttcccgtgc ttgcgcagca agataccaaa ggtgagtgag   2580
atatataccg atatgcaatt gtcgagattt gtttctgtga tataaattta accctccaca   2640
cacttgtttt tcagacactc gccattatca ttgctttcct agtctctgca gtctttcatg   2700
aggtatacat actttctaca ttgccctgtc tctagacgca tgaacacacg ctagtgaaag   2760
aaatgctaat attcaaagca ttgtttttac ttaacgatct tgtgttacaa atttcctttt   2820
gacagctatg catcgcagtt ccttgtcgtc tcttcaagct atgggctttt cttgggatta   2880
tgtttcaggt taaaaaatta ctaaactgct gcagtcgatt tttactaaac tctaatctca   2940
tattctgacc aaccaatttg tttgagtagg tgcctttggt cttcatcaca aactatctac   3000
aggaaaggtt tggctcaacg gtatgctctc aaaacccgag aaaatagaac gaataactct   3060
```

```
ttctttcata gcctagccat ttaaatcgca atgctgaaac ttaataataa aggtgatctg   3120
ttttggaatg ggatcatatt attaggtggg gaacatgatc ttctggttca tcttctgcat   3180
tttcggacaa ccgatgtgtg tgcttcttta ttaccacgac ctgatgaacc gaaaaggatc   3240
gatgtcatga aacaactgtt caaaaaatga ctttcttcaa acatctatgg cctcgttgga   3300
tctccgttga tgttgtggtg gttctgatgc taaaacgaca aatagtgtta taaccattga   3360
agaagaaaag aaaattagag ttgttgtatc tgcaaaaatt ttggtagaga cacgcgaacc   3420
cgtttggatt ttgttatggt gtaaagaaat ttcaatcaaa aaactgttgt aataattgtt   3480
accaaaaaga aatgcttttc tggaaacgag gggaaaaata gtagttttgt t            3531
```

<210> SEQ ID NO 117
<211> LENGTH: 6346
<212> TYPE: DNA
<213> ORGANISM: Zea mays

<400> SEQUENCE: 117

```
atggccccgc ccccctccat gcctgccgcc tccgatcgcg ccggccctgg ccgcgacgcg     60
ggcgactcgt cctcccttcg cctccgccgc gccccctcag ccgacgccgg cgaccttgcc    120
ggcgattcct cggtaggctt gcgggagaac ggcgagccgc aaccgccgac gaatccgccg    180
ccgcaggagc agcagcagca gcacgagatg ctatactacc gcgcgtcggc gcccgcccac    240
cgccgcgtca aggagagccc cctcagctct gacgccatct tccggcaggt gaggagacgc    300
gaattttagg ctcgctgttt gtaagcgatt gtttgatccc cgcgcttgtg cttcgatcca    360
cgccagttgc aaaatcctgc aaattgtttg ttgcttccag tcaactctgc ctctgttttt    420
ttttggttgg tgtgtgtgtg tgtgtgtgtg ttcaaatcac actttgtgct atcggtagct    480
taacactgcc ggttgccatc tcgcgcgcac ggatgtttta ttgtgggcct tgggcttcgg    540
aattgtggat agattgtgcg cgtgtactcg aatgggcaca attcgtttcg tggggggcat    600
atgctgctgc gattgaggtc ggtgtttact tgttttggga tcagggggac cagtgccggt    660
gcgcgggtgc cagatgcatg ccacgcagaa tttggcatcg gccggctgaa gcagcaaaca    720
acgagcgtaa ccgttaccac tggaggagct ttggcttgtc gaaacggatg actggatgag    780
cgaatgaatc attgaattca ttgttggcgg tactcactat agtgatgtgg acagttgttg    840
ggacagcacc tgcagtgccc ccagtattat taatgctgac ttttctaact acaatgcgtg    900
ttacattgtt tgtacacctt ggctttcctg cttggggcat tgcttcttgt tgaggaccat    960
ataactgtgc acctacatag aactgtattg gaccacttgt aagttttaac tggttagccc   1020
tccatttttt aataggtata ttattagaca atttttattg tcattgacat tatttttgtt   1080
tgctactctc ggagcccttt tcccagtgta atcttaatag ggctcaaatc acagcagaaa   1140
cacgtgagac gtaattttct agtgatactt ttattagact ttgttgtttc tgcacatact   1200
ctaaatctgt tttgaaggta ggagtgctta tttggatgat aaataatcct gggattacac   1260
agtggacaac gctttgataa ttgagtccat gctaacttga ttataatata tcagtattcc   1320
atatatcatt ttatcttgta cttcaactga gatcatcctt attttttgca aaccgtattt   1380
attggttgct ctggagaatt gaagtcttga aactaagcac ttctcctgat tgcagagcca   1440
tgctggtctt ctgaatctat gcattgttgt tctgatcgca gtgaacagca gactcattat   1500
tgagaattta atgaaggttt attactttct ttcttttttc attttcctca ccttcattta   1560
cagatccctc aatccatctc cttctgaaat acatctggtc ttcttcctgc gcatttgtct   1620
```

-continued

```
agtgtaaatc tgacacattc tgtgttttat ttaaattggc tggtgcagta tggcctgttg   1680
ataagagctg gattttggtt tagtgcaaga tcgctgggtg actggcccct tctaatgtgc   1740
tggtagaaat tgttgtcatt tttaattcag atgggtttca aataagaact gtggagtaat   1800
caatctgtca atttcagcct cactctacca gttttcccac tagttgcact catggctgag   1860
aagctgatca caagaaagct cattggtgaa catgtaagtt tgactcacaa gattgcgtag   1920
tattttgtag agaagttctc ttttgttatt tcttaggtat aagtgttgag gattgaatta   1980
gatgtaaaac tagacagtcc tctattctgc atcttccagg tgccatttat cgtttatgac   2040
ttctatacac ctcttgcagg tggttattct actccatatc attattacaa catctgccat   2100
tgtctatcca gttgttgtga ctcttaagta agcatttctt tctgctttgc agtttgtttg   2160
gatgcatctt attttgacat tcgttgagct ctagtatttc atggtatgga atacattcaa   2220
ttaatcttgt tcgtaatttg ctgtacttca tggtatggtg gccaactaca ttattgtgcc   2280
ccaaacattt agtctttccc ttcaagatac gtactatact atgcaaattg ggtggataaa   2340
aaggtagcta cataacactt ttatttaatt gtatctggtg actccacact ataatacaaa   2400
gaaacgcaac tctccagcat attcaagaaa aaaatgtatc tggtgataaa aatctattgc   2460
aaatgttcat ttatctctag tagaagaaat ccttactatc ttactctgtc ttgatctgtt   2520
cactgactgc atctaatagg gaagatttgt tagtccatca atattgatac acattttatt   2580
atgcagatat tttgtttctt tcatgtagct tctagcttgt aacccctttc ctaacatgaa   2640
gctgatcttt ccattgtaca agaaaaattg gatatatttg ttcacatgct tggaaattga   2700
ataaacaaac tgtagtattt ctgatgttga tgtgcaagta gtagactttg gttgagtcaa   2760
ttgttatctc tcaaaaagag ccattaggag caagttacct tttcattgat tatattttct   2820
gtgagactgc aagagttaag aatgttgtat ggttgatgcc ttatgctgtt tagtttaagt   2880
ttgttataat tgccaagaaa tgttacttga aaagatattg tcccatgcat caattatgga   2940
ttatcagttc agtcatattc cgaaaaattt caggtgtgac tcagcagtac tatctggatt   3000
tgtgctaatg tttcttgcga gcatcatgtg gatgaagctt gtctcttatg cacatacaaa   3060
ttatgatata agggtattgt ccaaaagtac tgagaaggta atgcattgac atgttaatct   3120
gaatcagttc aaatattttg ttaacatgtt gcccatttct caaaattgat ttgttgacgt   3180
tcaaactttt cttaaaactc cttttggtgg ccaaattttt ctgaagctag aatatctccc   3240
acttgtttaa acttcttttc cagtttcatt tcatgaatgt cttatatcta gtttcaattt   3300
ttgcatagga tgaaatgtgg tgccaatcaa tatacgttac catcaagaga gtaaaaaaat   3360
tgttcttaac ttctcataca gtgtttttgt tacatgggct gatcatatat actctcatgt   3420
gttagcttaa ctgttagtgt atacctctat tgtaatgggc cttggtccac ctaaccctgt   3480
tatatcaatg cattcccaac cctaattagg gttagggttt ccctcattct aacttcaggc   3540
aacggtagca tatgattata tcccttcatt ttcatttttc atgcaaataa ccactattgc   3600
tatattctta tttttagggt gctgcatatg gaaattatgt cgatcctgag aatatgaaag   3660
atccaacctt taaaagtcta gtgtacttca tgttggcccc aacactttgt taccaggtac   3720
tattattgga ccaatgcccc gtttttgttt ttaatgtcta cactctgctt ttcttcatcg   3780
cgtctatcta gttatgccag tgacaacatg aatttcctga tgtcactttg gcatgttatg   3840
cagccaactt atcctcaaac tacatgtatt agaaagggtt gggtgaccca gcaactcata   3900
aagtgcgtgg tttttacagg cttgatgggc ttcataattg agcaagtgag cctcctatat   3960
tccttaagta acttgtattt atacataact ttggattaaa ttaccaattt ttcttctatt   4020
```

```
ttgcagtata taaacccaat tgtgaagaat tccaaacatc cactgaaagg gaatttttg   4080
aatgctatag aaagagtctt aaaactctca gtgccaacat tatatgtatg gctttgcatg   4140
ttctattgct tttttcattt atggttagta tcttgcttca gttcaacagt accttaaatt   4200
tgtgcggcag tgattggttt atataacagg ttaattgggt tttgacctgc atgggacttt   4260
gatttccatt ttccatggca ttcttgtttg ctcttttggt tggtttcagg ctgaacattg   4320
tagctgaact cctctgtttc ggtgaccgtg aattctataa ggactggtgg aatgccaaaa   4380
ctgttgaaga ggtgagatgc ctgttaaaat tgagttcgtt tcttttgaag tgagaacttt   4440
aaataggact gacatcaatt atattctcat gtacttaaat gtgatggtat tttggggctt   4500
tacctcagta ctggaggatg tggaacatgg taatcttttt gttacttcta tattcagatt   4560
ctataccctt ttatttagtt gagactttgt tacttaacta aggacagttg tgatggtagt   4620
ggtactcttc tatttagtta agacttcctt aacttctgtc actgagcttg agatatttgt   4680
ctaataatat ctttcaaata actgacaatt agtctatttt ttgtcagcct gttcataagt   4740
ggatcatcag acacatatat tttccatgta taaggaaagg cttttccagg gtaattgctt   4800
ctatatgtgt acaaaactct acatttgttc tttgcttttg aattctccaa atgcagttta   4860
gtttggaaca tcgatgcaat atagaattca caatatacaa atgatgttct ttagaaaatg   4920
gggaagcaga gctggacaga gtgttagcac tcaattgtca atttgtcata ataataatga   4980
atacaactga acaagtggct gaaactgttg tgagaaaatc agaacactag tggtcaatat   5040
tatttgcata gtaaatcaat ttggtaatgt aaattaagat atgaagttct tacttcttat   5100
ataaagattt actatgcttg aattttatag tggctgaaac tttactgttc ttggataaag   5160
attttaaata aaaacaaagg atatctagac ttggcaacaa aatgctgcct tctgctgact   5220
ggcaaaagta aattagacaa tgtgaataca tggacataca taaaatttg ttggtccttt   5280
catttttgca gaactgacat gattttcact gcctacttct caaattcgta ttgtatctac   5340
actgcagggt gtagctattc taatctcgtt tctggtttca gctgtattcc atgaggtact   5400
ttaagttctt cagaagcctt tttcatgatc ggttcaattt ctgtttttcc taagacatgc   5460
tattgttcga attccactca gcacattact aacaatacgt ttgaccttac gtaccaatat   5520
atcatcacca catctctttt tacattgtga attcacagat atgtattgcg gtgccgtgcc   5580
acattttcaa attctgggca ttttctggga tcatgtttca ggtatagaaa taacactaat   5640
atataactac tacctccatt ccgaattata agtctttctg gcttggcttt tctagttaca   5700
ttatactagg tatatatcta gattataata gttatatatc tagacattgt gtatatctag   5760
atgcatacca aatgttacct atctagaaaa taggatcatg gtttcaggta tagaagtagt   5820
aataatataa taactactac ctccatttcg aactgtaagt cattatgact tggcttttat   5880
agataatgct aagagttata tatctggaca ttatctagat gcgtagctac gaatctagga   5940
aaactagaac gacttgtaat tatccctgcc ttttcttttg agtccatcag tgtctattct   6000
cttacgtttt gattccatca ttacatccat aagaacaata ctacatcttg gatacaatgt   6060
accttccact gttttcacat aggctgacac tggttgatgt ctgactcaca gataccgttg   6120
gtattcttga caagatatct ccatgctacg ttcaagcatg taatggtacg ctgtgtcaat   6180
tatgtccttt ttttcccatt acctcttgcc actacctaac catcatcttc ttatttggca   6240
ggtgggcaac atgatatttt ggttcttcag tatagtcgga cagccgatgt gtgtccttct   6300
atactaccat gacgtcatga acaggcaggc ccaggcaagt agatag                  6346
```

<210> SEQ ID NO 118
<211> LENGTH: 5848
<212> TYPE: DNA
<213> ORGANISM: Zea mays

<400> SEQUENCE: 118
tcgtcgaagg ctcgtagccc tagaagctcc aatggcggac tccgaagacg cgccgccagc 60
cgtgcaccgc cgcccaccgc gccccgctcg cggtgctgct gcagcccagg gcttcgcggc 120
cgcgttgcgc cgccggctga gatccggcgc tgcggtggcg gcacgcgcca gctttgccgc 180
agactccggg gacgagtctg gccccggcga gccctcttcg tctcgccgcc gcgacaacag 240
cgggggcgcc tcgtccgccg ccggcggccg ggccggggca ggggacttct ccgcgttcac 300
cttccgcgcc gcggcgcctg tccaccggaa agccaaggag agccctctga gctccgacgc 360
catcttcaag caggtcagag cagggaccta tttgattgcc gcgcccgcgc gacctgttcg 420
tcgagatgtc agctattctg cggccgattt taatttctcc gccatgcttg tttggtttca 480
tcagtaacga atttgaaact gatgtgtaac cgattaatcg tagcagggga attctcgagg 540
tgcatctacg catgtgggat aaaggcgtcg ccttttattc agagaatctg ggaggggaat 600 ttaactttc gtgctgcata tgcgtgcgag aagctcgaac gtagcaaaca gcgtgctgcc 660
cacagttcat tctgttttat tagcacacca accgtttggt gacagttact tagtggcatg 720
atatgtcttg attagtgtgg ataaaaggaa ctttttact agttgggagc tgtgagttca 780
aatcacgtga tctcctttat tggcatcgta cgtgacctgc cattttacaa atggatccag 840
tacatgataa tatgatatgt gtgcttcagc tcacatggta aggtcatagt gaggtcactt 900
aggaactagg aaaatttcc tgtttcctgt gtttttatg tgaaaataaa ctgattcttc 960
ctgtacgatt cctaagcaat tcatgtggct atgctgtttt ccctcaaaat tttgcttcat 1020
cagagaatat tgttttacca tgagattgag agctgttagc taatacttct attttggttt 1080
ctgacagagt catgcaggcc ttttcaacct atgtattgtt gttctggttg cggtgaatag 1140
caggctcatt attgagaacc tgatgaaggt tcttgtcata ctttttcgat tgagcaaatt 1200
gatgccattg ttcttgtgcc tttcactcaa catatttgag ctgttctttt ctgatgcctt 1260
ttgcagtatg gcttattaat aagatctggc ttttggttta atgctacatc attgcgagac 1320
tggccactgc taatgtgttg gtaatagtca atactgctct atcatccact tcttcaatgg 1380
cttcttaact ctgaaactta atcagctaat ttatattttc agccttagtc tacccatatt 1440
tccccttggt gcatttgcag tcgaaaagtt ggcattcaac aatctcatta gtgatcctgt 1500
aagcgcacac ctccttccta taaagcttac tttttctggt gtccaggttc tcattaacag 1560
tttatgcatt ttccatattg tggatggacg gcgaactatt agtttcattt atcaaaacag 1620
ttgtgagaca ccttttgttt gtattgtttc tccaaatttt gcttataaac catcgattta 1680
tggttctttc ctttttcagg ctactacctg ttttcacatc ctttttacaa catttgaaat 1740
tgtatatcca gtgctcgtga ttcttaagta agtatatgta ataaccttta aatatatgat 1800
tgattatgca cttccctctg cgtcaagata ttgccatgtt gtttatcaag aaagcaaatt 1860
tgagaataaa acacatgtgc cagtatgctg tttagttcat atgaatctac caaaattttc 1920
ttcgaatgtt aaatcgcatt tgtaactttt ggataatacc gttttcgtac aaatatcacg 1980
ccattttgcc ttgtgttaac accaagttct gtaactgggt tcaggtgtga ttctgcagtt 2040
ttatcaggct ttgtgttgat gtttattgcc tgcattgttt ggctgaagct tgtatctttt 2100
gcacatacaa accatgatat aagaaaactg atcacaagcg gcaagaaggt acattgtgtg 2160

-continued

```
ctatattttt tccttctccg tttgttttat atttgcttta aagctcttat tccaattatg   2220
taattagttg atcagaagga agcaaatatt cagtcctcgt ttttttctg ttatataaat    2280
acatctgaaa tgccatctat ggggattaga atcctttga tttgtttgaa taggtcacag    2340
attttcgttt gtaagagtcc ttatggaaga aggcatcagc atttatcctt ttggttatcc   2400
cgtttgttgt ccatataatt tgattgaatt gaacaagcac ttaggtactt agggcctagg   2460
gcctgtttgg aagcacctag tttttaagaa actggtttat gaaaactgag gtggttccaa   2520
acatactagt ttatgtccta gtttatagaa actggattct caatttctta aaaaccaaga   2580
agctagcctc ccctagctaa agccagttta tgaaaacagt ggtggttcca aacaacatta   2640
accagttttt tttcctcata aatcagtctc tagaaactgg attcttaaaa actaggttgc   2700
ttccaaacag ggccttagca aacgttttaa tctactctag tgattcttct cttactctgt   2760
cagaattctt tcggagttgt gacacttaat gcagcaaagg gattttaaca taataaatat   2820
ttacatttaa cattgatatg ttgctggacc tgctgcttct catcactggg ttttcctccc   2880
tctcctgact taacccttgt actctattac ttttagagat gttcatagta gtccagcctt   2940
ctctggccca aggtgctggg cttagcttgg tcgtgggctt gtaaatgaaa tgcaaaaata   3000
tgcaggtatc tgtatatgtt atgcttaaga ctattgttac taaaaatgta atatatccta   3060
ttcgtgttaa tatttttaaa gaaaaatata taaaaatatt aatatattgg gcttcaggtg   3120
aggagttgag agtttacggg tccaacctgg tccggtgcat gatcacctca attactacca   3180
tttatgtttt atatgtattt aactgttgtt agtttgttac ataagttaat ataccgttta   3240
tattaggttg ataatgaact gaccgcggct ggcatagata atttacaagc tccaactctt   3300
gggagtctaa catacttcat gatggctccg acactctgtt atcaggtaat tttccgatca   3360
tgtatgttga tctaaagcag atatatgatt tttttatta cctttcgact ggccatttct    3420
gattagcagc agaaagtgtg ctggcaaggt gaaacatttt agaaacgtac tacttttgtt   3480
ttgcatgcag ccaagttatc ctcgaacacc ttatgttaga aaaggttggc tggtccgtca   3540
agttattcta tacttgatat ttactggtct ccaaggattc attattgagc aagtaagctg   3600
tttatatgtc tccatatata tatcttgtaa aatatcctca tacatttctt aacctttttat  3660
tgattttaca atcttgcagt acataaatcc tattgttgtg aactctcaac atccattgat   3720
gggaggatta ctgaatgctg tagagactgt tttgaagctc tcattaccaa atgtctacct   3780
gtggctttgc atgttttatt gccttttcca tctgtggtag taaattatat tttctatcta   3840
ttcattcaaa ttcaaataca tgatcgatcc tgatattatt ctaatatcag tcatcgatgc   3900
ttcttctccg aacatgcatg ctctcggaga aaattatttc cttttatgct ctttcaaatt   3960
tgcatatttg cagtttcgaa cttatattca tctatacagg ttaaacatac ttgctgagat   4020
tcttcgattt ggtgaccgag aattctacaa agactggtgg aatgcaaaga caattgatga   4080
ggtgaaatac taccgtgttt gttgcaacct agtataactt cattttcaa ctaacaaaag    4140
gaatctaggt aagcatagct gatgttgtgt atgttgtttg ctgttgttgc ttgtgttgct   4200
gtgcttggat gggatcagta ctggagaaaa tggaacatgg tatgcctttt ctttcttggc   4260
aataataatt ctagcaagaa tgtactgcca gacatggtat acgcagttgt ggttagatgt   4320
aaccatctta aagcaactgc ataataaaaa tggcaagtca ctgtaagatt gttgagaact   4380
atgaaatctg gactcttggt acacagaact attctaattt gtatgttcca agtagtttga   4440
ataacaccca gaatttgatg gatttattct tctccaatga tctttgttgg tccatattaa   4500
```

```
tttcatttgc tgaaatatta tgactaataa tttgcacatt ttgacagcct gtgcataaat   4560

ggattgttcg tcatatatat ttcccttgca tgcgaaatgg tatatcaaag gtaaaataat   4620

atttgtgtgg atgttatgct cagggttgct tccagtgcat ataagactaa actgtacctt   4680

cactacagtt tgtgccttgt aaatccctta accagtcagt gcttgcttgt aatttctaat   4740

ttttcaaagt aactataaga attacttcca tgctgtttag ggcaatctaa ttagttcacc   4800

agtgaaacta aagttcatgt actcataaaa atctgtaagt tcaacagtaa aagtattctt   4860

ttgagtttat tgagcaataa gaatgtgttt aattttgtat ggatctactg tcctccagtc   4920

tagctcctat actgaaggtg ctatattttg ttatccagtc ttctgtgctg ttattattac   4980

tgtttaaagt tattcactta tttgtgctag tttgttacag gaagttgctg tttttatatc   5040

gttctttgtt tctgctgtac ttcatgaggt aacttattta ccttttcact cttcatctgc   5100

tatattaatt atatagttct ctattttcaa atgtgtcctt tcgagtttcg acatgctttt   5160

gttcaaactt accagctgca gattacttgg atgaagtgct ctatataaaa ttaaatattt   5220

cataatccag tccctttcga gaaaattatg atacattttg tttgcaattg tacaccagtt   5280

atgtgttgct gttccctgcc acatactcaa gttctgggct ttcttaggaa tcatgcttca   5340

ggtaaatata atacaacgcc agatgctgtg gatcaatatc caacatttat gtttttcttt   5400

actcattttt tcctttatta gttctttttt cattcgctat agtctgaggt cttatgagca   5460

ccagaaggca acagtcatct aatatggttc catgtattta tgttgtctcc taaacagaaa   5520

actgttctga caccatattt cttttcctct ttttaccaga ttcccctcat catattgaca   5580

tcatacctca aaaataaatt cagtgacaca atggtgagcc atatttttct tagttgatac   5640

ttgctaggat cgttttttat gggaacctgt ctaatttgtg gtatattcaa taggttggca   5700

atatgatctt ttggtttttt ttctgcatat acgggcagcc aatgtgtgtt ctattgtatt   5760

accatgatgt gatgaaccgg actgagaagg caaaataaaa gcaataatct gtgcacacag   5820

taaaccagca tcgtgtcttc cagttttt                                       5848


<210> SEQ ID NO 119
<211> LENGTH: 157
<212> TYPE: PRT
<213> ORGANISM: Arabidopsis thaliana

<400> SEQUENCE: 119

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
```

```
    130                 135                 140

Ala Val Asn Ser Arg Leu Ile Ile Glu Asn Leu Asn Lys
145                 150                 155


<210> SEQ ID NO 120
<211> LENGTH: 140
<212> TYPE: PRT
<213> ORGANISM: Brassica juncea

<400> SEQUENCE: 120

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Arg Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Pro Ile Ile Glu Asn Leu Met Lys
    130                 135                 140


<210> SEQ ID NO 121
<211> LENGTH: 140
<212> TYPE: PRT
<213> ORGANISM: Brassica napus

<400> SEQUENCE: 121

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Leu Ile Ile Glu Asn Leu Met Lys
    130                 135                 140


<210> SEQ ID NO 122
<211> LENGTH: 140
<212> TYPE: PRT
```

```
<213> ORGANISM: Brassica juncea

<400> SEQUENCE: 122

Met Ala Ile Leu Asp Ser Gly Thr Val Thr Met Ala Thr Glu Asn Gly
1               5                   10                  15

Val Ala Asp Leu Asp Met Leu Arg Arg Arg Lys Ser Arg Ser Asp Ser
            20                  25                  30

Ser Asn Gly Leu Leu Ser Glu Thr Ser Pro Ser Asp Asp Ala Gly Ala
        35                  40                  45

Pro Ala Asp Val Glu Asp Arg Val Asp Ser Ala Ala Gln Gly Thr Ala
    50                  55                  60

Asn Leu Ala Gly Asp Thr Glu Thr Arg Glu Ser Gly Gly Gly Gly Gly
65                  70                  75                  80

Gly Gly Asn Gly Glu Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Leu Ile Ile Glu Asn Leu Met Lys
    130                 135                 140


<210> SEQ ID NO 123
<211> LENGTH: 149
<212> TYPE: PRT
<213> ORGANISM: Tropaeolum majus

<400> SEQUENCE: 123

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Asn Lys
145


<210> SEQ ID NO 124
<211> LENGTH: 103
<212> TYPE: PRT
<213> ORGANISM: Echium pitardii

<400> SEQUENCE: 124

Met Thr Ile Trp Glu Ser Pro Glu Ile Ile Ser Ser Asp Glu Ala Ala
1               5                   10                  15
```

Ala Ala Leu Arg Arg Arg Gly Gly Ala Lys Glu Val Ala Glu Gln Arg
20 25 30

Leu Asp Ser Glu Glu Glu Lys Lys Lys Glu Glu Glu Asn Gly Lys Leu
35 40 45

Lys Tyr Thr Tyr Arg Ala Ser Ala Pro Ala His Arg Arg Ile Lys Glu
50 55 60

Ser Pro Leu Ser Ser Asp Ala Ile Phe Lys Gln Ser His Ala Gly Leu
65 70 75 80

Phe Asn Leu Cys Ile Val Val Leu Val Ala Val Asn Ser Arg Leu Ile
85 90 95

Ile Glu Asn Leu Pro Met Lys
100

<210> SEQ ID NO 125
<211> LENGTH: 152
<212> TYPE: PRT
<213> ORGANISM: Vernonia galamensis

<400> SEQUENCE: 125

Met Ala Leu Leu Asp Thr Pro Gln Ile Gly Glu Ile Thr Thr Thr Ala
1 5 10 15

Thr Thr Thr Ile Arg Arg Arg Thr Thr Val Lys Pro Asp Ala Gly Ile
20 25 30

Gly Asp Gly Leu Phe Asp Ser Ser Ser Ser Ser Lys Thr Asn Ser Ser
35 40 45

Phe Glu Asp Gly Asp Ser Leu Asn Gly Asp Phe Asn Asp Lys Phe Lys
50 55 60

Glu Gln Ile Gly Ala Gly Asp Glu Ser Lys Asp Asp Ser Lys Gly Asn
65 70 75 80

Gly Gln Lys Ile Asp His Gly Gly Val Lys Lys Gly Arg Glu Thr Thr
85 90 95

Val Val His Tyr Ala Tyr Arg Pro Ser Ser Pro Ala His Arg Arg Ile
100 105 110

Lys Glu Ser Pro Leu Ser Ser Asp Ala Ile Phe Lys Gln Ser His Ala
115 120 125

Gly Leu Phe Asn Leu Cys Ile Val Val Leu Val Ala Val Asn Gly Arg
130 135 140

Leu Ile Ile Glu Asn Leu Asn Lys
145 150

<210> SEQ ID NO 126
<211> LENGTH: 165
<212> TYPE: PRT
<213> ORGANISM: Nicotiana tabacum

<400> SEQUENCE: 126

Met Val Ile Met Glu Leu Pro Glu Ser Val Glu Met Thr Thr Thr Thr
1 5 10 15

Thr Thr Ser Gly Ile Glu Asn Leu Asn Ser Asp Leu Asn His Ser Val
20 25 30

Arg Arg Arg Arg Cys Ser Asn Gly Phe Glu Ala Ala Ser Ala Ile Asn
35 40 45

Ser Ser Asp Ala Asn Met Ser Glu Asp Arg Arg Asp Val Cys Gly Ser
50 55 60

Gly Ala Gly Leu Glu Thr Val Asn Glu Arg Ser Lys Ser Val Gly Glu
65 70 75 80

```
Ser Ser Asp Val Ile Arg Lys Glu Asp Asp Arg Asn Asp Asn Val Ala
                85                  90                  95

Asn Gly Glu Glu Ser Lys Ser Thr Glu Thr Thr Thr Thr Pro Phe Lys
            100                 105                 110

Phe Ala Tyr Arg Ala Ser Ala Pro Ala His Arg Arg Ile Lys Glu Ser
        115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Asn Lys
                165


<210> SEQ ID NO 127
<211> LENGTH: 163
<212> TYPE: PRT
<213> ORGANISM: Perilla frutescens

<400> SEQUENCE: 127

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Arg Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Asn Lys


<210> SEQ ID NO 128
<211> LENGTH: 141
<212> TYPE: PRT
<213> ORGANISM: Zea mays

<400> SEQUENCE: 128

Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60
```

-continued

```
Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys
    130                 135                 140


<210> SEQ ID NO 129
<211> LENGTH: 141
<212> TYPE: PRT
<213> ORGANISM: Sorghum bicolor

<400> SEQUENCE: 129

Met Ala Asp Thr Asp Asp Ala Pro Pro Ala Pro Ala Val His Arg Arg
1               5                   10                  15

Pro Pro Arg Pro Ala Arg Gly Ala Ala Ala Ala Gln Ala Ala Glu Leu
            20                  25                  30

Arg Arg Arg Leu Ser Ser Gly Ala Ala Ala Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Gly Gly Asp Ala Ser Ser Ala Ala Asp Gly Gly
65                  70                  75                  80

Arg Gly Gly Ala Gly Asp Phe Ser Ala Phe Ile Phe Arg Ala Ala Ala
                85                  90                  95

Pro Val His Phe Glu Ala Lys Glu Ser Pro Leu Ser Ser Asp Ala Ile
            100                 105                 110

Phe Glu Gln Ser His Ala Leu Glu Asn Leu Cys Ile Val Val Leu Val
        115                 120                 125

Ala Val Asn Ser Pro Leu Ile Ile Glu Asn Leu Asn Lys
    130                 135                 140


<210> SEQ ID NO 130
<211> LENGTH: 167
<212> TYPE: PRT
<213> ORGANISM: Oryza sativa

<400> SEQUENCE: 130

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Thr Val Glu Gly Phe Ala Ala Ala Leu Arg Arg
        35                  40                  45

Pro Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110
```

```
Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Asn Lys
                165


<210> SEQ ID NO 131
<211> LENGTH: 104
<212> TYPE: PRT
<213> ORGANISM: Oryza sativa

<400> SEQUENCE: 131

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys
            100


<210> SEQ ID NO 132
<211> LENGTH: 118
<212> TYPE: PRT
<213> ORGANISM: Sorghum bicolor

<400> SEQUENCE: 132

Met Ala Pro Pro Pro Ser Met Ala Ala Ala Ser Asp Arg Ala Val Pro
1               5                   10                  15

Gly Ala Asp Ala Thr Glu Ala Ser Ser Leu Arg Leu Arg Arg Ala Pro
            20                  25                  30

Ser Ala Asp Ala Gly Asp Leu Ala Asp Asp Ser Ser Gly Asp Arg Arg
        35                  40                  45

Glu Asn Gly Glu Pro Gln Pro Pro Gln Glu Gln Gln Gln Gln His Glu
    50                  55                  60

Met Leu Tyr Tyr Arg Ala Ser Ala Pro Ala His Arg Arg Val Lys Glu
65                  70                  75                  80

Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
            100                 105                 110

Ile Glu Asn Leu Met Lys
        115


<210> SEQ ID NO 133
<211> LENGTH: 122
<212> TYPE: PRT
<213> ORGANISM: Zea mays
```

<400> SEQUENCE: 133

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys
        115                 120

<210> SEQ ID NO 134
<211> LENGTH: 76
<212> TYPE: PRT
<213> ORGANISM: Physcomitrella patens

<400> SEQUENCE: 134

Met Pro Val Lys Ser Ser Asn Leu Ala Gly Glu Arg Ala Ala Thr Ser
1               5                   10                  15

His Ile Asn Ala Asn Thr Lys Phe Asp Leu Arg Gly Cys Thr Pro Ala
            20                  25                  30

His Arg Val Arg Arg Glu Ser Pro Leu Ser Ser Asp Ala Ile Phe His
        35                  40                  45

Gln Ser His Ala Gly Leu Phe Asn Leu Cys Ile Val Val Leu Ile Ala
    50                  55                  60

Val Asn Ser Arg Leu Ile Ile Glu Asn Leu Met Lys
65                  70                  75

<210> SEQ ID NO 135
<211> LENGTH: 51
<212> TYPE: PRT
<213> ORGANISM: Selaginella moellendorffii

<400> SEQUENCE: 135

Met Arg Pro Ser Leu Pro Ala His Arg Arg Ser Lys Glu Ser Pro Leu
1               5                   10                  15

Ser Ser Asp Ala Ile Phe Thr Gln Ser His Ala Gly Leu Phe Asn Leu
            20                  25                  30

Cys Ile Val Val Leu Val Ala Val Asn Ser Arg Leu Ile Ile Glu Asn
        35                  40                  45

Leu Met Lys
    50

<210> SEQ ID NO 136
<211> LENGTH: 136
<212> TYPE: PRT
<213> ORGANISM: Euonymus alatus

<400> SEQUENCE: 136

Met Ala Ala Asn Leu Asn Glu Ala Ser Asp Leu Asn Phe Ser Leu Arg
1               5                   10                  15

Arg Arg Thr Gly Gly Ile Ser Ser Thr Thr Val Pro Asp Ser Ser Ser
20 25 30

Glu Thr Ser Ser Ser Glu Ala Asp Phe Leu Asp Gly Gly Lys Gly Ala
35 40 45

Ala Asp Val Lys Asp Arg Gly Asp Gly Ala Val Glu Phe Gln Asn Ser
50 55 60

Met Lys Asn Val Glu Arg Ile Glu Lys His Glu Ser Arg Val Gly Leu
65 70 75 80

Asp Ser Arg Phe Thr Tyr Arg Pro Ser Val Pro Ala His Arg Thr Ile
85 90 95

Lys Glu Ser Pro Leu Ser Ser Asp Ala Ile Phe Lys Gln Ser His Ala
100 105 110

Gly Leu Phe Asn Leu Cys Ile Val Val Leu Val Ala Val Asn Ser Arg
115 120 125

Leu Ile Ile Glu Asn Leu Asn Lys
130 135

<210> SEQ ID NO 137
<211> LENGTH: 146
<212> TYPE: PRT
<213> ORGANISM: Vitis vinifera

<400> SEQUENCE: 137

Met Ala Ile Cys Asn Ser Phe Pro Ser Val Thr Thr Ser Ser Ser Ser
1 5 10 15

Ser His Ala Asp Ser Asp Leu Asp Phe Ser Ile Arg Lys Arg Phe Gly
20 25 30

Gly Lys Gly Lys Ala Val Ala Asp Ser Ser Leu Glu Thr Glu Thr Glu
35 40 45

Ala Ala Ala Ala Ala Val Leu Glu Ala Glu Lys Ser Val Gly Glu Val
50 55 60

Gly Ser Gly Gly Asp Arg Gly Glu Ser Gly Ser Gln Val Val Arg Asn
65 70 75 80

Gly Glu Asn Gly Val Ala Glu Val Ala Ala Lys Phe Ala Tyr Arg Pro
85 90 95

Cys Ala Pro Ala His Arg Lys Val Lys Glu Ser Pro Leu Ser Ser Asp
100 105 110

Ala Ile Phe Arg Gln Ser His Ala Cys Gly Leu Phe Asn Leu Cys Ile
115 120 125

Val Val Leu Val Ala Val Asn Ser Arg Leu Ile Ile Glu Asn Leu Asn
130 135 140

Asn Lys
145

<210> SEQ ID NO 138
<211> LENGTH: 128
<212> TYPE: PRT
<213> ORGANISM: Glycine max

<400> SEQUENCE: 138

Met Ala Ile Ser Asp Glu Pro Glu Thr Val Ala Thr Ala Leu Asn His
1 5 10 15

Ser Ser Leu Arg Arg Arg Pro Thr Ala Ala Gly Leu Phe Asn Ser Pro
20 25 30

Glu Thr Thr Thr Asp Ser Ser Gly Asp Asp Leu Ala Lys Asp Ser Gly
35 40 45

```
Ser Asp Asp Ser Ile Ser Ser Asp Ala Ala Asn Ser Gln Pro Gln Gln
    50                  55                  60

Lys Lys Gln Asp Thr Asp Phe Ser Val Leu Lys Phe Ala Tyr Arg Pro
65                  70                  75                  80

Ser Val Pro Ala His Arg Glu Val Glu Glu Ser Pro Leu Ser Ser Asp
                85                  90                  95

Thr Ile Phe Arg Gln Ser His Ala Gly Leu Phe Asn Leu Cys Ile Val
            100                 105                 110

Val Leu Val Ala Val Asn Ser Arg Leu Ile Ile Glu Asn Leu Met Lys
        115                 120                 125


<210> SEQ ID NO 139
<211> LENGTH: 133
<212> TYPE: PRT
<213> ORGANISM: Glycine max

<400> SEQUENCE: 139

Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Ser Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys
    130


<210> SEQ ID NO 140
<211> LENGTH: 139
<212> TYPE: PRT
<213> ORGANISM: Lotus japonicus

<400> SEQUENCE: 140

Met Ala Ile Ser Glu Asp Ser Glu Ser Leu Phe Ala Ala Ala Ala Ala
1               5                   10                  15

Ser Ser Val Ile Gln Ser Gly Ser Ser Val Arg Arg Arg Pro Ser Ala
            20                  25                  30

Ile Ser Ala Val Ala Thr Val Glu Asp Glu Ser Ser Ser Glu Glu Pro
        35                  40                  45

Val Pro Val Arg Asp Ser Gly Ser Asp Val Asp Asp Ser Val Ser Ser
    50                  55                  60

Glu Gln His Val Ser Pro Ala Thr Ala Asn Arg Glu Lys Asn Gln Val
65                  70                  75                  80

His Asp Ile Ser Ala Thr Lys Phe Ala Tyr Arg Pro Ser Ala Pro Ala
                85                  90                  95

His Arg Arg Val Lys Glu Ser Pro Leu Ser Ser Asp Asn Ile Phe Arg
            100                 105                 110
```

```
His His Ala Gly Leu Phe Asn Leu Cys Ile Val Val Leu Val Ala Val
        115                 120                 125

Asn Ser Arg Leu Ile Ile Glu Asn Leu Asn Lys
    130                 135


<210> SEQ ID NO 141
<211> LENGTH: 167
<212> TYPE: PRT
<213> ORGANISM: Medicago truncatula

<400> SEQUENCE: 141

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
            20                  25                  30

Arg Arg Pro Ser Ala Thr Ser Thr Ala Gly Gly Leu Phe Asp Ala Glu
        35                  40                  45

Ser Ala Ala Ala Asp Ala Val Arg Asp Ser Gly Ser Asp Asp Ser Leu
    50                  55                  60

Asn Gly Lys Ile Asn Asn Glu Glu Glu Val Lys Asp Arg Lys Thr Asp
65                  70                  75                  80

His Ala Glu Gly Ile Val Asp Asp Asp Asp Asp Asn Ala Val Lys Lys
                85                  90                  95

Asn Gly Gly Asn Asp Val Ile Asn Asp Arg Glu Asn Val Ala Val Asp
            100                 105                 110

Phe Lys Phe Thr Tyr Arg Pro Ser Val Pro Ala His Arg Arg Ser Lys
        115                 120                 125

Glu Ser Pro Leu Ser Ser Gly Asn Ile Phe Arg Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Asn Lys
                165


<210> SEQ ID NO 142
<211> LENGTH: 148
<212> TYPE: PRT
<213> ORGANISM: Jatropha curcas

<400> SEQUENCE: 142

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
    50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125
```

Leu Cys Ile Val Val Leu Val Ala Val Asn Ser Arg Leu Ile Ile Glu
    130                 135                 140

Asn Leu Asn Lys
145

<210> SEQ ID NO 143
<211> LENGTH: 153
<212> TYPE: PRT
<213> ORGANISM: Vernicia fordii

<400> SEQUENCE: 143

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
        35                  40                  45

Ile Asp Glu Leu Glu Ser Asp Ala Gly Gly Gly Gln Val Ile Lys Asp
    50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
            100                 105                 110

Leu Lys Glu Ser Pro Leu Ser Ser Asp Asn Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Ile Asn Lys
145                 150

<210> SEQ ID NO 144
<211> LENGTH: 153
<212> TYPE: PRT
<213> ORGANISM: Vernonia galamensis

<400> SEQUENCE: 144

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Arg Thr Ser Asn
            20                  25                  30

Asp Ser Asp Gly Ala Leu Ala Asp Leu Ala Ser Lys Phe Asp Asp Asp
        35                  40                  45

Asp Asp Val Arg Ser Glu Asp Ser Ala Glu Asn Ile Ile Glu Asp Pro
    50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

```
Arg Leu Ile Ile Glu Asn Leu Asn Lys
145                 150


<210> SEQ ID NO 145
<211> LENGTH: 79
<212> TYPE: PRT
<213> ORGANISM: Ricinus communis

<400> SEQUENCE: 145

Met Met Glu Ser Glu Asp Leu Lys Ser Asn Gly Lys Glu Cys Asp Lys
1               5                   10                  15

Val Thr Asn Glu Asn Arg Ser Asp Ile Lys Phe Asn Tyr Arg Pro Ser
            20                  25                  30

Met Pro Ala His Arg Gly Val Arg Glu Ser Pro Leu Ser Ser Asp Ala
        35                  40                  45

Ile Phe Lys Gln Ser His Ala Gly Leu Phe Asn Leu Cys Ile Val Val
    50                  55                  60

Leu Val Ala Ile Asn Ser Arg Leu Ile Ile Glu Asn Ile Ile Lys
65                  70                  75


<210> SEQ ID NO 146
<211> LENGTH: 120
<212> TYPE: PRT
<213> ORGANISM: Populus trichocarpa

<400> SEQUENCE: 146

Met Ala Glu Ser Glu Ser Pro Glu Asn Arg Ile Ala Ala Met Glu Ser
1               5                   10                  15

Thr Ser Ser Ser Thr Ser Asp Leu Asn Phe Ser Ile Arg Arg Arg Ser
            20                  25                  30

Thr Val Met Asp Ser Ala Ser Thr Glu Met Met Gly Ser Glu Gly Leu
        35                  40                  45

Lys Ser Ser Gly Lys Ala Cys Asp Lys Val Lys Ile Glu Lys Gln Ser
    50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
                85                  90                  95

Gly Leu Phe Asn Leu Cys Ile Val Val Leu Val Ala Val Asn Ser Arg
            100                 105                 110

Leu Ile Ile Glu Asn Leu Ile Lys
        115                 120
```

ACYLTRANSFERASE POLYNUCLEOTIDES, POLYPEPTIDES AND METHODS OF USE

CROSS-REFERENCE TO RELATED APPLICATIONS

This application is a U.S. National Stage Application filed under 35 U.S.C. § 371 of International Application No. PCT/IB2013/059525, filed Oct. 22, 2013, which claims the benefit of U.S. Provisional Patent Application No. 61/720, 136, filed Oct. 30, 2012. Both of these applications are hereby incorporated by reference in their entireties.

TECHNICAL FIELD

The invention relates to compositions and methods for the manipulation of cellular lipid production and/or cellular lipid profile.

BACKGROUND

Plant oil is an economically important product not only due to its broad utilization in the food industry and as a component of feed ingredients but it also has a wide range of applications as biofuels or in the manufacture of various nutraceutical and industrial products. Within the plant itself, oil is essential to carry out a number of metabolic processes which are vital to growth and development particularly during seed germination and early plant growth stages. Considering its value, there is a growing research interest within the biotechnology field to improve plant oil production and make the supply more sustainable.

The major component of plant oil is triacylglyceride (TAG). It is the main form of storage lipid in oil seeds and the primary source of energy for seed germination and seedling development. TAG biosynthesis via the Kennedy pathway involves sequential acylation steps starting from the precursor sn-glycerol-3-phosphate (G3P). Firstly, G3P is esterified by an acyl-CoA to form lysophosphatidic acid (LPA) in a reaction catalyzed by glycerol-3-phosphate acyltransferase (GPAT, EC 2.3.1.15). This is followed by a second acylation step catalyzed by lysophosphatidic acid acyltransferase (LPAT; EC 2.3.1.51) forming phosphatidic acid (PA), a key intermediate in the biosynthesis of glycerolipids. The PA is then dephosphorylated by the enzyme phosphatidic acid phosphatase (PAP; EC3.1.3.4) to release the immediate precursor for TAG, the sn-1,2-diacylglycerol (DAG). Finally, DAG is acylated in the sn-3 position by the enzyme diacylglycerol acyltransferase (DGAT; EC 2.3.1.20) to form TAG.

Since this last catalytic action is the only unique step in TAG biosynthesis, DGAT is termed as the committed triacylglycerol-forming enzyme. As DAG is located at the branch point between TAG and membrane phospholipid biosyntheses, DGAT potentially plays a decisive role in regulating the formation of TAG in the glycerolipid synthesis pathway (Lung and Weselake, 2006, Lipids. December 2006; 41(12):1073-88). There are two different families of DGAT proteins. The first family of DGAT proteins ("DGAT1") is related to the acyl-coenzyme A:cholesterol acyltransferase ("ACAT") and has been described in the U.A. at. U.S. Pat. Nos. 6,100,077 and 6,344,548. A second family of DGAT proteins ("DGAT2") is unrelated to the DGAT1 family and is described in PCT Patention Publication WO 2004/011671 published Feb. 5, 2004. Other references to DGAT genes and their use in plants include PCT Publication Nos. WO2004/011,671, WO1998/055,631, and WO2000/001,713, and US Patent Publication No. 20030115632.

DGAT1 is typically the major TAG synthesising enzyme in both the seed and senescing leaf (Kaup et al., 2002, Plant Physiol. 129(4):1616-26; for reviews see Lung and Weselake 2006, Lipids. 41(12):1073-88; Cahoon et al., 2007, Current Opinion in Plant Biology. 10:236-244; and Li et al., 2010, Lipids. 45:145-157).

Raising the yield of oilseed crops (canola, sunflower, safflower, soybean, corn, cotton, linseed, flax etc) has been a major target for the agricultural industry for decades. Many approaches (including traditional and mutational breeding as well as genetic engineering) have been tried, typically with modest success (Xu et al., 2008, Plant Biotechnol J., 6:799-818 and references therein).

Although liquid biofuels offer considerable promise the reality of utilising biological material is tempered by competing uses and the quantities available. Consequently, engineering plants and microorganisms to address this is the focus of multiple research groups; in particular the accumulation of triacylglcerol (TAG) in vegetative tissues and oleaginous yeasts and bacteria (Fortman et al., 2008, Trends Biotechnol 26, 375-381; Ohlrogge et al., 2009, Science 324, 1019-1020). TAG is a neutral lipid with twice the energy density of cellulose and can be used to generate biodiesel a high energy density desirable biofuel with one of the simplest and most efficient manufacturing processes. Engineering TAG accumulation in leaves has so far resulted in a 5-20 fold increase over WT utilising a variety of strategies which includes: the over-expression of seed development transcription factors (LEC1, LEC2 and WRI1); silencing of APS (a key gene involved in starch biosynthesis); mutation of CGI-58 (a regulator of neutral lipid accumulation); and upregulation of the TAG synthesising enzyme DGAT (diacylglycerol O acyltransferase, EC 2.3.1.20) in plants and also in yeast (Andrianov et al., 2009, Plant Biotech J 8, 1-11; Mu et al., 2008, Plant Physiol 148, 1042-1054; Sanjaya et al 2011, Plant Biotech J 9, 874-883; Santos-Mendoza et al., 2008, Plant J 54, 608-620; James et al., 2010, Proc Natl Acad Sci USA 107, 17833-17838; Beopoulos et al., 2011, Appl Microbiol Biotechnol 90, 1193-1206; Bouvier-Navé et al., 2000, Eur J Biochem 267, 85-96; Durrett et al., 2008, Plant J 54, 593-607. However, it has been acknowledged that to achieve further increases in TAG, preventing its catabolism may be crucial within non oleaginous tissues and over a range of developmental stages (Yang and Ohlrogge, 2009, Plant Physiol 150, 1981-1989.

Positively manipulating the yield and quality of triacylglycderides (TAG) in eukaryotes is difficult to achieve. The enzyme diacylglycerol-O-acyltransferase (DGAT) has the lowest specific activity of the Kennedy pathway enzymes and is regarded as a 'bottleneck' in TAG synthesis.

Attempts have been made previously to improve DGAT1 by biotechnological methods, with limited success. For example Nykiforuk et al., (2002, Biochimica et Biophysica Acta 1580:95-109) reported N-terminal truncation of the *Brassica napus* DGAT1 but reported approximately 50% lower activity. McFie et al., (2010, JBC., 285:37377-37387) reported that N-terminal truncation of the mouse DGAT1 resulted in increased specific activity of the enzyme, but also reported a large decline in the level of protein that accumulated.

Xu et al., (2008, Plant Biotechnology Journal, 6:799-818) recently identified a consensus sequence (X-Leu-X-Lys-X-X-Ser-X-X-X-Val) within *Tropaeolum majus* (garden nasturtium) DGAT1 (TmDGAT1) sequences as a targeting motif typical of members of the SNF1-related protein kinase-1 (SnRK1) with Ser being the residue for phosphorylation. The SnRK1 proteins are a class of Ser/Thr protein kinases that have been increasingly implicated in the global regulation of carbon metabolism in plants, e.g. the inactivation of sucrose phosphate synthase by phosphorylation (Halford & Hardie 1998, Plant Mol Biol. 37:735-48. Review). Xu et al., (2008, Plant Biotechnology Journal, 6:799-818) performed site-directed mutagenesis on six putative functional regions/motifs of the TmDGAT1 enzyme. Mutagenesis of a serine residue (S197) in a putative SnRK1 target site resulted in a 38%-80% increase in DGAT1 activity, and over-expression of the mutated TmDGAT1 in *Arabidopsis* resulted in a 20%-50% increase in oil content on a per seed basis.

It would be beneficial to provide improved forms of DGAT1, which overcome one or more of the deficiencies in the prior art, and which can be used to increase cellular oil production.

It is an object of the invention to provide an improved DGAT1 protein and methods for its use to increase cellular lipid production and/or at least to provide the public with a useful choice.

SUMMARY OF THE INVENTION

The inventors provide a novel DGAT1 protein with improved properties over known DGAT1 proteins, particularly known DGAT1 proteins from plants. The novel DGAT1 protein of the invention can be expressed in cells to increase cellular lipid accumulation. Expression of the DGAT1 protein of the invention in cells results in a higher level of lipid than any of several other plant DGAT1 proteins tested by the applicants.

Polynucleotide Encoding a Polypeptide

In the first aspect the invention provides an isolated polynucleotide encoding a DGAT1 polypeptide comprising the sequence of SEQ ID NO:39 (ZmDGAT1-long) or a variant or fragment thereof.

In one embodiment the variant has at least 70% identity to SEQ ID NO:39. In a further embodiment the variant has DGAT1 activity.

In a further embodiment the DGAT1 polypeptide has higher DGAT1 activity than at least one other DGAT1 protein.

In one embodiment the DGAT1 polypeptide has at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50% higher DGAT1 activity relative to the at least one other DGAT1 protein.

Preferably the at least one other DGAT1 protein has the amino acid sequence of the polypeptide of SEQ ID NO:44 (ZmDGAT1-short).

In one embodiment the DGAT1 polypeptide has the higher DGAT1 activity when expressed in a cell.

In a further embodiment the DGAT1 polypeptide has higher DGAT1 activity than any previously known DGAT1 protein.

In one embodiment the DGAT1 polypeptide has the higher DGAT1 activity when expressed in a cell.

In one embodiment the DGAT1 polypeptide has at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50% higher DGAT1 activity than any previously known DGAT1 protein.

In one embodiment the DGAT1 polypeptide has the higher DGAT1 activity when expressed in a cell.

In a further embodiment the polypeptide of the invention has altered substrate specificity relative to at least one other DGAT1 protein.

In one embodiment the DGAT1 polypeptide has the altered substrate specificity when expressed in a cell.

Preferably the at least one DGAT1 protein has the amino acid sequence of the polypeptide of SEQ ID NO:44 (ZmDGAT1-short).

In a further embodiment the polypeptide of the invention, when expressed in the cell, has altered substrate specificity relative to any previously known plant DGAT1 protein.

In one embodiment the DGAT1 polypeptide has the altered substrate specificity when expressed in a cell.

In a further embodiment the DGAT1 protein of the invention is not expressed in naturally occurring plants.

Polypeptide Fragment

Preferably the fragment comprises at least 50 contiguous amino acids, more preferably at least 100 contiguous amino acids, more preferably at least 150 contiguous amino acids, more preferably at least 200 contiguous amino acids, more preferably at least 250 contiguous amino acids, more preferably at least 300 contiguous amino acids, more preferably at least 350 contiguous amino acids, more preferably at least 400 contiguous amino acids, more preferably at least 450 contiguous amino acids of the polypeptide of the invention.

In one embodiment the fragment of the DGAT1 polypeptide of the invention can confer increased DGAT1 activity when added to at least part of another DGAT1 polypeptide.

Polynucleotide

In a further aspect the invention provides an isolated polynucleotide comprising the sequence of SEQ ID NO:10 (ZmDGAT1-long) or a variant or fragment thereof.

In one embodiment the variant has at least 70% identity to SEQ ID NO:10. In a further embodiment the variant encodes a polypeptide with DGAT1 activity.

Polynucleotide Fragment

In a preferred embodiment, the fragment of the polynucleotide of the invention, encodes a fragment of the polypeptide of the invention.

Polypeptide

In a further aspect the invention provides a polypeptide with the sequence of SEQ ID NO:39 (ZmDGAT1-long) or a variant or fragment thereof.

In one embodiment the variant has at least 70% identity to SEQ ID NO:39. In a further embodiment the variant has DGAT1 activity.

In a further embodiment the DGAT1 polypeptide has higher DGAT1 activity than at least one other DGAT1 protein.

In one embodiment the DGAT1 polypeptide has at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50% higher DGAT1 activity relative to the at least one other DGAT1 protein.

Preferably the at least one DGAT1 protein has the amino acid sequence of the polypeptide of SEQ ID NO:44 (ZmDGAT1-short).

In a further embodiment the DGAT1 polypeptide has higher DGAT1 activity than any previously known DGAT1 protein.

In a further embodiment the polypeptide of the invention, when expressed in the cell, has altered substrate specificity relative to at least one other DGAT1 protein.

Preferably the at least one DGAT1 protein has the amino acid sequence of the polypeptide of SEQ ID NO:44 (Zm-DGAT1-short).

In a further embodiment the polypeptide of the invention, when expressed in the cell, has altered substrate specificity relative to any previously known plant DGAT1 protein.

Preferably the fragment comprises at least 50 contiguous amino acids, more preferably at least 100 contiguous amino acids, more preferably at least 150 contiguous amino acids, more preferably at least 200 contiguous amino acids, more preferably at least 250 contiguous amino acids, more preferably at least 300 contiguous amino acids, more preferably at least 350 contiguous amino acids, more preferably at least 400 contiguous amino acids, more preferably at least 450 contiguous amino acids of the polypeptide of the invention.

In one embodiment the fragment of the DGAT1 polypeptide of the invention can confer increased DGAT1 activity when added to at least part of an other DGAT1 polypeptide.

Construct

In a further embodiment the invention provides a genetic construct comprising a polynucleotide of the invention.

Cells

In a further embodiment the invention provides a cell comprising a polynucleotide of the invention. Preferably the cell, or its predecessor, is transformed to comprise the polynucleotide of the invention.

In a further embodiment the invention provides a cell comprising a genetic construct of the invention.

In a preferred embodiment the cell expresses the polynucleotide of the invention.

In a preferred embodiment the cell expresses the polypeptide of the invention.

In a preferred embodiment the cell, or its predecessor, is transformed or genetically modified to expresses the polynucleotide or polypeptide of the invention.

In one embodiment the polypeptide of the invention, when expressed in the cell, has increased DGAT1 activity relative to at least one other DGAT1 protein.

In one embodiment the DGAT1 polypeptide has at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50% higher DGAT1 activity relative to the at least one other DGAT1 protein.

Preferably the at least one DGAT1 protein has the amino acid sequence of the polypeptide of SEQ ID NO:44 (Zm-DGAT1-short).

In a further embodiment the polypeptide of the invention, when expressed in the cell, has increased DGAT1 activity relative to any previously known plant DGAT1 protein.

In a further embodiment the cell produces more lipid than does a control cell.

In one embodiment the cell produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control cell.

In a further embodiment the polypeptide of the invention, when expressed in the cell, has altered substrate specificity relative to at least one other DGAT1 protein.

Preferably the at least one DGAT1 protein has the amino acid sequence of the polypeptide of SEQ ID NO:44 (Zm-DGAT1-short).

In a further embodiment the polypeptide of the invention, when expressed in the cell, has altered substrate specificity relative to any previously known plant DGAT1 protein.

In a further embodiment the cell has an altered lipid profile relative to a control cell.

In one embodiment the proportion of 16:0 in the triacylglycerol is altered relative to that in a control cell.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control cell.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control cell.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:1 in the triacylglycerol in the range 39% to 55%. In this embodiment the proportion of 18:1 in the triacylglycerol is altered within the range 39% to 55%.

The control cell may be any cell of the same type that is not transformed with the polynucleotide, or construct, of the invention to express the polypeptide of the invention. The control cell may also be transformed with an "empty" vector, wherein the empty vector does not include an insert sequence corresponding to a polynucleotide of the invention or expressing a polypeptide of the invention.

In one embodiment the control cell is an untransformed cell. In a further embodiment the control cell is transformed cell to express the polypeptide of SEQ ID NO:44 (ZmDGAT1-short). In a further embodiment the control cell is transformed cell to express any previously known plant DGAT1 protein.

Cells Also Transformed to Express an Oleosin

In one embodiment the cell is also transformed to express at least one of: an oleosin, steroleosin, caloleosin, polyoleosin, and an oleosin including at least one artificially introduced cysteine (WO2011/053169).

In one embodiment the cell is a plant cell.

Plant

In a further embodiment the invention provides a plant comprising a polynucleotide of the invention. Preferably the plant, or its predecessor, is transformed to comprise the polynucleotide of the invention.

In a further embodiment the invention provides a plant comprising a genetic construct of the invention.

In a further embodiment the invention provides a plant comprising a plant cell of the invention.

In a preferred embodiment the plant expresses the polynucleotide of the invention.

In a preferred embodiment the plant expresses the polypeptide of the invention.

In a preferred embodiment the plant, or its predecessor, is transformed or genetically modified to expresses the polynucleotide or polypeptide of the invention.

In one embodiment the polypeptide of the invention, when expressed in the plant, has increased DGAT1 activity relative to at least one other DGAT1 protein.

In one embodiment the DGAT1 protein of the invention has at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50% higher DGAT1 activity relative to the at least one other DGAT1 protein.

Preferably the at least one DGAT1 protein has the amino acid sequence of the polypeptide of SEQ ID NO:44 (ZmDGAT1-short).

In a further embodiment the polypeptide of the invention, when expressed in the plant, has increased DGAT1 activity relative to any previously know plant DGAT1 protein.

In a further embodiment the plant produces more lipid, in at least one of its tissues or parts, than does the equivalent tissue or part in a control plant.

In one embodiment the plant produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control plant.

In one embodiment the tissue is a vegetative tissue. In one embodiment the part is a leaf. In a further embodiment the part is a root. In a further embodiment the part is a tuber. In a further embodiment the part is a corn. In a further embodiment the part is a stalk. In a further embodiment the part is a stalk of a monoct plant. In a further embodiment the part is from stover (the dried stalks and leaves of a field crop). Stover is often used as animal fodder, for example, after the grain of the crop has been harvested In a preferred embodiment the tissue is seed tissue. In a preferred embodiment the part is a seed. In a preferred embodiment the tissue is endosperm tissue.

In a further embodiment the plant as a whole produces more lipid than does the control plant as a whole.

In a further embodiment the plant has an altered lipid profile, in at least one of its tissues or parts, relative to a control plant.

In one embodiment the proportion of 16:0 in the triacylglycerol is altered relative to that in a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control plant.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control plant.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control plant.

In a further embodiment the altered lipid profile has a proportion of 18:1 in the triacylglycerol in the range 39% to 55%. In this embodiment the proportion of 18:1 in the triacylglycerol is altered within the range 39% to 55%.

In one embodiment the tissue is a vegetative tissue. In one embodiment the part is a leaf. In a further embodiment the part is a root. In a further embodiment the part is a tuber. In a further embodiment the part is a corn. In a further embodiment the part is a stalk. In a further embodiment the part is a stalk of a monoct plant. In a further embodiment the part is a stovum (stalk and leaf blade).

In a preferred embodiment the tissue is seed tissue. In a preferred embodiment the part is a seed. In a preferred embodiment the tissue is endosperm tissue.

In a further embodiment the plant as a whole has an altered lipid profile relative to the control plant as a whole.

The control plant may be any plant of the same type that is not transformed with the polynucleotide, or construct, of the invention to express the polypeptide of the invention. The control plant may also be transformed with an "empty" vector, wherein the empty vector does not include an insert sequence corresponding to a polynucleotide of the invention or expressing a polypeptide of the invention.

In one embodiment the control plant is an untransformed plant. In a further embodiment the control cell is transformed cell to express the polypeptide of SEQ ID NO:44 (ZmDGAT1-short).

Plant Also Transformed to Express an Oleosin

In one embodiment the plant is also transformed to express at least one of: an oleo sin, a steroleosin, a caloleosin, a polyoleosin, and an oleosin including at least one artificially introduced cysteine (WO 2011/053169).

Plant Parts

In a further embodiment the invention provides a part, propagule or progeny of a plant of the invention.

In a preferred embodiment the part, propagule or progeny comprises at least one of a polynucleotide, construct, or polypeptide of the invention. Preferably the part, propagule or progeny, or its predecessor plant, is transformed to comprise the polynucleotide of the invention.

In a preferred embodiment the part, propagule or progeny expresses at least one of: a polynucleotide and a polypeptide of the invention.

In a preferred embodiment the part, propagule or progeny expresses a polypeptide of the invention.

In a preferred embodiment the part, propagule or progeny, or its predecessor plant, is transformed or genetically modified to expresses the polynucleotide or polypeptide of the invention.

In a further embodiment the part, propagule or progeny produces more lipid than does a control part, propagule or progeny, or part, propagule or progeny of a control plant.

In one embodiment the part, propagule or progeny produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control part, propagule or progeny, or part, propagule or progeny of a control plant.

In a further embodiment the part, propagule or progeny has an altered lipid profile relative to a control part, propagule or progeny, or part, propagule or progeny of a control plant.

In one embodiment the proportion of 16:0 in the triacylglycerol is altered relative to that in a control part, propagule or progeny, or part, propagule or progeny of a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in control part, propagule or progeny, or part, propagule or progeny of a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in control part, propagule or progeny, or part, propagule or progeny of a control plant.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control part, propagule or progeny, or part, propagule or progeny of a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 18:1 in the triacylglycerol in the range 39% to 55%. In this embodiment the proportion of 18:1 in the triacylglycerol is altered within the range 39% to 55%.

The control plant may be any plant of the same type that is not transformed with the polynucleotide, or construct, of the invention to express the polypeptide of the invention.

In one embodiment the control plant is an untransformed plant. In a further embodiment the control plant is transformed plant to express the polypeptide of SEQ ID NO:44 (ZmDGAT1-short).

Preferably the control the part, propagule or progeny is from a control plant as described above.

In one embodiment the part is from a vegetative tissue. In one embodiment the part is a leaf. In a further embodiment the part is a root. In a further embodiment the part is a tuber. In a further embodiment the part is a corn. In a further embodiment the part is a stalk. In a further embodiment the part is a stalk of a monocot plant. In a further embodiment the part is a stovum (stalk and leaf blade).

In a further embodiment the part is from a reproductive tissue. In a further embodiment the part is a seed. In a preferred embodiment the part is from or includes endosperm tissue.

Animal Feed

In a further aspect the invention provides an animal feedstock comprising at least one of a polynucleotide, polypeptide, construct, cell, plant cell, plant part, plant, propagule and progeny of the invention.

Biofuel Feedstock

In a further aspect the invention provides a biofuel feedstock comprising at least one of a polynucleotide, polypeptide, construct, cell, plant cell, plant part, plant, propagule and progeny of the invention.

Lipid

In one embodiment the lipid is an oil. In a further embodiment the lipid is triacylglycerol (TAG)

Method for Producing Lipid/Oil

In a further aspect the invention provides a method for producing a lipid, the method comprising growing a cell, plant cell or plant that is transformed, or genetically modified, to express and polynucleotide or polypeptide of the invention wherein the plant produces oil through the activity of the expressed polypeptide.

In one embodiment the cell, plant cell or plant produces the lipid as a result of the DGAT1 activity of the polypeptide.

In a further aspect the invention provides a method for producing lipid, the method comprising extracting lipid from at least one of a cell, plant cell, plant, plant part, propagule and progeny of the invention.

In one embodiment the lipid is triacylglycerol (TAG).

In a further embodiment the lipid is processed into at least one of:

a) a fuel,
b) an oleochemical,
c) a nutritional oil,
d) a cosmetic oil,
e) a polyunsaturated fatty acid (PUFA), and
f) a combination of any of a) to e).

In a further aspect the invention provides a method for producing lipid, the method comprising expressing a DGAT1 protein of the invention in a cell, plant cell or plant.

In a preferred embodiment expressing the DGAT1 protein of the invention in the plant leads production of the lipid in the cell, plant cell or plant.

In one embodiment the method includes the step of transforming a cell, plant cell or plant with a polynucleotide of the invention encoding the DGAT1 protein.

In a further embodiment the method includes the step of extracting the lipid from the cell, plant cell, or plant, or from a part, propagule or progeny of the plant.

In one embodiment the lipid is an oil. In a further embodiment the lipid is triacylglycerol (TAG)

In a further embodiment the lipid is processed into at least one of:

a) a fuel,
b) an oleochemical,
c) a nutritional oil,
d) a cosmetic oil,
e) a polyunsaturated fatty acid (PUFA), and
f) a combination of any of a) to e).

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. In some embodiments, the term "comprising" (and related terms such as "comprise" and "comprises") can be replaced by "consisting of" (and related terms "consist" and "consists").

The term "DGAT1" as used herein means acyl CoA: diacylglycerol acyltransferase (EC 2.3.1.20)

DGAT1 is typically the major TAG synthesising enzyme in both the seed and senescing leaf (Kaup et al., 2002, Plant Physiol. 129(4):1616-26; for reviews see Lung and Weselake 2006, Lipids. December 2006; 41(12):1073-88; Cahoon et al., 2007, Current Opinion in Plant Biology. 10:236-244; and Li et al., 2010, Lipids. 45:145-157).

DGAT1 contains approximately 500 amino acids and has 10 predicted transmembrane domains whereas DGAT2 has only 320 amino acids and is predicted to contain only two transmembrane domains; both proteins were also predicted to have their N- and C-termini located in the cytoplasm (Shockey et al., 2006, Plant Cell 18:2294-2313). Both DGAT1 and DGAT2 have orthologues in animals and fungi and are transmembrane proteins located in the ER.

In most dicotyledonous plants DGAT1 & DGAT2 appear to be single copy genes whereas there are typically two versions of each in the grasses which presumably arose during the duplication of the grass genome (Salse et al., 2008, Plant Cell, 20:11-24).

The phrase "increased DGAT1 activity" means increased specific activity relative to that of the first and/or DGAT1 protein.

An art skilled worker would know how to test the "specific activity" of a DGAT1 protein or variant thereof of the invention. This may typically be done by isolating, enriching and quantifying the recombinant DGAT1 then using this material to determine either the rate of triacylglyceride formation and/or the disappearance of precursor substrates (including various forms of acyl-CoA and DAG) as per Xu et al., (2008), Plant Biotechnology Journal. 6:799-818.

Lipid

In one embodiment the lipid is an oil. In a further embodiment the oil is triacylglycerol (TAG)

Lipid Production

In certain embodiments the cell, cells, tissues, plants and plant parts of the invention produces more lipid than control cells, tissues, plants and plant parts.

Those skilled in the art are well aware of methods for measuring lipid production. This may typically be done by quantitative fatty acid methyl ester gas chromatography mass spectral analysis (FAMES GC-MS). Suitable methods are also described in the examples section of this specification.

Substrate Specificity

In certain embodiments, the polypeptides of the invention have altered substrate specificity relative to other DGAT1 proteins. Plant DGAT1 proteins are relatively promiscuous in terms of the fatty acid substrates and DAG species they are capable of utilising to generate TAG. As such they can be considered to have relatively low substrate specificity. However, this can be modified such that certain fatty acids become a preferred substrate over others. This leads to an increase in the proportions of the preferred fatty acids in the TAG and decreases in the proportions of the non preferred fatty acid species. Substrate specificity can be determined by in vitro quantitative analysis of TAG production following the addition of specific and known quantities of purified substrates to known quantities of recombinant DGAT, as per Xu et al., (2008), Plant Biotechnology Journal. 6:799-818.

Lipid Profile

In a further embodiment the cell, cells, tissues, plants and plant parts of the invention have an altered lipid profile relative to the control cells, tissues, plants and plant parts.

Those skilled in the art are well aware of methods for assessing lipid profile. This may involve assessing the proportion or percentage of at least one of the 16:0, 16:1, 18:0, 18:1c9 fatty acid species present in the lipid. This may typically be done by fatty acid methyl ester (FAME) analysis (Browse et al., 1986, Anal. Biochem. 152, 141-145). Suitable methods are also described in the examples section of this specification.

Cells

The DGAT1 polypeptide of the invention, or as used in the methods of the invention, may be expressed in any cell type.

In one embodiment the cell is a prokaryotic cell. In a further embodiment the cell is a eukaryotic cell. In one embodiment the cell is selected from a bacterial cell, a yeast cell, a fungal cell, an insect cell, algal cell, and a plant cell. In one embodiment the cell is a bacterial cell. In a further embodiment the cell is a yeast cell. In one embodiment the yeast cell is a *S. ceriviseae* cell. In further embodiment the cell is a fungal cell. In further embodiment the cell is an insect cell. In further embodiment the cell is an algal cell. In a further embodiment the cell is a plant cell.

In one embodiment the cell is a non-plant cell. In one embodiment the non-plant is selected from *E. coli, P. pastoris, S. ceriviseae, D. salina* and *C. reinhardtii*. In a further embodiment the non-plant is selected from *P. pastoris, S. ceriviseae, D. Salina* and *C. reinhardtii*.

In one embodiment the cell is a microbial cell. In another embodiment, the microbial cell is an algal cell of the division of Chlorophyta (green algae), Rhodophyta (red algae), Phaeophyceae (brown algae), Bacillariophycaeae (diatoms), or Dinoflagellata (dinoflagellates). In another embodiment, the microbial cell is an algal cell of the species *Chlamydomonas, Dunaliella, Botrycoccus, Chlorella, Crypthecodinium, Gracilaria, Sargassum, Pleurochrysis, Porphyridium, Phaeodactylum, Haematococcus, Isochrysis, Scenedesmus, Monodus, Cyclotella, Nitzschia*, or *Parietochloris*. In another embodiment, the algal cell is *Chlamydomonas reinhardtii*. In yet another embodiment, the cell is from the genus *Yarrowia, Candida, Rhodotorula, Rhodosporidium, Cryptococcus, Trichosporon, Lipomyces, Pythium, Schizochytrium, Thraustochytrium*, or *Ulkenia*. In yet another embodiment, the cell is a bacterium of the genus *Rhodococcus, Escherichia*, or a *cyanobacterium*. In yet another embodiment, the cell is a yeast cell. In yet another embodiment, the cell is a synthetic cell.

Plants

The variant DGAT1 sequences of the invention may be naturally-occurring DGAT1 sequences. Preferably the variant DGAT1 sequences are from plants. In certain embodiments the cells into which the DGAT1 proteins of the invention are expressed are from plants. In other embodiments the DGAT1 proteins of the invention are expressed in plants.

The plant cells, from which the DGAT1 proteins of the invention are derived, the plants from which the plant cells are derived, and the plants in which the DGAT1 proteins of the invention are expressed may be from any plant species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Other preferred plants are forage plant species from a group comprising but not limited to the following genera: *Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago* and *Cichorium*.

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is *Trifolium*. Preferred *Trifolium* species include *Trifolium repens; Trifolium arvense; Trifolium affine*; and *Trifolium occidentale*. A particularly preferred *Trifolium* species is *Trifolium repens*.

Another preferred genus is *Medicago*. Preferred *Medicago* species include *Medicago sativa* and *Medicago truncatula*. A particularly preferred *Medicago* species is *Medicago sativa*, commonly known as alfalfa.

Another preferred genus is *Glycine*. Preferred *Glycine* species include *Glycine max* and *Glycine wightii* (also known as *Neonotonia wightii*). A particularly preferred *Glycine* species is *Glycine max*, commonly known as soy bean. A particularly preferred *Glycine* species is *Glycine wightii*, commonly known as perennial soybean.

Another preferred genus is *Vigna*. A particularly preferred *Vigna* species is *Vigna unguiculata* commonly known as cowpea.

Another preferred genus is *Mucana*. Preferred *Mucana* species include *Mucana pruniens*. A particularly preferred *Mucana* species is *Mucana pruniens* commonly known as velvetbean.

Another preferred genus is *Arachis*. A particularly preferred *Arachis* species is *Arachis glabrata* commonly known as perennial peanut.

Another preferred genus is *Pisum*. A preferred *Pisum* species is *Pisum sativum* commonly known as pea.

Another preferred genus is *Lotus*. Preferred *Lotus* species include *Lotus corniculatus, Lotus pedunculatus, Lotus glabar, Lotus tenuis* and *Lotus uliginosus*. A preferred *Lotus* species is *Lotus corniculatus* commonly known as Birdsfoot Trefoil. Another preferred *Lotus* species is *Lotus glabar* commonly known as Narrow-leaf Birdsfoot Trefoil. Another preferred *Lotus* species is *Lotus pedunculatus* commonly known as Big trefoil. Another preferred *Lotus* species is *Lotus tenuis* commonly known as Slender trefoil.

Another preferred genus is *Brassica*. A preferred *Brassica* species is *Brassica oleracea*, commonly known as forage kale and cabbage. A preferred *Brassica* genus is *Camelina*. A preferred *Camelina* species is *Camelina sativa*.

Other preferred species are oil seed crops including but not limited to the following genera: *Brassica, Carthumus, Helianthas, Zea* and *Sesamum*.

A preferred oil seed genera is *Brassica*. A preferred oil seed species is *Brassica napus*.

A preferred oil seed genera is *Brassica*. A preferred oil seed species is *Brassica oleraceae*.

A preferred oil seed genera is *Carthamus*. A preferred oil seed species is *Carthamus tinctorius*.

A preferred oil seed genera is *Helianthus*. A preferred oil seed species is *Helianthus annuus*.

A preferred oil seed genera is *Zea*. A preferred oil seed species is *Zea mays*.

A preferred oil seed genera is *Sesamum*. A preferred oil seed species is *Sesamum indicum*.

A preferred silage genera is *Zea*. A preferred silage species is *Zea mays*.

A preferred grain producing genera is *Hordeum*. A preferred grain producing species is *Hordeum vulgare*.

A preferred grazing genera is *Lolium*. A preferred grazing species is *Lolium perenne*.

A preferred grazing genera is *Lolium*. A preferred grazing species is *Lolium arundinaceum*.

A preferred grazing genera is *Trifolium*. A preferred grazing species is *Trifolium repens*.

A preferred grazing genera is *Hordeum*. A preferred grazing species is *Hordeum vulgare*.

Preferred plants also include forage, or animal feedstock plants. Such plants include but are not limited to the following genera: *Miscanthus, Saccharum, Panicum*.

A preferred biofuel genera is *Miscanthus*. A preferred biofuel species is *Miscanthus giganteus*.

A preferred biofuel genera is *Saccharum*. A preferred biofuel species is *Saccharum officinarum*.

A preferred biofuel genera is *Panicum*. A preferred biofuel species is *Panicum virgatum*.

Plant Parts, Propagues and Progeny

The term "plant" is intended to include a whole plant, any part of a plant, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting progeny, comprising the polynucleotides or constructs of the invention, and/or expressing the DGAT1 sequences of the invention, also form an part of the present invention.

Preferably the plants, plant parts, propagules and progeny comprise a polynucleotide or construct of the invention, and/or express a DGAT1 sequence of the invention.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques.

A "fragment" of a polypeptide is a subsequence of the polypeptide that preferably performs a function/activity of and/or influences three dimensional structure of the polypeptide.

The term "isolated" as applied to the polynucleotide or polypeptide sequences disclosed herein is used to refer to sequences that are removed from their natural cellular environment. The isolated sequence is preferably separated from the sequences that may be found flanking the sequence in its naturally occurring environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from the NCBI website on the World Wide Web at ftp://ftp.ncbi.nih.gov/blast/. The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from the World Wide Web at http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/.

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from the NCBI website on the World Wide Web at ftp://ftp.ncbi.nih.gov/blast/ via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp://ftp.ncbi.nih.gov/blast/. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http:/www.ebi.ac.uk/emboss/align/) and GAP (Huang, X. (1994) On Global Sequence Alignment. Computer Applications in the Biosciences 10, 227-235) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/. The similarity of polypeptide sequences may be examined using the following unix command line parameters:

bl2seq -i peptideseq1 -j peptideseq2 -F F -p blastp

Variant polypeptide sequences preferably exhibit an E value of less than 1×10−6 more preferably less than 1×10−9, more preferably less than 1×10−12, more preferably less than 1×10−15, more preferably less than 1×10−18, more preferably less than 1×10−21, more preferably less than 1×10−30, more preferably less than 1×10−40, more preferably less than 1×10−50, more preferably less than 1×10−60, more preferably less than 1×10−70, more preferably less than 1×10−80, more preferably less than 1×10−90 and most preferably 1×10−100 when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli.*

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

In certain embodiments the DGAT1 polynucleotides/polypeptides of the invention may be advantageously expressed under the control of selected promoter sequences as described below.

Vegetative Tissue Specific Promoters

An example of a vegetative specific promoter is found in U.S. Pat. Nos. 6,229,067; and 7,629,454; and 7,153,953; and 6,228,643.

Pollen Specific Promoters

An example of a pollen specific promoter is found in U.S. Pat. Nos. 7,141,424; and 5,545,546; and 5,412,085; and 5,086,169; and 7,667,097.

Seed Specific Promoters

An example of a seed specific promoter is found in U.S. Pat. Nos. 6,342,657; and 7,081,565; and 7,405,345; and 7,642,346; and 7,371,928. A preferred seed specific promoter is the napin promoter of *Brassica napus* (Josefsson et al., 1987, J Biol Chem. 262(25):12196-201; Ellerström et al, 1996, Plant Molecular Biology, Volume 32, Issue 6, pp 1019-1027).

Fruit Specific Promoters

An example of a fruit specific promoter is found in U.S. Pat. Nos. 5,536,653; and 6,127,179; and 5,608,150; and 4,943,674.

Non-photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corn Promoters

An example of a promoter capable of driving expression in a corn is found in Schenk et al., (2001) Plant Molecular Biology, 47:399-412.

Photosythetic Tissue Preferred Promoters

Photosythetic tissue preferred promoters include those that are preferentially expressed in photosynthetic tissues of the plants. Photosynthetic tissues of the plant include leaves, stems, shoots and above ground parts of the plant. Photosythetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

A "transgene" is a polynucleotide that is taken from one organism and introduced into a different organism by transformation. The transgene may be derived from the same species or from a different species as the species of the organism into which the transgene is introduced.

Host Cells

Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell, particularly a plant cell in a vegetative tissue of a plant.

A "transgenic plant" refers to a plant which contains new genetic material as a result of genetic manipulation or transformation. The new genetic material may be derived from a plant of the same species as the resulting transgenic plant or from a different species. Subsequent offspring or generations of the plant that still contain the new genetic material are also transgenic plants according to the invention.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens et al., (2000) Plant Mol Biol 42: 819-32, Hellens et al., Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues respond to internal developmental signals or external abiotic or biotic stresses are described in the scientific literature. Exemplary promoters are described, e.g., in WO 02/00894 and WO2011/053169, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183);

caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et at, 2006 Planta. 223(6):1219-30; Folta et at, 2006 Planta April 14; PMID: 16614818), rose (Li et al., 2003), *Rubus* (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412), Canola (*Brassica napus* L.). (Cardoza and Stewart, 2006 Methods Mol Biol. 343:257-66), safflower (Orlikowska et al., 1995, Plant Cell Tissue and Organ Culture 40:85-91), ryegrass (Altpeter et al., 2004 Developments in Plant Breeding 11(7):255-250), rice (Christou et al, 1991 Nature Biotech. 9:957-962), maize (Wang et al., 2009 In: Handbook of Maize pp. 609-639) and *Actinidia eriantha* (Wang et al., 2006, Plant Cell Rep. 25, 5: 425-31). Transformation of other species is also contemplated by the invention. Suitable methods and protocols are available in the scientific literature.

BRIEF DESCRIPTION OF THE FIGURES

FIG. 1 shows the nucleic acid sequence and three frame translation of the *Arabidopsis thaliana* DGAT1 transcribed region (SEQ ID NO:116). Exon coding sequences are shown in bold face, underlined, grey blocks.

FIG. 2 shows the nucleic acid sequence and three frame translation of the *Zea mays* short DGAT1 transcribed region (SEQ ID NO:117). This genomic sequence has F469 deleted and Q67 added compared to the cDNA (EU039830) and peptide (ABV91586) sequences actually used in this patent. Exon coding sequences are shown in bold face, underlined, grey blocks.

FIG. 3 shows the nucleic acid sequence and three frame translation of the *Zea mays* long DGAT1 transcribed region (SEQ ID NO:118) derived from CHORI-201 Maize B73 BAC Library (available from the World Wide Web at http://www.ncbi.nlm.nih.gov/nuccore/AC204647; http://bacpac.chori.org/maize201.htm). Exon coding sequences are shown in bold face, underlined, grey blocks.

FIG. 5 shows the line-bond structures of the amino acid residues lysine (K) and arginine (R).

EXAMPLES

Example 1

Figure 4:
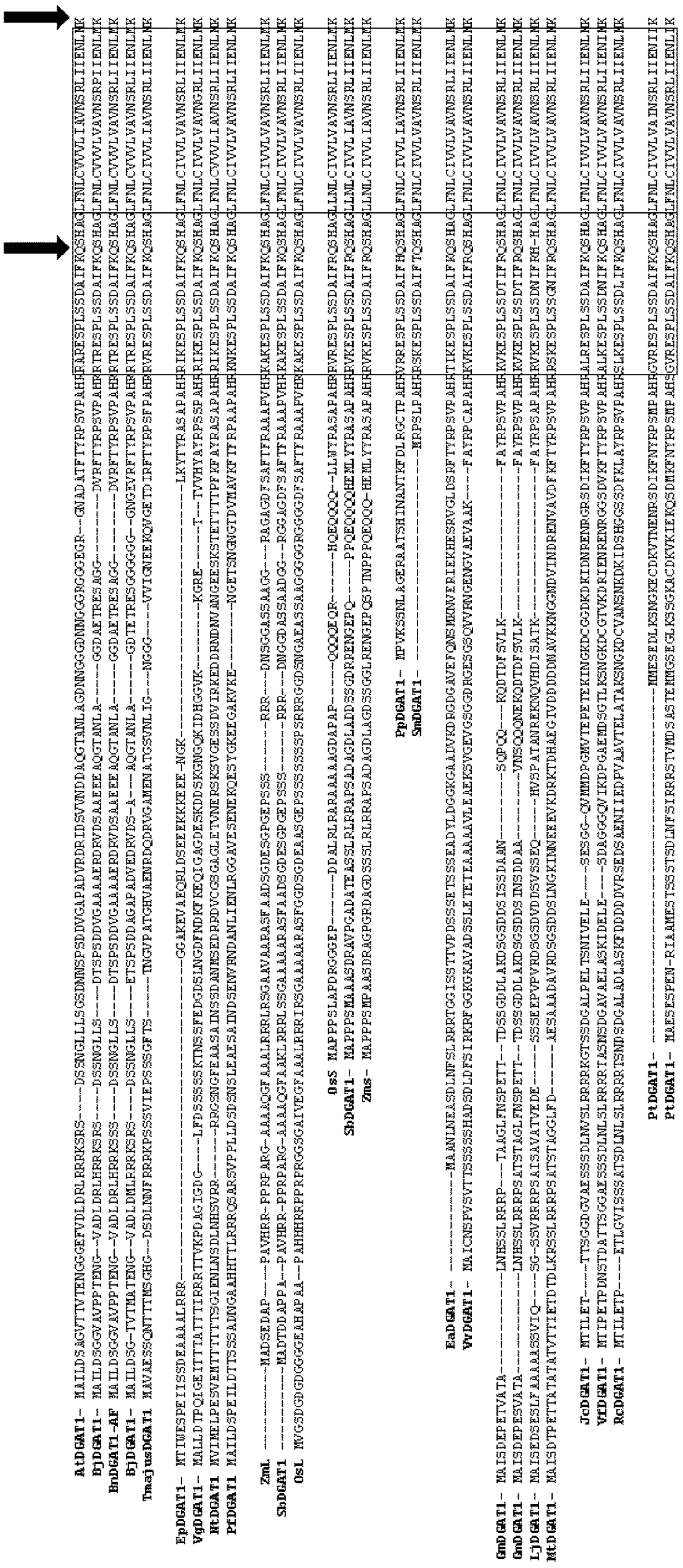
FIG. 4 shows the peptide sequence of the N-terminal cytoplasmic region of a number of plant DGAT1s including both long and short versions from the grasses as well as examples from dicotyledonous species. Left hand box represents acyl-CoA binding site (Nykiforuk et al., 2002, Biochimica et Biophysica Acta 1580:95-109). Right hand box represents first transmembrane region (McFie et al., 2010, JBC., 285:37377-37387). Left hand arrow represents boundary between exon 1 and exon 2. Right hand arrow represents boundary between exon 2 and exon 3. The sequences are AtDGAT1 (SEQ ID NO:119), BjDGAT1 (SEQ ID NO:120), BnDGAT1-AF (SEQ ID NO:121), BjDGAT1 (SEQ ID NO:122), TmajusDGAT1 (SEQ ID NO:123), EpDGAT1 (SEQ ID NO:124), VgDGAT1 (SEQ ID NO:125), NtDGAT1 (SEQ ID NO:126), PfDGAT1 (SEQ ID NO:127), ZmL (SEQ ID NO:128), SbDGAT1 (SEQ ID NO:129), OsL (SEQ ID NO:130), OsS (SEQ ID NO:131), SbDGAT1 (SEQ ID NO:132), ZmS (SEQ ID NO:133), PpDGAT1 (SEQ ID NO:132), SmDGAT1 (SEQ ID NO:135), EaDGAT1 (SEQ ID NO:136), VvDGAT1 (SEQ ID NO:137), GmDGAT1 (SEQ ID NO:138), GmDGAT1 (SEQ ID NO:139), LjDGAT1 (SEQ ID NO:140), MtDGAT1 (SEQ ID NO:141), JcDGAT1 (SEQ ID NO:142), VfDGAT1 (SEQ ID NO:143), RcDGAT1 (SEQ ID NO:144), PtDGAT1 (SEQ ID NO:145), Pt DGAT1 (SEQ ID NO:146).

Identification of the DGAT1 Sequence of the Invention

Several nucleic acid sequences and polypeptide sequences for the plant type 1 DGATs can be found by accession number in public domain libraries (Table 1). For creating initial alignments we used ClustalW (Thompson et al., 1994, Nucleic Acids Res., 22, 4673-4680); these were manually edited and used to create the models to search the DGAT sequences, using the HMMER2 package (HMMER 2.3.2 (October 2003) Copyright© 1992-2003 HHMI/Washington University School of Medicine, available from the World Wide Web at http://hmmer.org). Initial matching of protein sequences against genomic DNA with splice prediction was performed with the GeneWise package (Birney et al., 2004, Genome Res. 14: 988-995). Some of the sequences retrieved appeared to have errors; in particular incorrectly predicted splice sites which would result in internal deletions that would likely result in non-functional proteins. While both dicotyledonous and monocotyledonous type 1 DGATs have 16 exons there are some differences in the position of the splicing. Exon 8 in the dicotylendonous DGAT1 gene corresponds to exons 8 and 9 in the monocotyledonous DGAT1 gene, while exon 14 in the monocotyledonous gene corresponds to exons 13 and 14 in the dicotyledonous gene. We have found that the most accurate method for determining the likely genuine coding sequence from genomic data has been to use Vector NTI Advance (TM) 11.0 (© 2008 Invitrogen Corporation) to translate the genome in the three forward reading frames and align these with demonstrated functional DGAT1s from dicotyledonous or monocotyledous species as appropriate (for example *A. thaliana* cDNA NM_127503, protein NP_179535 and *Z. mays* cDNA EU039830, protein ABV91586). The genomic sequence and corresponding exon/intron boundary positions for *Arabidopsis thaliana* encoding NP_179535 and *Zea mays* encoding ABV91586 that can be used as a template for determining other plant DGAT coding regions are shown in FIG. 1 and FIG. 2, respectively.

Using this method, the applicants have assembled/identified a novel DGAT1 sequence from *Z. mays* DGAT1 (SEQ ID NO: 10 and SEQ ID NO: 39 [FIG. 3]). To the best of the applicant's knowledge, a functional portion of sequence is not present in any public cDNA database, which may indicate that the functional protein is not expressed in naturally occurring plants.

The applicants designated this sequence *Zea mays* DGAT-Long (ZmDGAT1-L or Zm-L DGAT1) because the encoded polypeptides is longer than the known *Zea mays* of SEQ ID NO: 44 (referred to as *Zea mays* DGAT1 -short or ZmDGAT1 -S or Zm-S DGAT1) as indicated in FIG. 4.

A similar relationship exists between *Oryza sativa* DGAT1 -short, or OsDGAT1-S, or Os-S DGAT1 (SEQ ID NO:41, and *Oryza sativa* DGAT1 -long, or OsDGAT1-L, or Os-L DGAT1 (SEQ ID NO:42).

TABLE 1

| DGAT1 Species Source | DNA accession #s & BAC # | SEQ ID NO: | PROTEIN accession #s & BAC # | SEQ ID NO: |
|---|---|---|---|---|
| *A. thaliana* | NM_127503 | 1 | NP_179535 | 30 |
| *B. juncea* | AF164434 | 2 | AAY40784 | 31 |
| *B. napus* | AF164434_1 | 3 | AAD45536.1 | 32 |
| *B. juncea* | DQ016107 | 4 | AAY40785 | 33 |
| *T. majus* | AY084052 | 5 | AAM03340 | 34 |
| *E. pitardii* | FJ226588 | 6 | ACO55635 | 35 |
| *V. galamensis* | EF653276 | 7 | ABV21945 | 36 |
| *N. tabacum* | AF129003_1 | 8 | AAF19345.1 | 37 |
| *P. frutescens* | AF298815_1 | 9 | AAG23696.1 | 38 |
| *Z. mays* | From: CHORI-201 Maize B73 BAC | 10 | From: CHORI-201 Maize B73 BAC | 39 |
| *S. bicolor* | XM_002439374 | 11 | XP_002439419 | 40 |
| *O. sativa* | Os05g0196800 | 12 | NP_001054869 | 41 |
| *O. sativa* | From: AP003714.1 | 13 | From: AP003714.1 | 42 |
| *S. bicolor* | XM_002437120.1 | 14 | XP_002437165 | 43 |
| *Z. mays* | EU039830 | 15 | ABV91586 | 44 |
| *P. patens* | XM_001770877.1 | 16 | XP_001770929 | 45 |
| *S. moellendorffii* | XM_002964119 | 17 | XP_002964165 | 46 |
| *E. alatus* | AY751297 | 18 | AAV31083 | 47 |
| *V. vinifera* | XM_002279309 | 19 | XP_002279345 | 48 |
| *G. max* | AY496439 | 20 | AAS78662 | 49 |
| *G. max* | AB257590 | 21 | BAE93461 | 50 |
| *L. japonicus* | AY859489 | 22 | AAW51456 | 51 |
| *M. truncatula* | AC174465.2 | 23 | ABN09107 | 52 |
| *J. curcas* | DQ278448.1 | 24 | ABB84383 | 53 |
| *V. fordii* | DQ356680.1 | 25 | ABC94472 | 54 |
| *V. galamensis* | EF653276.1 | 26 | ABV21945 | 55 |
| *R. communis* | XM_002514086.1 | 27 | XP_002514132 | 56 |
| *P. trichocarpa* | XM_002308242.1 | 28 | XP_002308278 | 57 |
| *P. trichocarpa* | XM_002330474.1 | 29 | XP_002330510 | 58 |

Example 2

The DGAT1 Sequence of the Invention has Surprisingly High Activity in Increasing Cellular Lipid Content, and Fragments of the DGAT1 Sequence of the Invention are Useful in Conferring Increased Activity to Other DGAT1 Proteins Summary The applicants compared the activity of the DGAT1 sequence of the invention to other known DGAT1 sequences. Surprisingly the DGAT1 sequence of the invention showed higher activity, in increasing cellular lipid content, than any of the other DGAT1 sequences tested.

Furthermore the applicants have shown that fragments of the DGAT1 protein of the invention are useful in conferring increase activity on at least parts of other DGAT proteins.

Materials and Methods

Nucleic acid constructs encoding the amino acid sequences, SEQ ID NO: 30 (*A. thaliana* DGAT1), 34 (*T. magus* DGAT1), 39 (*Zea mays* DGAT1-L), 41 (*O. sativa* DGAT1-S), 42 (*O. sativa* DGAT1-L) and 44 (Table 1) were optimised for expression in *Saccharomyces cerevisiae* by GeneArt AG (Germany). These were engineered to have an internal XhoI site within exon 1 encoding the conserved N-terminal acyl-Co binding region (identified by Lung and Weselake, 2006, Lipids. December 2006; 41(12):1073-88) without altering the amino acid sequence leucine-serine-serine (LSS). FIG. 4 shows alignment of a number of DGAT1 sequences from plants. The left box shows the position of the Acyl-CoA binding site.

An EcoRI site was engineered upstream of the 5' coding sequence while an XbaI site was placed downstream of the 3' stop codon. The internal XhoI and flanking EcoRI and XbaI sites were used to generate chimeras between the DGAT1 sequence of the invention and each of the other DGAT1 clones; essentially this fused the N-terminal reputed cytoplasmic region (based on Lung and Weselake, 2006, Lipids. December 2006; 41(12):1073-88 and McFie et al., 2010, JBC., 285:37377-37387) from one DGAT1 with the C-terminal ER luminal region of a different DGAT1. In some combinations this resulted in one amino acid change in the remaining cytoplasmic region downstream of the engineered XhoI site. The putative acyl-Co binding region the *A. thaliana* DGAT1, *T. majus* DGAT1, *Z. mays*-L DGAT1 and *O. sativa*-L DGAT1 have an identical amino acid sequence down stream of the XhoI site (LSSDAIFKQSHA). While in the *Z. mays*-S DGAT1 and *O. sativa*-S DGAT1 the lysine (K) residue is replaced by an arginine (R) residue (LSSDAIF RQSHA). Since the position of this residue is located 3' to the Xho I site encoded by LLS then chimeras deriving from one parent containing the lysine and one parent containing the arginine residue will effectively result in a substitution of this residue. This was considered to be a minimal disruption since both lysine and arginine are large, positively charged, hydrophilic, basic amino acids containing a free amine or guanidinium group, respectively at the end of an aliphatic side chain (FIG. 5). The N-terminal region/C-terminal region domain swapping constructs, and the parent constructs (highlighted in bold) are shown in Table 2, with their corresponding SEQ ID NOs.

TABLE 2

| DGAT1 N-terminal parent | DGAT1 C-terminal parent | C-terminal Tail Fusion | SEQ ID NO: |
|---|---|---|---|
| *A. thaliana* | *A. thaliana* | V5-6xHis | 59 |
| *A. thaliana* | *Z. mays*-L | V5-6xHis | 63 |
| *O. sativa*-S | *O. sativa*-S | V5-6xHis | 65 |
| *O. sativa*-S | *Z. mays*-L | V5-6xHis | 69 |
| *O. sativa*-L | *O. sativa*-L | V5-6xHis | 71 |
| *O. sativa*-L | *Z. mays*-L | V5-6xHis | 75 |
| *Z. mays*-S | *Z. mays*-S | V5-6xHis | 77 |
| *Z. mays*-S | *Z. mays*-L | V5-6xHis | 81 |
| *Z. mays*-L | *Z. mays*-L | Y5-6xHis | 83 |
| *Z. mays*-L | *Z. thaliana* | V5-6xHis | 84 |
| *Z. mays*-L | *O. sativa*-S | V5-6xHis | 85 |
| *Z. mays*-L | *O. sativa*-L | V5-6xHis | 86 |
| *Z. mays*-L | *Z. mays*-S | V5-6xHis | 87 |
| *Z. mays*-L | *T. majus* | V5-6xHis | 88 |
| *T. majus* | *T. majus* | V5-6xHis | 89 |
| *T. majus* | *Z. mays*-L | V5-6xHis | 94 |

Sequences were synthesised either by GENEART AG (Germany) or GeneScript (USA). Sequences were optimised for expression in *Saccharomyces cerevisiae* and flanked with appropriate incorporated appropriate restriction sites to facilitate the cloning into the pYES2.1 vector (Invitrogen).

Expression of Constructs in *S. cerevisiae*

The parent DGAT1 constructs and chimeric DGAT1 constructs were placed into the galactose-inducible yeast expression vector pYES2.1/V5-His TOPO® (Invitrogen). This resulted in the addition of an inframe C-terminal V5 epitope and 6× histidine tag. The chimeric constructs and the number of their corresponding polypeptide sequences are shown in Table 2 above.

The *Saccharomyces cerevisiae* quadruple mutant (H1246) in which all four neutral lipid biosynthesis genes have been disrupted (Sandager et at, 2002, The Journal of Biological Chemistry, 277:6478-6482) was transformed as per Elble (1992, BioTechniques 13, 18-20) and selected by the ability to grow in the absence of uracil. Routinely, yeast cells were grown aerobically overnight in a synthetic medium with 0.67% YNB, without uracil (SC-U) and containing 2% glucose. Cells from overnight culture were used to inoculate 200 mL of induction medium (SC-U containing 2% galactose and 1% raffinose) to an initial $OD_{600}$ of 0.4. Cells were allowed to further grow at 30° C., with shaking at 200 rpm until late stationary phase, normally 48 h. Cells were harvested by centrifugation at 1500×g for 5 min, then cell pellets were washed with distilled water and either used immediately for subsequent analysis or kept in −80° C. until required. Cell pellets for neutral lipid extraction were freeze-dried for 48 h and stored in −20° C. freezer until required.

Lipid Analysis of *S. cerevisiae*

Approximately 10 mg of freeze-dried yeast cell material was accurately weighed then disrupted using glass beads by vortexing for 1 minute. This lysate was extracted in hot methanolic HCl for fatty acid methyl ester (FAME) analysis (Browse et al., 1986, Anal. Biochem. 152, 141-145).

For FA profile analysis approximately 50 mg freeze dried yeast was placed in a 13-mm screw cap tube, and an equal volume of glass beads added before vortexing at high speed in 3×1 min bursts. Following addition of 50 μg of 19:0 TAG internal standard, 2.4 mL of 0.17 M NaCl in MeOH was added and the mixture vortexed for 15 sec followed by the addition of then 4.8 mL of heptane and the entire contents mixed.

The solution was then incubated in 80° C. water bath for 2 h without shaking. After incubation, the solution was cooled to room temperature. After cooling, the upper phase (lipidic phase) was transferred to fresh screw-cap tube and evaporated to dryness under stream of nitrogen gas. The dried residue was then dissolved in 1 mL heptane and mixed thoroughly for TAG SPE separation using Strata Si-1 Silica column (Phenomenwx, 8B-S012-EAK).

After preconditioning with methanol and equilibrating the Silica column with heptane the 1 mL TAG extract (including 50 μg 17:0 TAG Internal Standard was passed through the pre-equilibrated column, followed by 1.2 mL of heptane and then 2 mL of chloroform:heptane (1:9 v/v/) and the eluate collected. The total eluate collected was evaporated to dryness under the stream of N gas and the residue used for FAMEs extraction.

FAMEs of Extracted TAG

To the TAG residue above 10 μL of internal standard 15:0 FA (4 mg/mL dissolved in heptane) and 1 mL of methanolic HCl (1N) reagent containing 5% of 2,2-dimeethoxypropane (as water scavenger) were added.

The tube was then flushed with N gas, then sealed immediately with Teflon-lined cap, and heated at 80° C. in a water bath for 1 h. After cooling down, 0.6 mL heptane and 1.0 mL of 0.9% (w/v) NaCl was added, the mixture vortexed then spun at 500 rpm for 1 min.

From the top heptane layer, 100 μL was collected and transferred to a flat-bottom glass insert fitted into a vial for FAMES GC/MS analysis.

Protein Extraction and Trypsin Digestion

Yeast cell pellets were washed with lysis buffer (50 mM sodium phosphate, pH 7.4, 1 mM EDTA, 5% glycerol, 1 mM PMSF) then resuspended in 500 μL lysis buffer, glass beads were added and cells disrupted by vortexing 2× at medium speed for 30 seconds. Cell debris was pelleted by centrifugation at 1000×g for 5 min, the supernatant transferred to fresh tubes and total cellular membranes pelleted by ultracentrifugation at 100,000×g for 1 h. Membrane proteins were resuspended in lysis buffer with or without detergent (1% Dodecyl maltoside) and quantified in a Qubit Fluorometer using the Qubit IT Quantitation Kit.

Trypsin was added to give a final concentration of 25 μg/mL to 50 μL of protein extract and the mixture incubated at 30° C. for 30 min. The reaction was terminated by addition of Trypsin inhibitor from *Glycine max* (Sigma-Aldrich catalogue #T6414) to a final concentration of 0.4 μg/μL. After addition of trypsin inhibitor, 4×SDS loading dye and 10× reducing agent (Invitrogen) were added, and the protein incubated at 70° C. for 10 min prior to SDS-PAGE followed by immunoblotting. The blot was probed with either Anti V5-HRP antibody (Cat #R96125, Invitrogen) at 1:2500 dilution, or anti Kar2 (y-115) antibody produced in rabbit (SC-33630, Santa Cruz Biotechnology) at 1:200 dilution. Anti Kar2 was used to detect the yeast protein Kar2, an ER luminaly-located protein (Rose et al., 1989, Cell 57, 1211-1221) which serves as a control to demonstrate the presence of intact microsomes.

Expression of Chimeric DGAT1 in *Brassica napus*

The same strategy, as described above, was used to generate a variety of chimeric DGAT1 constructs for expression in the seeds of *Brassica napus*. This included the parent DGAT1s of *T. majus* DGAT1, *Z. mays*-L DGAT1 and *Z. mays*-S DGAT1 (amino acid SEQ ID NO: 34, 39 and 44 respectively, Table 1) optimised for expression in *Brassica napus* by GeneArt AG. The *T. majus* construct was engineered to contain a single point mutation $S_{197}A$ (Xu et al., 2008, Plant Biotechnology Journal, 6:799-818). All constructs were engineered to have an optimised Kozak, *Arabidopsis thaliana* UBQ10 intron, and tetranucleotide stop codon as per Scott et al., (2010, Plant Biotechnology Journal, 8:912-917) as indicated in Table 3 below.

TABLE 3

| DGAT1 Parent Species | Kozak, intron, stop codon | Residue modification | SEQ ID NO: |
|---|---|---|---|
| *T. majus* | yes | S197A | 95 |
| *Z. mays*-S | yes | none | 96 |
| *Z. mays*-L | yes | none | 97 |

The same digestion pattern used to generate the chimeras for expression in *S. cerevisiae* was used on the *B. napus*-optimised constructs to generate the chimeras Tm-ZmL and ZmL-Tm(S189A); resulting in the peptide sequences listed in Table 4.

TABLE 4

| DGAT1 N-terminal parent | DGAT1 C-terminal parent | Residue modification | SEQ ID NO: |
|---|---|---|---|
| *T. majus* | *T. majus* | S197A | 98 |
| *Z. mays*-L | *Z. mays*-L | none | 99 |
| *T. majus* | *Z. mays*-L | none | 100 |
| *Z. mays*-L | *T. majus* | S189A | 101 |

The parent DGATs and their chimeras were transferred into the Gateway®-compatible binary vector pMD107 (courtesy of Dr Mark Smith, NRC Saskatoon, SK, Canada, S7N 0W9) which placed them under the control of the seed-specific napin promoter (Ellerström et al., 1996, Plant Molecular Biology, Volume 32, Issue 6, pp 1019-1027).

Plant Transformation

*B. napus* (cv. DH12075) was transformed via *Agrobacterium tumefaciens* (GV3101) using the cotyledon co-cultivation method (adapted from that of Maloney et al., 1989, Plant Cell Rep. 8, 238-242). Control lines contained an empty-vector, and when identified, null sibling lines were subsequently used as true controls.

Approximately 200 $T_0$ transformed lines were produced and their corresponding $T_1$ selfed seeds were analysed for oil content by GC. Approximately 50 individual transgenic lines (including control lines) were selected for the next generation (10 plants/line) based on their oil content, or seed weight (8 lines).

A total of approximately $T_1$ plants were grown and screened by PCR for copy number and identification of null sibling lines. $T_2$ seeds were analysed in triplicate for oil content by NMR.

Expression of *Z. mays*-L and *T. majus* DGAT1 in *Camelina sativa*

The strategy above can also be used to generate a variety of chimeric DGAT1 constructs for expression in the seeds of *Camelina sativa* and other plants.

Sequences with modifications were synthesised either by GENEART AG (Germany) or GeneScript (USA). Sequences with modifications were synthesised either by GENEART AG (Germany) or GeneScript (USA). Sequences were optimised for expression in *Brassica* species and included an intron (SEQ ID NO:102) from *Arabidopsis thaliana* DGAT1 -intron 3. Each sequence was flanked with appropriate attL recombination sites to enable the cloning Gateway® adapted vectors.

TABLE 5

| DGAT1 N-terminal parent | DGAT1 C-terminal parent | Residue modification | C-terminal mod | Additional information | Type of sequence | SEQ ID NO: |
|---|---|---|---|---|---|---|
| *T. majus* | *T. majus* | S197A | V5-His tag | + intron | NUCLEIC | 103 |
| *T. majus* | *T. majus* | S197A | V5-His tag | ORF only | NUCLEIC | 104 |
| *T. majus* | *T. majus* | S197A | V5-His tag | | PEPTIDE | 105 |
| *Z. mays-L* | *Z. mays-L* | None | V5-His tag | + intron | NUCLEIC | 106 |
| *Z. mays-L* | *Z. mays-L* | None | V5-His tag | ORF only | NUCLEIC | 107 |
| *Z. mays-L* | *Z. mays-L* | None | V5-His tag | | PEPTIDE | 108 |
| *T. majus* | *Z. mays-L* | None | V5-His tag | + intron | NUCLEIC | 109 |
| *T. majus* | *Z. mays-L* | None | V5-His tag | ORF only | NUCLEIC | 110 |
| *T. majus* | *Z. mays-L* | None | V5-His tag | | PEPTIDE | 111 |
| *Z. mays-L* | *T. majus* | S189A | V5-His tag | + intron | NUCLEIC | 112 |
| *Z. mays-L* | *T. majus* | S189A | V5-His tag | ORF only | NUCLEIC | 113 |
| *Z. mays-L* | *T. majus* | S189A | V5-His tag | | PEPTIDE | 114 |

The parent DGATs and their modified forms were transferred into the Gateway®-compatible binary pRSh1 Gateway adapted binary vector (Winichayakul et al., 2009, Biotechnol. Appl. Biochem. 53, 111-122) modified by replacement of the CaMV35S promoter replaced with the *Brassica napus* Napin promoter (SEQ ID NO:115).

*Camelina sativa* Transformation

*C. sativa* (cf. Calena) were transformed via *Agrobacterium tumefaciens* (GV3101) using the floral dip method (adapted from that of Clough and Bent, 1998, Plant J. 16(6):735-745). Essentially seeds were sown in potting mix in 10 cm pots in a controlled environment, approximately 6 weeks after planting the flowers were dipped for 5-14 minutes under vacuum (70-80 inch Hg) in an overnight culture of appropriated *Agrobacterium* GV3101 cells re-suspended in a floral dip buffer. After vacuum-transformation, plants were kept for 24 h under low light conditions by partly covering with a black plastic sheet. Vacuum transformations can be repeated three times at approximately 10-12 days intervals, corresponding to the flowering duration. Plants were grown in potting mix in a controlled environment (16-h day length, 21-24° C., 65-70% relative humidity).

The $T_1$ seeds produced can be collected and screened for transformants by germinating and growing seedlings at 22° C. with continuous light on a half-strength MS medium (pH 5.6) selection plate containing 1% (w/v) sucrose, 300 mg/L Timentin, and 25 mg/L DL-phosphinothricin to select for herbicide resistance. $T_2$ selfed seed populations can also be screened by immuno blot for the presence of the V5 eptiope.

$T_2$ selfed seeds may be analysed for oil content by GC. Approximately 50 individual transgenic lines (including control lines) may be selected for the next generation (10 plants/line) based on their oil content, or seed weight. $T_2$ plants may be grown and screened by PCR for copy number and identification of null sibling lines. $T_2$ seeds may be analysed in triplicate for oil content by NMR or GC/MS.

Results

Addition of Fragments of the DGAT1 Polypeptide of the Invention to other DGAT1 Sequences Enhance Lipid Production in *Saccharomyces cerevisiae* Relative to that with the other DGAT1 Sequences Alone.

Tables 1-8 show the lipid yields of a variety of chimeric DGAT1s in which the N-terminal or C-terminal region has been derived from the DGAT1 sequence of the invention while the remainder of the protein has been derived from another plant DGAT1. The lipid yields are presented either as grams of lipid produced per liter (which therefore compensates for any differences in growth rate) or have been normalised as a percentage of the lipid yield of the corresponding unmodified parent DGAT1.

A comparison of parent DGAT1s with each other, and with each of the chimeric DGAT1s made using one donor parent for the N-terminal region, and a different donor parent for the C-terminal region are shown in Table 6. The parent DGAT1 sequences are highlighted in bold. Surprisingly the DGAT1 sequence of the invention shows higher activity, in lipid yield production, than any of the other sequences tested.

The lipid yields at 32 hr have been normalised against the highest lipid-producing parent (*Z. mays*-L) and are presented in ascending order.

TABLE 6

| N-terminal region DGAT1 Parent | C-terminal region DGAT1parent | SEQ ID NO: | Lipid yield as % *Z. mays*-L |
|---|---|---|---|
| Vector only | Vector only | N/A | 31.96 |
| *A. thaliana* | *Z. mays*-L | 63 | 38.28 |
| *A. thaliana* | *A. thaliana* | 59 | 64.69 |
| *T. majus* | *T. majus* | 89 | 77.62 |
| *Z. mays*-S | *Z. mays*-S | 77 | 81.79 |
| *Z. mays*-L | *T. majus* | 88 | 83.39 |
| *O. sativa*-S | *O. sativa*-S | 65 | 84.76 |
| *O. sativa*-L | *O. sativa*-L | 71 | 88.33 |
| *O. sativa*-S | *Z. mays*-L | 69 | 95.81 |
| *Z. mays*-L | *O. sativa*-L | 86 | 96.17 |
| *Z. mays*-L | *A. thaliana* | 84 | 97.53 |
| *Z. mays*-L | *Z. mays*-L | 83 | 100.00 |
| *T. majus* | *Z. mays*-L | 94 | 100.71 |
| *O. sativa*-L | *Z. mays*-L | 75 | 104.29 |
| *Z. mays*-L | *O. sativa*-S | 85 | 105.02 |

The results also show that addition of the *Z. mays*-L N-terminal region to the C-terminal region of the *A. thaliana* DGAT1 parent results in increased lipid yield over the full-length *A. thaliana* DGAT1 sequence (see SEQ ID NO: 84 versus SEQ ID NO: 59).

The results also show that addition of the *Z. mays*-L N-terminal or C-terminal region to the C-terminal or N-terminal region respectively, of the *T. majus* DGAT1 sequence results in increased lipid yield over the full-length *T. majus* DGAT1 sequence (see SEQ ID NO: 88 and 94 versus SEQ ID NO: 89).

The results also show that addition of the *Z. mays*-L N-terminal or C-terminal region to the C-terminal or N-terminal region respectively, of the *O. sativa*-S DGAT1 sequence results in increased lipid yield over the full-length *O. sativa*-S DGAT1 sequence (see SEQ ID NO: 85 and 69 versus SEQ ID NO: 65).

The results also show that addition of the *Z. mays*-L N-terminal or C-terminal region to the C-terminal or N-terminal region respectively, of the *O. sativa*-L DGAT1 sequence results in increased lipid yield over the full-length *O. sativa*-L (see SEQ ID NO: 86 and 75 versus SEQ ID NO: 71).

The results also show that addition of the *Z. mays*-L N-terminal or C-terminal region to C-terminal or N-terminal region respectively, of the *Z. mays*-S sequence results in increased lipid yield over the full-length *Z. mays*-S sequence (see SEQ ID NO: 87 and 81 versus SEQ ID NO: 77).

In summary addition of fragments (either the N-terminal region or C-terminal region) of the *Z. mays*-L polypeptide of the invention to another DGAT1 sequence can increase the cellular lipid yield attainable by the combined sequence over that of the other DGAT1 sequence.

Addition of Fragments of the DGAT1 Polypeptide of the Invention to other DGAT1 Sequences Enhance Lipid Production in *Brassica napus* Relative to that with the other DGAT1 Sequences Alone.

Fragments (N-terminal region or C-terminal region) of the *Z. mays*-L polypeptide of the invention can also be combined with fragments of other plant DGAT1s to raise the oil content in *Brassica napus* seeds. Tables 7-8 show the seed oil contents from a variety of transgenic plants expressing such chimeric DGAT1s. In Table 7 the seed oil contents are presented both as a % of Dry Matter (DM) and as a normalised percentage of the seed oil content of the corresponding unmodified DGAT1 parents.

TABLE 7

| Construct description | Transgenic plant ID # | Seed Oil as % DM | Oil Increase as % of Vector Control | Oil Increase as % of N-terminal DGAT1 Parent | Oil Increase as % of C-terminal DGAT1 Parent |
|---|---|---|---|---|---|
| Vector control | CV | 37.99 | 0.00 | N/A | N/A |
| *T. majus* | N2 | 39.07 | 2.84 | N/A | N/A |
| *Z. mays*-L | N6 | 38.96 | 2.55 | N/A | N/A |
| Tm-ZmS | 182-38-4 | 44.66 | 17.56 | 14.31 | 10.96 |
| Tm-ZmL | 183-60-6 | 44.47 | 17.06 | 13.82 | 14.14 |
| ZmL-Tm | 185-24-5 | 45.27 | 19.16 | 16.20 | 15.87 |
| ZmL-Tm | 185-24-9 | 45.14 | 18.82 | 15.86 | 15.54 |
| ZmL-Tm | 185-22-1 | 44.23 | 16.43 | 13.53 | 13.21 |
| ZmL-Tm | 185-22-4 | 43.20 | 13.71 | 10.88 | 10.57 |
| ZmL-Tm | 185-22-9 | 43.49 | 14.48 | 11.63 | 11.31 |
| ZmL-Tm | 185-14-10 | 44.77 | 17.85 | 14.91 | 14.59 |
| ZmL-Tm | 185-9-9 | 43.73 | 15.11 | 12.24 | 11.93 |
| ZmL-Tm | 185-8-4 | 44.02 | 15.87 | 12.99 | 12.67 |
| ZmL-Tm | 185-8-7 | 45.11 | 18.74 | 15.79 | 15.46 |
| ZmL-Tm | 185-8-8 | 44.62 | 17.45 | 14.53 | 14.21 |
| ZmL-Tm | 185-8-9 | 43.48 | 14.45 | 11.60 | 11.29 |

In Table 8 the oil contents are presented both on a % of DM basis and as a normalised percentage of the seed oil content of the corresponding segregating null sibling.

TABLE 8

| Construct description | Transgenic ID # | Seed Oil as % DM | Oil Increase as % of Null Sibling |
|---|---|---|---|
| Tm-ZmL | 183-17-10 | 43.8 | 29.43 |
| Tm-ZmL Null Sib | 183-17-4 | 33.84 | N/A |
| ZmL-Tm | 185-24-5 | 45.27 | 19.41 |
| ZmL-Tm | 185-24-9 | 45.14 | 19.07 |
| ZmL-Tm Null Sib | 185-24-10 | 37.91 | N/A |
| ZmL-Tm | 185-22-1 | 44.23 | 30.09 |
| ZmL-Tm | 185-22-4 | 43.2 | 27.06 |
| ZmL-Tm | 185-22-9 | 43.49 | 27.91 |
| ZmL-Tm Nun sib | 185-22-2 | 34 | N/A |
| ZmL-Tm | 185-9-9 | 43.73 | 15.60 |
| ZmL-Tm Null Sib | 185-9-8 | 37.83 | N/A |

Together these results show that addition of fragments (N-terminal or C-terminal) of the *Z. mays* DGAT1-L polypeptide of the invention can be added to parts of the *T. majus* DGATS1 sequence to increase oil yield relative to that produced by the full length *T. majus* DGAT1.

DISCUSSION

The applicants have thus shown that the novel *Z. mays* DGAT1-L protein of the invention can be used to manipulate cellular lipid accumulation. The DGAT1 of the invention also has higher activity in increasing cellular lipid content than any other DGAT1 proteins tested by the applicants. The applicants have also shown that subsequences, or fragments, of the DGAT1 of the invention can be combined with parts of other DGAT1 to increase activity over that shown over the other DGAT1 sequences.

The invention claimed is:

1. A cell transformed with a polynucleotide encoding a diacylglycerol acyltransferase 1 (DGAT1) polypeptide comprising at least one of:

a) a sequence with at least 99% identity to the sequence of SEQ ID NO:39 b) the sequence of SEQ ID NO:39 c) a sequence comprising at least 450 contiguous amino acids of the sequence of a) or b), wherein the polynucleotide is heterologous to the cell.

2. The cell of claim 1 wherein the polypeptide has DGAT1 activity.

3. The cell of claim 1, wherein the DGAT1 polypeptide, when expressed in the cell has at least one of:

a) higher DGAT1 activity than a DGAT1 protein having the amino acid sequence of SEQ ID NO: 44, and b) altered substrate specificity relative to a DGAT1 protein having the amino acid sequence of SEQ ID NO: 44.

4. A genetic construct comprising a polynucleotide encoding a DGAT1 polypeptide comprising at least one of:

a) a sequence with at least 99% identity to the sequence of SEQ ID NO:39 b) the sequence of SEQ ID NO:39 c) a sequence comprising at least 450 contiguous amino acids of the sequence of a) or b), wherein the polynucleotide is operably linked to a promoter, and wherein the polynucleotide and the promoter are not found operably linked in nature.

5. A cell comprising a genetic construct of claim 4.

6. The cell of claim 1 wherein the DGAT1 polypeptide has increased DGAT1 activity relative to a DGAT1 protein having the amino acid sequence of SEQ ID NO: 44.

7. The cell of claim 1 wherein the DGAT1 polypeptide has altered substrate specificity relative to a DGAT1 protein having the amino acid sequence of SEQ ID NO: 44.

8. The cell of claim 1 that produces more lipid than does a control cell that is not transformed with the polynucleotide.

9. The cell of claim 1 that has an altered lipid profile relative to a control cell that is not transformed with the polynucleotide.

10. The cell of claim 1 that is a plant cell.

11. The cell of claim 1 that is also transformed to express at least one of: an oleosin, steroleosin, caloleosin, polyoleosin, and an oleosin including at least one artificially introduced cysteine.

12. A plant comprising the cell of claim 1.

13. A plant comprising a genetic construct of claim 4.

14. A plant comprising a plant cell of claim 10.

15. The plant of claim 12 wherein the plant, or its predecessor, has been transformed or genetically modified to express the polynucleotide or encoded polypeptide.

16. The plant of claim 12 wherein the polypeptide expressed by the polynucleotide has increased DGAT1 activity relative to a DGAT1 protein having the amino acid sequence of SEQ ID NO: 44.

17. The plant of claim 12 wherein the plant produces more lipid, in at least one of its tissues or parts, or as a whole, than does a control plant that is not transformed with the polynucleotide.

18. The plant of claim 12 wherein the plant has an altered lipid profile, in at least one of its tissues or parts, or as a whole, relative to a control plant that is not transformed with the polynucleotide.

19. The plant of claim 12 wherein the plant is also transformed to express at least one of: an oleosin, a steroleosin, a caloleosin, a polyoleosin, and an oleosin including at least one artificially introduced cysteine.

20. A part, propagule or progeny of the plant of claim 12, wherein the part, propagule or progeny comprises the cell.

21. A part, propagule or progeny of the plant of claim 13 wherein the part, propagule or progeny comprises the construct.

22. The part, propagule or progeny of claim 20 wherein at least one of the following applies:

the part, propagule or progeny produces more lipid than does a control part, propagule or progeny, or part, propagule or progeny of a control plant, and the part, propagule or progeny has an altered lipid profile relative to a control part, propagule or progeny, or part, propagule or progeny of a control plant, wherein the control part, propagule or progeny, or part propagule or progeny of the control plant is not transformed to comprise the polynucleotide.

23. The part, propagule or progeny of claim 21, wherein at least one of the following applies:

the part, propagule or progeny produces more lipid than does a control part, propagule or progeny, or part, propagule or progeny of a control plant, and wherein the part, propagule or progeny has an altered lipid profile relative to a control part, propagule or progeny, or part, propagule or progeny of a control plant, wherein the control part, propagule or progeny, or part propagule or progeny of the control plant does not comprise at least one of:

a) a sequence with at least 99% identity to the sequence of SEQ ID NO:39 b) the sequence of SEQ ID NO:39 c) a sequence comprising at least 450 contiguous amino acids of the sequence of a) or b).

24. An animal or biofuel feedstock comprising a cell transformed with a polynucleotide encoding a polypeptide comprising at least one of:

a) a sequence with at least 99% identity to the sequence of SEQ ID NO:39 b) the sequence of SEQ ID NO:39 c) a sequence comprising at least 450 contiguous amino acids of the sequence of a) or b), wherein the polynucleotide is heterologous to the cell.

25. An animal feedstock or biofuel feedstock comprising at least one plant part, propagule or progeny as defined in claim 22.

26. A method for producing a lipid, the method comprising growing a cell, plant cell or plant that is transformed, or genetically modified, with a polynucleotide encoding a diacylglycerol acyltransferase 1 (DGAT1) polypeptide comprising at least one of:

a) a sequence with at least 99% identity to the sequence of SEQ ID NO:39 b) the sequence of SEQ ID NO:39 c) a sequence comprising at least 450 contiguous amino acids of the sequence of a) or b), wherein the cell, plant cell, or plant produces oil through the activity of the expressed polypeptide, and wherein the polynucleotide is heterologous to the cell.

27. The method of claim 26 wherein the cell, plant cell or plant produces the lipid as a result of the DGAT1 activity of the polypeptide.

28. A method for producing lipid, the method comprising extracting lipid from at least one cell of claim 14.

29. The method of claim 26 wherein the lipid is triacylglycerol (TAG).

30. The method of claim 26 wherein the lipid is processed into at least one of:

a) a fuel, b) an oleochemical, c) a nutritional oil, d) a cosmetic oil, e) a polyunsaturated fatty acid (PUFA), and f) a combination of any of a) to e).

* * * * *